(12) United States Patent
Jackson et al.

(10) Patent No.: US 11,998,447 B2
(45) Date of Patent: Jun. 4, 2024

(54) RETRIEVABLE PROSTHESIS DELIVERY SYSTEM

(71) Applicant: Neovasc Tiara Inc., Richmond (CA)

(72) Inventors: Keith Alan Jackson, Brooker, FL (US);
Karen Tsoek-Ji Wong, Richmond (CA); Christopher Brodeur, Plymouth, MN (US); Eric Soun-Sang Fung, Vancouver (CA); Kellen Bodell, Plymouth, MN (US); Fredericus Antonius Colen, Boca Raton, FL (US); Shmuel Banai, Tel Aviv (IL); Juzer Banatwala, Vancouver (CA)

(73) Assignee: Neovasc Tiara Inc., Richmond (CA)

( * ) Notice: Subject to any disclaimer, the term of this patent is extended or adjusted under 35 U.S.C. 154(b) by 0 days.

(21) Appl. No.: 16/811,693

(22) Filed: Mar. 6, 2020

(65) Prior Publication Data

US 2020/0281720 A1 Sep. 10, 2020

Related U.S. Application Data

(60) Provisional application No. 62/815,832, filed on Mar. 8, 2019.

(51) Int. Cl.
*A61F 2/24* (2006.01)
*A61F 2/95* (2013.01)
(Continued)

(52) U.S. Cl.
CPC .......... *A61F 2/2436* (2013.01); *A61F 2/2418* (2013.01); *A61F 2210/0019* (2013.01)

(58) Field of Classification Search
None
See application file for complete search history.

(56) References Cited

U.S. PATENT DOCUMENTS

| 2,967,856 A | 1/1961 | Coover, Jr. et al. |
| 4,204,283 A | 5/1980 | Bellhouse et al. |
| (Continued) | | |

FOREIGN PATENT DOCUMENTS

| CA | 3007660 A1 | 6/2017 |
| CA | 2874219 C | 7/2020 |
| (Continued) | | |

OTHER PUBLICATIONS

"U.S. Appl. No. 13/096,572, Examiner Interview Summary dated Sep. 6, 2013", 3 pgs.

(Continued)

*Primary Examiner* — Ann Schillinger
(74) *Attorney, Agent, or Firm* — Schwegman Lundberg & Woessner, P.A.

(57) ABSTRACT

A prosthetic delivery system may include a plurality of concentric shafts and an actuator mechanism for actuating one or more of the concentric shafts. A stop mechanism may be coupled to the actuator mechanism. The stop mechanism prevents advancement or retraction of at least some of the shafts beyond a predetermined position unless the stop mechanism is released. A second stop mechanism may be included in the system for controlling another of the shafts. A plurality of filaments may be coupled to a prosthesis carried by the delivery system and actuation of the filaments may be used to control deployment or retrieval of the prosthesis.

22 Claims, 67 Drawing Sheets

(51) Int. Cl.
*A61M 25/00* (2006.01)
*A61M 25/01* (2006.01)
*A61M 25/09* (2006.01)

(56) References Cited

U.S. PATENT DOCUMENTS

| | | | |
|---|---|---|---|
| 4,909,252 A * | 3/1990 | Goldberger | A61M 25/104 604/103.1 |
| 5,209,741 A * | 5/1993 | Spaeth | A61B 17/3439 604/528 |
| 5,415,664 A * | 5/1995 | Pinchuk | A61F 2/95 606/198 |
| 5,443,477 A * | 8/1995 | Marin | A61F 2/95 606/198 |
| 5,693,083 A * | 12/1997 | Baker | A61F 2/07 623/1.11 |
| 5,843,158 A * | 12/1998 | Lenker | A61F 2/90 623/1.13 |
| 5,910,154 A * | 6/1999 | Tsugita | A61F 2/0105 606/200 |
| 5,928,281 A | 7/1999 | Huynh et al. | |
| 6,074,417 A | 6/2000 | Peredo | |
| 6,312,465 B1 | 11/2001 | Griffin et al. | |
| 6,361,545 B1 * | 3/2002 | Macoviak | A61B 17/221 606/151 |
| 6,629,534 B1 | 10/2003 | St. Goar et al. | |
| 6,635,079 B2 * | 10/2003 | Unsworth | A61F 2/954 623/25 |
| 6,652,578 B2 | 11/2003 | Bailey et al. | |
| 6,676,692 B2 * | 1/2004 | Rabkin | A61B 17/221 606/191 |
| 7,018,406 B2 | 3/2006 | Seguin et al. | |
| 7,329,278 B2 | 2/2008 | Seguin et al. | |
| 7,338,520 B2 | 3/2008 | Bailey et al. | |
| 7,435,257 B2 | 10/2008 | Lashinski et al. | |
| 7,442,204 B2 | 10/2008 | Schwammenthal et al. | |
| 7,455,689 B2 | 11/2008 | Johnson | |
| 7,637,945 B2 | 12/2009 | Solem et al. | |
| 7,637,946 B2 | 12/2009 | Solem et al. | |
| 7,799,072 B2 | 9/2010 | Greenberg | |
| 7,914,569 B2 | 3/2011 | Nguyen et al. | |
| 7,914,575 B2 | 3/2011 | Guyenot et al. | |
| 7,972,377 B2 | 7/2011 | Lane | |
| 8,092,520 B2 | 1/2012 | Quadri | |
| 8,226,710 B2 | 7/2012 | Nguyen et al. | |
| 8,337,541 B2 | 12/2012 | Quadri et al. | |
| 8,398,708 B2 | 3/2013 | Meiri et al. | |
| 8,403,983 B2 | 3/2013 | Quadri et al. | |
| 8,408,214 B2 | 4/2013 | Spenser | |
| 8,414,644 B2 | 4/2013 | Quadri et al. | |
| 8,449,599 B2 | 5/2013 | Chau et al. | |
| 8,568,472 B2 * | 10/2013 | Marchand | A61F 2/2433 623/2.11 |
| 8,579,964 B2 | 11/2013 | Lane et al. | |
| 8,652,203 B2 | 2/2014 | Quadri et al. | |
| 8,795,356 B2 | 8/2014 | Quadri et al. | |
| 10,631,984 B2 * | 4/2020 | Nyuli | A61M 25/0074 |
| 2001/0002445 A1 * | 5/2001 | Vesely | A61F 2/2439 623/2.11 |
| 2004/0181238 A1 | 9/2004 | Zarbatany et al. | |
| 2005/0075727 A1 | 4/2005 | Wheatley | |
| 2005/0137689 A1 * | 6/2005 | Salahieh | A61F 2/243 623/2.11 |
| 2005/0137695 A1 * | 6/2005 | Salahieh | A61F 2/2412 623/2.11 |
| 2005/0137702 A1 * | 6/2005 | Haug | A61F 2/2427 623/2.38 |
| 2005/0228475 A1 | 10/2005 | Keeble et al. | |
| 2006/0020334 A1 | 1/2006 | Lashinski et al. | |
| 2006/0259136 A1 | 11/2006 | Nguyen et al. | |
| 2006/0293698 A1 | 12/2006 | Douk | |
| 2006/0293745 A1 | 12/2006 | Carpentier et al. | |
| 2007/0016286 A1 | 1/2007 | Herrmann et al. | |
| 2007/0050020 A1 | 3/2007 | Spence | |
| 2007/0055340 A1 * | 3/2007 | Pryor | A61F 2/95 623/1.11 |
| 2008/0065011 A1 | 3/2008 | Marchand et al. | |
| 2008/0071362 A1 | 3/2008 | Tuval et al. | |
| 2008/0071363 A1 | 3/2008 | Tuval et al. | |
| 2008/0071366 A1 | 3/2008 | Tuval et al. | |
| 2008/0221672 A1 | 9/2008 | Lamphere | |
| 2008/0228201 A1 | 9/2008 | Zarbalany et al. | |
| 2008/0255660 A1 | 10/2008 | Guyenot et al. | |
| 2009/0012602 A1 | 1/2009 | Quadri | |
| 2009/0062908 A1 | 3/2009 | Bonhoeffer et al. | |
| 2009/0171447 A1 | 7/2009 | Von Segesser et al. | |
| 2009/0216314 A1 | 8/2009 | Quadri | |
| 2009/0234428 A1 | 9/2009 | Snow et al. | |
| 2009/0234443 A1 | 9/2009 | Ottma et al. | |
| 2009/0259306 A1 | 10/2009 | Rowe | |
| 2009/0276040 A1 | 11/2009 | Rowe et al. | |
| 2009/0306768 A1 | 12/2009 | Quadri | |
| 2009/0318871 A1 | 12/2009 | Zarbatany et al. | |
| 2010/0036479 A1 | 2/2010 | Hill et al. | |
| 2010/0049313 A1 * | 2/2010 | Alon | A61F 2/2439 623/2.11 |
| 2010/0082094 A1 | 4/2010 | Quadri et al. | |
| 2010/0094411 A1 | 4/2010 | Tuval et al. | |
| 2010/0131054 A1 | 5/2010 | Tuval et al. | |
| 2010/0168839 A1 | 7/2010 | Braido et al. | |
| 2010/0268332 A1 | 10/2010 | Tuval et al. | |
| 2010/0280495 A1 * | 11/2010 | Paul | A61F 2/2439 604/528 |
| 2010/0298931 A1 * | 11/2010 | Quadri | A61F 2/243 623/2.11 |
| 2011/0015731 A1 | 1/2011 | Carpentier et al. | |
| 2011/0022157 A1 | 1/2011 | Essinger et al. | |
| 2011/0137397 A1 | 6/2011 | Chau et al. | |
| 2011/0178597 A9 | 7/2011 | Navia et al. | |
| 2011/0202128 A1 | 8/2011 | Duffy | |
| 2011/0208290 A1 | 8/2011 | Straubinger et al. | |
| 2011/0208297 A1 | 8/2011 | Tuval et al. | |
| 2011/0208298 A1 | 8/2011 | Tuval et al. | |
| 2011/0224785 A1 | 9/2011 | Hacohen | |
| 2011/0264191 A1 * | 10/2011 | Rothstein | A61F 2/2418 623/1.11 |
| 2011/0313515 A1 | 12/2011 | Quadri et al. | |
| 2011/0319989 A1 | 12/2011 | Lane et al. | |
| 2012/0022633 A1 * | 1/2012 | Olson | A61F 2/2433 623/2.11 |
| 2012/0078353 A1 | 3/2012 | Quadri et al. | |
| 2012/0101571 A1 | 4/2012 | Thambar et al. | |
| 2012/0179239 A1 | 7/2012 | Quadri | |
| 2012/0215303 A1 | 8/2012 | Quadri et al. | |
| 2013/0053950 A1 | 2/2013 | Rowe et al. | |
| 2013/0110227 A1 | 5/2013 | Quadri et al. | |
| 2013/0131788 A1 | 5/2013 | Quadri et al. | |
| 2013/0131793 A1 | 5/2013 | Quadri et al. | |
| 2013/0138203 A1 | 5/2013 | Quadri | |
| 2013/0138207 A1 | 5/2013 | Quadri et al. | |
| 2013/0144378 A1 | 6/2013 | Quadri et al. | |
| 2013/0144380 A1 | 6/2013 | Quadri et al. | |
| 2013/0144381 A1 | 6/2013 | Quadri et al. | |
| 2013/0184813 A1 | 7/2013 | Quadri et al. | |
| 2013/0274870 A1 | 10/2013 | Lombardi et al. | |
| 2014/0155990 A1 | 6/2014 | Nyuli et al. | |
| 2014/0172085 A1 | 6/2014 | Quadri et al. | |
| 2014/0172086 A1 | 6/2014 | Quadri et al. | |
| 2014/0200649 A1 | 7/2014 | Essinger et al. | |
| 2014/0236278 A1 * | 8/2014 | Argentine | A61F 2/966 623/1.11 |
| 2014/0277390 A1 | 9/2014 | Ratz et al. | |
| 2014/0277422 A1 | 9/2014 | Ratz et al. | |
| 2014/0277427 A1 | 9/2014 | Ratz et al. | |
| 2015/0127092 A1 | 5/2015 | Straubinger et al. | |
| 2015/0305867 A1 | 10/2015 | Liu et al. | |
| 2015/0306358 A1 | 10/2015 | Duffy et al. | |
| 2015/0342736 A1 | 12/2015 | Rabito et al. | |
| 2016/0270911 A1 * | 9/2016 | Ganesan | A61F 2/2436 |
| 2017/0165064 A1 | 6/2017 | Nyuli et al. | |
| 2018/0071490 A1 * | 3/2018 | Khuu | F16H 25/16 |
| 2018/0116790 A1 | 5/2018 | Ratz et al. | |

(56) References Cited

U.S. PATENT DOCUMENTS

| | | |
|---|---|---|
| 2018/0280171 A1 | 10/2018 | Gloss et al. |
| 2018/0280174 A1 | 10/2018 | Dwork |
| 2020/0205972 A1 | 7/2020 | Nyuli et al. |

FOREIGN PATENT DOCUMENTS

| | | |
|---|---|---|
| CN | 101553190 A | 10/2009 |
| CN | 103118630 A | 5/2013 |
| CN | 106170269 A | 11/2016 |
| CN | 108601645 A | 9/2018 |
| CN | 108992209 A | 12/2018 |
| CN | 108601645 B | 2/2021 |
| CN | 113747863 A | 12/2021 |
| DE | 10103955 B4 | 11/2001 |
| DE | 10033858 B4 | 1/2002 |
| DE | 102005052628 A1 | 5/2007 |
| DE | 102006013113 B4 | 12/2008 |
| DE | 102008015781 B4 | 9/2011 |
| DE | 102010051632 B4 | 9/2013 |
| DE | 102005032974 B4 | 11/2013 |
| DE | 202013011734 U1 | 4/2014 |
| DE | 102005052628 B4 | 6/2014 |
| DE | 10301026 B4 | 10/2014 |
| DE | 212013000104 U1 | 11/2014 |
| DE | 102008012438 B4 | 12/2014 |
| DE | 102011107551 B4 | 5/2015 |
| DE | 102011054176 B4 | 2/2016 |
| DE | 102014114762 B3 | 3/2016 |
| DE | 102013208038 B4 | 9/2016 |
| DE | 102010012677 B4 | 8/2017 |
| DE | 202011110951 U1 | 10/2017 |
| DE | 202011110985 U1 | 12/2017 |
| DE | 202016105963 U1 | 1/2018 |
| DE | 10394350 B4 | 5/2018 |
| DE | 102009024648 B4 | 5/2018 |
| DE | 102015206098 B4 | 9/2018 |
| DE | 10065824 B4 | 10/2018 |
| DE | 202017104793 U1 | 11/2018 |
| DE | 102011106928 B4 | 2/2019 |
| DE | 202016008737 U1 | 4/2019 |
| DE | 102013205519 B4 | 5/2019 |
| DE | 102008014730 B4 | 7/2019 |
| DE | 102018102940 B4 | 10/2019 |
| DE | 102009009158 B4 | 11/2020 |
| EP | 1077072 B1 | 11/2003 |
| EP | 1140244 B1 | 11/2003 |
| EP | 1214106 B1 | 11/2003 |
| EP | 1143864 B1 | 2/2004 |
| EP | 1220651 B1 | 3/2004 |
| EP | 1265534 B1 | 6/2004 |
| EP | 1347785 B1 | 7/2004 |
| EP | 1245202 B1 | 8/2004 |
| EP | 1161204 B1 | 9/2004 |
| EP | 1266641 B1 | 10/2004 |
| EP | 1102567 B1 | 11/2004 |
| EP | 1117446 B1 | 11/2004 |
| EP | 1107710 B1 | 12/2004 |
| EP | 1121070 B1 | 12/2004 |
| EP | 1217966 B1 | 12/2004 |
| EP | 1233731 B1 | 12/2004 |
| EP | 1294318 B1 | 12/2004 |
| EP | 1237510 B1 | 1/2005 |
| EP | 1034753 B1 | 2/2005 |
| EP | 1259194 B1 | 2/2005 |
| EP | 1121069 B1 | 3/2005 |
| EP | 1143879 B1 | 3/2005 |
| EP | 1023879 B1 | 4/2005 |
| EP | 1339356 B1 | 4/2005 |
| EP | 1214022 B1 | 5/2005 |
| EP | 1318774 B1 | 5/2005 |
| EP | 1088529 B1 | 6/2005 |
| EP | 1171060 B1 | 6/2005 |
| EP | 1251803 B1 | 6/2005 |
| EP | 1259776 B1 | 6/2005 |
| EP | 1272123 B1 | 6/2005 |
| EP | 1049422 B1 | 7/2005 |
| EP | 1230901 B1 | 8/2005 |
| EP | 1335683 B1 | 8/2005 |
| EP | 1307246 B1 | 9/2005 |
| EP | 1267753 B1 | 10/2005 |
| EP | 1284688 B1 | 10/2005 |
| EP | 1343536 B1 | 10/2005 |
| EP | 1027020 B1 | 11/2005 |
| EP | 1152780 B1 | 11/2005 |
| EP | 1171059 B1 | 11/2005 |
| EP | 1237508 B1 | 11/2005 |
| EP | 1303234 B1 | 11/2005 |
| EP | 1328215 B1 | 11/2005 |
| EP | 1341487 B1 | 11/2005 |
| EP | 1392197 B1 | 11/2005 |
| EP | 1469797 B1 | 11/2005 |
| EP | 1255505 B1 | 12/2005 |
| EP | 1360942 B1 | 12/2005 |
| EP | 1322260 B1 | 1/2006 |
| EP | 1359870 B1 | 1/2006 |
| EP | 1237586 B1 | 2/2006 |
| EP | 1112043 B1 | 4/2006 |
| EP | 1309360 B1 | 4/2006 |
| EP | 1322259 B1 | 5/2006 |
| EP | 1124592 B1 | 6/2006 |
| EP | 1237516 B1 | 6/2006 |
| EP | 1098673 B1 | 7/2006 |
| EP | 1124591 B1 | 7/2006 |
| EP | 1083845 B1 | 8/2006 |
| EP | 1155666 B1 | 8/2006 |
| EP | 1463462 B1 | 8/2006 |
| EP | 1684671 A1 | 8/2006 |
| EP | 1519695 B1 | 9/2006 |
| EP | 1444993 B1 | 10/2006 |
| EP | 1117350 B1 | 11/2006 |
| EP | 1212011 B1 | 11/2006 |
| EP | 1261294 B1 | 11/2006 |
| EP | 1318775 B1 | 11/2006 |
| EP | 1429690 B1 | 11/2006 |
| EP | 1173111 B1 | 12/2006 |
| EP | 1239795 B1 | 12/2006 |
| EP | 1299049 B1 | 12/2006 |
| EP | 1487382 B1 | 12/2006 |
| EP | 1112044 B1 | 1/2007 |
| EP | 1482997 B1 | 1/2007 |
| EP | 1117352 B1 | 2/2007 |
| EP | 1128849 B1 | 2/2007 |
| EP | 1392666 B1 | 2/2007 |
| EP | 1474077 B1 | 2/2007 |
| EP | 1251805 B1 | 3/2007 |
| EP | 1117334 B1 | 4/2007 |
| EP | 1263484 B1 | 5/2007 |
| EP | 1313410 B1 | 5/2007 |
| EP | 1370200 B1 | 5/2007 |
| EP | 1560526 B1 | 6/2007 |
| EP | 2007516044 A | 6/2007 |
| EP | 1173117 B1 | 7/2007 |
| EP | 1434615 B1 | 7/2007 |
| EP | 1465546 B1 | 7/2007 |
| EP | 1499366 B1 | 7/2007 |
| EP | 1225948 B1 | 8/2007 |
| EP | 1819304 A2 | 8/2007 |
| EP | 1519962 B1 | 9/2007 |
| EP | 1337285 B1 | 10/2007 |
| EP | 1112042 B1 | 11/2007 |
| EP | 1148821 B1 | 11/2007 |
| EP | 1143882 B1 | 12/2007 |
| EP | 1330189 B1 | 12/2007 |
| EP | 1489996 B1 | 12/2007 |
| EP | 1296618 B1 | 1/2008 |
| EP | 1401356 B1 | 1/2008 |
| EP | 1629795 B1 | 1/2008 |
| EP | 1128786 B1 | 2/2008 |
| EP | 1616532 B1 | 2/2008 |
| EP | 1289447 B1 | 3/2008 |
| EP | 1895942 A2 | 3/2008 |
| EP | 1115353 B1 | 5/2008 |
| EP | 1330190 B1 | 5/2008 |
| EP | 1383448 B1 | 6/2008 |

(56) References Cited

FOREIGN PATENT DOCUMENTS

| | | | |
|---|---|---|---|
| EP | 1251804 | B1 | 7/2008 |
| EP | 1294310 | B1 | 7/2008 |
| EP | 1313409 | B1 | 7/2008 |
| EP | 1395202 | B1 | 7/2008 |
| EP | 1395204 | B1 | 7/2008 |
| EP | 1395205 | B1 | 7/2008 |
| EP | 1423066 | B1 | 7/2008 |
| EP | 1560545 | B1 | 7/2008 |
| EP | 1605871 | B1 | 7/2008 |
| EP | 1671608 | B1 | 7/2008 |
| EP | 1690515 | B1 | 7/2008 |
| EP | 1180987 | B1 | 8/2008 |
| EP | 1337386 | B1 | 8/2008 |
| EP | 1492579 | B1 | 9/2008 |
| EP | 1524942 | B1 | 9/2008 |
| EP | 1627091 | B1 | 9/2008 |
| EP | 1827577 | B1 | 9/2008 |
| EP | 1259195 | B1 | 10/2008 |
| EP | 1704834 | B1 | 10/2008 |
| EP | 1146835 | B1 | 11/2008 |
| EP | 1498086 | B1 | 11/2008 |
| EP | 1622548 | B1 | 11/2008 |
| EP | 1235537 | B1 | 12/2008 |
| EP | 1237509 | B1 | 12/2008 |
| EP | 1355590 | B1 | 12/2008 |
| EP | 1455680 | B1 | 12/2008 |
| EP | 1472995 | B1 | 12/2008 |
| EP | 1513474 | B1 | 12/2008 |
| EP | 1562522 | B1 | 12/2008 |
| EP | 1620042 | B1 | 12/2008 |
| EP | 1690514 | B1 | 12/2008 |
| EP | 1258232 | B1 | 1/2009 |
| EP | 1420723 | B1 | 1/2009 |
| EP | 1570809 | B1 | 1/2009 |
| EP | 1395182 | B1 | 2/2009 |
| EP | 1408882 | B1 | 2/2009 |
| EP | 1482868 | B1 | 2/2009 |
| EP | 1255510 | B3 | 3/2009 |
| EP | 1330213 | B1 | 3/2009 |
| EP | 1429651 | B1 | 3/2009 |
| EP | 1610727 | B1 | 4/2009 |
| EP | 1617788 | B1 | 4/2009 |
| EP | 1634547 | B1 | 4/2009 |
| EP | 1790318 | B1 | 4/2009 |
| EP | 2040645 | A1 | 4/2009 |
| EP | 1250165 | B1 | 5/2009 |
| EP | 1842508 | B1 | 6/2009 |
| EP | 1968482 | B1 | 6/2009 |
| EP | 2072027 | A1 | 6/2009 |
| EP | 1343438 | B1 | 7/2009 |
| EP | 1406608 | B1 | 7/2009 |
| EP | 1509256 | B1 | 7/2009 |
| EP | 1626681 | B1 | 7/2009 |
| EP | 1723935 | B1 | 7/2009 |
| EP | 1803420 | B1 | 7/2009 |
| EP | 2073755 | A2 | 7/2009 |
| EP | 1401359 | B1 | 8/2009 |
| EP | 1411865 | B1 | 8/2009 |
| EP | 1485033 | B1 | 8/2009 |
| EP | 1581120 | B1 | 8/2009 |
| EP | 1620040 | B1 | 8/2009 |
| EP | 1684667 | B1 | 8/2009 |
| EP | 1872743 | B1 | 8/2009 |
| EP | 1100378 | B1 | 9/2009 |
| EP | 1198203 | B1 | 9/2009 |
| EP | 1370201 | B1 | 9/2009 |
| EP | 1408850 | B1 | 9/2009 |
| EP | 1478364 | B1 | 9/2009 |
| EP | 1653888 | B1 | 9/2009 |
| EP | 1785154 | B1 | 9/2009 |
| EP | 1881804 | B1 | 9/2009 |
| EP | 1903991 | B1 | 9/2009 |
| EP | 1418865 | B1 | 10/2009 |
| EP | 1561437 | B1 | 10/2009 |
| EP | 1615595 | B1 | 10/2009 |
| EP | 1353612 | B1 | 11/2009 |
| EP | 1348406 | B1 | 12/2009 |
| EP | 1370202 | B1 | 12/2009 |
| EP | 1603492 | B1 | 12/2009 |
| EP | 1670364 | B1 | 12/2009 |
| EP | 1759663 | B1 | 12/2009 |
| EP | 1994887 | B1 | 12/2009 |
| EP | 1615593 | B1 | 1/2010 |
| EP | 1643938 | B1 | 1/2010 |
| EP | 1863402 | B1 | 1/2010 |
| EP | 1943942 | B1 | 1/2010 |
| EP | 2010101 | B1 | 1/2010 |
| EP | 2081518 | B1 | 1/2010 |
| EP | 1703865 | B1 | 2/2010 |
| EP | 1276437 | B1 | 3/2010 |
| EP | 1276439 | B1 | 3/2010 |
| EP | 1411867 | B1 | 3/2010 |
| EP | 1458313 | B1 | 3/2010 |
| EP | 1520519 | B1 | 3/2010 |
| EP | 1648340 | B1 | 3/2010 |
| EP | 1682048 | B1 | 3/2010 |
| EP | 1773239 | B1 | 3/2010 |
| EP | 1935377 | B1 | 3/2010 |
| EP | 1994912 | B1 | 3/2010 |
| EP | 1154738 | B1 | 4/2010 |
| EP | 1531762 | B1 | 4/2010 |
| EP | 1600178 | B1 | 4/2010 |
| EP | 1626682 | B1 | 4/2010 |
| EP | 1511445 | B1 | 5/2010 |
| EP | 1198213 | B1 | 6/2010 |
| EP | 1250097 | B1 | 6/2010 |
| EP | 1272249 | B1 | 6/2010 |
| EP | 1978895 | B1 | 6/2010 |
| EP | 1572033 | B1 | 7/2010 |
| EP | 1968491 | B1 | 7/2010 |
| EP | 2019652 | B1 | 7/2010 |
| EP | 1610722 | B1 | 8/2010 |
| EP | 1682047 | B1 | 8/2010 |
| EP | 1952772 | B1 | 8/2010 |
| EP | 1427356 | B1 | 9/2010 |
| EP | 1631218 | B1 | 9/2010 |
| EP | 1765224 | B1 | 9/2010 |
| EP | 1871290 | B1 | 9/2010 |
| EP | 1895288 | B1 | 9/2010 |
| EP | 1895913 | B1 | 9/2010 |
| EP | 2014257 | B1 | 9/2010 |
| EP | 1176913 | B1 | 10/2010 |
| EP | 1178758 | B1 | 10/2010 |
| EP | 1248579 | B1 | 10/2010 |
| EP | 1913899 | B1 | 10/2010 |
| EP | 1259193 | B1 | 11/2010 |
| EP | 1928357 | B1 | 11/2010 |
| EP | 1968660 | B1 | 11/2010 |
| EP | 2249711 | A2 | 11/2010 |
| EP | 1408895 | B1 | 12/2010 |
| EP | 1465554 | B1 | 12/2010 |
| EP | 1732473 | B1 | 12/2010 |
| EP | 1768610 | B1 | 12/2010 |
| EP | 1827314 | B1 | 12/2010 |
| EP | 1940321 | B1 | 12/2010 |
| EP | 1964532 | B1 | 12/2010 |
| EP | 2078498 | B1 | 12/2010 |
| EP | 1600182 | B1 | 1/2011 |
| EP | 1617789 | B1 | 1/2011 |
| EP | 1663332 | B1 | 1/2011 |
| EP | 2147659 | B1 | 1/2011 |
| EP | 2268231 | A2 | 1/2011 |
| EP | 2273951 | A1 | 1/2011 |
| EP | 1187582 | B1 | 2/2011 |
| EP | 1450733 | B1 | 2/2011 |
| EP | 1803421 | B1 | 2/2011 |
| EP | 1833425 | B1 | 2/2011 |
| EP | 2029053 | B1 | 2/2011 |
| EP | 2068770 | B1 | 2/2011 |
| EP | 1441784 | B1 | 3/2011 |
| EP | 1534177 | B1 | 3/2011 |
| EP | 1893132 | B1 | 3/2011 |
| EP | 1951153 | B1 | 3/2011 |
| EP | 2289467 | A1 | 3/2011 |

(56) References Cited

FOREIGN PATENT DOCUMENTS

| | | | |
|---|---|---|---|
| EP | 2299938 | A2 | 3/2011 |
| EP | 1359978 | B1 | 4/2011 |
| EP | 1667750 | B1 | 4/2011 |
| EP | 1718249 | B1 | 4/2011 |
| EP | 1903989 | B1 | 4/2011 |
| EP | 2018122 | B1 | 4/2011 |
| EP | 1610728 | B1 | 5/2011 |
| EP | 2105110 | B1 | 5/2011 |
| EP | 1347717 | B1 | 6/2011 |
| EP | 2331018 | A1 | 6/2011 |
| EP | 1347791 | B1 | 7/2011 |
| EP | 1862128 | B1 | 7/2011 |
| EP | 2120795 | B1 | 7/2011 |
| EP | 2229920 | B1 | 7/2011 |
| EP | 1637087 | B1 | 8/2011 |
| EP | 2153799 | B1 | 8/2011 |
| EP | 2247263 | B1 | 8/2011 |
| EP | 2349095 | A1 | 8/2011 |
| EP | 2349097 | A1 | 8/2011 |
| EP | 2349098 | A1 | 8/2011 |
| EP | 2358307 | A1 | 8/2011 |
| EP | 1441672 | B1 | 9/2011 |
| EP | 1625832 | B1 | 9/2011 |
| EP | 2173279 | B1 | 9/2011 |
| EP | 2367505 | A1 | 9/2011 |
| EP | 2160150 | B1 | 10/2011 |
| EP | 2370138 | A2 | 10/2011 |
| EP | 1626679 | B1 | 11/2011 |
| EP | 1719476 | B1 | 11/2011 |
| EP | 1928355 | B1 | 11/2011 |
| EP | 2237747 | B1 | 11/2011 |
| EP | 2381895 | A2 | 11/2011 |
| EP | 2389121 | A1 | 11/2011 |
| EP | 1572031 | B1 | 12/2011 |
| EP | 1603493 | B1 | 12/2011 |
| EP | 1945109 | B1 | 12/2011 |
| EP | 1998688 | B1 | 12/2011 |
| EP | 2393442 | A2 | 12/2011 |
| EP | 2395944 | A1 | 12/2011 |
| EP | 1443877 | B1 | 1/2012 |
| EP | 2400922 | A1 | 1/2012 |
| EP | 1281375 | B1 | 2/2012 |
| EP | 1699501 | B1 | 2/2012 |
| EP | 1788984 | B1 | 2/2012 |
| EP | 1833415 | B1 | 2/2012 |
| EP | 1952785 | B1 | 2/2012 |
| EP | 2055266 | B1 | 2/2012 |
| EP | 2205184 | B1 | 2/2012 |
| EP | 2416736 | A1 | 2/2012 |
| EP | 1337188 | B1 | 3/2012 |
| EP | 1443974 | B1 | 3/2012 |
| EP | 1542623 | B1 | 3/2012 |
| EP | 1942835 | B1 | 3/2012 |
| EP | 2074964 | B1 | 3/2012 |
| EP | 2244661 | B1 | 3/2012 |
| EP | 2273928 | B1 | 3/2012 |
| EP | 2427144 | A1 | 3/2012 |
| EP | 2429455 | A1 | 3/2012 |
| EP | 1401336 | B1 | 4/2012 |
| EP | 1749544 | B1 | 4/2012 |
| EP | 2119417 | B1 | 4/2012 |
| EP | 2152330 | B1 | 4/2012 |
| EP | 2231069 | B1 | 4/2012 |
| EP | 2437688 | A1 | 4/2012 |
| EP | 2020958 | B1 | 5/2012 |
| EP | 2192875 | B1 | 5/2012 |
| EP | 2218425 | B1 | 5/2012 |
| EP | 2445450 | A2 | 5/2012 |
| EP | 1411847 | B1 | 6/2012 |
| EP | 1727499 | B1 | 6/2012 |
| EP | 2082690 | B1 | 6/2012 |
| EP | 1740747 | B1 | 7/2012 |
| EP | 1861044 | B1 | 7/2012 |
| EP | 2052699 | B1 | 7/2012 |
| EP | 2470121 | A2 | 7/2012 |
| EP | 2471492 | A1 | 7/2012 |
| EP | 1887975 | B1 | 8/2012 |
| EP | 2000116 | B1 | 8/2012 |
| EP | 2222247 | B1 | 8/2012 |
| EP | 2486894 | A1 | 8/2012 |
| EP | 1605870 | B1 | 9/2012 |
| EP | 1887980 | B1 | 9/2012 |
| EP | 2497445 | A1 | 9/2012 |
| EP | 1740126 | B1 | 10/2012 |
| EP | 1865889 | B1 | 10/2012 |
| EP | 2033593 | B1 | 10/2012 |
| EP | 2124824 | B1 | 10/2012 |
| EP | 2139431 | B1 | 10/2012 |
| EP | 2506777 | A1 | 10/2012 |
| EP | 2512952 | A2 | 10/2012 |
| EP | 1430853 | B1 | 11/2012 |
| EP | 1928512 | B1 | 11/2012 |
| EP | 2008615 | B1 | 11/2012 |
| EP | 2088965 | B1 | 11/2012 |
| EP | 2520249 | A1 | 11/2012 |
| EP | 2522307 | A1 | 11/2012 |
| EP | 1557138 | B1 | 12/2012 |
| EP | 1924221 | B1 | 12/2012 |
| EP | 2023859 | B1 | 12/2012 |
| EP | 2250970 | B1 | 12/2012 |
| EP | 2285317 | B1 | 12/2012 |
| EP | 2536353 | A1 | 12/2012 |
| EP | 2537486 | A1 | 12/2012 |
| EP | 1494731 | B1 | 1/2013 |
| EP | 1610752 | B1 | 1/2013 |
| EP | 1796597 | B1 | 1/2013 |
| EP | 1919397 | B1 | 1/2013 |
| EP | 1942834 | B1 | 1/2013 |
| EP | 2015709 | B1 | 1/2013 |
| EP | 2079400 | B1 | 1/2013 |
| EP | 2238947 | B1 | 1/2013 |
| EP | 2241287 | B1 | 1/2013 |
| EP | 2359774 | B1 | 1/2013 |
| EP | 2538878 | A1 | 1/2013 |
| EP | 2538881 | A1 | 1/2013 |
| EP | 2538882 | A1 | 1/2013 |
| EP | 2538883 | A1 | 1/2013 |
| EP | 1512383 | B1 | 2/2013 |
| EP | 1578474 | B1 | 2/2013 |
| EP | 1648339 | B1 | 2/2013 |
| EP | 1750622 | B1 | 2/2013 |
| EP | 1994482 | B1 | 2/2013 |
| EP | 2250975 | B1 | 2/2013 |
| EP | 2257242 | B1 | 2/2013 |
| EP | 2265225 | B1 | 2/2013 |
| EP | 2558032 | A1 | 2/2013 |
| EP | 1659992 | B1 | 3/2013 |
| EP | 1701668 | B1 | 3/2013 |
| EP | 2151216 | B1 | 3/2013 |
| EP | 2340075 | B1 | 3/2013 |
| EP | 2568924 | A2 | 3/2013 |
| EP | 1781183 | B1 | 4/2013 |
| EP | 1786367 | B1 | 4/2013 |
| EP | 1850795 | B1 | 4/2013 |
| EP | 1861041 | B1 | 4/2013 |
| EP | 2319458 | B1 | 4/2013 |
| EP | 2526898 | B1 | 4/2013 |
| EP | 2537487 | B1 | 4/2013 |
| EP | 2575681 | A1 | 4/2013 |
| EP | 1901682 | B1 | 5/2013 |
| EP | 1951166 | B1 | 5/2013 |
| EP | 1994913 | B1 | 5/2013 |
| EP | 2231070 | B1 | 5/2013 |
| EP | 2401970 | B1 | 5/2013 |
| EP | 2409651 | B1 | 5/2013 |
| EP | 2594230 | A1 | 5/2013 |
| EP | 1694246 | B1 | 6/2013 |
| EP | 1948087 | B1 | 6/2013 |
| EP | 2135559 | B1 | 6/2013 |
| EP | 1115335 | B1 | 7/2013 |
| EP | 1663339 | B1 | 7/2013 |
| EP | 1864687 | B1 | 7/2013 |
| EP | 1977719 | B1 | 7/2013 |
| EP | 2111337 | B1 | 7/2013 |

(56) References Cited

FOREIGN PATENT DOCUMENTS

| | | | |
|---|---|---|---|
| EP | 2298237 | B1 | 7/2013 |
| EP | 2309949 | B1 | 7/2013 |
| EP | 2608741 | A2 | 7/2013 |
| EP | 2611388 | A2 | 7/2013 |
| EP | 2611389 | A2 | 7/2013 |
| EP | 2618781 | A2 | 7/2013 |
| EP | 1599151 | B1 | 8/2013 |
| EP | 1761211 | B1 | 8/2013 |
| EP | 2047871 | B1 | 8/2013 |
| EP | 2142144 | B1 | 8/2013 |
| EP | 2150206 | B1 | 8/2013 |
| EP | 2319459 | B1 | 8/2013 |
| EP | 2397108 | B1 | 8/2013 |
| EP | 2623068 | A1 | 8/2013 |
| EP | 1758523 | B1 | 9/2013 |
| EP | 1545392 | B1 | 10/2013 |
| EP | 1638627 | B1 | 10/2013 |
| EP | 1779868 | B1 | 10/2013 |
| EP | 2073756 | B1 | 10/2013 |
| EP | 2111190 | B1 | 10/2013 |
| EP | 2651336 | A1 | 10/2013 |
| EP | 1848375 | B1 | 11/2013 |
| EP | 1928356 | B1 | 11/2013 |
| EP | 1933766 | B1 | 11/2013 |
| EP | 2109417 | B1 | 11/2013 |
| EP | 2194925 | B1 | 11/2013 |
| EP | 2387977 | B1 | 11/2013 |
| EP | 2476394 | B1 | 11/2013 |
| EP | 2529701 | B1 | 11/2013 |
| EP | 1945142 | B1 | 12/2013 |
| EP | 2387972 | B1 | 12/2013 |
| EP | 2477555 | B1 | 12/2013 |
| EP | 2670349 | A2 | 12/2013 |
| EP | 2670351 | A1 | 12/2013 |
| EP | 2117476 | B1 | 1/2014 |
| EP | 2526895 | B1 | 1/2014 |
| EP | 2526899 | B1 | 1/2014 |
| EP | 2529696 | B1 | 1/2014 |
| EP | 2529697 | B1 | 1/2014 |
| EP | 2529698 | B1 | 1/2014 |
| EP | 2529699 | B1 | 1/2014 |
| EP | 2679198 | A1 | 1/2014 |
| EP | 2688516 | A1 | 1/2014 |
| EP | 1395214 | B1 | 2/2014 |
| EP | 1499266 | B1 | 2/2014 |
| EP | 1838241 | B1 | 2/2014 |
| EP | 2520250 | B1 | 2/2014 |
| EP | 2526977 | B1 | 2/2014 |
| EP | 2693985 | A1 | 2/2014 |
| EP | 2698129 | A1 | 2/2014 |
| EP | 2699302 | A2 | 2/2014 |
| EP | 1629794 | B1 | 3/2014 |
| EP | 1919398 | B1 | 3/2014 |
| EP | 2099508 | B1 | 3/2014 |
| EP | 2399549 | B1 | 3/2014 |
| EP | 2422823 | B1 | 3/2014 |
| EP | 2706958 | A1 | 3/2014 |
| EP | 1804860 | B1 | 4/2014 |
| EP | 1926455 | B1 | 4/2014 |
| EP | 2081519 | B1 | 4/2014 |
| EP | 2117477 | B1 | 4/2014 |
| EP | 2405966 | B1 | 4/2014 |
| EP | 2420205 | B1 | 4/2014 |
| EP | 2593048 | B1 | 4/2014 |
| EP | 2713894 | A2 | 4/2014 |
| EP | 2713955 | A2 | 4/2014 |
| EP | 2723273 | A2 | 4/2014 |
| EP | 1499265 | B1 | 5/2014 |
| EP | 1594569 | B1 | 5/2014 |
| EP | 2029056 | B1 | 5/2014 |
| EP | 2257243 | B1 | 5/2014 |
| EP | 1791500 | B1 | 6/2014 |
| EP | 2073753 | B1 | 6/2014 |
| EP | 2306933 | B1 | 6/2014 |
| EP | 2331017 | B1 | 6/2014 |
| EP | 2337522 | B1 | 6/2014 |
| EP | 2389897 | B1 | 6/2014 |
| EP | 2606723 | B1 | 6/2014 |
| EP | 2739250 | A1 | 6/2014 |
| EP | 1487350 | B1 | 7/2014 |
| EP | 1977718 | B1 | 7/2014 |
| EP | 2117469 | B1 | 7/2014 |
| EP | 2124826 | B1 | 7/2014 |
| EP | 2258316 | B1 | 7/2014 |
| EP | 2747708 | A1 | 7/2014 |
| EP | 2750630 | A1 | 7/2014 |
| EP | 2750631 | A1 | 7/2014 |
| EP | 1667604 | B1 | 8/2014 |
| EP | 1786368 | B1 | 8/2014 |
| EP | 2211779 | B1 | 8/2014 |
| EP | 2217174 | B1 | 8/2014 |
| EP | 2293740 | B1 | 8/2014 |
| EP | 2367504 | B1 | 8/2014 |
| EP | 2453942 | B1 | 8/2014 |
| EP | 2475328 | B1 | 8/2014 |
| EP | 2545884 | B1 | 8/2014 |
| EP | 2571460 | B1 | 8/2014 |
| EP | 2763708 | A2 | 8/2014 |
| EP | 2765954 | A1 | 8/2014 |
| EP | 1935378 | B1 | 9/2014 |
| EP | 2246011 | B1 | 9/2014 |
| EP | 2422749 | B1 | 9/2014 |
| EP | 2531139 | B1 | 9/2014 |
| EP | 2609893 | B1 | 9/2014 |
| EP | 2777616 | A1 | 9/2014 |
| EP | 2779945 | A1 | 9/2014 |
| EP | 1853199 | B1 | 10/2014 |
| EP | 2133039 | B1 | 10/2014 |
| EP | 2549955 | B1 | 10/2014 |
| EP | 2549956 | B1 | 10/2014 |
| EP | 2651335 | B1 | 10/2014 |
| EP | 2785281 | A1 | 10/2014 |
| EP | 2793743 | A1 | 10/2014 |
| EP | 2793749 | A1 | 10/2014 |
| EP | 2793752 | A1 | 10/2014 |
| EP | 2049721 | B1 | 11/2014 |
| EP | 2142143 | B1 | 11/2014 |
| EP | 2229921 | B1 | 11/2014 |
| EP | 2288403 | B1 | 11/2014 |
| EP | 2415421 | B1 | 11/2014 |
| EP | 1551274 | B1 | 12/2014 |
| EP | 1768735 | B1 | 12/2014 |
| EP | 1959865 | B1 | 12/2014 |
| EP | 2077718 | B1 | 12/2014 |
| EP | 2303185 | B1 | 12/2014 |
| EP | 2334857 | B1 | 12/2014 |
| EP | 2365840 | B1 | 12/2014 |
| EP | 2420207 | B1 | 12/2014 |
| EP | 2422750 | B1 | 12/2014 |
| EP | 2707073 | B1 | 12/2014 |
| EP | 1768630 | B1 | 1/2015 |
| EP | 2254515 | B1 | 1/2015 |
| EP | 2641569 | B1 | 1/2015 |
| EP | 2709559 | B1 | 1/2015 |
| EP | 2825203 | A1 | 1/2015 |
| EP | 1903990 | B1 | 2/2015 |
| EP | 2255753 | B1 | 2/2015 |
| EP | 2335649 | B1 | 2/2015 |
| EP | 2522308 | B1 | 2/2015 |
| EP | 2591754 | B1 | 2/2015 |
| EP | 2835112 | A1 | 2/2015 |
| EP | 2838473 | A1 | 2/2015 |
| EP | 1861045 | B1 | 3/2015 |
| EP | 2029057 | B1 | 3/2015 |
| EP | 2193761 | B1 | 3/2015 |
| EP | 2379010 | B1 | 3/2015 |
| EP | 2416737 | B1 | 3/2015 |
| EP | 2849678 | A1 | 3/2015 |
| EP | 1791495 | B1 | 4/2015 |
| EP | 2298252 | B1 | 4/2015 |
| EP | 2536359 | B1 | 4/2015 |
| EP | 2538879 | B1 | 4/2015 |
| EP | 2609894 | B1 | 4/2015 |
| EP | 2693984 | B1 | 4/2015 |

(56) References Cited

FOREIGN PATENT DOCUMENTS

| | | | |
|---|---|---|---|
| EP | 2712633 | B1 | 4/2015 |
| EP | 2747707 | B1 | 4/2015 |
| EP | 2856973 | A1 | 4/2015 |
| EP | 2862546 | A1 | 4/2015 |
| EP | 2863842 | A1 | 4/2015 |
| EP | 1465555 | B1 | 5/2015 |
| EP | 1924224 | B1 | 5/2015 |
| EP | 1992369 | B1 | 5/2015 |
| EP | 2410947 | B1 | 5/2015 |
| EP | 2484311 | B1 | 5/2015 |
| EP | 2654616 | B1 | 5/2015 |
| EP | 2866741 | A1 | 5/2015 |
| EP | 1646332 | B1 | 6/2015 |
| EP | 2745805 | B1 | 6/2015 |
| EP | 2749254 | B1 | 6/2015 |
| EP | 2877123 | A2 | 6/2015 |
| EP | 2882374 | A1 | 6/2015 |
| EP | 2884906 | A1 | 6/2015 |
| EP | 1729685 | B1 | 7/2015 |
| EP | 1976439 | B1 | 7/2015 |
| EP | 2068767 | B1 | 7/2015 |
| EP | 2068769 | B1 | 7/2015 |
| EP | 2444031 | B1 | 7/2015 |
| EP | 2455041 | B1 | 7/2015 |
| EP | 2498719 | B1 | 7/2015 |
| EP | 2558030 | B1 | 7/2015 |
| EP | 2752209 | B1 | 7/2015 |
| EP | 2892467 | A1 | 7/2015 |
| EP | 1702247 | B1 | 8/2015 |
| EP | 1729688 | B1 | 8/2015 |
| EP | 1887979 | B1 | 8/2015 |
| EP | 2032079 | B1 | 8/2015 |
| EP | 2219558 | B1 | 8/2015 |
| EP | 2234657 | B1 | 8/2015 |
| EP | 2250976 | B1 | 8/2015 |
| EP | 2262447 | B1 | 8/2015 |
| EP | 2303384 | B1 | 8/2015 |
| EP | 2387366 | B1 | 8/2015 |
| EP | 2560579 | B1 | 8/2015 |
| EP | 2575621 | B1 | 8/2015 |
| EP | 2590595 | B1 | 8/2015 |
| EP | 2709560 | B1 | 8/2015 |
| EP | 2755603 | B1 | 8/2015 |
| EP | 2906147 | A1 | 8/2015 |
| EP | 1534185 | B1 | 9/2015 |
| EP | 1765225 | B1 | 9/2015 |
| EP | 1778127 | B1 | 9/2015 |
| EP | 2094194 | B1 | 9/2015 |
| EP | 2201911 | B1 | 9/2015 |
| EP | 2306934 | B1 | 9/2015 |
| EP | 2397113 | B1 | 9/2015 |
| EP | 2453843 | B1 | 9/2015 |
| EP | 2459127 | B1 | 9/2015 |
| EP | 2675396 | B1 | 9/2015 |
| EP | 2675397 | B1 | 9/2015 |
| EP | 2736454 | B1 | 9/2015 |
| EP | 2754414 | A4 | 9/2015 |
| EP | 2790609 | B1 | 9/2015 |
| EP | 2805693 | B1 | 9/2015 |
| EP | 2911611 | A1 | 9/2015 |
| EP | 2916781 | A2 | 9/2015 |
| EP | 2919712 | A1 | 9/2015 |
| EP | 1734903 | B1 | 10/2015 |
| EP | 1863546 | B1 | 10/2015 |
| EP | 1900343 | B1 | 10/2015 |
| EP | 2081515 | B1 | 10/2015 |
| EP | 2191792 | B1 | 10/2015 |
| EP | 2254513 | B1 | 10/2015 |
| EP | 2381896 | B1 | 10/2015 |
| EP | 2450008 | B1 | 10/2015 |
| EP | 2544626 | B1 | 10/2015 |
| EP | 2561830 | B1 | 10/2015 |
| EP | 2600798 | B1 | 10/2015 |
| EP | 2626039 | B1 | 10/2015 |
| EP | 2647354 | B1 | 10/2015 |
| EP | 2729093 | B1 | 10/2015 |
| EP | 2836165 | B1 | 10/2015 |
| EP | 1863545 | B1 | 11/2015 |
| EP | 2303395 | B1 | 11/2015 |
| EP | 2497446 | B1 | 11/2015 |
| EP | 2772228 | B1 | 11/2015 |
| EP | 1482869 | B1 | 12/2015 |
| EP | 1551473 | B1 | 12/2015 |
| EP | 1748745 | B1 | 12/2015 |
| EP | 1755459 | B1 | 12/2015 |
| EP | 1850796 | B1 | 12/2015 |
| EP | 1922030 | B1 | 12/2015 |
| EP | 1954212 | B1 | 12/2015 |
| EP | 2424472 | B1 | 12/2015 |
| EP | 2470120 | B1 | 12/2015 |
| EP | 2542179 | B1 | 12/2015 |
| EP | 2948100 | A1 | 12/2015 |
| EP | 2948103 | A2 | 12/2015 |
| EP | 2950752 | A2 | 12/2015 |
| EP | 2959866 | A1 | 12/2015 |
| EP | 1991168 | B1 | 1/2016 |
| EP | 2254512 | B1 | 1/2016 |
| EP | 2422748 | B1 | 1/2016 |
| EP | 2962664 | A1 | 1/2016 |
| EP | 2964153 | A1 | 1/2016 |
| EP | 2967700 | A1 | 1/2016 |
| EP | 2967807 | A2 | 1/2016 |
| EP | 2967834 | A1 | 1/2016 |
| EP | 2967856 | A1 | 1/2016 |
| EP | 2967858 | A2 | 1/2016 |
| EP | 2967860 | A1 | 1/2016 |
| EP | 2967866 | A2 | 1/2016 |
| EP | 2977026 | A1 | 1/2016 |
| EP | 1754684 | B1 | 2/2016 |
| EP | 1835948 | B1 | 2/2016 |
| EP | 2012712 | B1 | 2/2016 |
| EP | 2285318 | B1 | 2/2016 |
| EP | 2731550 | B1 | 2/2016 |
| EP | 2926766 | B1 | 2/2016 |
| EP | 2982337 | A1 | 2/2016 |
| EP | 1585463 | B1 | 3/2016 |
| EP | 1638621 | B1 | 3/2016 |
| EP | 1804726 | B1 | 3/2016 |
| EP | 1865886 | B1 | 3/2016 |
| EP | 1887982 | B1 | 3/2016 |
| EP | 2150205 | B1 | 3/2016 |
| EP | 2278944 | B1 | 3/2016 |
| EP | 2291126 | B1 | 3/2016 |
| EP | 2517674 | B1 | 3/2016 |
| EP | 2520253 | B1 | 3/2016 |
| EP | 2526897 | B1 | 3/2016 |
| EP | 2621409 | A4 | 3/2016 |
| EP | 2670353 | B1 | 3/2016 |
| EP | 2674130 | B1 | 3/2016 |
| EP | 2780042 | B1 | 3/2016 |
| EP | 2991584 | A1 | 3/2016 |
| EP | 2991587 | A2 | 3/2016 |
| EP | 2991588 | A1 | 3/2016 |
| EP | 2994072 | A1 | 3/2016 |
| EP | 2994075 | A1 | 3/2016 |
| EP | 2996632 | A1 | 3/2016 |
| EP | 2996633 | A1 | 3/2016 |
| EP | 2996641 | A1 | 3/2016 |
| EP | 2999435 | A1 | 3/2016 |
| EP | 1420730 | B1 | 4/2016 |
| EP | 1545371 | B1 | 4/2016 |
| EP | 1592367 | B1 | 4/2016 |
| EP | 1708649 | B1 | 4/2016 |
| EP | 1871300 | B1 | 4/2016 |
| EP | 2168536 | B1 | 4/2016 |
| EP | 2399550 | B1 | 4/2016 |
| EP | 2433591 | B1 | 4/2016 |
| EP | 2478871 | B1 | 4/2016 |
| EP | 2536355 | B1 | 4/2016 |
| EP | 2572676 | B1 | 4/2016 |
| EP | 2606852 | B1 | 4/2016 |
| EP | 2621408 | B1 | 4/2016 |
| EP | 2626041 | B1 | 4/2016 |
| EP | 2633821 | B1 | 4/2016 |

(56) References Cited

FOREIGN PATENT DOCUMENTS

| | | | |
|---|---|---|---|
| EP | 2670354 | B1 | 4/2016 |
| EP | 2702965 | B1 | 4/2016 |
| EP | 2704669 | B1 | 4/2016 |
| EP | 2815725 | B1 | 4/2016 |
| EP | 3007651 | A1 | 4/2016 |
| EP | 3010564 | A1 | 4/2016 |
| EP | 2194933 | B1 | 5/2016 |
| EP | 2237746 | B1 | 5/2016 |
| EP | 2378947 | B1 | 5/2016 |
| EP | 2542184 | B1 | 5/2016 |
| EP | 2572684 | B1 | 5/2016 |
| EP | 2582326 | B1 | 5/2016 |
| EP | 2618784 | B1 | 5/2016 |
| EP | 2654623 | B1 | 5/2016 |
| EP | 2656816 | B1 | 5/2016 |
| EP | 2680791 | B1 | 5/2016 |
| EP | 2693986 | B1 | 5/2016 |
| EP | 2806805 | B1 | 5/2016 |
| EP | 2866739 | B1 | 5/2016 |
| EP | 2889020 | B1 | 5/2016 |
| EP | 2926767 | B1 | 5/2016 |
| EP | 2949292 | B1 | 5/2016 |
| EP | 3019092 | A1 | 5/2016 |
| EP | 1734902 | B1 | 6/2016 |
| EP | 1906884 | B1 | 6/2016 |
| EP | 2111800 | B1 | 6/2016 |
| EP | 2160156 | B1 | 6/2016 |
| EP | 2190379 | B1 | 6/2016 |
| EP | 2193762 | B1 | 6/2016 |
| EP | 2416739 | B1 | 6/2016 |
| EP | 2453969 | B1 | 6/2016 |
| EP | 2515800 | B1 | 6/2016 |
| EP | 2558031 | B1 | 6/2016 |
| EP | 2563236 | B1 | 6/2016 |
| EP | 2572675 | B1 | 6/2016 |
| EP | 2626040 | B1 | 6/2016 |
| EP | 2704668 | B1 | 6/2016 |
| EP | 2777611 | B1 | 6/2016 |
| EP | 2815724 | B1 | 6/2016 |
| EP | 2854710 | B1 | 6/2016 |
| EP | 2901966 | B1 | 6/2016 |
| EP | 3024527 | A2 | 6/2016 |
| EP | 1605866 | B1 | 7/2016 |
| EP | 1933756 | B1 | 7/2016 |
| EP | 2393452 | B1 | 7/2016 |
| EP | 2410948 | B1 | 7/2016 |
| EP | 2412397 | B1 | 7/2016 |
| EP | 2724690 | B1 | 7/2016 |
| EP | 2815723 | B1 | 7/2016 |
| EP | 2870945 | B1 | 7/2016 |
| EP | 3038567 | A1 | 7/2016 |
| EP | 3040054 | A1 | 7/2016 |
| EP | 3042635 | A1 | 7/2016 |
| EP | 3043745 | A1 | 7/2016 |
| EP | 3043747 | A1 | 7/2016 |
| EP | 3043755 | A1 | 7/2016 |
| EP | 1401358 | B1 | 8/2016 |
| EP | 1915105 | B1 | 8/2016 |
| EP | 1937186 | B1 | 8/2016 |
| EP | 2292186 | B1 | 8/2016 |
| EP | 2379012 | B1 | 8/2016 |
| EP | 2385809 | B1 | 8/2016 |
| EP | 2536345 | B1 | 8/2016 |
| EP | 2537490 | B1 | 8/2016 |
| EP | 2549954 | B1 | 8/2016 |
| EP | 2618779 | B1 | 8/2016 |
| EP | 2670352 | B1 | 8/2016 |
| EP | 2829235 | B1 | 8/2016 |
| EP | 2853238 | B1 | 8/2016 |
| EP | 2866738 | B1 | 8/2016 |
| EP | 2906150 | B1 | 8/2016 |
| EP | 3052053 | A1 | 8/2016 |
| EP | 3052611 | A1 | 8/2016 |
| EP | 3060171 | A1 | 8/2016 |
| EP | 3060174 | A1 | 8/2016 |
| EP | 3061421 | A1 | 8/2016 |
| EP | 3061422 | A1 | 8/2016 |
| EP | 1156755 | B1 | 9/2016 |
| EP | 1492478 | B1 | 9/2016 |
| EP | 1912697 | B1 | 9/2016 |
| EP | 2393449 | B1 | 9/2016 |
| EP | 2670356 | B1 | 9/2016 |
| EP | 2793969 | B1 | 9/2016 |
| EP | 2809271 | B1 | 9/2016 |
| EP | 2896425 | B1 | 9/2016 |
| EP | 3068345 | A1 | 9/2016 |
| EP | 3068346 | A1 | 9/2016 |
| EP | 3071148 | A1 | 9/2016 |
| EP | 3071149 | A1 | 9/2016 |
| EP | 2023858 | B1 | 10/2016 |
| EP | 2112912 | B1 | 10/2016 |
| EP | 2640319 | B1 | 10/2016 |
| EP | 2663257 | B1 | 10/2016 |
| EP | 2727612 | B1 | 10/2016 |
| EP | 2760384 | B1 | 10/2016 |
| EP | 2806829 | B1 | 10/2016 |
| EP | 2858599 | B1 | 10/2016 |
| EP | 2918250 | B1 | 10/2016 |
| EP | 2922592 | A4 | 10/2016 |
| EP | 2934387 | B1 | 10/2016 |
| EP | 3076901 | A1 | 10/2016 |
| EP | 3079633 | A1 | 10/2016 |
| EP | 1539047 | B1 | 11/2016 |
| EP | 2282700 | B1 | 11/2016 |
| EP | 2400926 | B1 | 11/2016 |
| EP | 2467104 | B1 | 11/2016 |
| EP | 2525743 | B1 | 11/2016 |
| EP | 2549953 | B1 | 11/2016 |
| EP | 2575696 | B1 | 11/2016 |
| EP | 2598045 | B1 | 11/2016 |
| EP | 2670355 | B1 | 11/2016 |
| EP | 2676640 | B1 | 11/2016 |
| EP | 2680792 | B1 | 11/2016 |
| EP | 2707053 | B1 | 11/2016 |
| EP | 2717803 | B1 | 11/2016 |
| EP | 2773297 | B1 | 11/2016 |
| EP | 2801387 | B1 | 11/2016 |
| EP | 2844192 | B1 | 11/2016 |
| EP | 2849679 | B1 | 11/2016 |
| EP | 2877122 | B1 | 11/2016 |
| EP | 2908778 | B1 | 11/2016 |
| EP | 2922500 | B1 | 11/2016 |
| EP | 2922501 | B1 | 11/2016 |
| EP | 2967854 | B1 | 11/2016 |
| EP | 3020365 | B1 | 11/2016 |
| EP | 3090703 | A1 | 11/2016 |
| EP | 3096713 | A1 | 11/2016 |
| EP | 1645244 | B1 | 12/2016 |
| EP | 1667614 | B1 | 12/2016 |
| EP | 1684656 | B1 | 12/2016 |
| EP | 1684670 | B1 | 12/2016 |
| EP | 1750592 | B1 | 12/2016 |
| EP | 1883375 | B1 | 12/2016 |
| EP | 2293739 | B1 | 12/2016 |
| EP | 2339988 | B1 | 12/2016 |
| EP | 2512375 | B1 | 12/2016 |
| EP | 2754417 | B1 | 12/2016 |
| EP | 2754418 | B1 | 12/2016 |
| EP | 2755562 | B1 | 12/2016 |
| EP | 2889019 | B1 | 12/2016 |
| EP | 3010442 | B1 | 12/2016 |
| EP | 3099271 | A1 | 12/2016 |
| EP | 3102150 | A1 | 12/2016 |
| EP | 3107495 | A1 | 12/2016 |
| EP | 3107498 | A2 | 12/2016 |
| EP | 3107500 | A1 | 12/2016 |
| EP | 1893127 | B1 | 1/2017 |
| EP | 1951352 | B1 | 1/2017 |
| EP | 2109419 | B1 | 1/2017 |
| EP | 2185107 | B1 | 1/2017 |
| EP | 2266503 | B1 | 1/2017 |
| EP | 2340055 | B1 | 1/2017 |
| EP | 2395941 | B1 | 1/2017 |
| EP | 2400923 | B1 | 1/2017 |

(56) References Cited

FOREIGN PATENT DOCUMENTS

| | | | |
|---|---|---|---|
| EP | 2629699 B1 | 1/2017 |
| EP | 2645963 B1 | 1/2017 |
| EP | 2654622 B1 | 1/2017 |
| EP | 2706952 B1 | 1/2017 |
| EP | 2760347 B1 | 1/2017 |
| EP | 2771064 B1 | 1/2017 |
| EP | 2780077 B1 | 1/2017 |
| EP | 2809272 B1 | 1/2017 |
| EP | 2934385 B1 | 1/2017 |
| EP | 2986255 B1 | 1/2017 |
| EP | 3119351 A1 | 1/2017 |
| EP | 1507493 B1 | 2/2017 |
| EP | 2563238 B1 | 2/2017 |
| EP | 2752170 B1 | 2/2017 |
| EP | 2760371 B1 | 2/2017 |
| EP | 2793709 B1 | 2/2017 |
| EP | 2793748 B1 | 2/2017 |
| EP | 2793763 B1 | 2/2017 |
| EP | 2832317 B1 | 2/2017 |
| EP | 2921135 B1 | 2/2017 |
| EP | 2967931 B1 | 2/2017 |
| EP | 2974693 B1 | 2/2017 |
| EP | 3025680 B1 | 2/2017 |
| EP | 3025681 B1 | 2/2017 |
| EP | 3125826 A1 | 2/2017 |
| EP | 3125827 A2 | 2/2017 |
| EP | 3128927 A1 | 2/2017 |
| EP | 3131502 A1 | 2/2017 |
| EP | 1845895 B1 | 3/2017 |
| EP | 2190385 B1 | 3/2017 |
| EP | 2266504 B1 | 3/2017 |
| EP | 2341871 B1 | 3/2017 |
| EP | 2379011 B1 | 3/2017 |
| EP | 2379013 B1 | 3/2017 |
| EP | 2640316 B1 | 3/2017 |
| EP | 2731552 B1 | 3/2017 |
| EP | 2756109 B1 | 3/2017 |
| EP | 2773298 B1 | 3/2017 |
| EP | 2832316 B1 | 3/2017 |
| EP | 2854718 B1 | 3/2017 |
| EP | 2881083 B1 | 3/2017 |
| EP | 2934390 B1 | 3/2017 |
| EP | 2934391 B1 | 3/2017 |
| EP | 3010564 A4 | 3/2017 |
| EP | 3145451 A2 | 3/2017 |
| EP | 3146938 A1 | 3/2017 |
| EP | 2014239 B1 | 4/2017 |
| EP | 2111189 B1 | 4/2017 |
| EP | 2393451 B1 | 4/2017 |
| EP | 2617388 B1 | 4/2017 |
| EP | 2629700 B1 | 4/2017 |
| EP | 2832318 B1 | 4/2017 |
| EP | 2893904 B1 | 4/2017 |
| EP | 2982340 B1 | 4/2017 |
| EP | 3000436 B1 | 4/2017 |
| EP | 3001979 B1 | 4/2017 |
| EP | 3043749 B1 | 4/2017 |
| EP | 3045147 B1 | 4/2017 |
| EP | 3054893 B1 | 4/2017 |
| EP | 3154474 A1 | 4/2017 |
| EP | 3156007 A1 | 4/2017 |
| EP | 3157469 A1 | 4/2017 |
| EP | 3158975 A1 | 4/2017 |
| EP | 1855614 B1 | 5/2017 |
| EP | 2001402 B1 | 5/2017 |
| EP | 2032080 B1 | 5/2017 |
| EP | 2262451 B1 | 5/2017 |
| EP | 2470119 B1 | 5/2017 |
| EP | 2478869 B1 | 5/2017 |
| EP | 2538880 B1 | 5/2017 |
| EP | 2545850 B1 | 5/2017 |
| EP | 2600799 B1 | 5/2017 |
| EP | 2717926 B1 | 5/2017 |
| EP | 2726024 B1 | 5/2017 |
| EP | 2805678 B1 | 5/2017 |
| EP | 2809270 B1 | 5/2017 |
| EP | 2918245 B1 | 5/2017 |
| EP | 2953579 B1 | 5/2017 |
| EP | 2976043 B1 | 5/2017 |
| EP | 2979666 B1 | 5/2017 |
| EP | 3011931 B1 | 5/2017 |
| EP | 3025682 B1 | 5/2017 |
| EP | 3033135 B1 | 5/2017 |
| EP | 3160396 A1 | 5/2017 |
| EP | 3167847 A1 | 5/2017 |
| EP | 3169245 A1 | 5/2017 |
| EP | 3169276 A1 | 5/2017 |
| EP | 2351541 B1 | 6/2017 |
| EP | 2384165 B1 | 6/2017 |
| EP | 2400924 B1 | 6/2017 |
| EP | 2419041 B1 | 6/2017 |
| EP | 2419050 B1 | 6/2017 |
| EP | 2489331 B1 | 6/2017 |
| EP | 2493417 B1 | 6/2017 |
| EP | 2560585 B1 | 6/2017 |
| EP | 2611387 B1 | 6/2017 |
| EP | 2645967 B1 | 6/2017 |
| EP | 2677965 B1 | 6/2017 |
| EP | 2760349 B1 | 6/2017 |
| EP | 2826443 B1 | 6/2017 |
| EP | 2906148 B1 | 6/2017 |
| EP | 2929860 B1 | 6/2017 |
| EP | 2934669 B1 | 6/2017 |
| EP | 2967852 B1 | 6/2017 |
| EP | 3076901 A4 | 6/2017 |
| EP | 3174502 A1 | 6/2017 |
| EP | 3175823 A1 | 6/2017 |
| EP | 3178443 A1 | 6/2017 |
| EP | 3178445 A1 | 6/2017 |
| EP | 3184081 A1 | 6/2017 |
| EP | 1624810 B1 | 7/2017 |
| EP | 2026703 B1 | 7/2017 |
| EP | 2293718 B1 | 7/2017 |
| EP | 2339989 B1 | 7/2017 |
| EP | 2344076 B1 | 7/2017 |
| EP | 2486893 B1 | 7/2017 |
| EP | 2536356 B1 | 7/2017 |
| EP | 2548534 B1 | 7/2017 |
| EP | 2608742 B1 | 7/2017 |
| EP | 2673038 B1 | 7/2017 |
| EP | 2676638 B1 | 7/2017 |
| EP | 2774630 B1 | 7/2017 |
| EP | 2825107 B1 | 7/2017 |
| EP | 2841020 B1 | 7/2017 |
| EP | 2934386 B1 | 7/2017 |
| EP | 2943151 B1 | 7/2017 |
| EP | 3058894 B1 | 7/2017 |
| EP | 3071151 B1 | 7/2017 |
| EP | 3191025 A1 | 7/2017 |
| EP | 3193740 A2 | 7/2017 |
| EP | 3193782 A1 | 7/2017 |
| EP | 1530441 B1 | 8/2017 |
| EP | 1722716 B1 | 8/2017 |
| EP | 1971289 B1 | 8/2017 |
| EP | 2323591 B1 | 8/2017 |
| EP | 2344070 B1 | 8/2017 |
| EP | 2393442 A4 | 8/2017 |
| EP | 2413842 B1 | 8/2017 |
| EP | 2427143 B1 | 8/2017 |
| EP | 2459077 B1 | 8/2017 |
| EP | 2480167 B1 | 8/2017 |
| EP | 2482749 B1 | 8/2017 |
| EP | 2496181 B1 | 8/2017 |
| EP | 2568925 B1 | 8/2017 |
| EP | 2617389 B1 | 8/2017 |
| EP | 2713954 B1 | 8/2017 |
| EP | 2755602 B1 | 8/2017 |
| EP | 2800602 B1 | 8/2017 |
| EP | 2809263 B1 | 8/2017 |
| EP | 2830536 B1 | 8/2017 |
| EP | 2841009 B1 | 8/2017 |
| EP | 2844190 B1 | 8/2017 |
| EP | 2849681 B1 | 8/2017 |
| EP | 2858600 B1 | 8/2017 |

(56) References Cited

FOREIGN PATENT DOCUMENTS

| | | | |
|---|---|---|---|
| EP | 2897556 | B1 | 8/2017 |
| EP | 2934388 | B1 | 8/2017 |
| EP | 2979667 | B1 | 8/2017 |
| EP | 3197397 | A1 | 8/2017 |
| EP | 3202371 | A1 | 8/2017 |
| EP | 3206629 | A1 | 8/2017 |
| EP | 3206631 | A2 | 8/2017 |
| EP | 1799093 | B1 | 9/2017 |
| EP | 2010103 | B1 | 9/2017 |
| EP | 2114304 | B1 | 9/2017 |
| EP | 2344090 | B1 | 9/2017 |
| EP | 2398421 | B1 | 9/2017 |
| EP | 2437687 | B1 | 9/2017 |
| EP | 2453970 | B1 | 9/2017 |
| EP | 2509538 | B1 | 9/2017 |
| EP | 2713956 | B1 | 9/2017 |
| EP | 2772227 | B1 | 9/2017 |
| EP | 2787924 | B1 | 9/2017 |
| EP | 2803335 | B1 | 9/2017 |
| EP | 2811939 | B1 | 9/2017 |
| EP | 2830537 | B1 | 9/2017 |
| EP | 2865355 | B1 | 9/2017 |
| EP | 2872047 | B1 | 9/2017 |
| EP | 2934389 | B1 | 9/2017 |
| EP | 3213715 | A1 | 9/2017 |
| EP | 3213716 | A1 | 9/2017 |
| EP | 3215061 | A1 | 9/2017 |
| EP | 3220856 | A2 | 9/2017 |
| EP | 3220857 | A1 | 9/2017 |
| EP | 1945141 | B1 | 10/2017 |
| EP | 2317956 | B1 | 10/2017 |
| EP | 2613737 | B1 | 10/2017 |
| EP | 2620125 | B1 | 10/2017 |
| EP | 2720642 | B1 | 10/2017 |
| EP | 2741682 | B1 | 10/2017 |
| EP | 2872077 | B1 | 10/2017 |
| EP | 3021925 | B1 | 10/2017 |
| EP | 3231395 | A1 | 10/2017 |
| EP | 3232989 | A1 | 10/2017 |
| EP | 1651148 | B1 | 11/2017 |
| EP | 1913901 | B1 | 11/2017 |
| EP | 2222248 | B1 | 11/2017 |
| EP | 2296581 | B1 | 11/2017 |
| EP | 2326264 | B1 | 11/2017 |
| EP | 2427142 | B1 | 11/2017 |
| EP | 2456483 | B1 | 11/2017 |
| EP | 2493423 | B1 | 11/2017 |
| EP | 2611391 | B1 | 11/2017 |
| EP | 2618780 | B1 | 11/2017 |
| EP | 2658480 | B1 | 11/2017 |
| EP | 2710978 | B1 | 11/2017 |
| EP | 2832315 | B1 | 11/2017 |
| EP | 2954875 | B1 | 11/2017 |
| EP | 2967861 | B1 | 11/2017 |
| EP | 2982338 | B1 | 11/2017 |
| EP | 3027144 | B1 | 11/2017 |
| EP | 3043746 | B1 | 11/2017 |
| EP | 3049026 | B1 | 11/2017 |
| EP | 3068311 | B1 | 11/2017 |
| EP | 3110368 | B1 | 11/2017 |
| EP | 3110369 | B1 | 11/2017 |
| EP | 3132773 | B1 | 11/2017 |
| EP | 3238662 | A1 | 11/2017 |
| EP | 3245980 | A1 | 11/2017 |
| EP | 3247312 | A1 | 11/2017 |
| EP | 1667603 | B1 | 12/2017 |
| EP | 1874954 | B1 | 12/2017 |
| EP | 2427145 | B1 | 12/2017 |
| EP | 2542185 | B1 | 12/2017 |
| EP | 2670351 | A4 | 12/2017 |
| EP | 2723274 | B1 | 12/2017 |
| EP | 2736455 | B1 | 12/2017 |
| EP | 2736457 | B1 | 12/2017 |
| EP | 2830534 | B1 | 12/2017 |
| EP | 2830535 | B1 | 12/2017 |
| EP | 2911592 | B1 | 12/2017 |
| EP | 2916772 | B1 | 12/2017 |
| EP | 2967922 | B1 | 12/2017 |
| EP | 3009105 | B1 | 12/2017 |
| EP | 3088037 | B1 | 12/2017 |
| EP | 3115023 | B1 | 12/2017 |
| EP | 3251633 | A1 | 12/2017 |
| EP | 3253332 | A2 | 12/2017 |
| EP | 3256073 | A1 | 12/2017 |
| EP | 3256074 | A1 | 12/2017 |
| EP | 3256076 | A1 | 12/2017 |
| EP | 3256178 | A1 | 12/2017 |
| EP | 1492458 | B1 | 1/2018 |
| EP | 1768604 | B1 | 1/2018 |
| EP | 1951154 | B1 | 1/2018 |
| EP | 2091465 | B1 | 1/2018 |
| EP | 2345380 | B1 | 1/2018 |
| EP | 2456363 | B1 | 1/2018 |
| EP | 2621407 | B1 | 1/2018 |
| EP | 2631143 | B1 | 1/2018 |
| EP | 2694123 | B1 | 1/2018 |
| EP | 2775962 | B1 | 1/2018 |
| EP | 2874568 | B1 | 1/2018 |
| EP | 2967863 | B1 | 1/2018 |
| EP | 2967869 | B1 | 1/2018 |
| EP | 3033047 | B1 | 1/2018 |
| EP | 3037065 | B1 | 1/2018 |
| EP | 3049025 | B1 | 1/2018 |
| EP | 3052052 | B1 | 1/2018 |
| EP | 3078350 | B1 | 1/2018 |
| EP | 3266417 | A1 | 1/2018 |
| EP | 3267946 | A1 | 1/2018 |
| EP | 3269331 | A1 | 1/2018 |
| EP | 3273911 | A1 | 1/2018 |
| EP | 3275404 | A1 | 1/2018 |
| EP | 2197512 | B1 | 2/2018 |
| EP | 2248486 | B1 | 2/2018 |
| EP | 2344066 | B1 | 2/2018 |
| EP | 2381854 | B1 | 2/2018 |
| EP | 2667823 | B1 | 2/2018 |
| EP | 2699169 | B1 | 2/2018 |
| EP | 2714177 | B1 | 2/2018 |
| EP | 2736544 | B1 | 2/2018 |
| EP | 2846736 | B1 | 2/2018 |
| EP | 2886082 | B1 | 2/2018 |
| EP | 2886084 | B1 | 2/2018 |
| EP | 2931178 | B1 | 2/2018 |
| EP | 2934392 | B1 | 2/2018 |
| EP | 3150173 | B1 | 2/2018 |
| EP | 3277221 | A1 | 2/2018 |
| EP | 3277222 | A1 | 2/2018 |
| EP | 3280358 | A1 | 2/2018 |
| EP | 3281608 | A1 | 2/2018 |
| EP | 3283009 | A1 | 2/2018 |
| EP | 3283011 | A1 | 2/2018 |
| EP | 3287099 | A1 | 2/2018 |
| EP | 1959864 | B1 | 3/2018 |
| EP | 2513200 | B1 | 3/2018 |
| EP | 2608815 | B1 | 3/2018 |
| EP | 2858711 | B1 | 3/2018 |
| EP | 2938292 | B1 | 3/2018 |
| EP | 2943132 | B1 | 3/2018 |
| EP | 2983620 | B1 | 3/2018 |
| EP | 3003219 | B1 | 3/2018 |
| EP | 3005979 | B1 | 3/2018 |
| EP | 3037064 | B1 | 3/2018 |
| EP | 3046511 | B1 | 3/2018 |
| EP | 3142603 | B1 | 3/2018 |
| EP | 3288479 | A1 | 3/2018 |
| EP | 3288491 | A1 | 3/2018 |
| EP | 3288494 | A1 | 3/2018 |
| EP | 3288497 | A2 | 3/2018 |
| EP | 3288498 | A1 | 3/2018 |
| EP | 3288499 | A1 | 3/2018 |
| EP | 3290004 | A1 | 3/2018 |
| EP | 3290007 | A1 | 3/2018 |
| EP | 3294214 | A1 | 3/2018 |
| EP | 3294215 | A1 | 3/2018 |
| EP | 3294218 | A1 | 3/2018 |

(56) References Cited

FOREIGN PATENT DOCUMENTS

| | | |
|---|---|---|
| EP | 3296979 A1 | 3/2018 |
| EP | 3298970 A1 | 3/2018 |
| EP | 3298987 A1 | 3/2018 |
| EP | 3298988 A1 | 3/2018 |
| EP | 2209440 B1 | 4/2018 |
| EP | 2536357 B1 | 4/2018 |
| EP | 2605725 B1 | 4/2018 |
| EP | 2608743 B1 | 4/2018 |
| EP | 2709561 B1 | 4/2018 |
| EP | 2787925 B1 | 4/2018 |
| EP | 2789314 B1 | 4/2018 |
| EP | 2900150 B1 | 4/2018 |
| EP | 2908779 B1 | 4/2018 |
| EP | 2922502 B1 | 4/2018 |
| EP | 2964441 B1 | 4/2018 |
| EP | 2967868 B1 | 4/2018 |
| EP | 2979665 B1 | 4/2018 |
| EP | 2994073 B1 | 4/2018 |
| EP | 3095394 B1 | 4/2018 |
| EP | 3128927 A4 | 4/2018 |
| EP | 3134033 B1 | 4/2018 |
| EP | 3137146 A4 | 4/2018 |
| EP | 3280482 A4 | 4/2018 |
| EP | 3302297 A2 | 4/2018 |
| EP | 3302362 A1 | 4/2018 |
| EP | 3302367 A1 | 4/2018 |
| EP | 3307208 A1 | 4/2018 |
| EP | 3308745 A1 | 4/2018 |
| EP | 3310301 A1 | 4/2018 |
| EP | 3311774 A1 | 4/2018 |
| EP | 3311775 A1 | 4/2018 |
| EP | 3311783 A1 | 4/2018 |
| EP | 1945112 B1 | 5/2018 |
| EP | 2007313 B1 | 5/2018 |
| EP | 2316381 B2 | 5/2018 |
| EP | 2377469 B1 | 5/2018 |
| EP | 2531115 B1 | 5/2018 |
| EP | 2561831 B1 | 5/2018 |
| EP | 2605724 B1 | 5/2018 |
| EP | 2723277 B1 | 5/2018 |
| EP | 2741711 B1 | 5/2018 |
| EP | 2755573 B1 | 5/2018 |
| EP | 2768429 B1 | 5/2018 |
| EP | 2819618 B1 | 5/2018 |
| EP | 2833836 B1 | 5/2018 |
| EP | 2886083 B1 | 5/2018 |
| EP | 2926840 B1 | 5/2018 |
| EP | 2943157 B1 | 5/2018 |
| EP | 2948099 B1 | 5/2018 |
| EP | 3000437 B1 | 5/2018 |
| EP | 3145448 B1 | 5/2018 |
| EP | 3154475 B1 | 5/2018 |
| EP | 3316819 A1 | 5/2018 |
| EP | 3316821 A1 | 5/2018 |
| EP | 3322381 A1 | 5/2018 |
| EP | 3322383 A1 | 5/2018 |
| EP | 3323353 A1 | 5/2018 |
| EP | 3323439 A1 | 5/2018 |
| EP | 3324892 A1 | 5/2018 |
| EP | 3326584 A1 | 5/2018 |
| EP | 2150312 B1 | 6/2018 |
| EP | 2379322 B1 | 6/2018 |
| EP | 2400925 B1 | 6/2018 |
| EP | 2552355 B1 | 6/2018 |
| EP | 2560589 B1 | 6/2018 |
| EP | 2563277 B1 | 6/2018 |
| EP | 2661305 B1 | 6/2018 |
| EP | 2736456 B1 | 6/2018 |
| EP | 2782523 B1 | 6/2018 |
| EP | 3056170 B1 | 6/2018 |
| EP | 3062745 B1 | 6/2018 |
| EP | 3130320 B1 | 6/2018 |
| EP | 3187150 B1 | 6/2018 |
| EP | 3334378 A1 | 6/2018 |
| EP | 3334380 A1 | 6/2018 |
| EP | 3334381 A1 | 6/2018 |
| EP | 3335670 A1 | 6/2018 |
| EP | 3337412 A1 | 6/2018 |
| EP | 3337424 A1 | 6/2018 |
| EP | 2478872 B1 | 7/2018 |
| EP | 2563278 B1 | 7/2018 |
| EP | 2616004 B1 | 7/2018 |
| EP | 2779943 B1 | 7/2018 |
| EP | 2802290 B1 | 7/2018 |
| EP | 2816980 B1 | 7/2018 |
| EP | 2938293 B1 | 7/2018 |
| EP | 3107496 B1 | 7/2018 |
| EP | 3178450 B1 | 7/2018 |
| EP | 3212097 B1 | 7/2018 |
| EP | 3340923 A1 | 7/2018 |
| EP | 3340932 A1 | 7/2018 |
| EP | 3340934 A1 | 7/2018 |
| EP | 3340936 A1 | 7/2018 |
| EP | 3340945 A1 | 7/2018 |
| EP | 3342355 A1 | 7/2018 |
| EP | 3342377 A1 | 7/2018 |
| EP | 3344158 A1 | 7/2018 |
| EP | 3346952 A1 | 7/2018 |
| EP | 3347182 A1 | 7/2018 |
| EP | 3348235 A1 | 7/2018 |
| EP | 3349693 A1 | 7/2018 |
| EP | 2536354 B1 | 8/2018 |
| EP | 2616006 B1 | 8/2018 |
| EP | 2797556 B1 | 8/2018 |
| EP | 2822473 B1 | 8/2018 |
| EP | 2854711 B1 | 8/2018 |
| EP | 2866847 B1 | 8/2018 |
| EP | 2918246 B1 | 8/2018 |
| EP | 2967845 B1 | 8/2018 |
| EP | 2999436 B1 | 8/2018 |
| EP | 3013281 B1 | 8/2018 |
| EP | 3060170 B1 | 8/2018 |
| EP | 3104811 B1 | 8/2018 |
| EP | 3143944 B1 | 8/2018 |
| EP | 3157467 B1 | 8/2018 |
| EP | 3193791 B1 | 8/2018 |
| EP | 3241526 B1 | 8/2018 |
| EP | 3355800 A1 | 8/2018 |
| EP | 3360513 A1 | 8/2018 |
| EP | 3360514 A1 | 8/2018 |
| EP | 3361988 A1 | 8/2018 |
| EP | 3361991 A1 | 8/2018 |
| EP | 2114305 B1 | 9/2018 |
| EP | 2155115 B1 | 9/2018 |
| EP | 2601910 B1 | 9/2018 |
| EP | 2617390 B1 | 9/2018 |
| EP | 2734157 B1 | 9/2018 |
| EP | 2968674 B1 | 9/2018 |
| EP | 2999415 B1 | 9/2018 |
| EP | 3106130 B1 | 9/2018 |
| EP | 3151763 B1 | 9/2018 |
| EP | 3213717 B1 | 9/2018 |
| EP | 3245985 B1 | 9/2018 |
| EP | 3367979 A1 | 9/2018 |
| EP | 3370649 A1 | 9/2018 |
| EP | 3370650 A1 | 9/2018 |
| EP | 3377000 A1 | 9/2018 |
| EP | 1827256 B1 | 10/2018 |
| EP | 1850790 B1 | 10/2018 |
| EP | 2063823 B1 | 10/2018 |
| EP | 2124825 B1 | 10/2018 |
| EP | 2249746 B1 | 10/2018 |
| EP | 2254514 B1 | 10/2018 |
| EP | 2285309 B1 | 10/2018 |
| EP | 2455042 B1 | 10/2018 |
| EP | 2571561 B1 | 10/2018 |
| EP | 2616008 B1 | 10/2018 |
| EP | 2647393 B1 | 10/2018 |
| EP | 2739214 B1 | 10/2018 |
| EP | 2739247 B1 | 10/2018 |
| EP | 2776114 B1 | 10/2018 |
| EP | 2836171 B1 | 10/2018 |
| EP | 2842581 B1 | 10/2018 |
| EP | 2870946 B1 | 10/2018 |

(56) References Cited

FOREIGN PATENT DOCUMENTS

| | | | |
|---|---|---|---|
| EP | 2923665 B1 | 10/2018 |
| EP | 2964277 B1 | 10/2018 |
| EP | 3001978 B1 | 10/2018 |
| EP | 3010562 B1 | 10/2018 |
| EP | 3072475 B1 | 10/2018 |
| EP | 3081161 B1 | 10/2018 |
| EP | 3081195 B1 | 10/2018 |
| EP | 3099345 B1 | 10/2018 |
| EP | 3120809 B1 | 10/2018 |
| EP | 3238663 B1 | 10/2018 |
| EP | 3275404 A4 | 10/2018 |
| EP | 3384879 A1 | 10/2018 |
| EP | 3388027 A1 | 10/2018 |
| EP | 3389557 A1 | 10/2018 |
| EP | 3390706 A1 | 10/2018 |
| EP | 1708650 B1 | 11/2018 |
| EP | 1945143 B1 | 11/2018 |
| EP | 2205183 B1 | 11/2018 |
| EP | 2663258 B1 | 11/2018 |
| EP | 2790615 B1 | 11/2018 |
| EP | 2854709 B1 | 11/2018 |
| EP | 2898859 B1 | 11/2018 |
| EP | 2921139 B1 | 11/2018 |
| EP | 2928538 B1 | 11/2018 |
| EP | 3075354 B1 | 11/2018 |
| EP | 3082949 B1 | 11/2018 |
| EP | 3145452 B1 | 11/2018 |
| EP | 3216424 B1 | 11/2018 |
| EP | 3260084 B1 | 11/2018 |
| EP | 3397206 A1 | 11/2018 |
| EP | 3398562 A1 | 11/2018 |
| EP | 3400908 A1 | 11/2018 |
| EP | 3403616 A1 | 11/2018 |
| EP | 3405139 A1 | 11/2018 |
| EP | 1858450 B1 | 12/2018 |
| EP | 2150208 B1 | 12/2018 |
| EP | 2326261 B1 | 12/2018 |
| EP | 2344075 B1 | 12/2018 |
| EP | 2370028 B1 | 12/2018 |
| EP | 2555709 B1 | 12/2018 |
| EP | 2564812 B1 | 12/2018 |
| EP | 2777618 B1 | 12/2018 |
| EP | 2814427 B1 | 12/2018 |
| EP | 2829240 B1 | 12/2018 |
| EP | 2911594 B1 | 12/2018 |
| EP | 2911729 B1 | 12/2018 |
| EP | 2954876 B1 | 12/2018 |
| EP | 2958520 B1 | 12/2018 |
| EP | 2958605 B1 | 12/2018 |
| EP | 3010446 B1 | 12/2018 |
| EP | 3064174 B1 | 12/2018 |
| EP | 3206628 B1 | 12/2018 |
| EP | 3242629 B1 | 12/2018 |
| EP | 3260085 B1 | 12/2018 |
| EP | 3266416 B1 | 12/2018 |
| EP | 3326583 B1 | 12/2018 |
| EP | 3407834 A1 | 12/2018 |
| EP | 3410984 A1 | 12/2018 |
| EP | 3410987 A1 | 12/2018 |
| EP | 3415120 A1 | 12/2018 |
| EP | 3417813 A1 | 12/2018 |
| EP | 2129332 B1 | 1/2019 |
| EP | 2196159 B1 | 1/2019 |
| EP | 2370025 B1 | 1/2019 |
| EP | 2549957 B1 | 1/2019 |
| EP | 2819619 B1 | 1/2019 |
| EP | 2849680 B1 | 1/2019 |
| EP | 2856972 B1 | 1/2019 |
| EP | 2866742 B1 | 1/2019 |
| EP | 2884946 B1 | 1/2019 |
| EP | 2948102 B1 | 1/2019 |
| EP | 2979664 B1 | 1/2019 |
| EP | 3043748 B1 | 1/2019 |
| EP | 3145449 B1 | 1/2019 |
| EP | 3288491 A4 | 1/2019 |
| EP | 3332743 B1 | 1/2019 |
| EP | 3427695 A1 | 1/2019 |
| EP | 3429507 A1 | 1/2019 |
| EP | 3432832 A1 | 1/2019 |
| EP | 3432834 A1 | 1/2019 |
| EP | 1895943 B1 | 2/2019 |
| EP | 2070490 B1 | 2/2019 |
| EP | 2308425 B1 | 2/2019 |
| EP | 2379009 B1 | 2/2019 |
| EP | 2575685 B1 | 2/2019 |
| EP | 2688562 B1 | 2/2019 |
| EP | 2714068 B1 | 2/2019 |
| EP | 2720641 B1 | 2/2019 |
| EP | 2760375 B1 | 2/2019 |
| EP | 2862590 B1 | 2/2019 |
| EP | 2925259 B1 | 2/2019 |
| EP | 2931179 B1 | 2/2019 |
| EP | 3005983 B1 | 2/2019 |
| EP | 3023117 B1 | 2/2019 |
| EP | 3184083 B1 | 2/2019 |
| EP | 3202333 B1 | 2/2019 |
| EP | 3261583 B1 | 2/2019 |
| EP | 3278832 B1 | 2/2019 |
| EP | 3409454 A4 | 2/2019 |
| EP | 3435919 A1 | 2/2019 |
| EP | 3441045 A1 | 2/2019 |
| EP | 3442469 A1 | 2/2019 |
| EP | 3443937 A1 | 2/2019 |
| EP | 3445290 A1 | 2/2019 |
| EP | 1771132 B1 | 3/2019 |
| EP | 1959866 B1 | 3/2019 |
| EP | 2120794 B1 | 3/2019 |
| EP | 2259728 B1 | 3/2019 |
| EP | 2344074 B1 | 3/2019 |
| EP | 2552356 B1 | 3/2019 |
| EP | 2598044 B1 | 3/2019 |
| EP | 2659861 B1 | 3/2019 |
| EP | 2670357 B1 | 3/2019 |
| EP | 2898902 B1 | 3/2019 |
| EP | 2948098 B1 | 3/2019 |
| EP | 2948101 B1 | 3/2019 |
| EP | 2967865 B1 | 3/2019 |
| EP | 2974695 B1 | 3/2019 |
| EP | 3027243 B1 | 3/2019 |
| EP | 3116446 B1 | 3/2019 |
| EP | 3145445 B1 | 3/2019 |
| EP | 3151783 B1 | 3/2019 |
| EP | 3151784 B1 | 3/2019 |
| EP | 3278768 B1 | 3/2019 |
| EP | 3320943 B1 | 3/2019 |
| EP | 3448314 A1 | 3/2019 |
| EP | 3448315 A1 | 3/2019 |
| EP | 3449969 A1 | 3/2019 |
| EP | 3454785 A1 | 3/2019 |
| EP | 3454786 A1 | 3/2019 |
| EP | 3454789 A1 | 3/2019 |
| EP | 3454794 A1 | 3/2019 |
| EP | 3454795 A1 | 3/2019 |
| EP | 3457987 A1 | 3/2019 |
| EP | 3457988 A1 | 3/2019 |
| EP | 3457990 A1 | 3/2019 |
| EP | 3458136 A2 | 3/2019 |
| EP | 3459499 A2 | 3/2019 |
| EP | 1793745 B1 | 4/2019 |
| EP | 1855623 B1 | 4/2019 |
| EP | 2129333 B1 | 4/2019 |
| EP | 2149349 B1 | 4/2019 |
| EP | 2438888 B1 | 4/2019 |
| EP | 2484309 B1 | 4/2019 |
| EP | 2519268 B1 | 4/2019 |
| EP | 2528545 B1 | 4/2019 |
| EP | 2536358 B1 | 4/2019 |
| EP | 2661239 B1 | 4/2019 |
| EP | 2709563 B1 | 4/2019 |
| EP | 2736451 B1 | 4/2019 |
| EP | 2810619 B1 | 4/2019 |
| EP | 2810622 B1 | 4/2019 |
| EP | 2879589 B1 | 4/2019 |
| EP | 2921198 B1 | 4/2019 |

(56) References Cited

FOREIGN PATENT DOCUMENTS

| | | | |
|---|---|---|---|
| EP | 2986256 | B1 | 4/2019 |
| EP | 3090704 | B1 | 4/2019 |
| EP | 3116445 | B1 | 4/2019 |
| EP | 3141217 | B1 | 4/2019 |
| EP | 3193745 | B1 | 4/2019 |
| EP | 3241525 | B1 | 4/2019 |
| EP | 3344167 | A4 | 4/2019 |
| EP | 3461531 | A1 | 4/2019 |
| EP | 3463120 | A1 | 4/2019 |
| EP | 3466373 | A1 | 4/2019 |
| EP | 3471662 | A1 | 4/2019 |
| EP | 1703870 | B1 | 5/2019 |
| EP | 1708642 | B1 | 5/2019 |
| EP | 2240121 | B1 | 5/2019 |
| EP | 2663259 | B1 | 5/2019 |
| EP | 2695586 | B1 | 5/2019 |
| EP | 2726018 | B1 | 5/2019 |
| EP | 2954872 | B1 | 5/2019 |
| EP | 3071150 | B1 | 5/2019 |
| EP | 3110370 | B1 | 5/2019 |
| EP | 3111890 | B1 | 5/2019 |
| EP | 3182932 | B1 | 5/2019 |
| EP | 3192472 | B1 | 5/2019 |
| EP | 3238661 | B1 | 5/2019 |
| EP | 3284503 | B1 | 5/2019 |
| EP | 3302364 | B1 | 5/2019 |
| EP | 3315094 | B1 | 5/2019 |
| EP | 3316818 | B1 | 5/2019 |
| EP | 3474778 | A1 | 5/2019 |
| EP | 3476366 | A1 | 5/2019 |
| EP | 3476424 | A1 | 5/2019 |
| EP | 3478224 | A1 | 5/2019 |
| EP | 3479797 | A1 | 5/2019 |
| EP | 3481335 | A1 | 5/2019 |
| EP | 3481336 | A1 | 5/2019 |
| EP | 3481338 | A1 | 5/2019 |
| EP | 3481339 | A1 | 5/2019 |
| EP | 3482718 | A1 | 5/2019 |
| EP | 3484412 | A1 | 5/2019 |
| EP | 3485847 | A1 | 5/2019 |
| EP | 3485848 | A1 | 5/2019 |
| EP | 3485933 | A1 | 5/2019 |
| EP | 3487420 | A1 | 5/2019 |
| EP | 3487451 | A1 | 5/2019 |
| EP | 3487452 | A1 | 5/2019 |
| EP | 3488822 | A1 | 5/2019 |
| EP | 1624792 | B1 | 6/2019 |
| EP | 1737394 | B1 | 6/2019 |
| EP | 1858451 | B1 | 6/2019 |
| EP | 1895944 | B1 | 6/2019 |
| EP | 1968487 | B1 | 6/2019 |
| EP | 2004095 | B1 | 6/2019 |
| EP | 2010102 | B1 | 6/2019 |
| EP | 2131788 | B1 | 6/2019 |
| EP | 2560580 | B1 | 6/2019 |
| EP | 2618782 | B1 | 6/2019 |
| EP | 2868296 | B1 | 6/2019 |
| EP | 2961358 | B1 | 6/2019 |
| EP | 2967847 | B1 | 6/2019 |
| EP | 2985006 | B1 | 6/2019 |
| EP | 3033048 | B1 | 6/2019 |
| EP | 3119451 | B1 | 6/2019 |
| EP | 3131503 | B1 | 6/2019 |
| EP | 3213718 | B1 | 6/2019 |
| EP | 3275390 | B1 | 6/2019 |
| EP | 3300692 | B1 | 6/2019 |
| EP | 3326585 | B1 | 6/2019 |
| EP | 3338737 | B1 | 6/2019 |
| EP | 3357457 | B1 | 6/2019 |
| EP | 3372198 | B1 | 6/2019 |
| EP | 3490465 | A1 | 6/2019 |
| EP | 3490500 | A1 | 6/2019 |
| EP | 3490657 | A1 | 6/2019 |
| EP | 3490659 | A1 | 6/2019 |
| EP | 3496626 | A1 | 6/2019 |
| EP | 3496664 | A1 | 6/2019 |
| EP | 3498224 | A1 | 6/2019 |
| EP | 3501454 | A1 | 6/2019 |
| EP | 1659981 | B1 | 7/2019 |
| EP | 1924223 | B1 | 7/2019 |
| EP | 2249745 | B1 | 7/2019 |
| EP | 2296744 | B1 | 7/2019 |
| EP | 2331019 | B1 | 7/2019 |
| EP | 2368527 | B1 | 7/2019 |
| EP | 2509542 | B1 | 7/2019 |
| EP | 2555710 | B1 | 7/2019 |
| EP | 2575682 | B1 | 7/2019 |
| EP | 2575683 | B1 | 7/2019 |
| EP | 2640431 | B1 | 7/2019 |
| EP | 2641572 | B1 | 7/2019 |
| EP | 2649964 | B1 | 7/2019 |
| EP | 2767260 | B1 | 7/2019 |
| EP | 2777615 | B1 | 7/2019 |
| EP | 2838476 | B1 | 7/2019 |
| EP | 2861186 | B1 | 7/2019 |
| EP | 2877124 | B1 | 7/2019 |
| EP | 2877132 | B1 | 7/2019 |
| EP | 2921565 | B1 | 7/2019 |
| EP | 2938291 | B1 | 7/2019 |
| EP | 2999433 | B1 | 7/2019 |
| EP | 3145450 | B1 | 7/2019 |
| EP | 3254644 | B1 | 7/2019 |
| EP | 3315093 | B1 | 7/2019 |
| EP | 3344189 | B1 | 7/2019 |
| EP | 3503813 | A1 | 7/2019 |
| EP | 3503846 | A1 | 7/2019 |
| EP | 3503847 | A1 | 7/2019 |
| EP | 3503848 | A1 | 7/2019 |
| EP | 3505077 | A1 | 7/2019 |
| EP | 3512465 | A1 | 7/2019 |
| EP | 3515365 | A1 | 7/2019 |
| EP | 3517075 | A1 | 7/2019 |
| EP | 1861043 | B1 | 8/2019 |
| EP | 2303190 | B1 | 8/2019 |
| EP | 2593171 | B1 | 8/2019 |
| EP | 2632393 | B1 | 8/2019 |
| EP | 2663355 | B1 | 8/2019 |
| EP | 2665509 | B1 | 8/2019 |
| EP | 2688525 | B1 | 8/2019 |
| EP | 2699201 | B1 | 8/2019 |
| EP | 2755564 | B1 | 8/2019 |
| EP | 2769681 | B1 | 8/2019 |
| EP | 2793751 | B1 | 8/2019 |
| EP | 2900177 | B1 | 8/2019 |
| EP | 2967536 | B1 | 8/2019 |
| EP | 3050541 | B1 | 8/2019 |
| EP | 3102152 | B1 | 8/2019 |
| EP | 3157607 | B1 | 8/2019 |
| EP | 3231392 | B1 | 8/2019 |
| EP | 3284411 | B1 | 8/2019 |
| EP | 3328318 | B1 | 8/2019 |
| EP | 3348233 | B1 | 8/2019 |
| EP | 3366262 | B1 | 8/2019 |
| EP | 3527170 | A1 | 8/2019 |
| EP | 3530236 | A1 | 8/2019 |
| EP | 2358297 | B1 | 9/2019 |
| EP | 2368525 | B1 | 9/2019 |
| EP | 2542186 | B1 | 9/2019 |
| EP | 2656863 | B1 | 9/2019 |
| EP | 3003221 | B1 | 9/2019 |
| EP | 3003452 | B1 | 9/2019 |
| EP | 3220971 | B1 | 9/2019 |
| EP | 3223874 | B1 | 9/2019 |
| EP | 3288495 | B1 | 9/2019 |
| EP | 3311776 | B1 | 9/2019 |
| EP | 3334379 | B1 | 9/2019 |
| EP | 3531975 | A1 | 9/2019 |
| EP | 3534840 | A1 | 9/2019 |
| EP | 3534841 | A1 | 9/2019 |
| EP | 3534845 | A2 | 9/2019 |
| EP | 3535010 | A1 | 9/2019 |
| EP | 3538026 | A1 | 9/2019 |
| EP | 3538027 | A1 | 9/2019 |
| EP | 3539508 | A1 | 9/2019 |

(56) References Cited

FOREIGN PATENT DOCUMENTS

| | | | |
|---|---|---|---|
| EP | 3539509 | A1 | 9/2019 |
| EP | 3541316 | A1 | 9/2019 |
| EP | 3541325 | A1 | 9/2019 |
| EP | 3541328 | A1 | 9/2019 |
| EP | 3542758 | A1 | 9/2019 |
| EP | 1740265 | B1 | 10/2019 |
| EP | 2039756 | B1 | 10/2019 |
| EP | 2456506 | B1 | 10/2019 |
| EP | 2470122 | B1 | 10/2019 |
| EP | 2613738 | B1 | 10/2019 |
| EP | 2637607 | B1 | 10/2019 |
| EP | 2674174 | B1 | 10/2019 |
| EP | 2811923 | B1 | 10/2019 |
| EP | 2901967 | B1 | 10/2019 |
| EP | 3010431 | B1 | 10/2019 |
| EP | 3019091 | B1 | 10/2019 |
| EP | 3019123 | B1 | 10/2019 |
| EP | 3057522 | B1 | 10/2019 |
| EP | 3067075 | B1 | 10/2019 |
| EP | 3146937 | B1 | 10/2019 |
| EP | 3238777 | B1 | 10/2019 |
| EP | 3359211 | B1 | 10/2019 |
| EP | 3388026 | B1 | 10/2019 |
| EP | 3432806 | B1 | 10/2019 |
| EP | 3496626 | A4 | 10/2019 |
| EP | 3544548 | A1 | 10/2019 |
| EP | 3545905 | A1 | 10/2019 |
| EP | 3547936 | A1 | 10/2019 |
| EP | 3547966 | A1 | 10/2019 |
| EP | 3549555 | A1 | 10/2019 |
| EP | 3549556 | A1 | 10/2019 |
| EP | 3552585 | A1 | 10/2019 |
| EP | 3554424 | A1 | 10/2019 |
| EP | 3556323 | A1 | 10/2019 |
| EP | 3558165 | A1 | 10/2019 |
| EP | 3558168 | A1 | 10/2019 |
| EP | 3558169 | A2 | 10/2019 |
| EP | 2043559 | B1 | 11/2019 |
| EP | 2358308 | B1 | 11/2019 |
| EP | 2405863 | B1 | 11/2019 |
| EP | 2701633 | B1 | 11/2019 |
| EP | 2898857 | B1 | 11/2019 |
| EP | 2967853 | B1 | 11/2019 |
| EP | 3009104 | B1 | 11/2019 |
| EP | 3021792 | B1 | 11/2019 |
| EP | 3076900 | B1 | 11/2019 |
| EP | 3111889 | B1 | 11/2019 |
| EP | 3142607 | B1 | 11/2019 |
| EP | 3167850 | B1 | 11/2019 |
| EP | 3397205 | B1 | 11/2019 |
| EP | 3563799 | A1 | 11/2019 |
| EP | 3563806 | A1 | 11/2019 |
| EP | 3570779 | A1 | 11/2019 |
| EP | 3572045 | A1 | 11/2019 |
| EP | 3572117 | A1 | 11/2019 |
| EP | 3479800 | A4 | 12/2019 |
| EP | 3576677 | A1 | 12/2019 |
| EP | 3579761 | A2 | 12/2019 |
| EP | 3579788 | A1 | 12/2019 |
| EP | 3582697 | A1 | 12/2019 |
| EP | 3583922 | A1 | 12/2019 |
| EP | 3445443 | A4 | 1/2020 |
| EP | 3590471 | A1 | 1/2020 |
| EP | 3590472 | A1 | 1/2020 |
| EP | 3592284 | A1 | 1/2020 |
| EP | 3592288 | A1 | 1/2020 |
| EP | 3592289 | A1 | 1/2020 |
| EP | 3593763 | A1 | 1/2020 |
| EP | 3595588 | A1 | 1/2020 |
| EP | 3600156 | A1 | 2/2020 |
| EP | 3600159 | A1 | 2/2020 |
| EP | 3606443 | A1 | 2/2020 |
| EP | 3606472 | A1 | 2/2020 |
| EP | 2241287 | B2 | 3/2020 |
| EP | 2376013 | B1 | 3/2020 |
| EP | 2911593 | B1 | 3/2020 |
| EP | 2995279 | B1 | 3/2020 |
| EP | 3009103 | B1 | 3/2020 |
| EP | 3038664 | B1 | 3/2020 |
| EP | 3167848 | B1 | 3/2020 |
| EP | 3175822 | B1 | 3/2020 |
| EP | 3179960 | B1 | 3/2020 |
| EP | 3280479 | B1 | 3/2020 |
| EP | 3616651 | A1 | 3/2020 |
| EP | 3619136 | A1 | 3/2020 |
| EP | 3626208 | A1 | 3/2020 |
| EP | 1667614 | B2 | 4/2020 |
| EP | 2119417 | B2 | 4/2020 |
| EP | 2155114 | B1 | 4/2020 |
| EP | 2299937 | B1 | 4/2020 |
| EP | 2331016 | B1 | 4/2020 |
| EP | 2376013 | B8 | 4/2020 |
| EP | 2413843 | B1 | 4/2020 |
| EP | 2854705 | B1 | 4/2020 |
| EP | 2918249 | B1 | 4/2020 |
| EP | 2922593 | B1 | 4/2020 |
| EP | 2950753 | B1 | 4/2020 |
| EP | 2967810 | B1 | 4/2020 |
| EP | 3110367 | B1 | 4/2020 |
| EP | 3111888 | B1 | 4/2020 |
| EP | 3128927 | B1 | 4/2020 |
| EP | 3134032 | B1 | 4/2020 |
| EP | 3142606 | B1 | 4/2020 |
| EP | 3270825 | B1 | 4/2020 |
| EP | 3300696 | B1 | 4/2020 |
| EP | 3316823 | B1 | 4/2020 |
| EP | 3334487 | B1 | 4/2020 |
| EP | 3342355 | B1 | 4/2020 |
| EP | 3373863 | B1 | 4/2020 |
| EP | 3459498 | B1 | 4/2020 |
| EP | 3470105 | B1 | 4/2020 |
| EP | 3628239 | A1 | 4/2020 |
| EP | 3628274 | A1 | 4/2020 |
| EP | 3632338 | A1 | 4/2020 |
| EP | 3636312 | A1 | 4/2020 |
| EP | 3639792 | A1 | 4/2020 |
| EP | 3639888 | A1 | 4/2020 |
| EP | 3643273 | A1 | 4/2020 |
| EP | 1895942 | B1 | 5/2020 |
| EP | 2120821 | B1 | 5/2020 |
| EP | 2437688 | B1 | 5/2020 |
| EP | 2785281 | B1 | 5/2020 |
| EP | 2852354 | B1 | 5/2020 |
| EP | 2884906 | B1 | 5/2020 |
| EP | 2999412 | B1 | 5/2020 |
| EP | 3060174 | B1 | 5/2020 |
| EP | 3071147 | B1 | 5/2020 |
| EP | 3104812 | B1 | 5/2020 |
| EP | 3139861 | B1 | 5/2020 |
| EP | 3232989 | B1 | 5/2020 |
| EP | 3294219 | B1 | 5/2020 |
| EP | 3298970 | B1 | 5/2020 |
| EP | 3302366 | B1 | 5/2020 |
| EP | 3323389 | B1 | 5/2020 |
| EP | 3332744 | B1 | 5/2020 |
| EP | 3402440 | B1 | 5/2020 |
| EP | 3417813 | B1 | 5/2020 |
| EP | 3417831 | B1 | 5/2020 |
| EP | 3457987 | B1 | 5/2020 |
| EP | 3484413 | B1 | 5/2020 |
| EP | 3531975 | B1 | 5/2020 |
| EP | 3644866 | A1 | 5/2020 |
| EP | 3646822 | A1 | 5/2020 |
| EP | 3646824 | A1 | 5/2020 |
| EP | 3646825 | A1 | 5/2020 |
| EP | 3648706 | A1 | 5/2020 |
| EP | 3648709 | A1 | 5/2020 |
| EP | 3656354 | A1 | 5/2020 |
| EP | 1648339 | B2 | 6/2020 |
| EP | 2072027 | B1 | 6/2020 |
| EP | 2331016 | B8 | 6/2020 |
| EP | 2616007 | B1 | 6/2020 |
| EP | 2967856 | B1 | 6/2020 |
| EP | 3042635 | B1 | 6/2020 |

(56) References Cited

FOREIGN PATENT DOCUMENTS

| | | | |
|---|---|---|---|
| EP | 3060165 | B1 | 6/2020 |
| EP | 3280338 | B1 | 6/2020 |
| EP | 3283010 | B1 | 6/2020 |
| EP | 3400908 | B1 | 6/2020 |
| EP | 3494928 | B1 | 6/2020 |
| EP | 3498225 | B1 | 6/2020 |
| EP | 3583920 | B1 | 6/2020 |
| EP | 3659553 | A1 | 6/2020 |
| EP | 3661429 | A1 | 6/2020 |
| EP | 3661436 | A1 | 6/2020 |
| EP | 3668450 | A1 | 6/2020 |
| EP | 3668452 | A1 | 6/2020 |
| EP | 3669828 | A1 | 6/2020 |
| EP | 3669829 | A1 | 6/2020 |
| EP | 2271284 | B1 | 7/2020 |
| EP | 2291145 | B1 | 7/2020 |
| EP | 2512952 | B1 | 7/2020 |
| EP | 2558029 | B1 | 7/2020 |
| EP | 2693985 | B1 | 7/2020 |
| EP | 2858708 | B1 | 7/2020 |
| EP | 2862546 | B1 | 7/2020 |
| EP | 2967807 | B1 | 7/2020 |
| EP | 2967866 | B1 | 7/2020 |
| EP | 3061421 | B1 | 7/2020 |
| EP | 3107497 | B1 | 7/2020 |
| EP | 3139862 | B1 | 7/2020 |
| EP | 3423000 | B1 | 7/2020 |
| EP | 3441045 | B1 | 7/2020 |
| EP | 3451972 | B1 | 7/2020 |
| EP | 3501454 | B1 | 7/2020 |
| EP | 3512466 | B1 | 7/2020 |
| EP | 3616652 | B1 | 7/2020 |
| EP | 3672528 | A1 | 7/2020 |
| EP | 3672529 | A1 | 7/2020 |
| EP | 3672532 | A1 | 7/2020 |
| EP | 3673925 | A1 | 7/2020 |
| EP | 3679894 | A1 | 7/2020 |
| EP | 3681439 | A1 | 7/2020 |
| EP | 3681441 | A1 | 7/2020 |
| EP | 3682852 | A1 | 7/2020 |
| EP | 3682854 | A1 | 7/2020 |
| EP | 3685802 | A1 | 7/2020 |
| EP | 2367505 | B1 | 8/2020 |
| EP | 2497445 | B1 | 8/2020 |
| EP | 2537486 | B1 | 8/2020 |
| EP | 2777616 | B1 | 8/2020 |
| EP | 3007651 | B1 | 8/2020 |
| EP | 3052053 | B1 | 8/2020 |
| EP | 3237033 | B1 | 8/2020 |
| EP | 3388005 | B1 | 8/2020 |
| EP | 3410986 | B1 | 8/2020 |
| EP | 3451974 | B1 | 8/2020 |
| EP | 3463192 | B1 | 8/2020 |
| EP | 3554423 | B1 | 8/2020 |
| EP | 3568089 | A4 | 8/2020 |
| EP | 3573544 | B1 | 8/2020 |
| EP | 3634255 | B1 | 8/2020 |
| EP | 3689299 | A1 | 8/2020 |
| EP | 3691567 | A1 | 8/2020 |
| EP | 3695810 | A1 | 8/2020 |
| EP | 3697342 | A1 | 8/2020 |
| EP | 3697346 | A1 | 8/2020 |
| EP | 2485795 | B1 | 9/2020 |
| EP | 3125777 | B1 | 9/2020 |
| EP | 3182930 | B1 | 9/2020 |
| EP | 3285690 | B1 | 9/2020 |
| EP | 3459500 | B1 | 9/2020 |
| EP | 3570782 | B1 | 9/2020 |
| EP | 3700467 | A1 | 9/2020 |
| EP | 3711711 | A1 | 9/2020 |
| EP | 3714936 | A1 | 9/2020 |
| EP | 2979667 | B2 | 10/2020 |
| EP | 3193783 | B1 | 10/2020 |
| EP | 3490501 | B1 | 10/2020 |
| EP | 3718509 | A1 | 10/2020 |
| EP | 3720363 | A1 | 10/2020 |
| EP | 3721811 | A1 | 10/2020 |
| EP | 2387973 | B1 | 11/2020 |
| EP | 2427144 | B1 | 11/2020 |
| EP | 2506777 | B1 | 11/2020 |
| EP | 2793743 | B1 | 11/2020 |
| EP | 2825203 | B1 | 11/2020 |
| EP | 2863842 | B1 | 11/2020 |
| EP | 2967700 | B1 | 11/2020 |
| EP | 2977026 | B1 | 11/2020 |
| EP | 3139864 | B1 | 11/2020 |
| EP | 3145451 | B1 | 11/2020 |
| EP | 3156007 | B1 | 11/2020 |
| EP | 3244834 | B1 | 11/2020 |
| EP | 3298987 | B1 | 11/2020 |
| EP | 3302362 | B1 | 11/2020 |
| EP | 3311777 | B1 | 11/2020 |
| EP | 3316819 | B1 | 11/2020 |
| EP | 3361988 | B1 | 11/2020 |
| EP | 3503813 | B1 | 11/2020 |
| EP | 3527170 | B1 | 11/2020 |
| EP | 3530236 | B1 | 11/2020 |
| EP | 3590471 | B1 | 11/2020 |
| EP | 3593762 | B1 | 11/2020 |
| EP | 3737336 | A1 | 11/2020 |
| EP | 3740162 | A1 | 11/2020 |
| EP | 2370138 | B1 | 12/2020 |
| EP | 2445450 | B1 | 12/2020 |
| EP | 2739250 | B1 | 12/2020 |
| EP | 2877123 | B1 | 12/2020 |
| EP | 2967834 | B1 | 12/2020 |
| EP | 2996632 | B1 | 12/2020 |
| EP | 3090703 | B1 | 12/2020 |
| EP | 3191025 | B1 | 12/2020 |
| EP | 3202371 | B1 | 12/2020 |
| EP | 3316822 | B1 | 12/2020 |
| EP | 3334382 | B1 | 12/2020 |
| EP | 3337424 | B1 | 12/2020 |
| EP | 3367896 | B1 | 12/2020 |
| EP | 3368582 | B1 | 12/2020 |
| EP | 3397208 | B1 | 12/2020 |
| EP | 3476366 | B1 | 12/2020 |
| EP | 3481303 | B1 | 12/2020 |
| EP | 3538028 | B1 | 12/2020 |
| EP | 3539510 | B1 | 12/2020 |
| EP | 3544548 | B1 | 12/2020 |
| EP | 3545906 | B1 | 12/2020 |
| EP | 3572117 | B1 | 12/2020 |
| EP | 3593763 | B1 | 12/2020 |
| EP | 3744291 | A1 | 12/2020 |
| EP | 3749254 | A1 | 12/2020 |
| EP | 3753535 | A1 | 12/2020 |
| EP | 3756623 | A1 | 12/2020 |
| EP | 1906883 | B1 | 1/2021 |
| EP | 2334261 | B1 | 1/2021 |
| EP | 2349096 | B1 | 1/2021 |
| EP | 2568924 | B1 | 1/2021 |
| EP | 2699202 | B1 | 1/2021 |
| EP | 2713894 | B1 | 1/2021 |
| EP | 2835112 | B1 | 1/2021 |
| EP | 3040054 | B1 | 1/2021 |
| EP | 3131502 | B1 | 1/2021 |
| EP | 3197397 | B1 | 1/2021 |
| EP | 3256178 | B1 | 1/2021 |
| EP | 3290007 | B1 | 1/2021 |
| EP | 3316821 | B1 | 1/2021 |
| EP | 3337412 | B1 | 1/2021 |
| EP | 3432834 | B1 | 1/2021 |
| EP | 3454786 | B1 | 1/2021 |
| EP | 3474778 | B1 | 1/2021 |
| EP | 3528748 | B1 | 1/2021 |
| EP | 3547966 | B1 | 1/2021 |
| EP | 3603576 | B1 | 1/2021 |
| EP | 3758651 | A1 | 1/2021 |
| EP | 3760164 | A1 | 1/2021 |
| EP | 3763331 | A1 | 1/2021 |
| EP | 3769721 | A1 | 1/2021 |
| EP | 2273951 | B1 | 2/2021 |
| EP | 2379008 | B1 | 2/2021 |

(56) References Cited

FOREIGN PATENT DOCUMENTS

| | | | |
|---|---|---|---|
| EP | 2996641 | B1 | 2/2021 |
| EP | 3043747 | B1 | 2/2021 |
| EP | 3340936 | B1 | 2/2021 |
| EP | 3457985 | B1 | 2/2021 |
| EP | 3503847 | B1 | 2/2021 |
| EP | 3538027 | B1 | 2/2021 |
| EP | 3558168 | B1 | 2/2021 |
| EP | 3581232 | B1 | 2/2021 |
| EP | 3656354 | B1 | 2/2021 |
| EP | 3697324 | B1 | 2/2021 |
| EP | 3773271 | A1 | 2/2021 |
| EP | 3773329 | A1 | 2/2021 |
| EP | 2299938 | B1 | 3/2021 |
| EP | 2470121 | B1 | 3/2021 |
| EP | 2564811 | B1 | 3/2021 |
| EP | 2679198 | B1 | 3/2021 |
| EP | 3068346 | B1 | 3/2021 |
| EP | 3160394 | B1 | 3/2021 |
| EP | 3169245 | B1 | 3/2021 |
| EP | 3178443 | B1 | 3/2021 |
| EP | 3184081 | B1 | 3/2021 |
| EP | 3226956 | B1 | 3/2021 |
| EP | 3324892 | B1 | 3/2021 |
| EP | 3334354 | B1 | 3/2021 |
| EP | 3402446 | B1 | 3/2021 |
| EP | 3442469 | B1 | 3/2021 |
| EP | 3503851 | B1 | 3/2021 |
| EP | 3506855 | B1 | 3/2021 |
| EP | 3531979 | B1 | 3/2021 |
| EP | 3535010 | B1 | 3/2021 |
| EP | 3581151 | B1 | 3/2021 |
| EP | 3590472 | B1 | 3/2021 |
| EP | 3593760 | B1 | 3/2021 |
| EP | 3646825 | B1 | 3/2021 |
| EP | 3649985 | B1 | 3/2021 |
| EP | 3787561 | A1 | 3/2021 |
| EP | 3790501 | A1 | 3/2021 |
| EP | 3791795 | A1 | 3/2021 |
| EP | 3791828 | A1 | 3/2021 |
| EP | 3796872 | A1 | 3/2021 |
| EP | 3796873 | A1 | 3/2021 |
| EP | 3796875 | A1 | 3/2021 |
| EP | 3796876 | A1 | 3/2021 |
| EP | 1734872 | B1 | 4/2021 |
| EP | 2594230 | B1 | 4/2021 |
| EP | 2624785 | B1 | 4/2021 |
| EP | 2670349 | B1 | 4/2021 |
| EP | 2793752 | B1 | 4/2021 |
| EP | 2823769 | B1 | 4/2021 |
| EP | 2964152 | B1 | 4/2021 |
| EP | 3253331 | B1 | 4/2021 |
| EP | 3290004 | B1 | 4/2021 |
| EP | 3311778 | B1 | 4/2021 |
| EP | 3367979 | B1 | 4/2021 |
| EP | 3454794 | B1 | 4/2021 |
| EP | 3487420 | B1 | 4/2021 |
| EP | 3558165 | B1 | 4/2021 |
| EP | 3616651 | B1 | 4/2021 |
| EP | 3619136 | B1 | 4/2021 |
| EP | 3626208 | B1 | 4/2021 |
| EP | 3632379 | B1 | 4/2021 |
| EP | 3646823 | B1 | 4/2021 |
| EP | 3646824 | B1 | 4/2021 |
| EP | 3653173 | B1 | 4/2021 |
| EP | 1951155 | B1 | 5/2021 |
| EP | 2073755 | B1 | 5/2021 |
| EP | 2948100 | B1 | 5/2021 |
| EP | 3099270 | B1 | 5/2021 |
| EP | 3150172 | B1 | 5/2021 |
| EP | 3178445 | B1 | 5/2021 |
| EP | 3310301 | B1 | 5/2021 |
| EP | 3582697 | B1 | 5/2021 |
| EP | 3592295 | B1 | 5/2021 |
| EP | 3639888 | B1 | 5/2021 |
| EP | 3669828 | B1 | 5/2021 |
| EP | 2471492 | B1 | 6/2021 |
| EP | 2486894 | B1 | 6/2021 |
| EP | 2750630 | B1 | 6/2021 |
| EP | 3247312 | B1 | 6/2021 |
| EP | 3294215 | B1 | 6/2021 |
| EP | 3323353 | B1 | 6/2021 |
| EP | 3360513 | B1 | 6/2021 |
| EP | 3488821 | B1 | 6/2021 |
| EP | 3549555 | B1 | 6/2021 |
| EP | 3576677 | B1 | 6/2021 |
| EP | 3632338 | B1 | 6/2021 |
| EP | 3834879 | A1 | 6/2021 |
| EP | 2381895 | B1 | 7/2021 |
| EP | 2611389 | B1 | 7/2021 |
| EP | 2779945 | B1 | 7/2021 |
| EP | 3193740 | B1 | 7/2021 |
| EP | 3206629 | B1 | 7/2021 |
| EP | 3277222 | B1 | 7/2021 |
| EP | 3400907 | B1 | 7/2021 |
| EP | 3435919 | B1 | 7/2021 |
| EP | 3522800 | B1 | 7/2021 |
| EP | 3539508 | B1 | 7/2021 |
| EP | 3539509 | B1 | 7/2021 |
| EP | 3572044 | B1 | 7/2021 |
| EP | 3592289 | B1 | 7/2021 |
| EP | 3668450 | B1 | 7/2021 |
| EP | 3681439 | B1 | 7/2021 |
| EP | 3691567 | B1 | 7/2021 |
| EP | 3789077 | A4 | 7/2021 |
| EP | 3846740 | A1 | 7/2021 |
| EP | 3849472 | A1 | 7/2021 |
| EP | 2558032 | B1 | 8/2021 |
| EP | 2992857 | B1 | 8/2021 |
| EP | 2994075 | B1 | 8/2021 |
| EP | 3038539 | B1 | 8/2021 |
| EP | 3287099 | B1 | 8/2021 |
| EP | 3348235 | B1 | 8/2021 |
| EP | 3643273 | B1 | 8/2021 |
| EP | 3646822 | B1 | 8/2021 |
| EP | 3658215 | B1 | 8/2021 |
| EP | 3659553 | B1 | 8/2021 |
| EP | 3723665 | B1 | 8/2021 |
| EP | 3744290 | B1 | 8/2021 |
| EP | 3860530 | A1 | 8/2021 |
| EP | 3863567 | A1 | 8/2021 |
| EP | 2040645 | B1 | 9/2021 |
| EP | 2329796 | B1 | 9/2021 |
| EP | 3125827 | B1 | 9/2021 |
| EP | 3137146 | B1 | 9/2021 |
| EP | 3288494 | B1 | 9/2021 |
| EP | 3288497 | B1 | 9/2021 |
| EP | 3446660 | B1 | 9/2021 |
| EP | 3454784 | B1 | 9/2021 |
| EP | 3456293 | B1 | 9/2021 |
| EP | 3457989 | B1 | 9/2021 |
| EP | 3496664 | B1 | 9/2021 |
| EP | 3503848 | B1 | 9/2021 |
| EP | 3512465 | B1 | 9/2021 |
| EP | 3544664 | B1 | 9/2021 |
| EP | 3568089 | B1 | 9/2021 |
| EP | 3592288 | B1 | 9/2021 |
| EP | 3606472 | B1 | 9/2021 |
| EP | 3669829 | B1 | 9/2021 |
| EP | 3672528 | B1 | 9/2021 |
| EP | 3833302 | A4 | 9/2021 |
| EP | 3870110 | A1 | 9/2021 |
| EP | 2249711 | B1 | 10/2021 |
| EP | 2538883 | B1 | 10/2021 |
| EP | 2723273 | B1 | 10/2021 |
| EP | 3119351 | B1 | 10/2021 |
| EP | 3267946 | B1 | 10/2021 |
| EP | 3275404 | B1 | 10/2021 |
| EP | 3280482 | B1 | 10/2021 |
| EP | 3334381 | B1 | 10/2021 |
| EP | 3639792 | B1 | 10/2021 |
| EP | 3886762 | A1 | 10/2021 |
| EP | 3886763 | A1 | 10/2021 |
| EP | 3892240 | A1 | 10/2021 |
| EP | 3897454 | A1 | 10/2021 |

(56) References Cited

FOREIGN PATENT DOCUMENTS

| | | | |
|---|---|---|---|
| EP | 3900679 | A1 | 10/2021 |
| EP | 2331018 | B1 | 11/2021 |
| EP | 2429455 | B1 | 11/2021 |
| EP | 2538878 | B1 | 11/2021 |
| EP | 2699302 | B1 | 11/2021 |
| EP | 2706958 | B1 | 11/2021 |
| EP | 2892467 | B1 | 11/2021 |
| EP | 2999434 | B1 | 11/2021 |
| EP | 3024527 | B1 | 11/2021 |
| EP | 3061422 | B1 | 11/2021 |
| EP | 3107500 | B1 | 11/2021 |
| EP | 3110468 | B1 | 11/2021 |
| EP | 3154474 | B1 | 11/2021 |
| EP | 3213715 | B1 | 11/2021 |
| EP | 3256076 | B1 | 11/2021 |
| EP | 3288499 | B1 | 11/2021 |
| EP | 3360514 | B1 | 11/2021 |
| EP | 3429507 | B1 | 11/2021 |
| EP | 3445443 | B1 | 11/2021 |
| EP | 3454785 | B1 | 11/2021 |
| EP | 3505077 | B1 | 11/2021 |
| EP | 3672529 | B1 | 11/2021 |
| EP | 3760164 | B1 | 11/2021 |
| EP | 3908228 | A1 | 11/2021 |
| EP | 3912595 | A1 | 11/2021 |
| EP | 3912596 | A1 | 11/2021 |
| EP | 2358307 | B1 | 12/2021 |
| EP | 2765954 | B1 | 12/2021 |
| EP | 2777608 | B1 | 12/2021 |
| EP | 2991584 | B1 | 12/2021 |
| EP | 3283011 | B1 | 12/2021 |
| EP | 3288479 | B1 | 12/2021 |
| EP | 3344167 | B1 | 12/2021 |
| EP | 3410987 | B1 | 12/2021 |
| EP | 3481339 | B1 | 12/2021 |
| EP | 3482718 | B1 | 12/2021 |
| EP | 3490465 | B1 | 12/2021 |
| EP | 3498224 | B1 | 12/2021 |
| EP | 3503846 | B1 | 12/2021 |
| EP | 3592284 | B1 | 12/2021 |
| EP | 3624705 | B1 | 12/2021 |
| EP | 3749254 | B1 | 12/2021 |
| EP | 3914191 | A1 | 12/2021 |
| EP | 3915493 | A1 | 12/2021 |
| EP | 2400922 | B1 | 1/2022 |
| EP | 2545885 | B1 | 1/2022 |
| EP | 2747708 | B1 | 1/2022 |
| EP | 2763708 | B1 | 1/2022 |
| EP | 2994072 | B1 | 1/2022 |
| EP | 3220856 | B1 | 1/2022 |
| EP | 3288498 | B1 | 1/2022 |
| EP | 3534840 | B1 | 1/2022 |
| EP | 3558169 | B1 | 1/2022 |
| EP | 3668452 | B1 | 1/2022 |
| EP | 3682854 | B1 | 1/2022 |
| EP | 3697346 | B1 | 1/2022 |
| EP | 3700467 | B1 | 1/2022 |
| EP | 3740162 | B1 | 1/2022 |
| EP | 3294218 | B1 | 2/2022 |
| EP | 3457988 | B1 | 2/2022 |
| EP | 3481336 | B1 | 2/2022 |
| EP | 3673925 | B1 | 2/2022 |
| EP | 3689299 | B1 | 2/2022 |
| EP | 3753535 | B1 | 2/2022 |
| EP | 3860530 | B1 | 2/2022 |
| EP | 2520249 | B1 | 3/2022 |
| EP | 2558033 | B1 | 3/2022 |
| EP | 2623068 | B1 | 3/2022 |
| EP | 2866737 | B1 | 3/2022 |
| EP | 3107495 | B1 | 3/2022 |
| EP | 3160396 | B1 | 3/2022 |
| EP | 3193782 | B1 | 3/2022 |
| EP | 3334380 | B1 | 3/2022 |
| EP | 3355800 | B1 | 3/2022 |
| EP | 3479797 | B1 | 3/2022 |
| EP | 3479800 | B1 | 3/2022 |
| EP | 3547936 | B1 | 3/2022 |
| EP | 3628274 | B1 | 3/2022 |
| EP | 3679894 | B1 | 3/2022 |
| EP | 3711711 | B1 | 3/2022 |
| EP | 3714936 | B1 | 3/2022 |
| EP | 3787561 | B1 | 3/2022 |
| EP | 3791795 | B1 | 3/2022 |
| EP | 3962415 | A1 | 3/2022 |
| EP | 2488126 | B1 | 4/2022 |
| EP | 2536360 | B1 | 4/2022 |
| EP | 2611388 | B1 | 4/2022 |
| EP | 2651336 | B1 | 4/2022 |
| EP | 2699200 | B1 | 4/2022 |
| EP | 2916781 | B1 | 4/2022 |
| EP | 3174502 | B1 | 4/2022 |
| EP | 3209221 | B1 | 4/2022 |
| EP | 3302297 | B1 | 4/2022 |
| EP | 3349693 | B1 | 4/2022 |
| EP | 3487451 | B1 | 4/2022 |
| EP | 3500184 | B1 | 4/2022 |
| EP | 3600159 | B1 | 4/2022 |
| EP | 3628239 | B1 | 4/2022 |
| EP | 3644866 | B1 | 4/2022 |
| EP | 3681441 | B1 | 4/2022 |
| EP | 3796873 | B1 | 4/2022 |
| EP | 2268231 | B1 | 5/2022 |
| EP | 2856973 | B1 | 5/2022 |
| EP | 2962664 | B1 | 5/2022 |
| EP | 3311774 | B1 | 5/2022 |
| EP | 3335670 | B1 | 5/2022 |
| EP | 3403616 | B1 | 5/2022 |
| EP | 3445290 | B1 | 5/2022 |
| EP | 3541316 | B1 | 5/2022 |
| EP | 3648709 | B1 | 5/2022 |
| EP | 3695810 | B1 | 5/2022 |
| EP | 3721811 | B1 | 5/2022 |
| EP | 3773271 | B1 | 5/2022 |
| EP | 2538893 | B1 | 6/2022 |
| EP | 2575681 | B1 | 6/2022 |
| EP | 2583640 | B1 | 6/2022 |
| EP | 3071149 | B1 | 6/2022 |
| EP | 3253332 | B1 | 6/2022 |
| EP | 3283009 | B1 | 6/2022 |
| EP | 3296979 | B1 | 6/2022 |
| EP | 3298988 | B1 | 6/2022 |
| EP | 3342377 | B1 | 6/2022 |
| EP | 3365349 | B1 | 6/2022 |
| EP | 3397206 | B1 | 6/2022 |
| EP | 3426194 | B1 | 6/2022 |
| EP | 3595588 | B1 | 6/2022 |
| EP | 3636312 | B1 | 6/2022 |
| EP | 3661436 | B1 | 6/2022 |
| EP | 3790501 | B1 | 6/2022 |
| EP | 3846740 | B1 | 6/2022 |
| EP | 3849472 | B1 | 6/2022 |
| EP | 3897454 | B1 | 6/2022 |
| EP | 4014928 | A1 | 6/2022 |
| EP | 2621409 | B1 | 7/2022 |
| EP | 2787926 | B1 | 7/2022 |
| EP | 2838473 | B1 | 7/2022 |
| EP | 2950752 | B1 | 7/2022 |
| EP | 3060171 | B1 | 7/2022 |
| EP | 3206631 | B1 | 7/2022 |
| EP | 3245980 | B1 | 7/2022 |
| EP | 3256073 | B1 | 7/2022 |
| EP | 3311783 | B1 | 7/2022 |
| EP | 3347182 | B1 | 7/2022 |
| EP | 3389557 | B1 | 7/2022 |
| EP | 3463120 | B1 | 7/2022 |
| EP | 3579788 | B1 | 7/2022 |
| EP | 3756623 | B1 | 7/2022 |
| EP | 3796872 | B1 | 7/2022 |
| EP | 3796876 | B1 | 7/2022 |
| EP | 2313152 | B1 | 8/2022 |
| EP | 2688516 | B1 | 8/2022 |
| EP | 2849678 | B1 | 8/2022 |
| EP | 2950751 | B1 | 8/2022 |
| EP | 2964153 | B1 | 8/2022 |

(56) References Cited

FOREIGN PATENT DOCUMENTS

| | | |
|---|---|---|
| EP | 3019092 B1 | 8/2022 |
| EP | 3184082 B1 | 8/2022 |
| EP | 3231395 B1 | 8/2022 |
| EP | 3266417 B1 | 8/2022 |
| EP | 3407834 B1 | 8/2022 |
| EP | 3458136 B1 | 8/2022 |
| EP | 3459499 B1 | 8/2022 |
| EP | 3471662 B1 | 8/2022 |
| EP | 3484412 B1 | 8/2022 |
| EP | 3534841 B1 | 8/2022 |
| EP | 3541328 B1 | 8/2022 |
| EP | 3672532 B1 | 8/2022 |
| EP | 3718509 B1 | 8/2022 |
| EP | 3769721 B1 | 8/2022 |
| EP | 3789077 B1 | 8/2022 |
| EP | 3908228 B1 | 8/2022 |
| EP | 3915493 B1 | 8/2022 |
| EP | 3967274 B1 | 8/2022 |
| EP | 2670351 B1 | 9/2022 |
| EP | 2777617 B1 | 9/2022 |
| EP | 2810620 B1 | 9/2022 |
| EP | 2922592 B1 | 9/2022 |
| EP | 3038567 B1 | 9/2022 |
| EP | 3096713 B1 | 9/2022 |
| EP | 3220857 B1 | 9/2022 |
| EP | 3448315 B1 | 9/2022 |
| EP | 3481335 B1 | 9/2022 |
| EP | 3520715 B1 | 9/2022 |
| EP | 3645065 B1 | 9/2022 |
| EP | 3737336 B1 | 9/2022 |
| EP | 2104470 B1 | 10/2022 |
| EP | 2536353 B1 | 10/2022 |
| EP | 2991588 B1 | 10/2022 |
| EP | 3043755 B1 | 10/2022 |
| EP | 3288491 B1 | 10/2022 |
| EP | 3466373 B1 | 10/2022 |
| EP | 3552585 B1 | 10/2022 |
| EP | 3791828 B1 | 10/2022 |
| EP | 3914191 B1 | 10/2022 |
| EP | 2538882 B1 | 11/2022 |
| EP | 2698129 B1 | 11/2022 |
| EP | 2959866 B1 | 11/2022 |
| EP | 3175823 B1 | 11/2022 |
| EP | 3280358 B1 | 11/2022 |
| EP | 3340923 B1 | 11/2022 |
| EP | 3478224 B1 | 11/2022 |
| EP | 3490659 B1 | 11/2022 |
| EP | 3744291 B1 | 11/2022 |
| FR | 2815844 B1 | 1/2003 |
| FR | 2826863 B1 | 9/2003 |
| FR | 2828091 B1 | 11/2003 |
| FR | 2847800 B1 | 10/2005 |
| FR | 2858543 B1 | 2/2006 |
| FR | 2828263 B1 | 5/2007 |
| FR | 2874812 B1 | 6/2007 |
| FR | 2874813 B1 | 6/2007 |
| FR | 2883721 B1 | 6/2007 |
| FR | 2894131 B1 | 12/2008 |
| FR | 2899096 B1 | 12/2008 |
| FR | 2910269 B1 | 2/2009 |
| FR | 2909857 B1 | 3/2009 |
| FR | 2906454 B1 | 4/2009 |
| FR | 2906998 B1 | 4/2009 |
| FR | 2913879 B1 | 6/2009 |
| FR | 2916959 B1 | 9/2009 |
| FR | 2892939 B1 | 1/2010 |
| FR | 2915678 B1 | 4/2010 |
| FR | 2930137 B1 | 4/2010 |
| FR | 2915903 B1 | 6/2010 |
| FR | 2916627 B1 | 9/2010 |
| FR | 2920664 B1 | 9/2010 |
| FR | 2932376 B1 | 4/2011 |
| FR | 2947716 B1 | 9/2011 |
| FR | 2945440 B1 | 12/2012 |
| FR | 2951549 B1 | 8/2013 |
| FR | 2964855 B1 | 10/2013 |
| FR | 2977792 B1 | 10/2013 |
| FR | 2980968 B1 | 12/2013 |
| FR | 2986149 B1 | 12/2014 |
| FR | 2997288 B1 | 1/2015 |
| FR | 2998167 B1 | 1/2015 |
| FR | 2996747 B1 | 2/2015 |
| FR | 2996748 B1 | 2/2015 |
| FR | 3004638 B1 | 5/2015 |
| FR | 2982763 B1 | 7/2015 |
| FR | 2991162 B1 | 7/2015 |
| FR | 3006582 B1 | 7/2015 |
| FR | 3001121 B1 | 1/2016 |
| FR | 2998166 B1 | 2/2016 |
| FR | 3021862 B1 | 5/2016 |
| FR | 3004917 B1 | 6/2016 |
| FR | 3006884 B1 | 6/2016 |
| FR | 3023704 B1 | 8/2016 |
| FR | 3008885 B1 | 12/2016 |
| FR | 3033494 B1 | 3/2017 |
| FR | 3057154 B1 | 10/2018 |
| FR | 3058631 B1 | 1/2019 |
| FR | 3058632 B1 | 1/2019 |
| FR | 3060292 B1 | 1/2019 |
| FR | 3063631 B1 | 3/2019 |
| FR | 3020265 B1 | 9/2019 |
| FR | 3072013 B1 | 9/2019 |
| GB | 243370 A | 8/1926 |
| GB | 2407146 B | 4/2006 |
| GB | 2398245 B | 3/2007 |
| GB | 2433700 B | 12/2007 |
| GB | 2478498 B | 7/2012 |
| GB | 2530487 B | 12/2016 |
| GB | 2517609 B | 5/2017 |
| GB | 2538749 B | 8/2017 |
| GB | 2538072 B | 11/2017 |
| GB | 2536538 B | 7/2018 |
| GB | 2548891 B | 7/2018 |
| JP | 2022523856 A | 4/2022 |
| JP | 7430732 B2 | 2/2024 |
| WO | WO-0236048 A1 | 5/2002 |
| WO | WO-2006097931 A2 | 9/2006 |
| WO | WO-2006113906 A1 | 10/2006 |
| WO | WO-2006097931 A3 | 7/2007 |
| WO | WO-2007097983 A2 | 8/2007 |
| WO | WO-2007122459 A2 | 11/2007 |
| WO | WO-2007122459 A3 | 1/2008 |
| WO | WO-2008013915 A2 | 1/2008 |
| WO | WO-2007097983 A3 | 3/2008 |
| WO | WO-2008013915 A3 | 7/2008 |
| WO | WO-2008103722 A2 | 8/2008 |
| WO | WO-2008103722 A3 | 10/2008 |
| WO | WO-2009033469 A1 | 3/2009 |
| WO | WO-2009108615 A1 | 9/2009 |
| WO | WO-2009134701 A2 | 11/2009 |
| WO | WO-2010004546 A1 | 1/2010 |
| WO | WO-2009134701 A3 | 2/2010 |
| WO | WO-2010037141 A1 | 4/2010 |
| WO | WO-2010045297 A2 | 4/2010 |
| WO | WO-2011072084 A2 | 6/2011 |
| WO | WO-2011126758 A1 | 10/2011 |
| WO | WO-2011139747 A1 | 11/2011 |
| WO | WO-2013056898 A1 | 4/2013 |
| WO | WO-2013075215 A1 | 5/2013 |
| WO | WO-2015038875 A1 | 3/2015 |
| WO | WO-2017096289 A1 | 6/2017 |
| WO | WO-2017100927 A1 | 6/2017 |
| WO | WO-2018213209 A1 | 11/2018 |
| WO | WO-2020185597 A1 | 9/2020 |

OTHER PUBLICATIONS

"U.S. Appl. No. 13/096,572, Non Final Office Action dated Jun. 4, 2013", 11 pgs.

"U.S. Appl. No. 13/096,572, Notice of Allowance dated Sep. 26, 2013", 8 pgs.

"U.S. Appl. No. 13/096,572, Preliminary Amendment filed Sep. 9, 2011", 15 pgs.

(56) References Cited

OTHER PUBLICATIONS

"U.S. Appl. No. 13/096,572, Response filed Mar. 25, 2013 to Restriction Requirement dated Mar. 4, 2018", 2 pgs.
"U.S. Appl. No. 13/096,572, Response filed Aug. 30, 2013 to Non Final Office Action dated Jun. 4, 2013", 11 pgs.
"U.S. Appl. No. 13/096,572, Restriction Requirement dated Mar. 4, 2013", 10 pgs.
"U.S. Appl. No. 15/379,748, Corrected Notice of Allowability dated Feb. 10, 2020", 6 pgs.
"U.S. Appl. No. 15/379,748, Corrected Notice of Allowability dated Apr. 1, 2020", 4 pgs.
"U.S. Appl. No. 15/379,748, Non Final Office Action dated Jun. 13, 2019", 18 pgs.
"U.S. Appl. No. 15/379,748, Notice of Allowance dated Dec. 13, 2019", 12 pgs.
"U.S. Appl. No. 15/379,748, Response filed Apr. 3, 2019 to Restriction Requirement dated Oct. 3, 2018", 9 pgs.
"U.S. Appl. No. 15/379,748, Response filed Sep. 25, 2019 to Non-Final Office Action dated Jun. 25, 2019", 12 pgs.
"U.S. Appl. No. 15/379,748, Restriction Requirement dated Oct. 3, 2018", 6 pgs.
"CardiAQ Valve Technologies", Medical Devices Today, [Online]. Retrieved from the Internet: <http:/www.medicaldevicestoday.com/2009/07/medical-device-start-up-cardiaq-valve-technologies-percutaneous-mitral-valve-replacement.html> Accessed: Mar. 8, 2012, (Jul. 17, 2009), 2 pgs.
"*CardiAQ Valve Technologies* v *NeoVasc*", Case 1:14-cv-12405-NMG. Document 31—main, (Aug. 19, 2014), 3 pgs.
"*CardiAQ Valve Technologies* v *NeoVasc*", Case 1:14-cv-12405-NMG. Document 32—main, (Aug. 19, 2014), 4 pgs.
"*CardiAQ Valve Technologies* v *NeoVasc*", Case 1:14-cv-12405-NMG. Document 34—main, (Aug. 20, 2014), 3 pgs.
"*CardiAQ Valve Technologies* v *NeoVasc*", Case 1:14-cv-12405-NMG. Document 35—main, (Aug. 20, 2014), 6 pgs.
"*CardiAQ Valve Technologies* v *NeoVasc*", Case 1:14-cv-12405-NMG. Document 36—main, (Aug. 20, 2014), 2 pgs.
"*CardiAQ Valve Technologies* v *NeoVasc*", Case 1:14-cv-12405-NMG. Document 38—main, (Aug. 28, 2014), 3 pgs.
"*CardiAQ Valve Technologies* v *NeoVasc*", Case 1:14-cv-12405-NMG. Document 39—main, (Aug. 28, 2014), 28 pgs.
"*CardiAQ Valve Technologies* v *NeoVasc*", Case 1:14-cv-12405-NMG. Document 40—main, (Sep. 11, 2014), 4 pgs.
"*CardiAQ Valve Technologies* v *NeoVasc*", Case 1:14-cv-12405-NMG. Document 41—main, (Sep. 11, 2014), 17 pgs.
"*CardiAQ Valve Technologies* v *NeoVasc*", Case 1:14-cv-12405-NMG. Document 42—main, (Oct. 3, 2014), 6 pgs.
"*CardiAQ Valve Technologies* v *NeoVasc*", Case 1:14-cv-12405-NMG. Document 43—main, (Oct. 7, 2014), 1 pg.
"*CardiAQ Valve Technologies* v *NeoVasc*", Case 1 :14-cv-12405-ADB. Document 583, (Oct. 31, 2016), 40 pgs.
"*CardiAQ Valve Technologies* v *NeoVasc*", Case 1:14-cv-12405-NMG. Document 01-1, (Jun. 6, 2014), 1 pg.
"*CardiAQ Valve Technologies* v *NeoVasc*", Case 1:14-cv-12405-NMG. Document 01-2, (Jun. 6, 2014), 1 pg.
"*CardiAQ Valve Technologies* v *NeoVasc*", Case 1:14-cv-12405-NMG. Document 01—main, (Jun. 6, 2014), 20 pgs.
"*CardiAQ Valve Technologies* v *NeoVasc*", Case 1:14-cv-12405-NMG. Document 02—main, (Jun. 6, 2014), 2 pgs.
"*CardiAQ Valve Technologies* v *NeoVasc*", Case 1:14-cv-12405-NMG. Document 03-1, (Jun. 6, 2014), 1 pg.
"*CardiAQ Valve Technologies* v *NeoVasc*", Case 1:14-cv-12406-NMG. Document 03-2, (Jun. 6, 2014), 3 pgs.
"*CardiAQ Valve Technologies* v *NeoVasc*", Case 1:14-cv-12405-NMG. Document 03-3, (Jun. 6, 2014), 1 pg.
"*CardiAQ Valve Technologies* v *NeoVasc*", Case 1:14-cv-12405-NMG. Document 03-4, (Jun. 6, 2014), 1 pg.
"*CardiAQ Valve Technologies* v *NeoVasc*", Case 1:14-cv-12405-NMG. Document 03-5, (Jun. 6, 2014), 2 pgs.
"*CardiAQ Valve Technologies* v *NeoVasc*", Case 1:14-cv-12405-NMG. Document 03—main, (Jun. 6, 2014), 20 pgs.
"*CardiAQ Valve Technologies* v *NeoVasc*", Case 1:14-cv-12405-NMG. Document 05—main, (Jun. 6, 2014), 2 pgs.
"*CardiAQ Valve Technologies* v *NeoVasc*", Case 1:14-cv-12405-NMG. Document 06—main, (Jul. 21, 2014), 3 pgs.
"*CardiAQ Valve Technologies* v *NeoVasc*", Case 1:14-cv-12405-NMG. Document 07—main, (Jul. 21, 2014), 3 pgs.
"*CardiAQ Valve Technologies* v *NeoVasc*", Case 1:14-cv-12405-NMG. Document 08-1, (Jul. 25, 2014), 3 pgs.
"*CardiAQ Valve Technologies* v *NeoVasc*", Case 1:14-cv-12405-NMG. Document 08—main, (Jul. 25, 2014), 2 pgs.
"*CardiAQ Valve Technologies* v *NeoVasc*", Case 1:14-cv-12405-NMG. Document 09-1, (Jul. 25, 2014), 3 pgs.
"*CardiAQ Valve Technologies* v *NeoVasc*", Case 1:14-cv-12405-NMG. Document 09—main, (Jul. 25, 2014), 2 pgs.
"*CardiAQ Valve Technologies* v *NeoVasc*", Case 1:14-cv-12405-NMG. Document 11-1, (Jul. 28, 2014), 3 pgs.
"*CardiAQ Valve Technologies* v *NeoVasc*", Case 1:14-cv-12405-NMG. Document 11—main, Jul. 28, 2014), 2 pgs.
"*CardiAQ Valve Technologies* v *NeoVasc*", Case 1:14-cv-12405-NMG. Document 13-1, (Jul. 29, 2014), 3 pgs.
"*CardiAQ Valve Technologies* v *NeoVasc*", Case 1:14-cv-12405-NMG. Document 13-2, (Jul. 29, 2014), 1 pg.
"*CardiAQ Valve Technologies* v *NeoVasc*", Case 1:14-cv-12405-NMG. Document 13—main, (Jul. 29, 2014), 3 pgs.
"*CardiAQ Valve Technologies* v *NeoVasc*", Case 1:14-cv-12405-NMG. Document 14-1, (Jul. 29, 2014), 3 pgs.
"*CardiAQ Valve Technologies* v *NeoVasc*", Case 1:14-cv-12405-NMG. Document 14-2, (Jul. 29, 2014), 1 pg.
"*CardiAQ Valve Technologies* v *NeoVasc*", Case 1:14-cv-12405-NMG. Document 14—main, (Jul. 29, 2014), 3 pgs.
"*CardiAQ Valve Technologies* v *NeoVasc*", Case 1:14-cv-12405-NMG. Document 15-1, (Jul. 29, 2014), 3 pgs.
"*CardiAQ Valve Technologies* v *NeoVasc*", Case 1:14-cv-12405-NMG. Document 15-2, (Jul. 29, 2014), 2 pgs.
"*CardiAQ Valve Technologies* v *NeoVasc*", Case 1:14-cv-12405-NMG. Document 15—main, (Jul. 29, 2014), 3 pgs.
"*CardiAQ Valve Technologies* v *NeoVasc*", Case 1:14-cv-12405-NMG. Document 16-1, (Jul. 29, 2014), 4 pgs.
"*CardiAQ Valve Technologies* v *NeoVasc*", Case 1:14-cv-12405-NMG. Document 16-2, Jul. 29, 2014), 1 pg.
"*CardiAQ Valve Technologies* v *NeoVasc*", Case 1:14-cv-12405-NMG. Document 16—main, (Jul. 29, 2014), 3 pgs.
"*CardiAQ Valve Technologies* v *NeoVasc*", Case 1:14-cv-12405-NMG. Document 17-1, (Jul. 29, 2014), 3 pg.
"*CardiAQ Valve Technologies* v *NeoVasc*", Case 1:14-cv-12405-NMG. Document 17—main, (Jul. 29, 2014), 2 pgs.
"*CardiAQ Valve Technologies* v *NeoVasc*", Case 1:14-cv-12405-NMG. Document 18—main, (Jul. 29, 2014), 27 pgs.
"*CardiAQ Valve Technologies* v *NeoVasc*", Case 1:14-cv-12405-NMG. Document 19-1, (Jul. 29, 2014), 1 pg.
"*CardiAQ Valve Technologies* v *NeoVasc*", Case 1:14-cv-12405-NMG. Document 19—main, (Jul. 29, 2014), 2 pgs.
"*CardiAQ Valve Technologies* v *NeoVasc*", Case 1:14-cv-12405-NMG. Document 20—main, (Jul. 29, 2014), 25 pgs.
"*CardiAQ Valve Technologies* v *NeoVasc*", Case 1:14-cv-12405-NMG. Document 21—main, (Jul. 29, 2014), 5 pgs.
"*CardiAQ Valve Technologies* v *NeoVasc*", Case 1:14-cv-12405-NMG. Document 22-1, (Jul. 29, 2014), 89 pgs.
"*CardiAQ Valve Technologies* v *NeoVasc*", Case 1:14-cv-12405-NMG, Document 22—main, (Jul. 29, 2014), 4 pgs.
"*CardiAQ Valve Technologies* v *NeoVasc*", Case 1:14-cv-12405-NMG. Document 24-1, (Aug. 12, 2014), 17 pgs.
"*CardiAQ Valve Technologies* v *NeoVasc*", Case 1:14-cv-12405-NMG. Document 24-2, (Aug. 12, 2014), 4 pgs.
"*CardiAQ Valve Technologies* v *NeoVasc*", Case 1:14-cv-12405-NMG. Document 24-3, (Aug. 12, 2014), 2 pgs.
"*CardiAQ Valve Technologies* v *NeoVasc*", Case 1:14-cv-12405-NMG. Document 24-4, (Aug. 12, 2014), 2 pgs.
"*CardiAQ Valve Technologies* v *NeoVasc*", Case 1:14-cv-12405-NMG. Document 24-5, (Aug. 12, 2014), 3 pgs.
"*CardiAQ Valve Technologies* v *NeoVasc*", Case 1:14-cv-12405-NMG. Document 24—main, (Aug. 12, 2014), 21 pgs.

(56) References Cited

OTHER PUBLICATIONS

"CardiAQ Valve Technologies v NeoVasc", Case 1:14-cv-12405-NMG. Document 25—main, (Aug. 12, 2014), 15 pgs.
"CardiAQ Valve Technologies v NeoVasc", Case 1:14-cv-12405-NMG. Document 26—main, (Aug. 12, 2014), 4 pgs.
"CardiAQ Valve Technologies v NeoVasc", Case 1:14-cv-12405-NMG. Document 27-1, (Aug. 12, 2014), 28 pgs.
"CardiAQ Valve Technologies v NeoVasc", Case 1:14-cv-12405-NMG. Document 27-2, (Aug. 12, 2014), 51 pgs.
"CardiAQ Valve Technologies v NeoVasc", Case 1:14-cv-12405-NMG. Document 27-3, (Aug. 12, 2014), 3 pgs.
"CardiAQ Valve Technologies v NeoVasc", Case 1:14-cv-12405-NMG. Document 27—main, (Aug. 12, 2014), 4 pgs.
"CardiAQ Valve Technologies v NeoVasc", Case 1:14-cv-12405-NMG. Document 28—main, (Aug. 12, 2014), 16 pgs.
"CardiAQ Valve Technologies v NeoVasc", Case 1:14-cv-12405-NMG. Document 29—main, (Aug. 13, 2014), 2 pgs.
"CardiAQ Valve Technologies v NeoVasc", Case 1:14-cv-12405-NMG. Document 30—main, (Aug. 19, 2014), 2 pgs.
"CardiAQ Valve Technologies v NeoVasc", Case 1:14-cv-12405-NMG. Document 31-1, (Aug. 19, 2014), 6 pgs.
"CardiAQ Valve Technologies vNeoVasc", Case 1:14-cv-12405-NMG. Document 31-2, (Aug. 19, 2014), 2 pgs.
"CardiAQ Valve Technologies: Percutaneous Mitral Valve Replacement", Start Up Windhover Review of Emerging Medical Ventures, vol. 14. No. 6, (Jun. 2009), 48-49.
"Chinese Application Serial No. 201680081812.0, Office Action dated Oct. 31, 2019", w/English Translation, 22 pgs.
"European Application Serial No. 11777065.1, Extended European Search Report dated Dec. 10, 2013", 6 pgs.
"European Application Serial No. 16874205.4, Extended European Search Report dated Jul. 5, 2019", 9 pgs.
"European Application Serial No. 16874205.4, Response filed Feb. 3, 2020 to Extended European Search Report dated Jul. 5, 2019", 17 pgs.
"International Application Serial No. PCT/CA2011/000662, International Search Report dated Sep. 27, 2011", 5 pgs.
"International Application Serial No. PCT/CA2011/000662, Written Opinion dated Sep. 27, 2011", 6 pgs.
"International Application Serial No. PCT/CA2016/051482, International Preliminary Report on Patentability dated Jun. 28, 2018", 10 pgs.
"International Application Serial No. PCT/CA2016/051482, International Search Report dated Feb. 27, 2017", 8 pgs.
"International Application Serial No. PCT/CA2016/051482, Written Opinion dated Feb. 27, 2017", 8 pgs.
Bavaria, "CardiAQ Valve Technologies (CVT) discloses successful results of acute in vivo study of its novel transcatheter mitral valve implantation (TMVI) system", [Online]. Retrieved from the Internet: <http://eon.businesswire.com/news/eon/20090928005120/en/CardiAQ-Valve-Technologies/Heart/heart-failure>, (Sep. 28, 2009), 2 pgs.
Bavaria, "CardiAQ Valve Technologies. TOT Company Overview", Transcatheter Cardiovascular Therapeutics Conference. San Francisco, CA, (Sep. 21-25, 2009), 11 pgs.
Carpentier-Edwards, "Why compromise in the mitral position?", Edwards Lifesciences, (2004), 4 pgs.
Fitzgerald, "Tomorrow's technology: percutaneous mitral valve replacement, chordal shortening and beyond", Transcatheter Valve Therapies (TVT) Conference. Seattle, WA, (Jun. 7, 2010), 8 pgs.
Mack, "Advantages and limitations of surgical mitral valve replacement; lessons for the transcatheter approach", Texas Cardiovascular Innovative Ventures (TCIV) Conference. Dallas, TX, (Jun. 7, 2010), 5 pgs.
Ostrovsky, "Transcatheter mitral valve implantation technology from CardiAQ", [Online]. Retrieved from the Internet: <http://medgadget.com/2010/01/transcatheter_mitral_valveimplantation_technologyfrom_cardiaq.html>, Accessed Jun. 27, 2012 from, (Jan. 15, 2010), 2 pgs.
Ratz, "CardiAQ Valve Technologies. Innovations in heartvalve therapy", IN3 San Francisco PowerPoint presentation in 19 slides, (Jun. 18, 2008), 19 pgs.
Ruiz, "Overview of novel transcatheter valve technologies", Glimpse into the future. New transcatheter mitral valve treatment. Euro PCR. Paris, France, (May 27, 2010), 14 pgs.
"Canadian Application Serial No. 3,132,873, Office Action dated Oct. 19, 2021", 3 pgs.
"International Application Serial No. PCT/US2020/021493, International Preliminary Report on Patentability dated Sep. 23, 2021", 8 pgs.
"U.S. Appl. No. 16/812,865, Preliminary Amendment filed Sep. 22, 2020", 6 pgs.
"International Application Serial No. PCT/US2020/021493, International Search Report dated Jul. 6, 2020", 4 pgs.
"International Application Serial No. PCT/US2020/021493, Invitation to Pay Additional Fees dated May 14, 2020", 2 pgs.
"International Application Serial No. PCT/US2020/021493, Written Opinion dated Jul. 6, 2020", 6 pgs.
"Australian Application Serial No. 2020233892, First Examination Report dated May 25, 2022", 4 pgs.
"European Application Serial No. 20770471.9, Response to Communication pursuant to Rules 161 and 162 filed May 18, 2022", 14 pgs.
"Canadian Application Serial No. 3,132,873, Non Final Office Action dated Jun. 9, 2022", 4 pgs.
"European Application Serial No. 20770471.9, Response filed May 18, 2022 to Communication dated Nov. 8, 2021", 16 pgs.
"Canadian Application Serial No. 3,132,873, Response filed Feb. 9, 2022 to Office Action dated Oct. 19, 2021", 17 pgs.
"Canadian Application Serial No. 3,132,873, Response filed Oct. 6, 2022 to Non Final Office Action dated Jun. 9, 2022", 18 pgs.
"European Application Serial No. 20770471.9, Extended European Search Report dated Oct. 26, 2022", 13 pgs.
"Japanese Application Serial No. 2021-553368, Notification of Reasons for Refusal dated Nov. 18, 2022", w/ English Translation, 9 pgs.
"U.S. Appl. No. 16/812,865, Response filed Oct. 10, 2023 to Restriction Requirement dated Sep. 15, 2023", 6 pgs.
"Japanese Application Serial No. 2021-553368, Response filed Oct. 19, 2023 to Notification of Reasons for Rejection dated Aug. 24, 2023", W English Claims, 6 pgs.
"U.S. Appl. No. 17/358,757, Non Final Office Action dated Oct. 25, 2023", 12 pgs.
"European Application Serial No. 20770471.9, Communication Pursuant to Article 94(3) EPC dated Sep. 20, 2023", 6 pgs.
"U.S. Appl. No. 16/812,865, Restriction Requirement dated Sep. 15, 2023", 8 pgs.
"Canadian Application Serial No. 3,132,873, Examiners Rule 86(2) Report dated Feb. 8, 2023", 3 pgs.
"Canadian Application Serial No. 3,132,873, Response filed May 24, 2023 to Examiners Rule 86(2) Report dated Feb. 8, 2023", 8 pgs.
"European Application Serial No. 20770471.9, Response filed May 25, 2023 to Extended European Search Report dated Oct. 26, 2022", 123 pgs.
"Japanese Application Serial No. 2021-553368, Notification of Reasons for Rejection dated Aug. 24, 2023", W/English Translation, 4 pgs.
"Japanese Application Serial No. 2021-553368, Response filed May 15, 2023 to Notification of Reasons for Refusal dated Nov. 18, 2022", w/ English Claims, 11 pgs.
"Chinese Application Serial No. 202080030790.1, Office Action mailed Mar. 11, 2024", with English translation, 16 pgs.
"Chinese Application Serial No. 202080030790.1, Response filed Feb. 29, 2024 to Notification of Paying the Restoration Fee mailed Dec. 18, 2023", with machine translation, 4 pgs.
"European Application Serial No. 20770471.9, Response filed Jan. 30, 2024 to Communication Pursuant to Article 94(3) EPC mailed Sep. 20, 2023", 24 pgs.
"U.S. Appl. No. 16/812,865, Final Office Action mailed Mar. 18, 2024", 8 pgs.

(56) References Cited

OTHER PUBLICATIONS

"U.S. Appl. No. 16/812,865, Response filed Jan. 25, 2024 to Non Final Office Action mailed Oct. 25, 2023", 19 pgs.

* cited by examiner

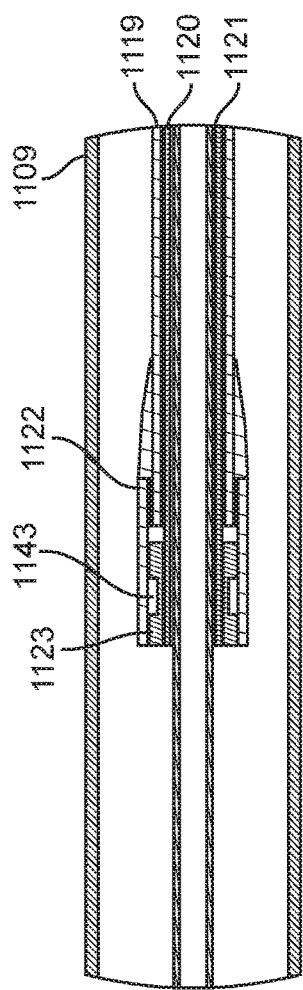
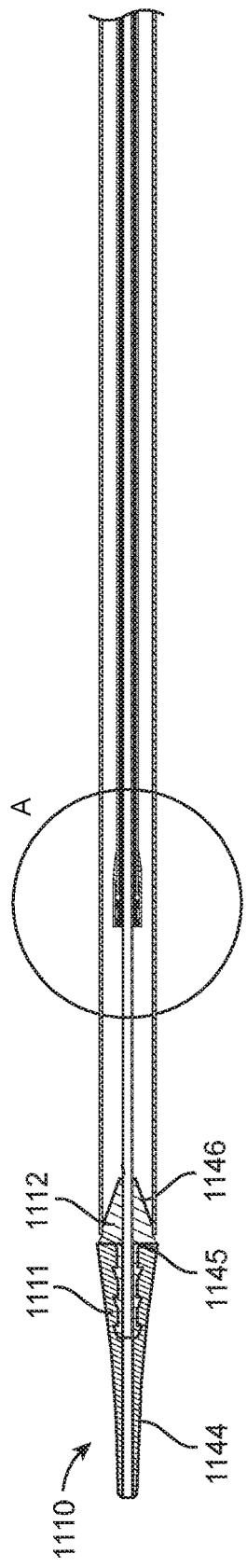
DETAIL A
FIG. 15A

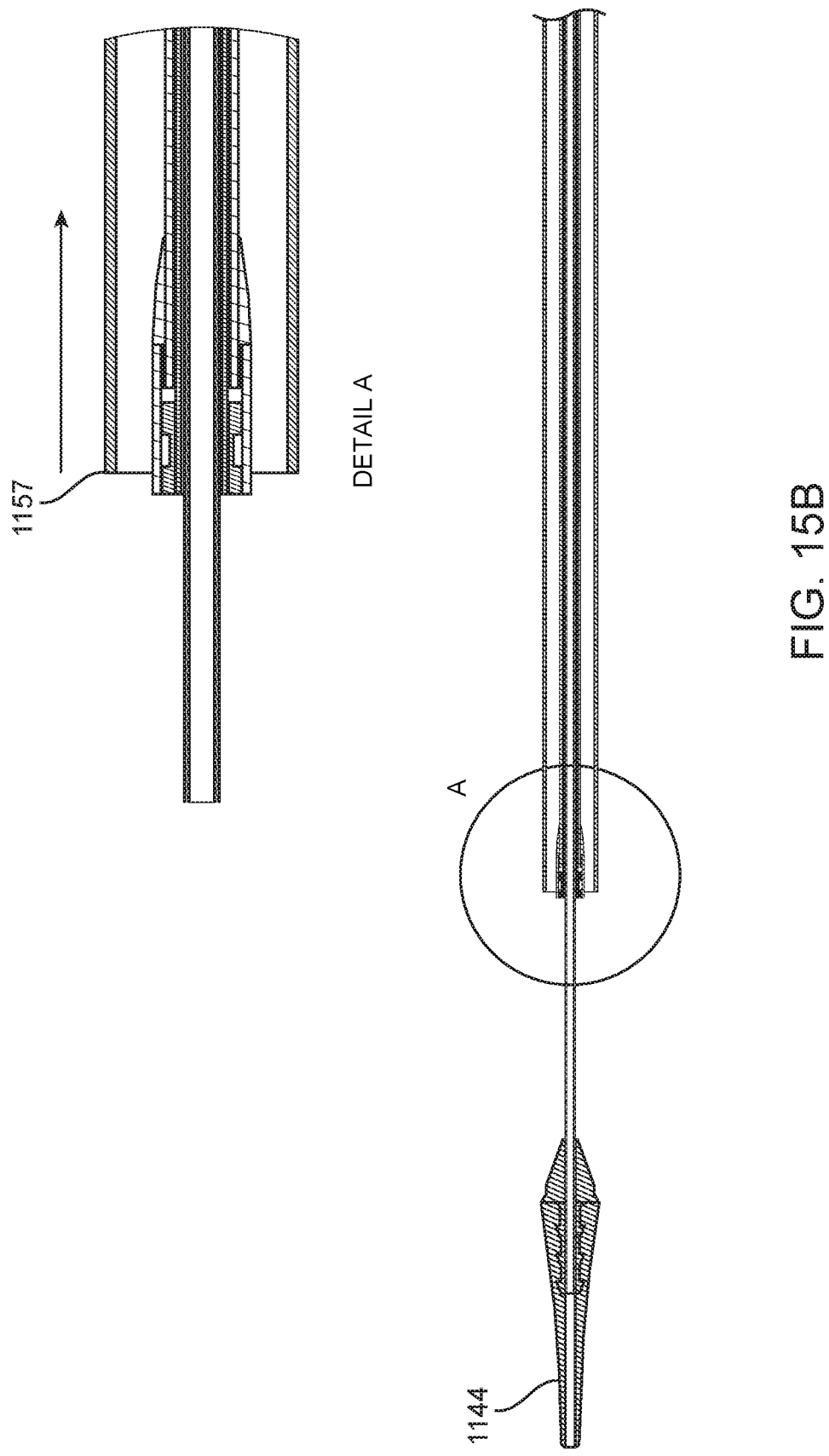

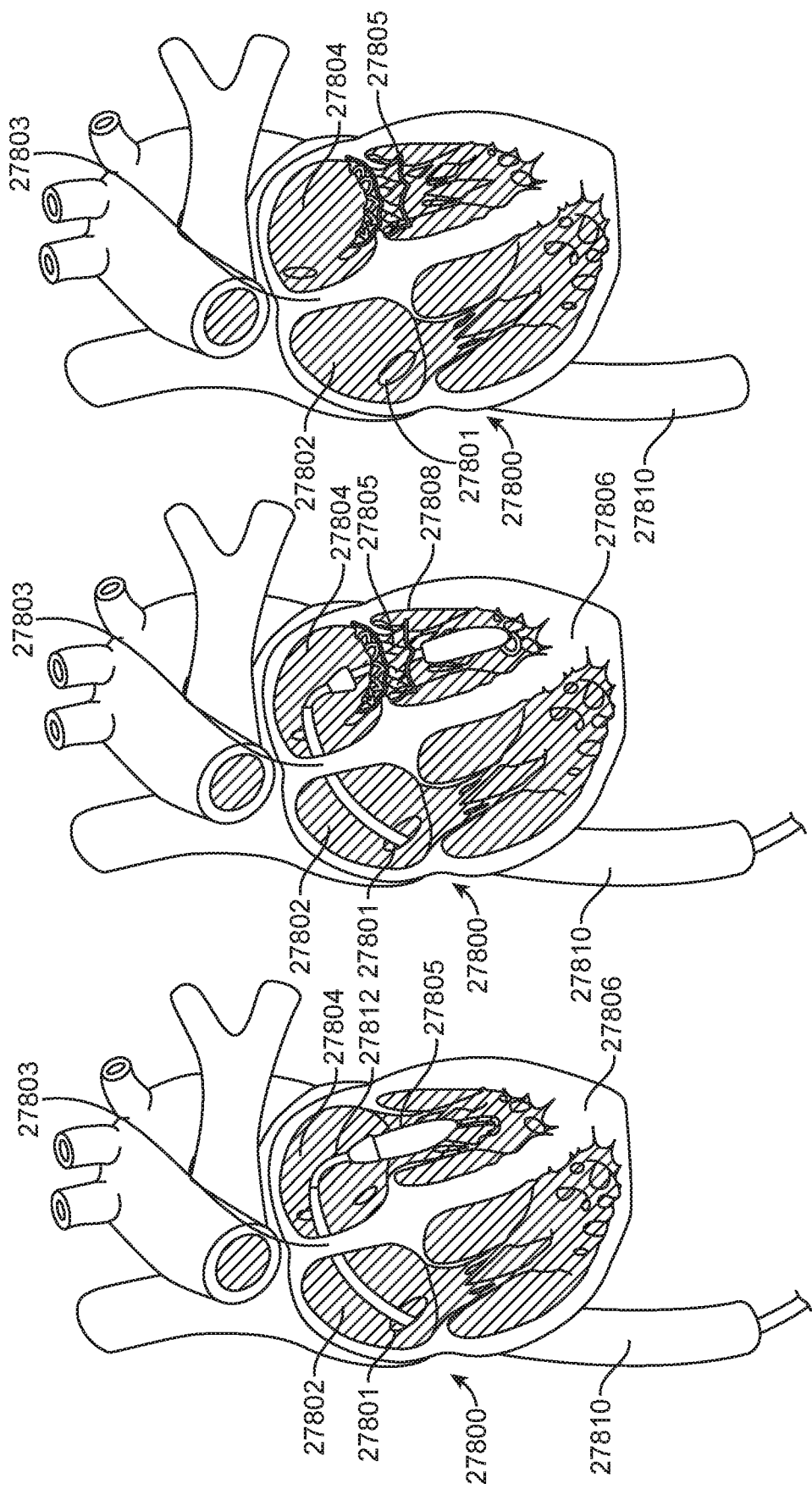

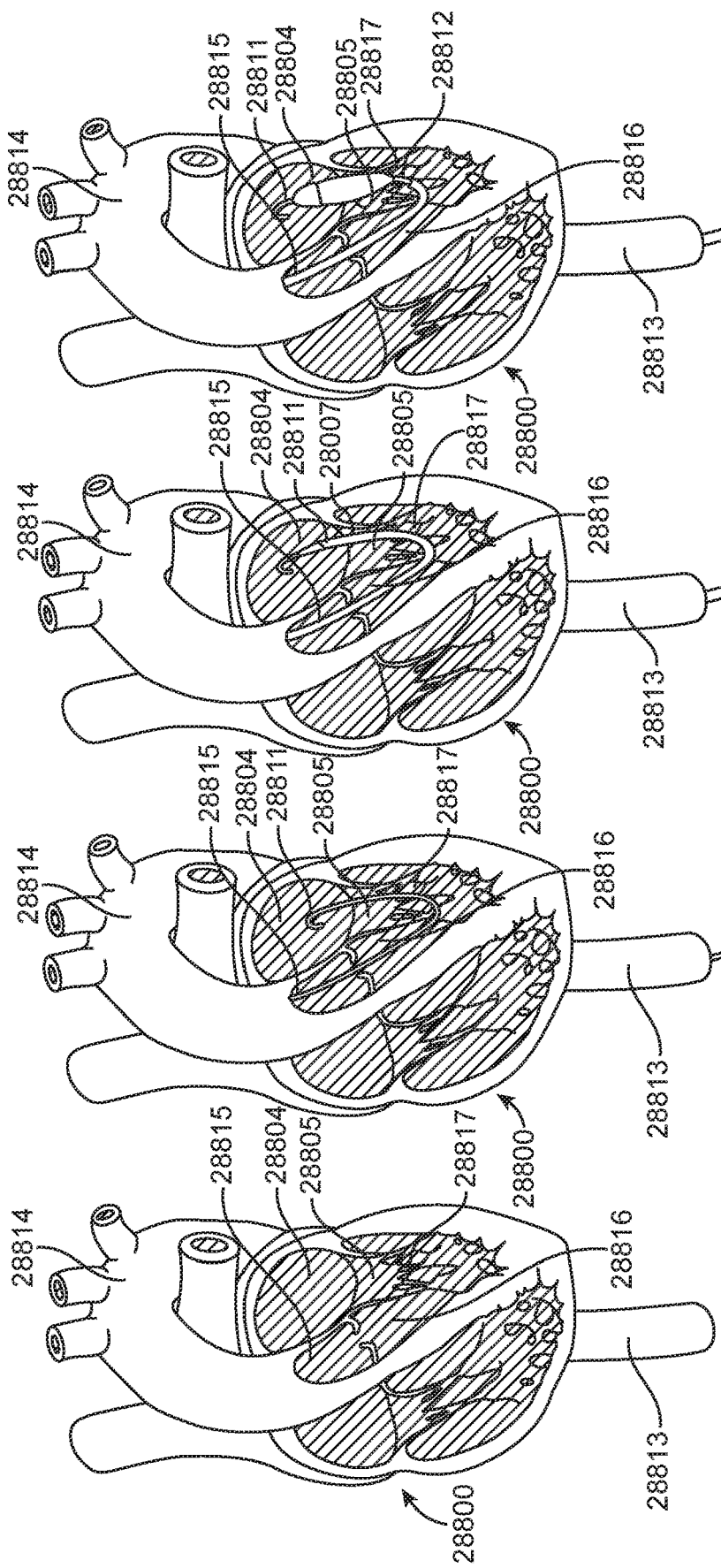

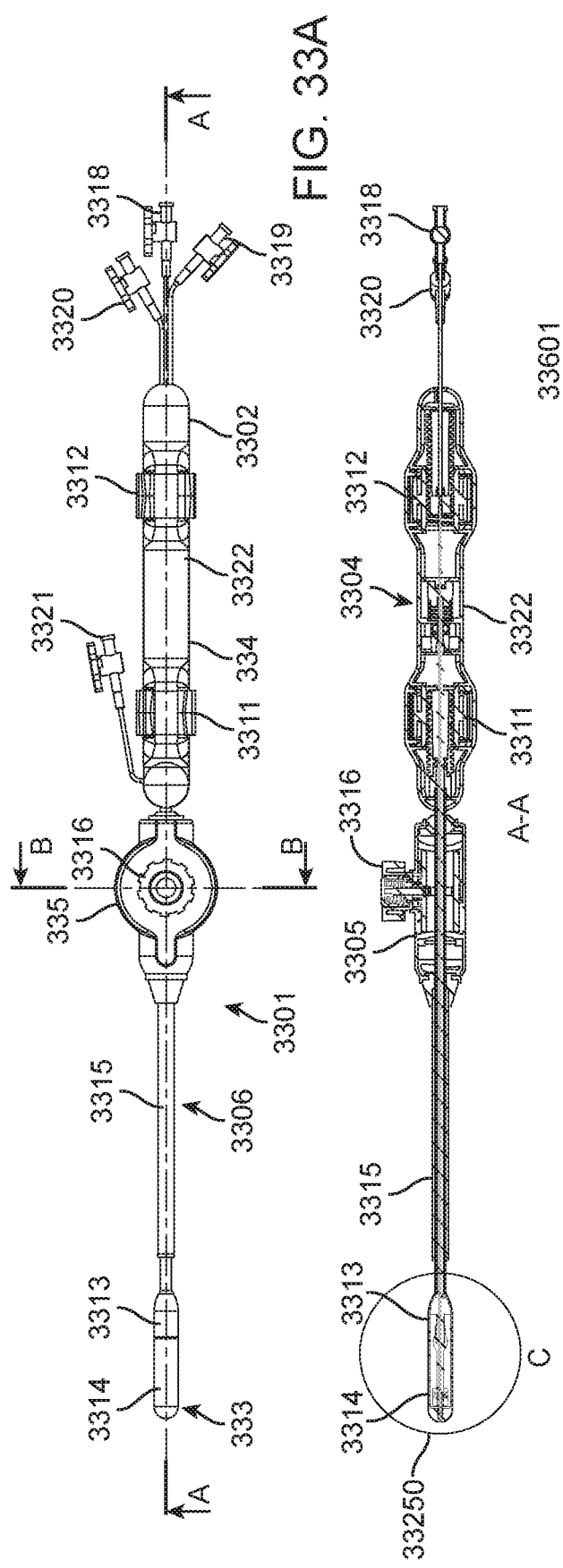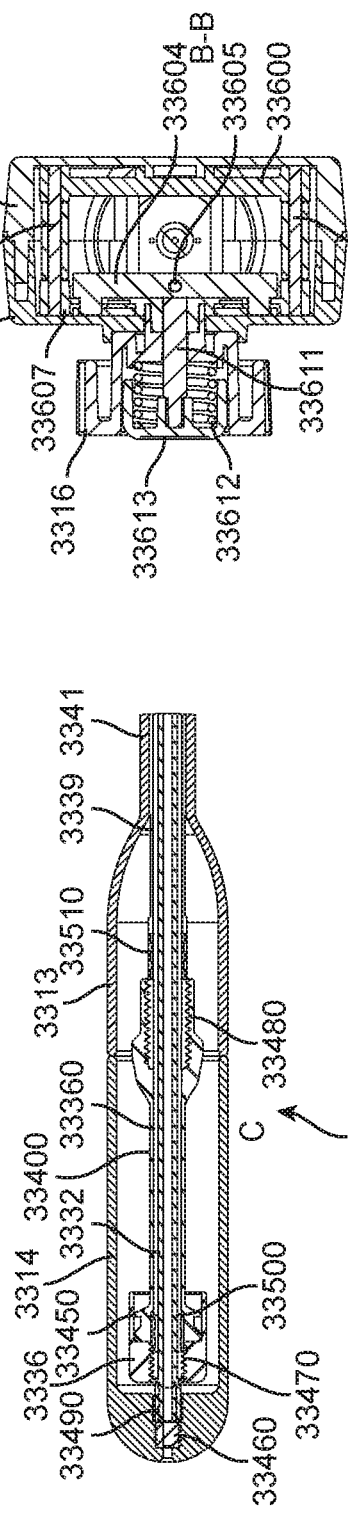
FIG. 33A
FIG. 33B
FIG. 33C
FIG. 33D

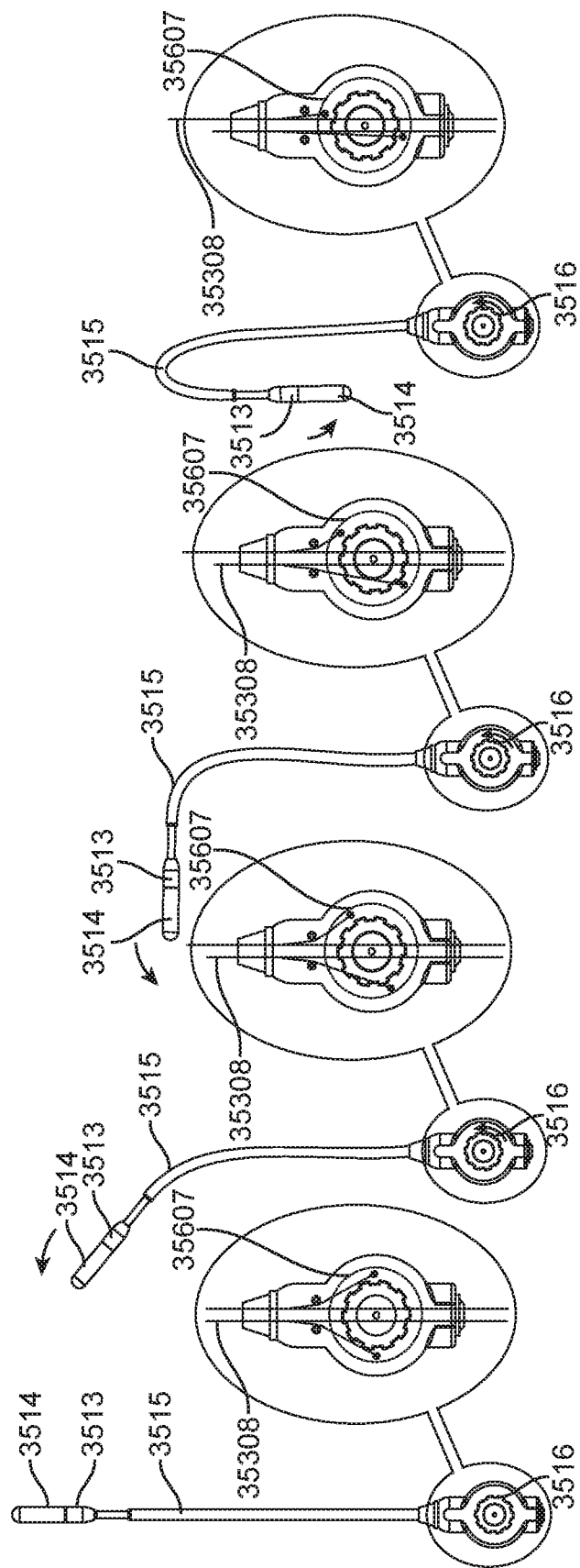

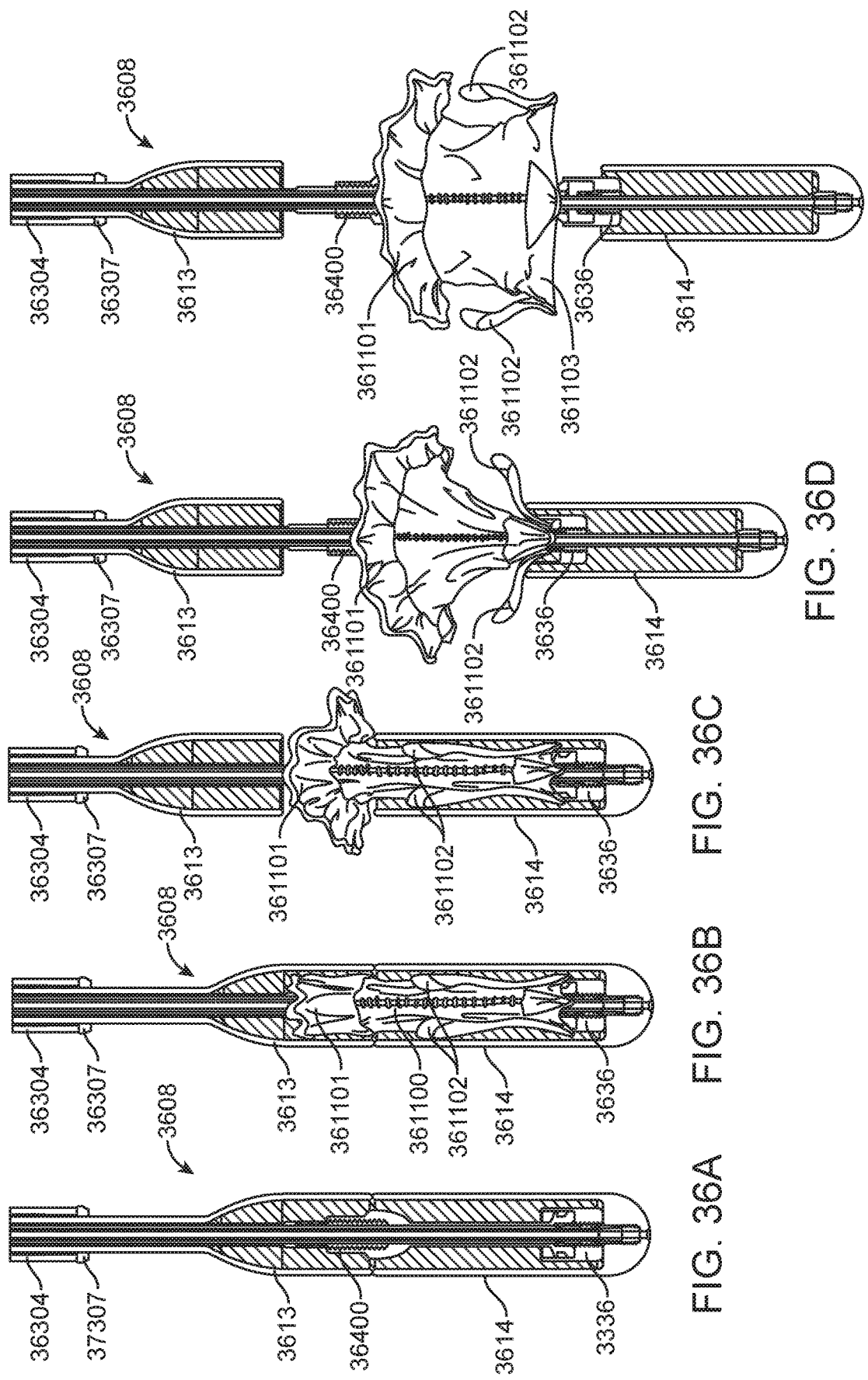

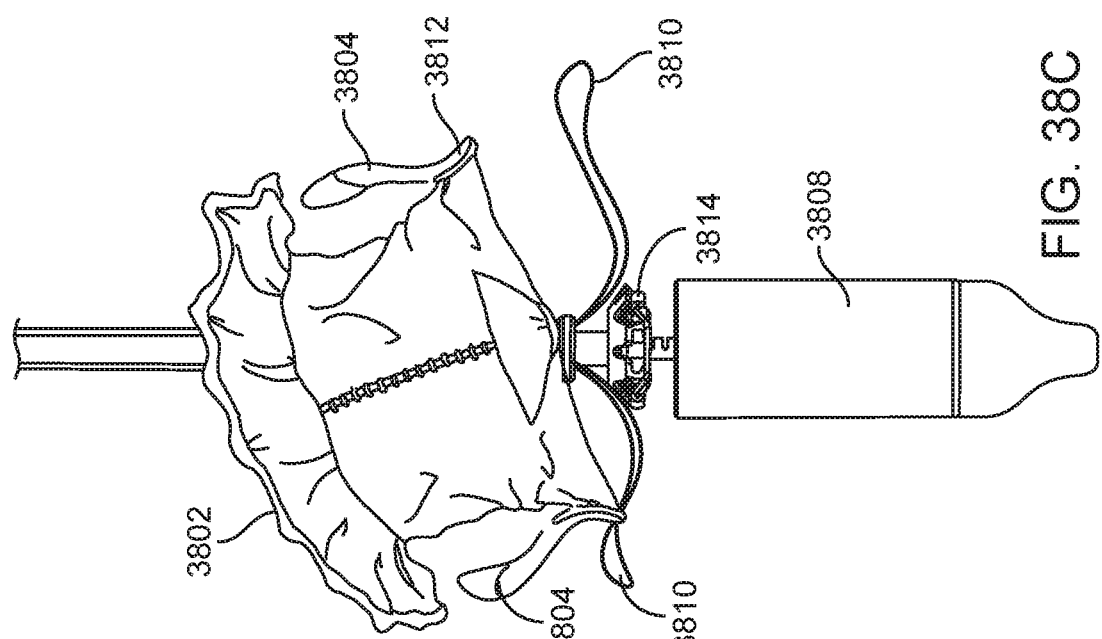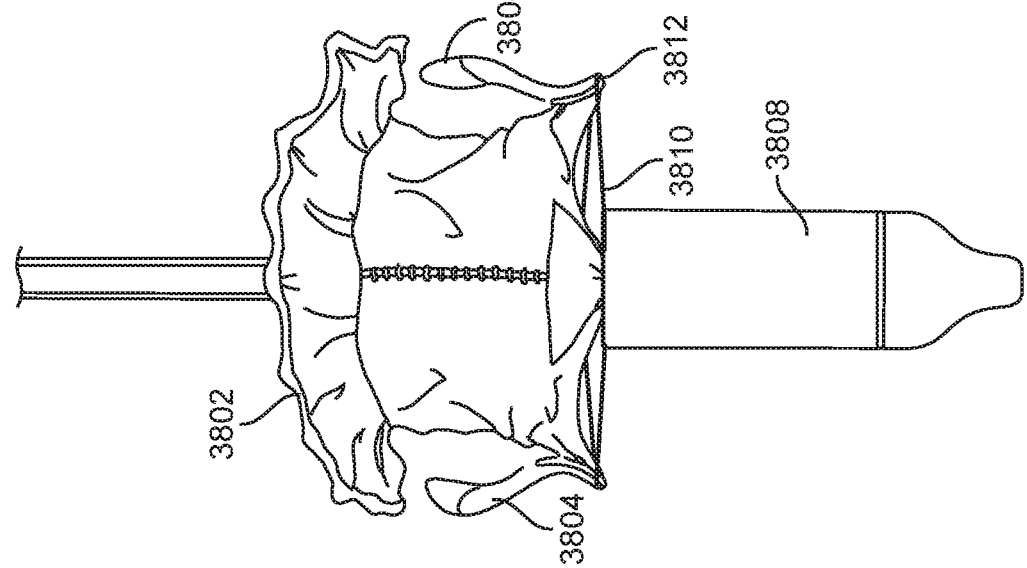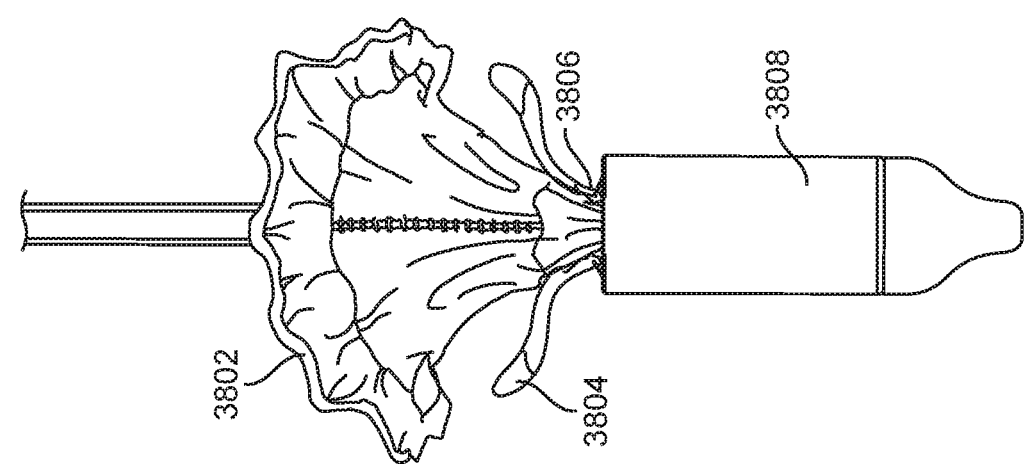

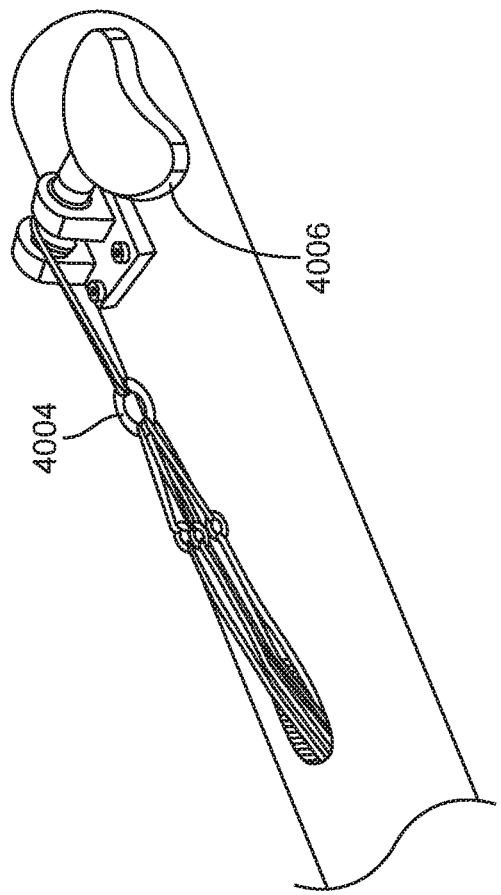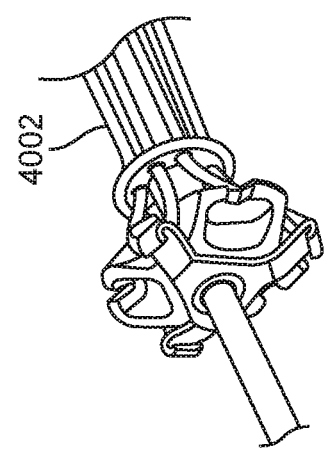
FIG. 40 a# RETRIEVABLE PROSTHESIS DELIVERY SYSTEM

CLAIM OF PRIORITY

The present application is a non-provisional of, and claims the benefit of U.S. Provisional Patent Application No. 62/815,832 filed on Mar. 8, 2019, the entire contents of which are incorporated herein by reference.

CROSS-REFERENCE TO RELATED PATENT DOCUMENTS

This patent application is related to U.S. Pat. No. 8,579,964 and US Patent Publication No. 2017/0165064; the entire contents of which are incorporated herein by reference.

BACKGROUND

Less invasive and minimally invasive procedures are increasingly being used to treat patients for a variety of conditions in lieu of traditional open surgical techniques. For example, delivery catheters may be used for advancing a prosthesis or other device to a target area such as a diagnostic or treatment region of interest.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 15A-15C are cross-sectional views of a distal portion of the delivery device in FIG. 11.

FIGS. 27A-27F are sequential views of the procedural pathway traversed by the prosthesis during a transseptal implantation procedure.

FIGS. 28A-28D are sequential views of the procedural pathway traversed by the prosthesis during a transaortic implantation procedure.

FIG. 33A is a side view of the delivery system in FIG. 26.

FIG. 33B is a cross-sectional view of the delivery system taken along line A-A in FIG. 33A.

FIGS. 33C-33D show other cross-sections of the delivery system.

FIGS. 35A-35D are sequential views of the steering handle portion of the delivery system of FIG. 26.

FIGS. 36A-36E are sequential cross-sectional views of the valve capsule portion taken along the line A-A in FIG. 33A.

FIGS. 38A-38C show the use of tethers to control deployment of a prosthesis.

FIG. 40 shows a tension equalizer.

DETAILED DESCRIPTION

Delivery system are used to advance a therapeutic or diagnostic device to a target area. Often times the delivery system must navigate an obstructed, tortuous, or otherwise challenging path to the target area. Therefore, it may be desirable to provide delivery systems that can accommodate the challenging path. Furthermore, sometimes once a prosthesis or other medical device is delivered to the target area and released from the delivery system, the physician determines that the prosthesis or medical device has not been delivered to the optimal location and therefore it may be desirable to move the prosthesis or medical device after it has been partially or fully deployed. Additionally, it may be desirable to provide a delivery system with controls or other indicators which allow the operator to know when critical deployment steps are performed or about to be performed, and it may be desirable to provide controls that allow an operator to acknowledge and confirm that he/she would like to proceed with the next step of deployment so that inadvertent deployment is avoided. At least some of these challenges will be addressed by the examples disclosed herein.

While the present examples will be discussed primarily with respect to prosthetic mitral valves used to treat mitral valve insufficiency, one of skill in the art will appreciate that this is not intended to be limiting and the examples disclosed herein may be used in any heart valve (e.g. aortic valve, tricuspid valve, pulmonary valve, etc.) as well as other anatomic valves (e.g. venous valves) or in any other region of the body.

Prosthetic heart valves such as prosthetic mitral valves may be implanted during an open heart procedure which is highly invasive and requires a lengthy hospital stay and recovery period.

More recently, prosthetic heart valves are being delivered either transapically or transseptally with a delivery system such as a delivery catheter. Examples of prosthetic valves, transapical and transseptal delivery systems are disclosed in U.S. Pat. No. 8,579,964; previously incorporated by reference. Any of the delivery systems disclosed in U.S. Pat. No. 8,579,964 may be used with any of the examples disclosed herein.

Additional transseptal delivery systems are disclosed in US Patent Publication No. 2017/0165064; previously incorporated herein by reference. Any of the prostheses or delivery systems disclosed in these references may be modified to include the features disclosed herein.

In some situations it may be desirable to add additional features to a transseptal or transapical delivery system. Any of the following features may be incorporated into a delivery system.

Specific embodiments of the disclosed device, delivery system, and method will now be described with reference to the drawings. Nothing in this detailed description is intended to imply that any particular component, feature, or step is essential to the invention.

Figure 1:
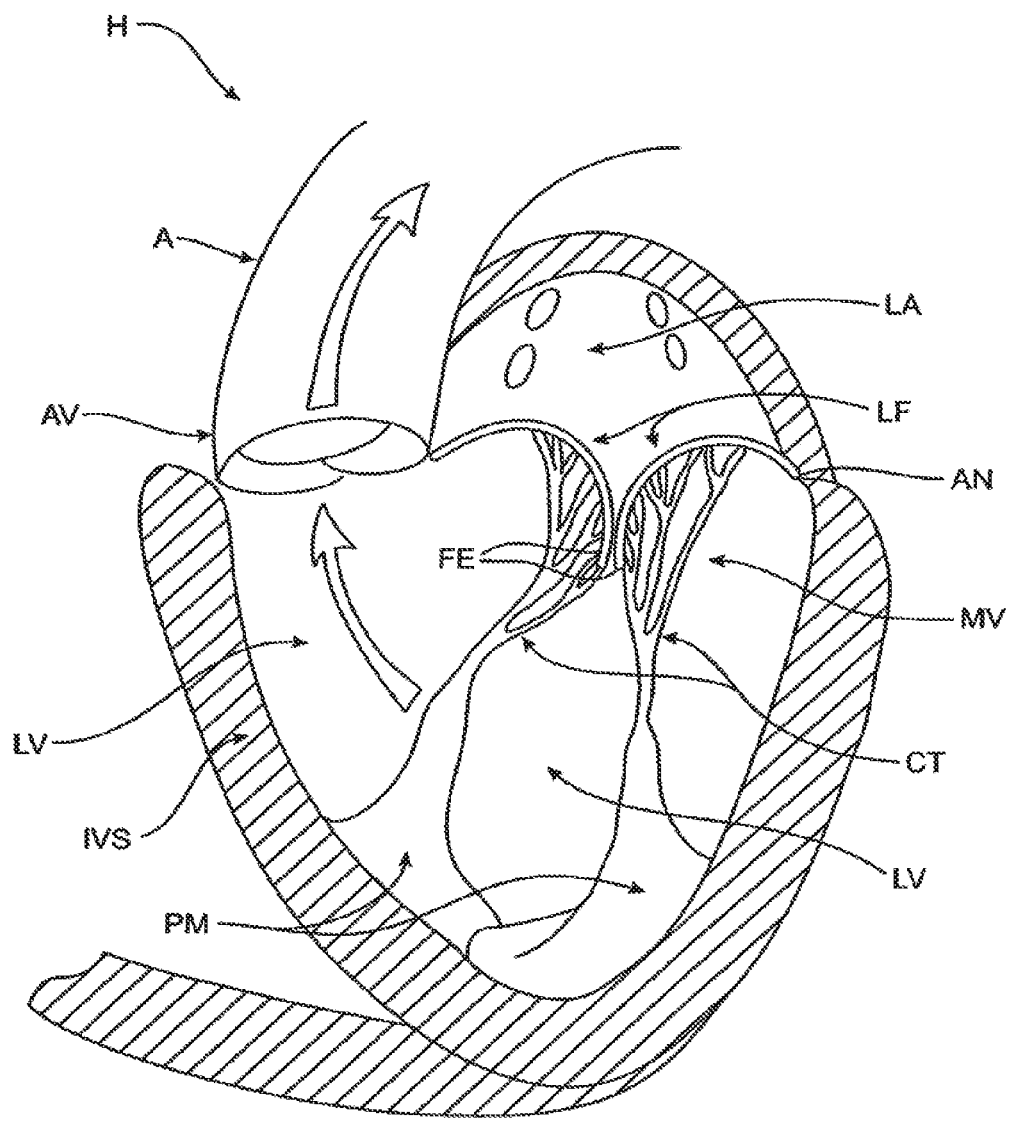
FIG. 1 is a schematic illustration of the left ventricle of a heart showing blood flow during systole with arrows.

Cardiac Anatomy. The left ventricle LV of a normal heart H in systole is illustrated in FIG. 1. The left ventricle LV is contracting and blood flows outwardly through the aortic valve AV, a tricuspid valve in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1. The opposite ends of the leaflets LF are attached to the surrounding heart structure along an annular region referred to as the annulus AN. The free edges FE of the leaflets LF are secured to the lower portions of the left ventricle LV through chordae tendineae CT (also referred to herein as the chordae) which include a plurality of branching tendons secured over the lower surfaces of each of the valve leaflets LF. The chordae CT in turn, are attached to the papillary muscles PM which extend upwardly from the lower portions of the left ventricle and interventricular septum IVS.

Figure 2:
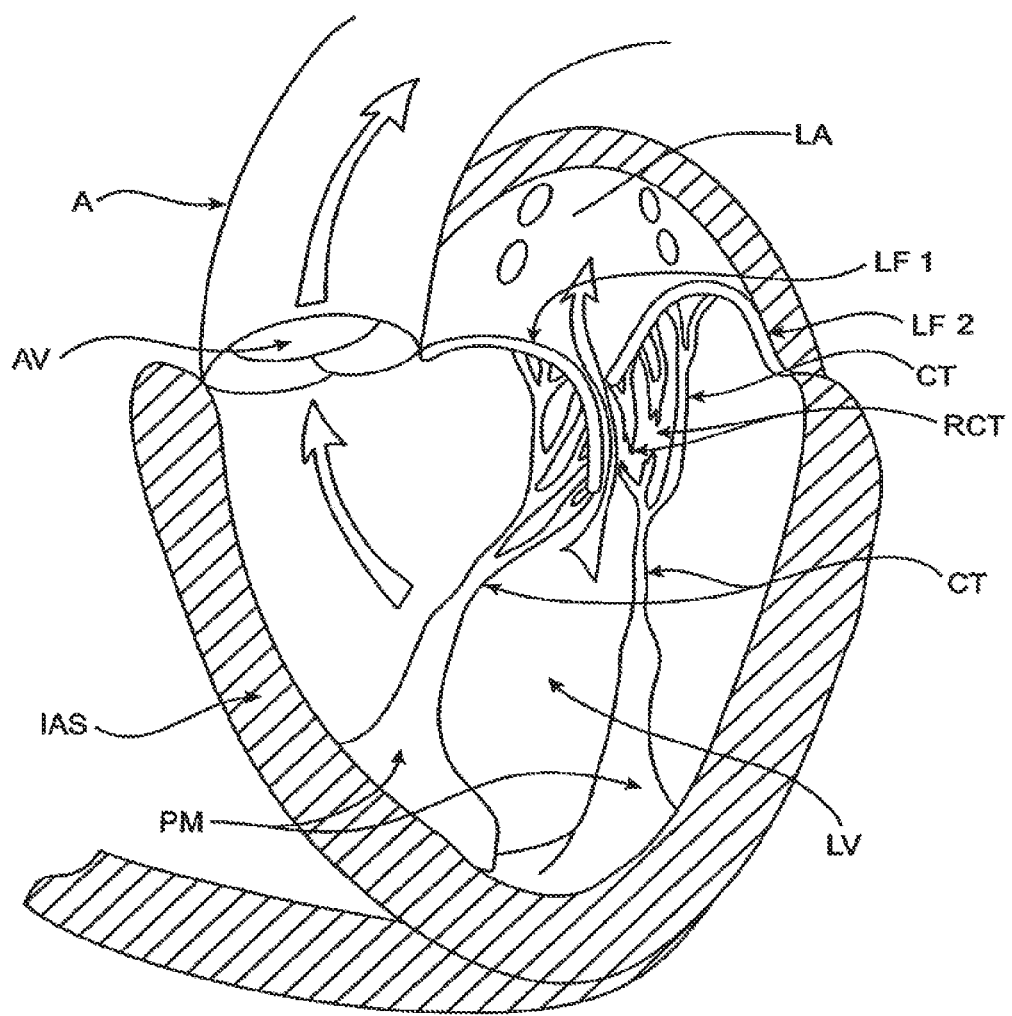
FIG. 2 is a schematic illustration of the left ventricle of a heart having prolapsed leaflets in the mitral valve.
Figure 3:
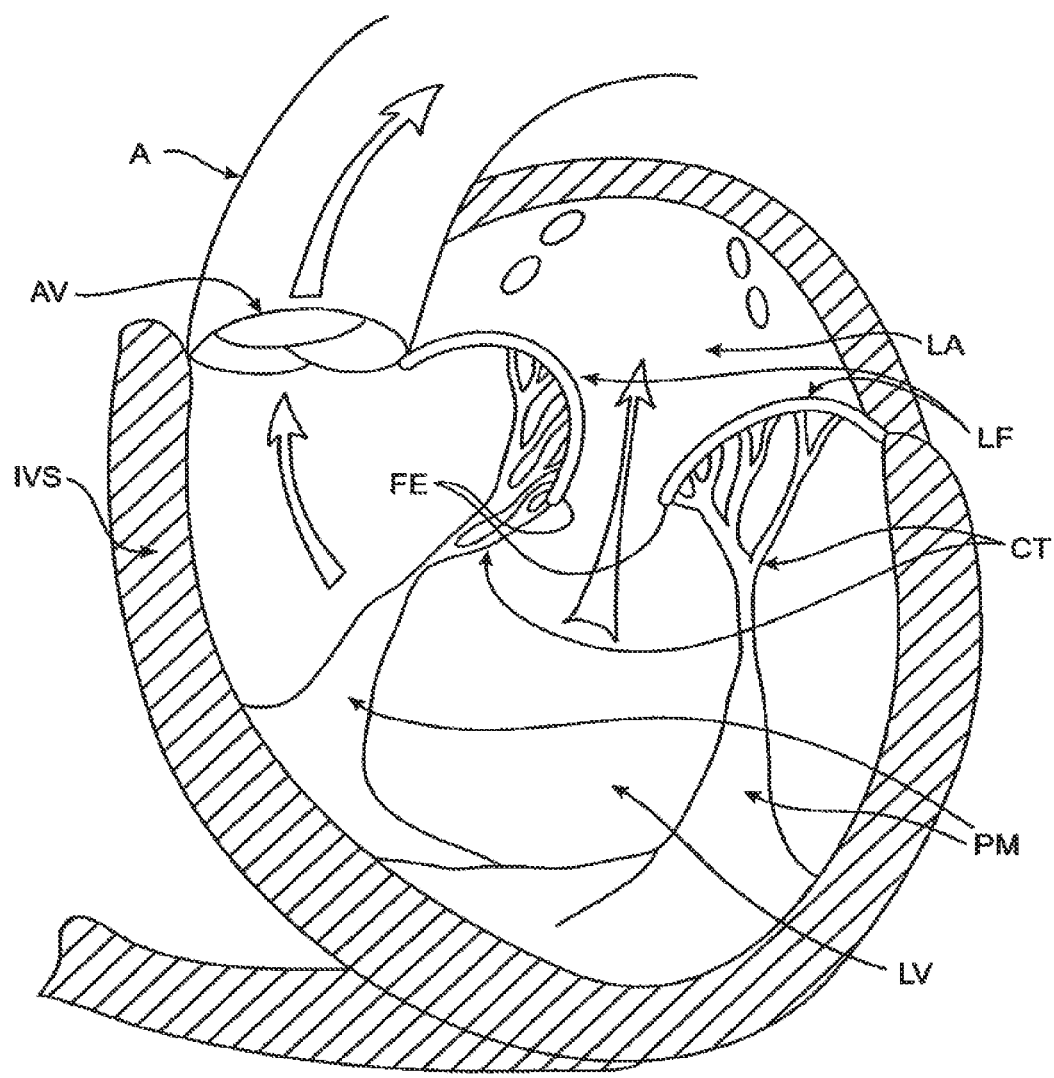
FIG. 3 is a schematic illustration of a heart in a patient suffering from cardiomyopathy where the heart is dilated and the leaflets do not meet.
Figure 4:
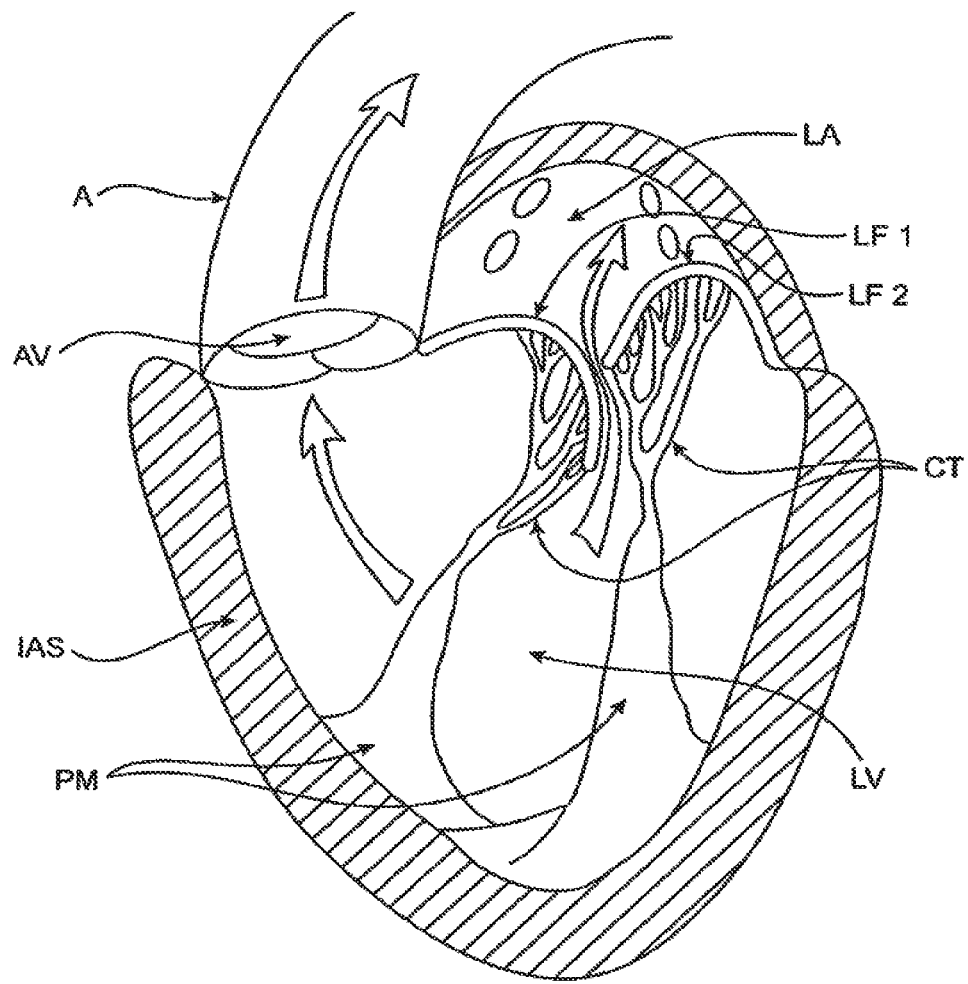
FIG. 4 illustrates mitral valve regurgitation in the left ventricle of a heart having impaired papillary muscles.

Referring now to FIGS. 2-4, a number of structural defects in the heart can cause mitral prolapse since inadequate tension is transmitted to the leaflet via the chordae. While the other leaflet LF1 maintains a normal profile, the two valve leaflets do not properly meet and leakage from the left ventricle LV into the left atrium LA will occur, as shown by the arrow.

Figure 3A:
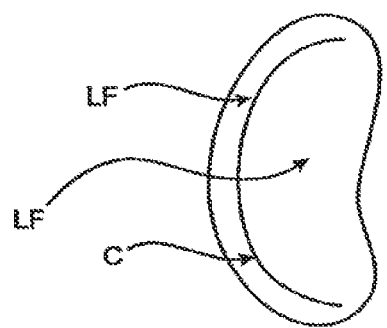
FIG. 3A shows, normal closure of the leaflets.
Figure 3B:
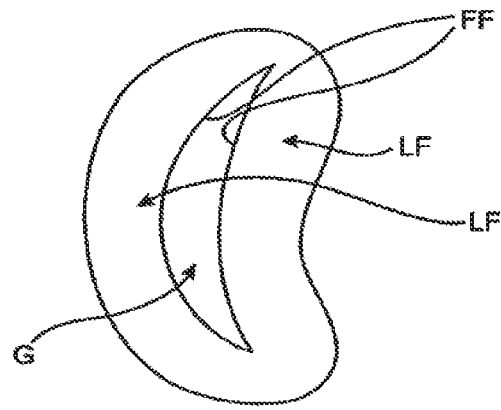
FIG. 3B shows abnormal closure in the dilated heart.

Regurgitation also occurs in the patients suffering from cardiomyopathy where the heart is dilated and the increased size prevents the valve leaflets LF from meeting properly, as shown in FIG. 3. The enlargement of the heart causes the mitral annulus to become enlarged, making it impossible for the free edges FE to meet during systole. The free edges of the anterior and posterior leaflets normally meet along a line of coaptation C as shown in FIG. 3A, but a significant gap G can be left in patients suffering from cardiomyopathy, as shown in FIG. 3B.

Mitral valve regurgitation can also occur in patients who have suffered ischemic heart disease where the functioning of the papillary muscles PM is impaired, as illustrated in FIG. 4. As the left ventricle LV contracts during systole, the papillary muscles PM do not contract sufficiently to effect proper closure. The leaflets LF1 and LF2 then prolapse, as illustrated. Leakage again occurs from the left ventricle LV to the left atrium LA, as shown by the arrow.

Figure 5A:
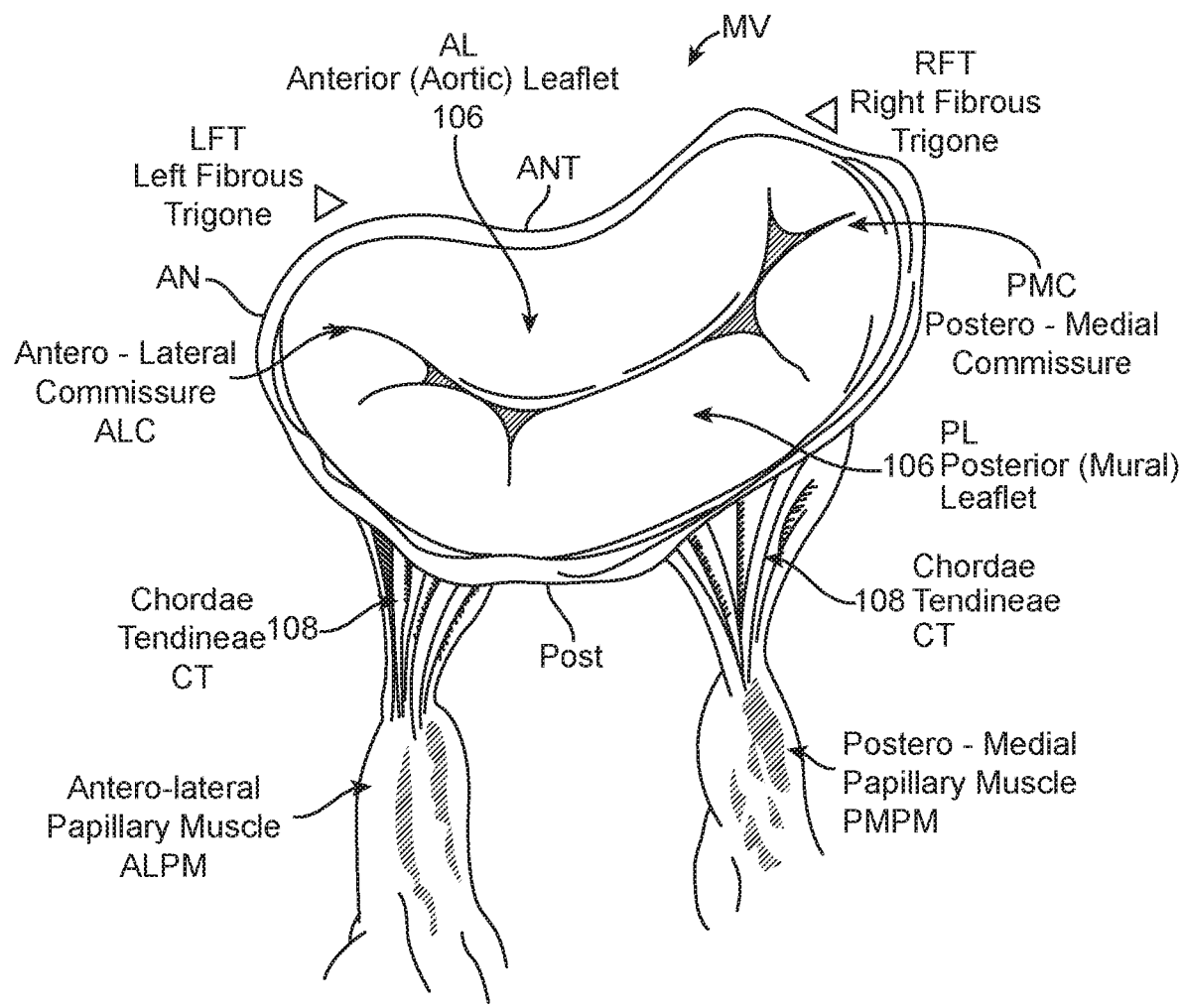
FIGS. 5A-5B illustrate the mitral valve.
Figure 5B:
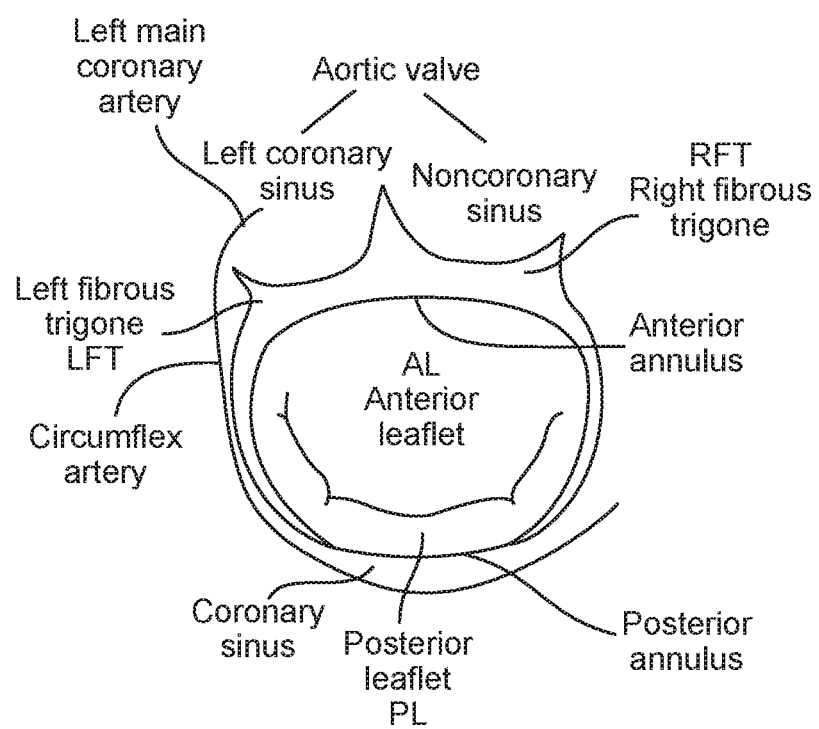

FIG. 5A more clearly illustrates the anatomy of a mitral valve MV which is a bicuspid valve having an anterior side ANT and a posterior side POST. The valve includes an anterior (aortic) leaflet AL and a posterior (mural) leaflet PL. Chordae tendineae CT couple the valve leaflets AL, PL with the antero-lateral papillary muscle ALPM and the postero-medial papillary muscle PMPM. The valve leaflets AL, PL join one another along a line referred to as the antero-lateral commissure ALC and the posterior-medial commissure PMC. The annulus AN circumscribes the valve leaflets, and two regions adjacent an anterior portion of the annulus, on opposite sides of the anterior leaflet are referred to as the left fibrous trigone LFT and also the right fibrous trigone RFT. These areas are indicted by generally by the solid triangles. FIG. 5B more clearly illustrates the left and right fibrous trigones, LFT, RFT.

While various surgical techniques as well as implantable devices have been proposed and appear to be promising treatments for mitral regurgitation, surgical approaches can require a lengthy recovery period, and implantable devices have varying clinical results. Therefore, there still is a need for improved devices and methods for treating mitral regurgitation. While the embodiments disclosed herein are directed to an implantable prosthetic mitral valve for treating mitral regurgitation, one of skill in the art will appreciate that this is not intended to be limiting, and the device and methods disclosed herein may also be used to treat other cardiac valves such as the tricuspid valve, aortic valve, pulmonary valve, etc., as well as other valves in the body such as venous valves.

Prosthetic Valve

Prosthetic valves have been surgically implanted in the heart as a treatment for mitral regurgitation. Some of these valves have been valves harvested from animals such as porcine valves, and others have been prosthetic mechanical valves with or without a tissue covering. More recently, minimally invasive catheter technology has been used to deliver prosthetic valves to the heart. These valves typically include an anchor for securing the valve to the patient's heart, and a valve mechanism, either a mechanical valve, a valve with animal tissue, or combinations thereof. The prosthetic valve once implanted, takes over for malfunctioning native valve, thereby reducing or eliminating valvar insufficiency. While some of these valves appear promising, there still is a need for improved valves. The following discloses exemplary embodiments of a prosthetic valve, a delivery system for the prosthetic valve, and methods of delivering the valve that overcome some of the challenges associated with existing prosthetic valves.

Figure 6:
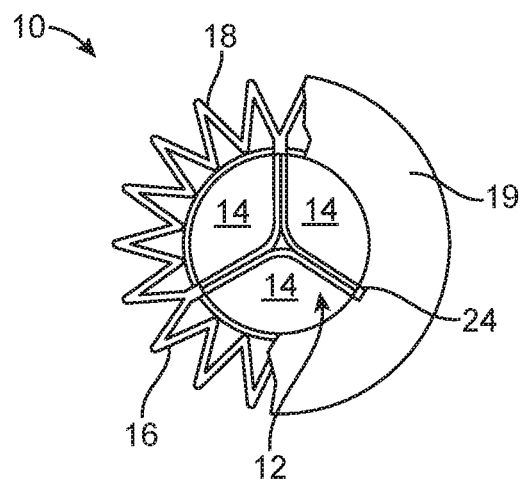
FIG. 6 illustrates a bottom, partial cross-sectional view of an exemplary prosthetic mitral valve.
Figure 7:
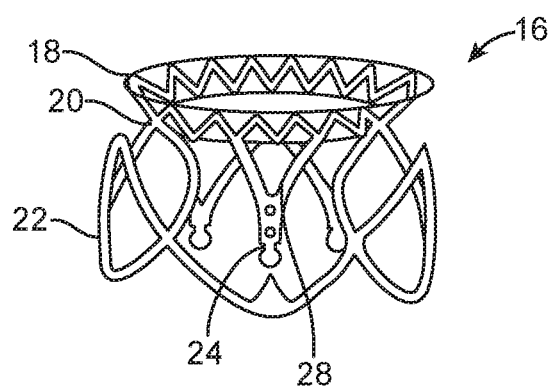
FIG. 7 is a perspective view of the anchor portion of the prosthetic mitral valve seen in FIG. 6.

Referring now to FIGS. 6-7, exemplary embodiments of a mitral valve prosthesis generally designated with reference numeral 10 comprise tricuspid tissue-type prosthetic one-way valve structure 12 comprising leaflets 14 affixed within self-expanding or expandable anchor portion 16 having a geometry that expands into low profile atrial skirt region 18, annular region 20, ventricular skirt region 22, and a plurality of leaflet commissures 24 (also referred to herein as commissure posts) extending axially in a cantilevered fashion downstream into the sub-annular space defined by ventricular skirt region 22. FIG. 6 shows a partial cross-section of the valve 10 from the patient's left ventricle looking upward toward the right atrium. The atrial skirt region 18 is anchored to a lower portion of the right atrium 19. The valve leaflets 14 have an open position (not illustrated) and a closed position illustrated in FIG. 6. In the open position, the leaflets 14 are displaced away from one another to allow blood flow therepast, and in the closed position, the leaflets 14 engage one another to close the valve and prevent retrograde blood flow therepast. The valve commissures 24 may be configured to optimize the efficiency of the prosthetic valve structure 12 and the load distribution on the leaflets 14 by providing for the attachment of the leaflets 14 along arcuate seams 28 (best seen in FIG. 7), and by being made selectively flexible at different points or zones along their axial length through the addition/deletion of reinforcing struts.

FIG. 7 shows a perspective view of the anchor portion 16 of the valve 10 which has been formed from a series of interconnected struts. The atrial skirt region 18 forms an annular flanged region on the anchor to help secure an upper portion of the prosthetic valve in the atrium, and the annular region 20 is a cylindrical region for anchoring the valve along the native valve annulus. The ventricular skirt region 22 similarly is cylindrically shaped and helps anchor a lower portion of the valve in the patient's left ventricle. Any portion, or all of the anchor may be covered with tissue such as pericardium or other tissues disclosed herein, or a synthetic material such as Dacron or ePTFE may be used to cover the anchor. The covering helps to seal the anchor to the native valve, and this helps funnel blood into and through the prosthetic valve, rather than around the valve. In some embodiments, the anchor may remain uncovered. The prosthetic valve has an expanded configuration and a collapsed configuration. The collapsed configuration has a low profile cylindrical shape that is suitable for mounting on a delivery system and delivery is preferably made either transluminally on a catheter, or transapically through the heart wall. The expanded configuration (as illustrated) allow the prosthetic valve to be anchored into a desired position.

Figure 8A:
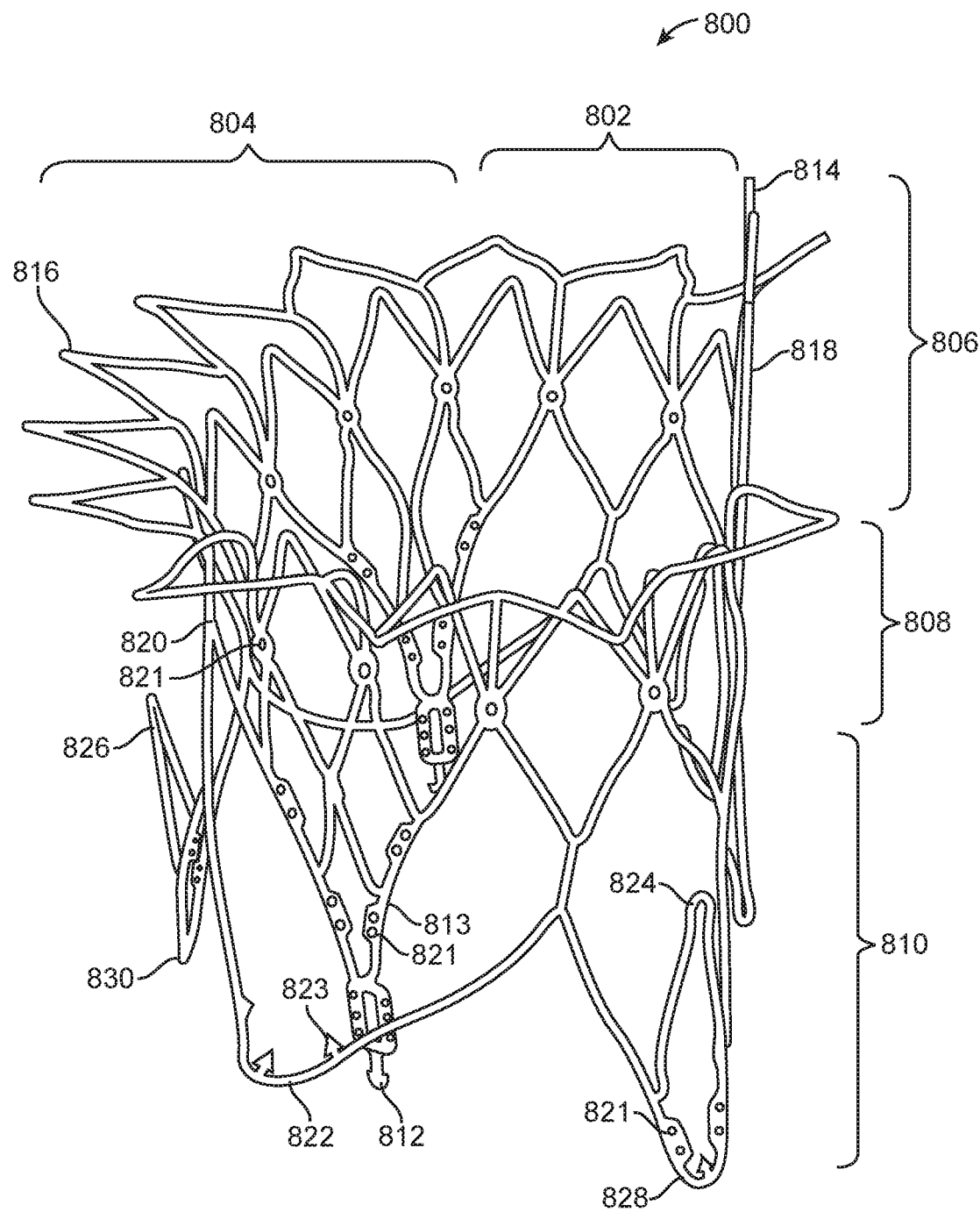
FIG. 8A is a perspective view of a prosthetic mitral valve.
Figure 8B:
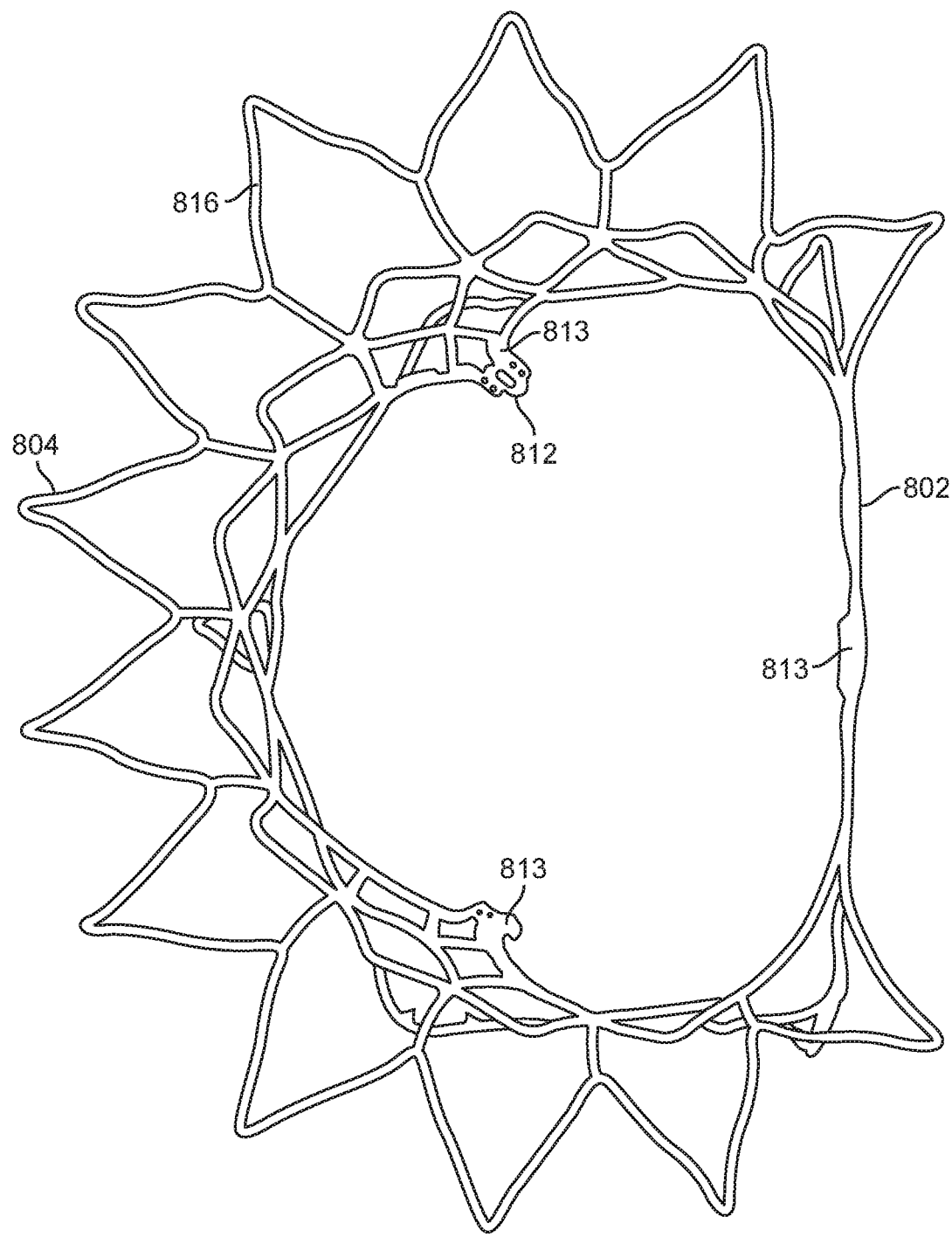
FIG. 8B is a top view from the atrium of the prosthetic valve in FIG. 8A.

FIG. 8A illustrates a perspective view of a preferred embodiment of a prosthetic mitral valve with optional coverings removed to allow visibility of the anchor struts. FIG. 8B illustrates a top view of the prosthetic valve in FIG. 8A from the atrium looking down into the ventricle. The valve 800 includes an asymmetrical expanded anchor portion having a D-shaped cross-section. As shown, the anchor portion generally comprises anterior 802 and posterior 804 aspects along the longitudinal axis thereof, as well as atrial 806, annular 808 and ventricular 810 regions that correspond generally to the atrial skirt 18, annular 20 and ventricular skirt 22 regions of the embodiment described above in FIGS. 6-7. Commissures (also referred to herein as commissure posts) 813 also correspond generally to the leaflets 14 of the embodiment in FIGS. 6-7. The prosthetic valve 800 has a collapsed configuration and an expanded configuration. The collapsed configuration is adapted to loading on a shaft such as a delivery catheter for transluminal delivery to the heart, or on a shaft for transapical delivery through the heart wall. The radially expanded configuration is adapted to anchor the valve to the patient's native heart adjacent the damaged valve. In order to allow the valve to expand from the collapsed configuration to the expanded configuration, the anchor portion of the valve may be fabricated from a self-expanding material such as a nickel titanium alloy like nitinol, or it may also be made from spring temper stainless steel, or a resilient polymer. In still other embodiments, the anchor may be expandable with an expandable member such as a balloon. In preferred embodiments, the anchor is fabricated by laser cutting, electrical discharge machining (EDM), or photochemically etching a tube. The anchor may also be fabricated by photochemically etching a flat sheet of material which is then rolled up with the opposing ends welded together.

The atrial skirt portion 816 forms a flanged region that helps to anchor the prosthetic valve to the atrium, above the mitral valve. The atrial skirt includes a plurality of triangular fingers which extend radially outward from the anchor to form the flange. The posterior 804 portion of the atrial skirt 816 is generally round or circular, while a portion of the anterior 802 part of the atrial skirt 816 is flat. Thus, the atrial skirt region preferably has a D-shaped cross-section. This allows the prosthetic valve to conform to the patient's cardiac anatomy without obstructing other portions of the heart, as will be discussed below. Each triangular finger is formed from a pair of interconnected struts. The triangular fingers of the atrial skirt generally are bent radially outward from the central axis of the prosthetic valve and lie in a plane that is transverse to the valve central axis. In some embodiments, the atrial skirt lies in a plane that is substantially perpendicular to the central axis of the valve. The anterior portion 802 of the atrial skirt 806 optionally includes an alignment element 814 which may be one or more struts which extend vertically upward and substantially parallel to the prosthetic valve. The alignment element 814 may include radiopaque markers (not illustrated) to facilitate visualization under fluoroscopy. The alignment element helps the physician to align the prosthetic valve with the native mitral valve anatomy, as will be discussed later.

Disposed under the atrial skirt region is the annular region 820 which also has a collapsed configuration for delivery, and an expanded configuration for anchoring the prosthetic valve along the native valve annulus. The annular region is also comprised of a plurality of interconnected struts that form a series of cells, preferably closed. Suture holes 821 in some of the struts allow tissue or other coverings (not illustrated) to be attached to the annular region. Covering all or a portion of the anchor with tissue or another covering helps seal the anchor against the heart valve and adjacent tissue, thereby ensuring that blood is funneled through the valve, and not around it. The annular region may be cylindrical, but in preferred embodiments has a posterior portion 804 which is circular, and an anterior portion 802 which is flat, thereby forming a D-shaped cross-section. This D-shaped cross-section conforms better to the native mitral valve anatomy without obstructing blood flow in other areas of the heart.

The lower portion of the prosthetic valve includes the ventricular skirt region 828. The ventricular skirt region also has a collapsed configuration for delivery, and an expanded configuration for anchoring. It is formed from a plurality of interconnected struts that form a series of cells, preferably closed, that can radially expand. The ventricular skirt in the expanded configuration anchors the prosthetic valve to the ventricle by expanding against the native mitral valve leaflets. Optional barbs 823 in the ventricular skirt may be used to further help anchor the prosthetic valve into the ventricular tissue. Barbs may optionally also be included in the atrial skirt portion as well as the annular region of the anchor. Additionally, optional suture holes 821 in the ventricular skirt may be used to help suture tissue or another material to the ventricular skirt region, similarly as discussed above. The anterior 802 portion of the ventricular skirt may be flat, and the posterior 804 portion of the ventricular skirt may be circular, similarly forming a D-shaped cross-section to anchor and conform to the native anatomy without obstructing other portions of the heart. Also, the lower portions of the ventricular skirt serve as deployment control regions since the lower portions can remain sheathed thereby constraining the ventricular skirt from radial expansion until after the optional ventricular trigonal tabs and posterior tab have expanded, as will be explained in greater detail below.

The ventricular skirt portion may optionally also include a pair of ventricular trigonal tabs 824 on the anterior portion of the anchor (only 1 visible in this view) for helping to anchor the prosthetic valve as will be discussed in greater detail below. The ventricular skirt may also optionally include a posterior tab 826 on a posterior portion 804 of the ventricular skirt for anchoring the prosthetic valve to a posterior portion of the annulus. The trigonal tabs 824 or the posterior tab 826 are tabs that extend radially outward from the anchor, and they are inclined upward in the upstream direction.

The actual valve mechanism is formed from three commissures posts (also referred to as commissures) 813 which extend radially inward toward the central axis of the anchor in a funnel or cone-like shape. The commissures 813 are formed from a plurality of interconnected struts that create the triangular shaped commissures. The struts of the commissures may include one or more suture holes 821 that allow tissue or a synthetic material to be attached to the commissures. In this exemplary embodiment, the valve is a tricuspid valve, therefore it includes three commissures 813. The tips of the commissures may include a commissure tab 812 (also referred to as a tab) for engaging a delivery catheter. In this embodiment, the tabs have enlarged head regions connected to a narrower neck, forming a mushroom-like shape. The commissures may be biased in any position, but preferably angle inward slightly toward the central axis of the prosthetic valve so that retrograde blood flow forces the commissures into apposition with one another to close the valve, and antegrade blood flow pushes the commissures radially outward, to fully open the valve. FIG. 8B is a top view illustrating the prosthetic valve of FIG. 8A from the atrial side, and shows the preferred D-shaped cross-section.

Figure 9A:
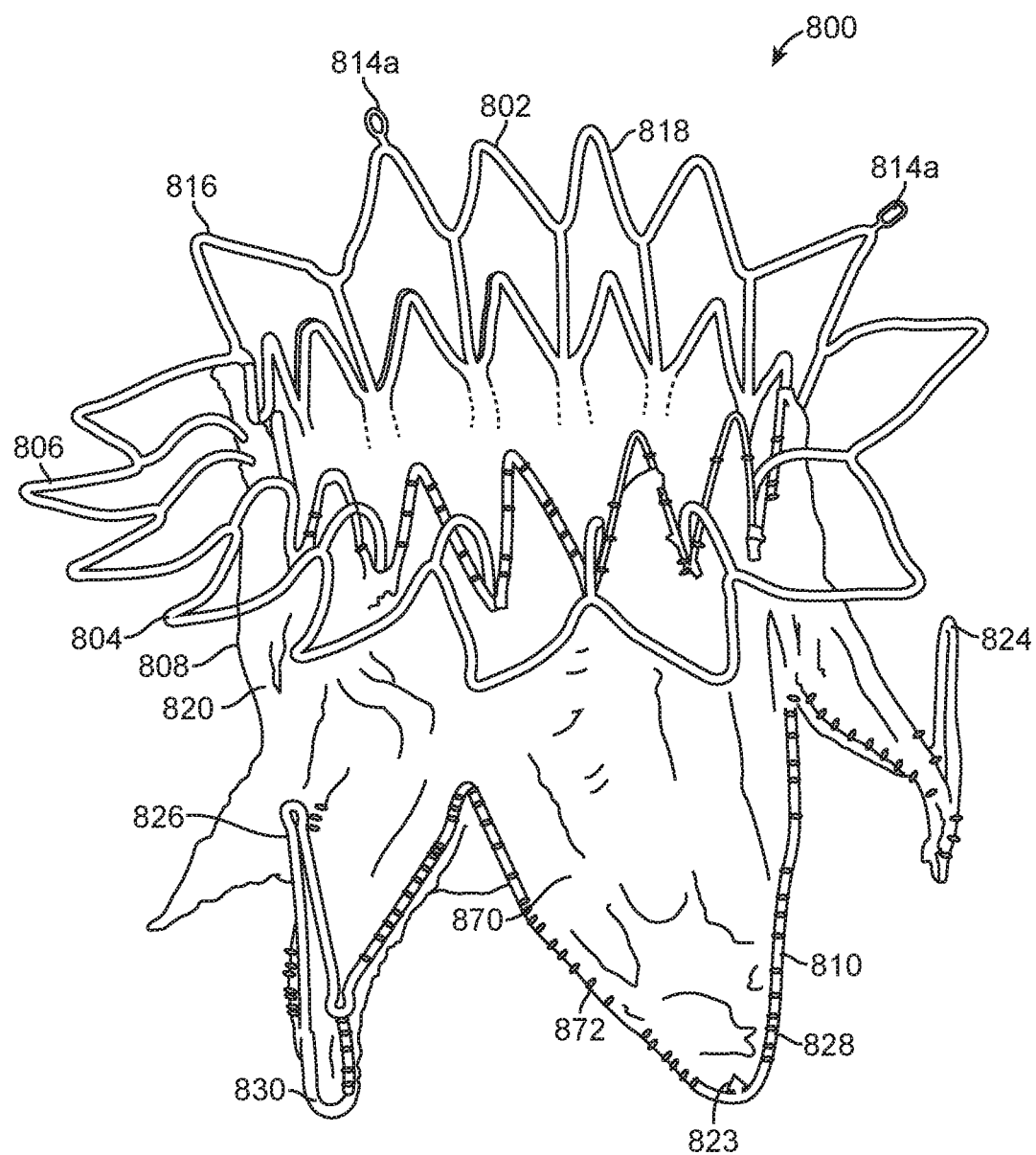
FIG. 9A illustrates a perspective view of the prosthetic valve in FIG. 8A from the atrium.

FIG. 9A illustrates the prosthetic mitral valve of FIGS. 8A-8B with a covering 870 coupled to portions of the anchor with suture 872. This view is taken from an atrial perspective. In this embodiment, the covering is preferably pericardium which may come from a number of sources as disclosed elsewhere in this specification. In alternative embodiments, the covering may be a polymer such as Dacron polyester, ePTFE, or another synthetic material. The covering is preferably disposed over the annular region 820 and the ventricular skirt region 828, and in some embodiments the anterior ventricular trigonal 824 tabs and the ventricular posterior tab 830 may also be covered with the same or a different material. The covering helps seal the anchor against the adjacent tissue so that blood funnels through the valve mechanism. In this embodiment, the atrial skirt is left uncovered, as well as tabs 824, 830. Additionally, radiopaque markers 814a form a portion of the alignment element and facilitate visualization of the prosthetic valve under fluoroscopy which is important during alignment of the valve.

Figure 9B:
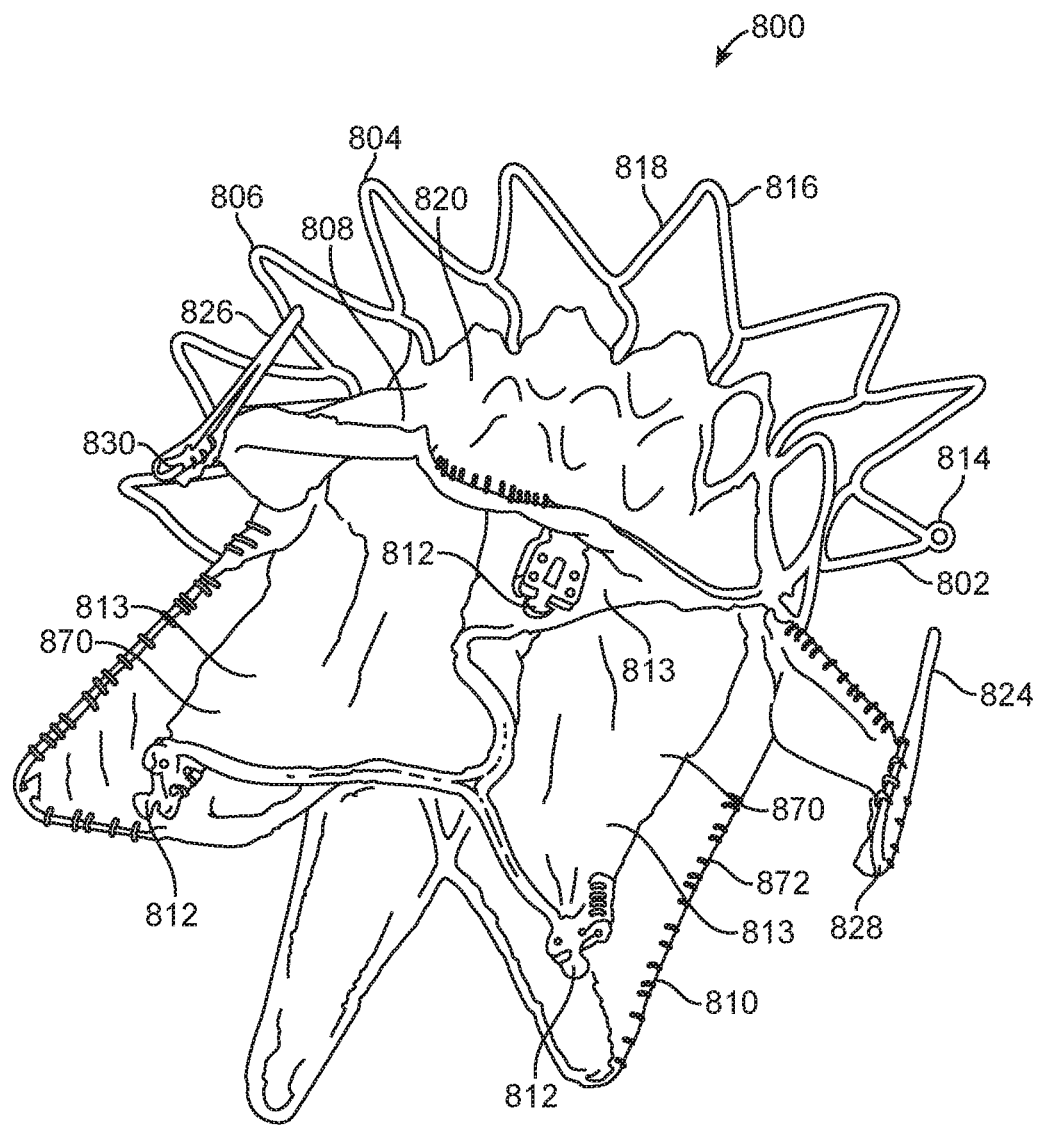
FIG. 9B illustrates a perspective view of the prosthetic valve in FIG. 8A from the ventricle.

FIG. 9B is a perspective view of the prosthetic mitral valve seen in FIG. 9A, as seen from the ventricle. The struts of the valve commissures are covered with the same material or a different material as the annular and ventricular regions as discussed above, thereby forming the tricuspid valve leaflets 813. FIG. 9B shows the valve in the closed configuration where the three leaflets are engaged with one another preventing retrograde blood flow. Commissure tabs 812 remain uncovered and allow the commissures to be coupled with a delivery device as will be explained below. The prosthetic valve in FIGS. 9A-9B may be sterilized so they are suitable for implantation in a patient using methods known in the art.

Figure 10:
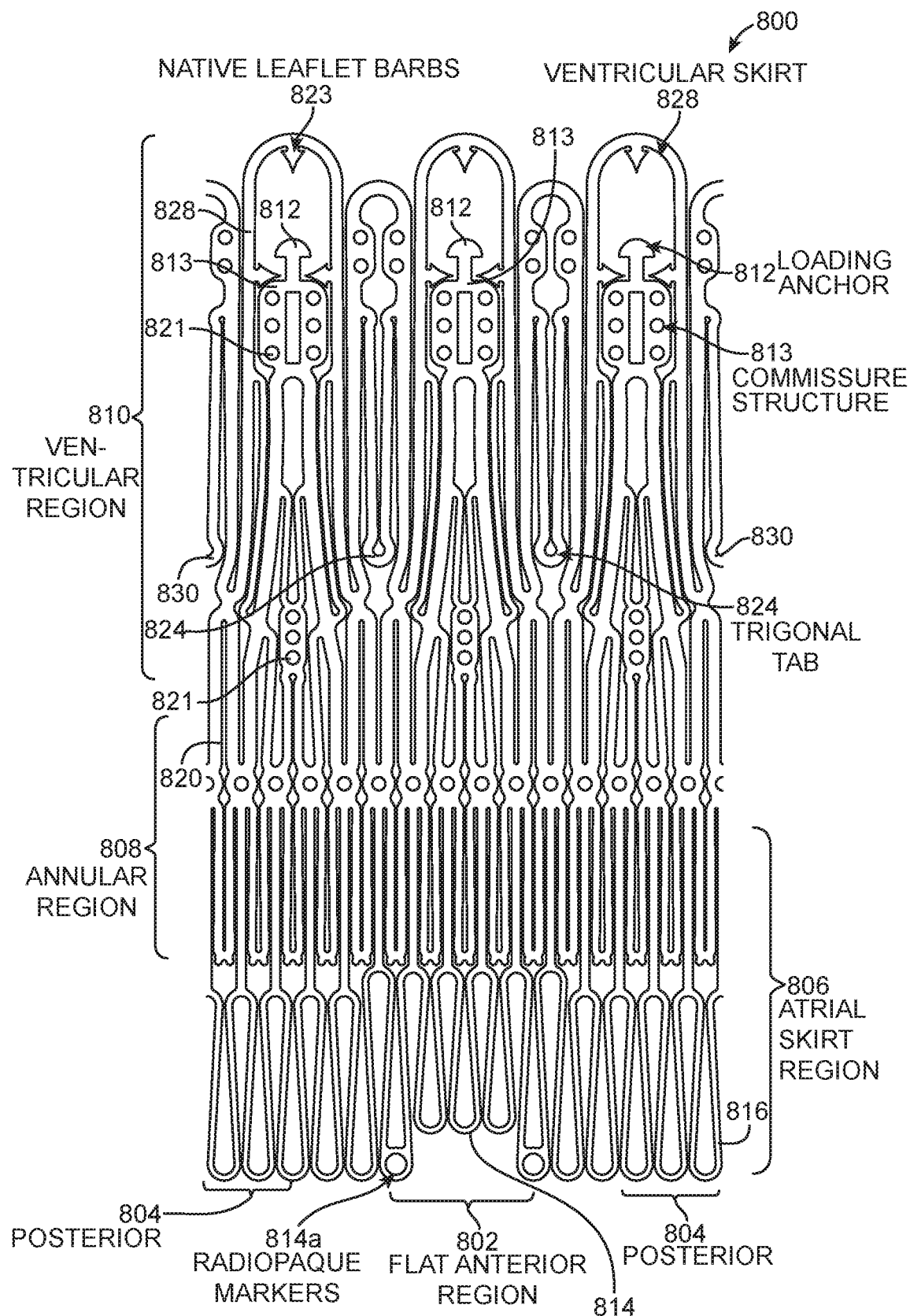
FIG. 10 illustrates the prosthetic valve of FIG. 8A uncovered and unrolled in a flat pattern.

FIG. 10 illustrates the prosthetic valve of FIG. 9A with the covering removed, and the remaining anchor unrolled and flattened out. The prosthetic valve 800 is formed from a plurality of interconnected struts. For example, the atrial skirt region 806 includes a plurality of interconnected struts that form a series of peaks and valleys. The flat anterior region 802 of the prosthetic valve has its peaks and valleys axially offset from those of the remaining portion of the atrial skirt, and this region becomes a part of the alignment element 814. Radiopaque markers 814a are disposed on either side of the offset peaks and valleys and help with visualization during implantation of the valve. An axially oriented connector joins the struts of the skirt region 806 with the struts of the annular region 808. The annular region is also comprised of a plurality of axially oriented and interconnected struts that form peaks and valleys. Connector struts couple struts of the annular region with the struts of the ventricular region 810. The ventricular region also includes a plurality of interconnected struts that form peaks and valleys. Additionally, the struts form the leaflet commissures 813, the ventricular skirt 828, as well as the trigonal and posterior tabs 824, 830. Suture holes 821 are disposed along the struts of the annular region as well as the ventricular region to allow attachment of a cover such as pericardium or a polymer such as Dacron or ePTFE. Barbs 823 are disposed along the ventricular skirt 828 to help anchor the prosthetic valve to adjacent tissue. Commissure tabs or tabs 812 are disposed on the tips of the commissures 813 and may be used to releasably couple the prosthetic valve with a delivery system as will be described below. One of skill in the art will appreciate that a number of strut geometries may be used, and additionally that strut dimensions such as length, width, thickness, etc. may be adjusted in order to provide the anchor with the desired mechanical properties such as stiffness, radial crush strength, commissure deflection, etc. Therefore, the illustrated geometry is not intended to be limiting.

Once the flat anchor pattern has been formed by EDM, laser cutting, photochemical etching, or other techniques known in the art, the anchor is radially expanded into a desired geometry. The anchor is then heat treated using known processes to set the shape. Thus, the anchor may be loaded onto a delivery catheter in a collapsed configuration and constrained in the collapsed configuration with a constraining sheath. Removal of the constraining sheath will allow the anchor to self-expand into its unbiased pre-set shape. In other embodiments, an expandable member such as a balloon may be used to radially expand the anchor into its preferred expanded configuration.

Transapical Delivery Systems

FIGS. 11-15C show a delivery apparatus 1124 fashioned to deliver a prosthetic mitral valve to the heart transapically. However, one of skill in the art will appreciate that the delivery system may be modified and relative motion of the various components adjusted to allow the device to be used to deliver a prosthetic mitral valve transseptally. The delivery apparatus is generally comprised of a handle 1101 that is the combination of a handle section 1102 and a handle section 1103 (best seen in FIG. 12), as well as a flexible tip 1110 that can smoothly penetrate the apex of the heart, and a sheath catheter 1109 which houses several additional catheters that are designed to translate axially and will be described in detail below.

The handle 1101 includes a female threaded Luer adaptor 1113 which connects to a Tuohy Borst adaptor 1114 in order to provide a hemostatic seal with a 0.035" diameter guide wire (not shown). The female threaded Luer adaptor 1113 is in threaded contact with the proximal section of the handle 1101 through a threaded port 1131 (best seen in FIG. 12).

Figure 11:
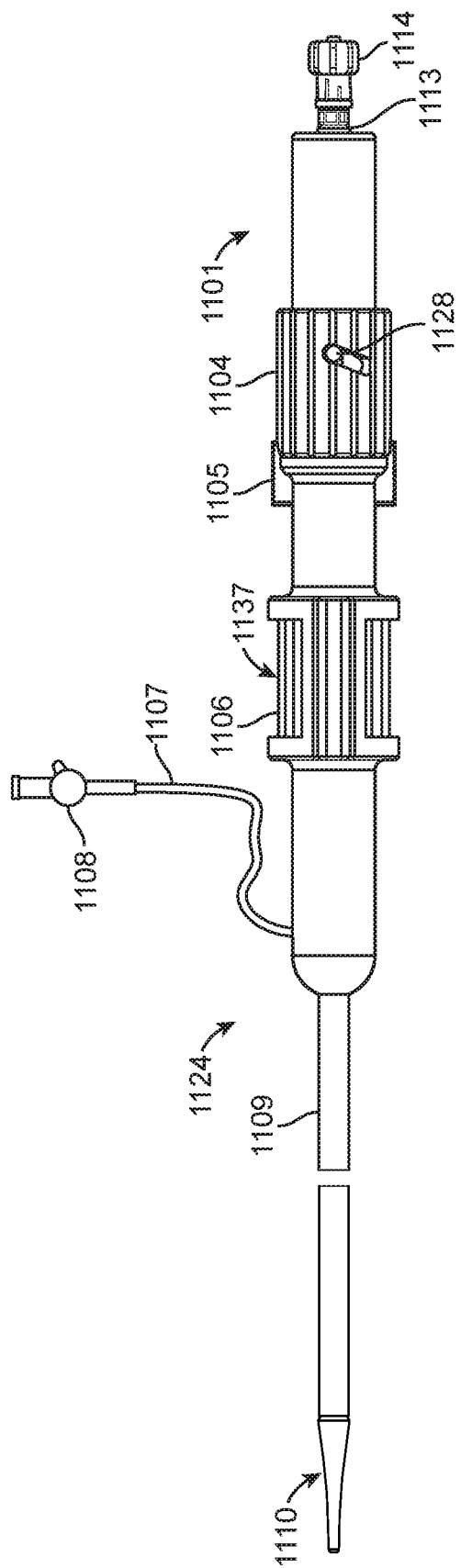
FIG. 11 is a side view of a delivery device for implantation of a prosthetic valve.

As can be seen in FIG. 11, the handle 1101 provides location for the control mechanisms used to position and deploy a prosthetic mitral valve. The handle 1101 provides housing for a thumbwheel 1106 that can be accessed through a window 1137 that appears on both the top and bottom of the handle 1101. The thumbwheel 1106 internally mates with a threaded insert 1115 (best seen in FIG. 12) that actuates the sheath catheter 1109, and the mechanics of this interaction will be explained in detail below.

FIG. 11 also shows a deployment thumbwheel 1104 that provides linear translation to a deployment catheter 1120 (best seen in FIG. 12) when turned, since the turning motion of the deployment thumbwheel 1104 acts as a power screw, pushing the peg 1128 forward and distally from the user. The mechanics behind the peg 1128 will be further detailed below. The thumbwheel lock 1105 provides a security measure against unwanted rotation of the deployment thumbwheel 1104 by acting as a physical barrier to rotation. In order to turn the deployment thumbwheel 1104 the user must push forward the thumbwheel lock 1105, disengaging it from two slots 1147 (seen in FIG. 12) in the deployment thumbwheel 1105.

As can also be seen in FIG. 11, a bleed valve 1108 and fluid line 1107 are connected to an internal mechanism in the distal portion of the handle 1101, which provides a hemostatic seal for the sheath catheter 1109. The details of this connection will be described below.

Figure 12:
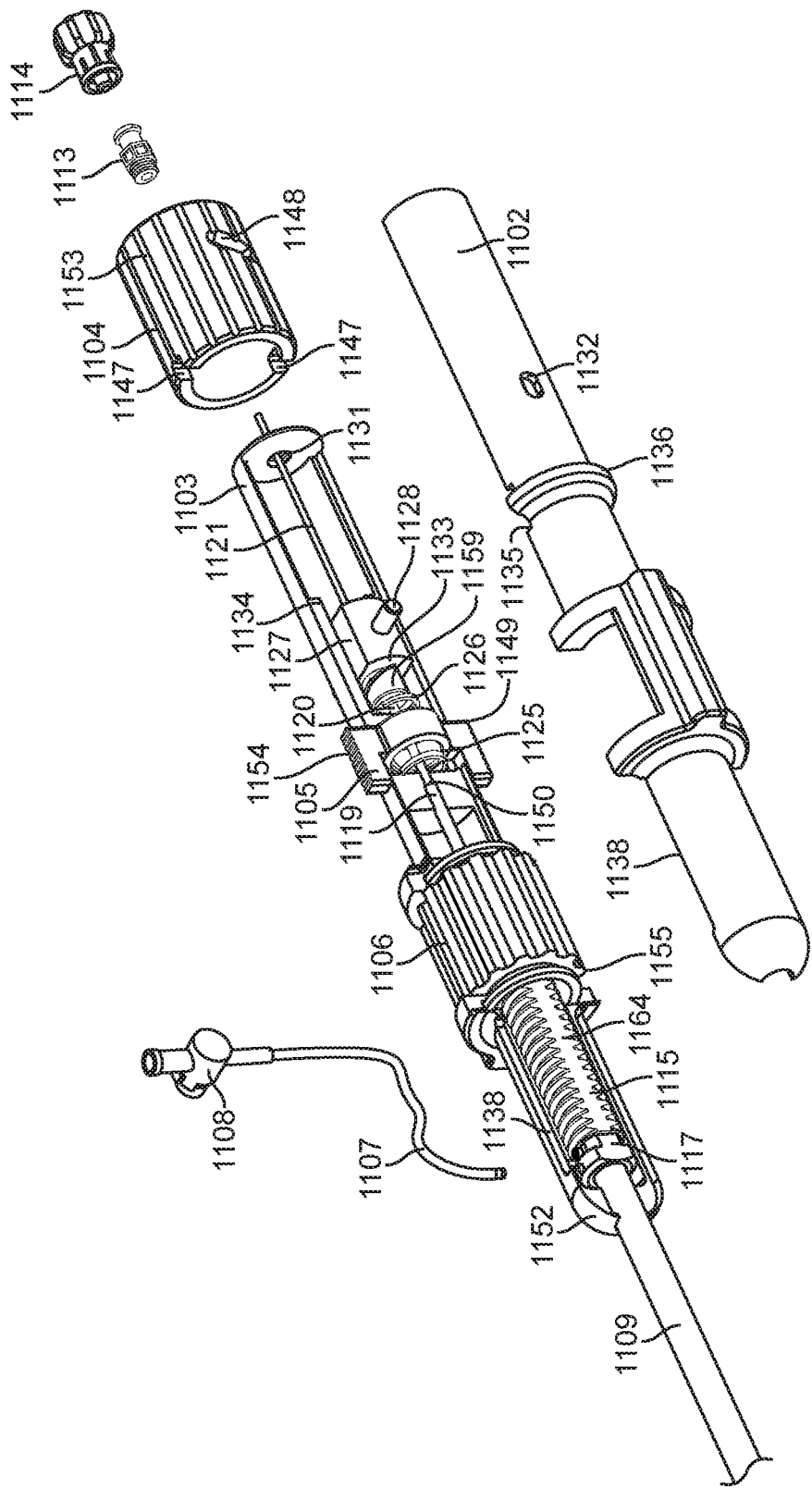
FIG. 12 is a perspective exploded view of a proximal portion of the delivery device in FIG. 11.

Internal mechanics of the delivery apparatus 1124 are illustrated in detail in FIG. 12, and the following descriptions will reveal the interactions between individual components, and the manner in which those components combine in order to achieve a prosthetic heart valve delivery apparatus.

As seen in FIG. 12, a handle section 1103 and handle section 1102 combine to create a handle 1101 that forms the basis of the delivery apparatus 1124. In order to advance the sheath catheter 1109 during valve loading, or retract the sheath catheter 1109 during deployment, a rotatable thumbwheel 1106 is in threaded contact (internal threads 1129 seen in FIG. 14) with a threaded insert 1115 (external threads 1130 of FIG. 13) that translates linearly along the axis of the delivery apparatus, from a proximal position to a distal position. The sheath catheter 1109 is in mating contact with the threaded insert 1115 and is fastened through the use of a collar 1117 that aligns and mates the collar with the insert. The collar 1117 is fastened with screws 1116 (best seen in DETAIL A in FIG. 14) to the threaded insert 1115 and contains a fluid port 1142 (best seen in DETAIL A in FIG. 14) that provides location for the fluid line 1117 so that hemostasis can be maintained between the patient and delivery apparatus. An O-ring 1118 (best seen in DETAIL A in FIG. 14) seals the stationary catheter 1119 (best seen in FIG. 14) against the sheath catheter 1109. The fluid line 1107 also provides a means of visually locating the sheath catheter 1109 with respect to position, as a slot 1138 in the handle 1101 allows the fluid line 1107 to translate with the sheath catheter 1109 (through a hole 1151 (best seen in DETAIL A in FIG. 14) during operation, and this translation is highly visible. In order to prevent rotation of the threaded insert during translation, a flat face 1164 has been machined onto both sides of the threaded insert 1115. The flat faces 1164 remain in contact with bosses 1139 and 1140 that are located on both handle section 1102 and handle section 1103 so that the bosses 1139 and 1140 act to grip the threaded insert 1115 and prevent rotation. A textured pattern 1155 allows the user to easily turn the thumbwheel 1106 in the surgical field. Detents 1141 (best seen in FIG. 14) locate flanges 63 (seen in FIG. 14) on the thumbwheel 1116 in order to allow for rotation.

The manner in which individual catheters (there are four catheters) move with respect to each other is illustrated in FIG. 12. Sheath catheter 1109 provides housing for the stationary catheter 1119, which in turn provides housing for the movable hub catheter 1120. The hub catheter 1120 translates linearly with respect to the nose catheter 1121 which can also be translated with respect to each previous catheter, and the handle 1101. The stationary catheter 1119 is mated to a handle section 1103 in an internal bore 1150 which also forms a seal between the stationary catheter 1119 and the hub catheter 1120. The distal portion of the stationary catheter 1119 is formed in the shape of a bell 1122 (see DETAIL A in FIG. 15A) which acts as a housing to retain the hub capture 1123 (seen in DETAIL A in FIG. 15A).

As previously stated a thumbwheel lock 1105 prevents rotation of the deployment thumbwheel 1104. In order to provide a seating force that keeps the thumbwheel lock 1105 in a locked position until manipulated, a spring 1125 is housed in an internal bore 62 (best seen in FIG. 14) and abuts against a shoulder 1161 (best seen in FIG. 14) that is located inside the thumbwheel lock 1105. This spring 1125 maintains the leading edge 1149 of the thumbwheel lock 1105 in a locked position within the two slots 1147 of the deployment thumbwheel 1104. Gripping texture 1154 is provided on the thumbwheel lock 1105 for ease of use. In order to locate and retain the thumbwheel lock 1105 inside of the handle 1101, a slot 1135 has been provided in both a handle section 1102 and a handle section 1103.

As shown in FIG. 12, a sliding block 1127 is housed inside of flat parallel faces 1134 which appear on the inside of the handle 1101. This sliding block 1127 is in mating contact with hub catheter 1120 and is the physical mechanism that linearly actuates the catheter. A spring 1126 is mounted on an external post 1159 and abuts against a shoulder 1133 that is located on the distal end of the sliding block 1127. This spring 1126 forces a peg 1128 (located inside a thru-hole 1156 of FIG. 14) into contact with the proximal edge of an angled slot 1148 that is cut into the deployment thumbwheel 1104. The deployment thumbwheel 1104 is contained between a shoulder 1136 and a snap ring (not shown), both of which are features of the handle 1101. Gripping texture 1153 on the deployment thumbwheel 1104 allows the user to easily rotate the thumbwheel in a clockwise direction, actuating the peg 1128 to ride distally along the slot 1148 and move the sliding block 1127, which pushes the hub catheter 1120 and hub 1123 (best seen in DETAIL A of FIG. 15A) forward and out of the bell 1122 (seen in DETAIL A of FIG. 15A). A slot 1132 appears in a handle section 1102 and a handle section 1103 and prevents the peg 1128 from translating beyond a desired range.

A nose catheter 1121 extends from a Tuohy Borst adaptor 1114 on the proximal end of the handle 1101, and internally throughout the handle and the respective catheters (sheath catheter 1109, stationary catheter 1119, and hub catheter 1120), terminating inside the rigid insert 1112 (seen in FIG. 15A) of the flexible tip 1110 (seen in FIG. 15A) that abuts with the distal end of the sheath catheter 1109.

Figure 13:
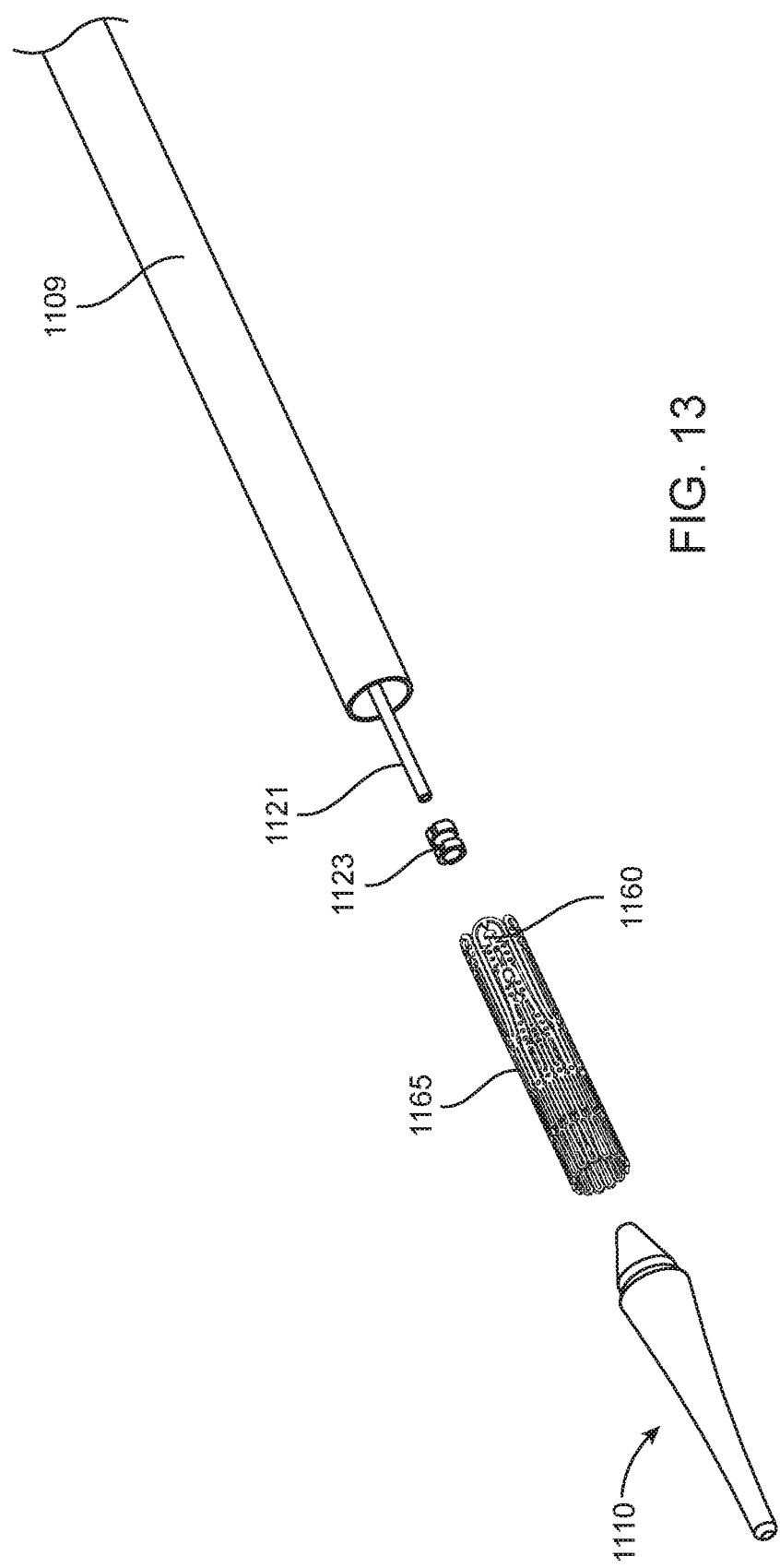
FIG. 13 is a perspective exploded view of a distal portion of the delivery device in FIG. 11.
Figure 14:
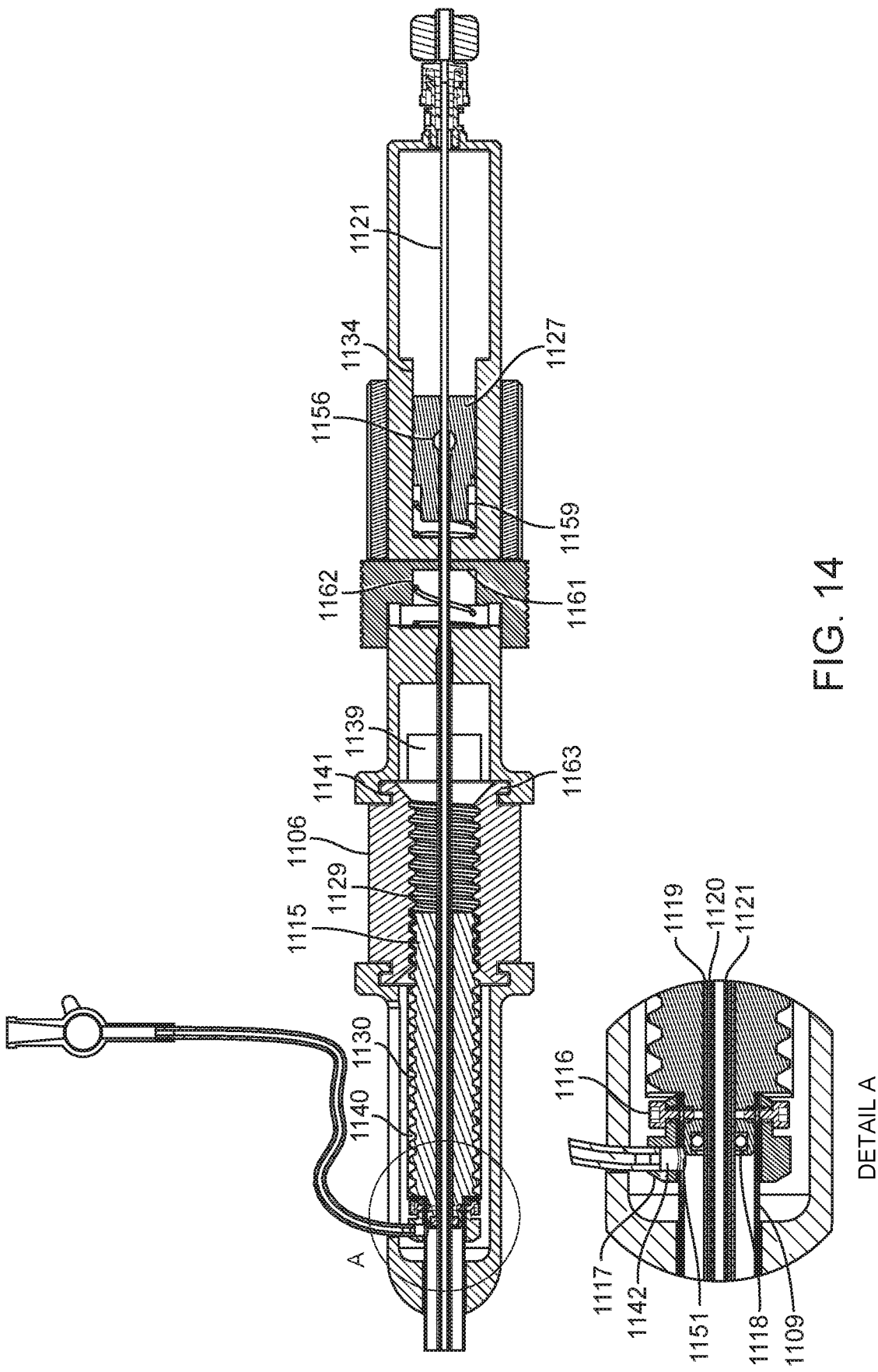
FIG. 14 is a cross-section of the proximal portion of the delivery device in FIG. 11.

FIG. 13 displays an exploded view of the tip section of the delivery apparatus 1124, and shows the relation between prosthetic mitral valve 1165 and the internal and external catheters. When crimped and loaded, the prosthetic mitral valve 1165 is encased between the internal surface of the sheath catheter 1109 and the external surface of the nose catheter 1121. In order to capture and anchor the prosthetic mitral valve 1165 within the delivery apparatus 1124, three commissure tabs 1160 (circumferentially spaced at 120.degree.apart) appearing on the proximal end of the prosthetic mitral valve 1165 provide points of contact between the valve and three slots 1143 (seen in FIG. 15A) that are machined into the outer surface of the hub 1123 (circumferentially spaced at 120.degree.apart). After first advancing the hub catheter 1120 (FIG. 15A) by rotating the deployment thumbwheel 1104 (seen in FIG. 12) clockwise, the three commissure tabs 1160 can be captured within the three slots 1143 (seen in FIG. 15A). The hub 1123 can then be retracted into the bell 1122 by releasing the deployment thumbwheel 1104 (seen in FIG. 12). In this position the prosthetic mitral valve 1165 is anchored to the delivery apparatus 1124, and further crimping of the valve will allow the sheath catheter 1109 to be advanced over the valve.

Figure 15C:
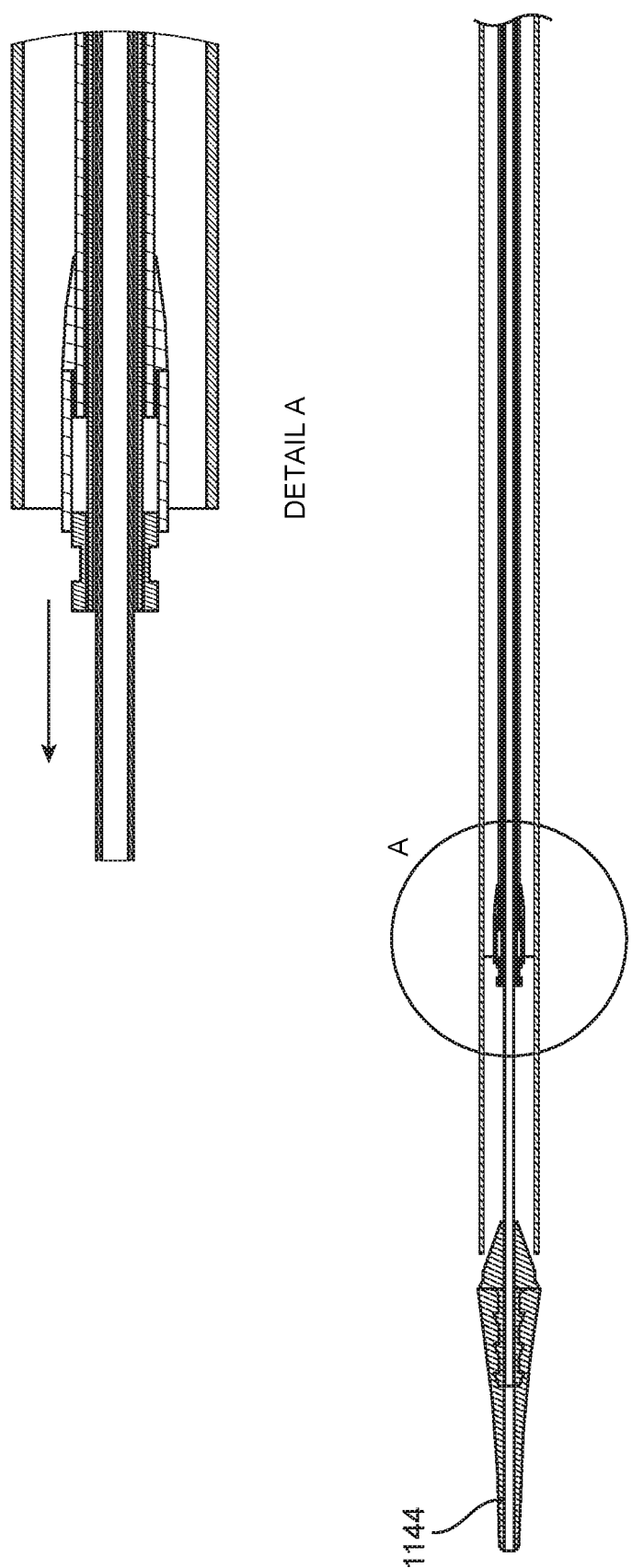

FIGS. 15A-15C further detail the manner in which loading of the prosthetic mitral valve 1165 (seen in FIG. 13) into the delivery apparatus 1124 can be achieved. Initially, the flexible tip 1110 is abutted against the distal edge 1157 of the sheath catheter 1109. The flexible tip 1110 is comprised of a rigid insert 1112, and a soft and flexible tip portion 1111 which is over-molded onto the rigid insert 1112. The shoulder 1145 and tapered face 1146 of the rigid insert 1112 act to guide and locate the distal edge 1157 of the sheath catheter 1109, so that the catheter may rest against and be stiffened by the flexible tip 1110, and be more easily introduced into the apex of the heart.

An initial position from which loading can be achieved is illustrated in FIG. 15A. As a first step in the loading of a prosthetic mitral valve 1165 (seen in FIG. 13) into the delivery apparatus 1124, the sheath catheter 1109 is withdrawn by rotation of the thumbwheel 1106 in a clockwise direction. The distal edge 1157 of the sheath catheter 1109 is retracted until it passes the distal edge of the bell 1122, as illustrated in DETAIL A of FIG. 15B. As a second step in the loading of a prosthetic mitral valve 1165 (seen in FIG. 13) into the delivery apparatus 1124, the hub 1123 is advanced from beneath the bell 1122 by clockwise turning of the deployment thumbwheel 1104 (seen in FIG. 12), as illustrated in DETAIL A of FIG. 15C. The deployment thumbwheel may only be turned once the thumbwheel lock 1105 (see FIG. 12) has been set in the forward position, disengaging it from contact with the thumbwheel. Advancement of the hub 1123 uncovers three slots 1143 into which three commissure tabs 1160 of the prosthetic mitral valve 1165 (seen in FIG. 13) will fit and be anchored. After anchoring of the commissure tabs 1160 into the slots 1143 by retraction of the hub 1123 has been achieved, a third step in the loading of a prosthetic mitral valve 1165 (seen in FIG. 13) into the delivery apparatus 1124 may be performed. The prosthetic mitral valve 1165 (seen in FIG. 13) can be crimped down to a minimum diameter by a loading mechanism (not shown), and then the sheath cannula 1109 can be advanced forward so as to cover the valve, by rotation of the thumbwheel 1106 in a counter-clockwise direction. The delivery apparatus 1124 and prosthetic mitral valve 1165 are then ready for deployment.

FIGS. 16-19B illustrate another exemplary embodiment of a delivery device for implanting a prosthetic valve in the heart transapically. However, one of skill in the art will appreciate that the delivery system may be modified and relative motion of the various components adjusted to allow the device to be used to deliver a prosthetic transseptally. The delivery apparatus is generally comprised of a handle 1601 that is the combination of two halves (1610 and 1635), as well as a tip 1603 that can smoothly penetrate the apex of the heart, and a flexible sheath 1602 which is comprised of concentric catheters that are designed to translate axially and will be described in detail below.

The handle 1601 includes a handle cap 1611 which connects to a female threaded Luer adaptor 1612 in order to provide a sealable exit for a 0.035" diameter guide-wire (not shown). The handle cap 1611 is attached to the handle 1601 with threaded fasteners 1613. The female threaded Luer adaptor 1612 is in threaded contact with the handle cap 1611 through a tapped port, and when fully inserted squeezes against an O-ring (1636 best seen in FIG. 18) which seals against the outer diameter of a guide-wire catheter (1621 best seen in FIG. 18).

Figure 17:
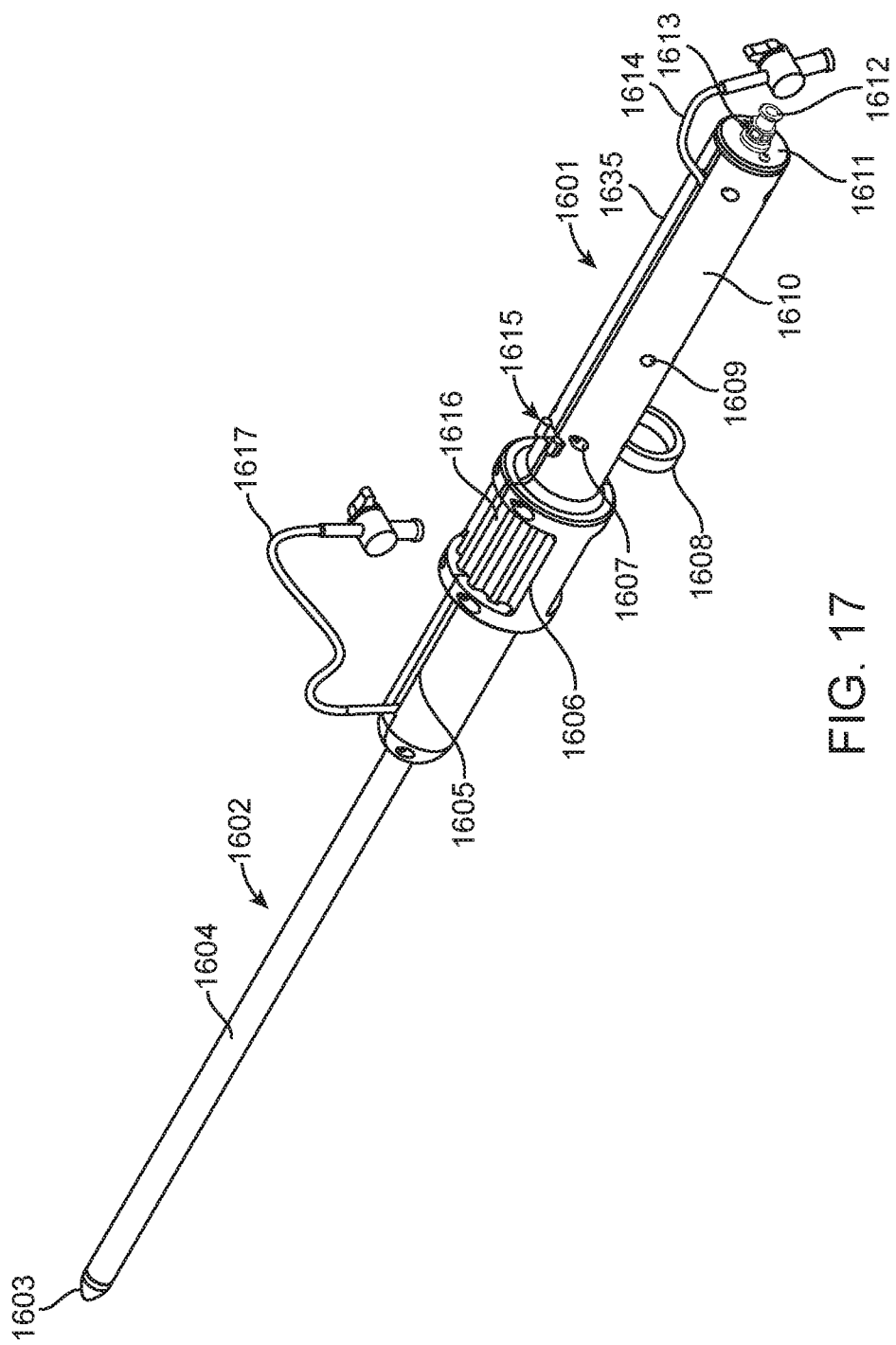
FIG. 17 is a perspective view of the delivery device in FIG. 16.

As can be seen in FIG. 17, the handle 1601 provides location for the control mechanisms used to position and deploy a prosthetic mitral valve. The handle 1601 provides housing for a thumbwheel 1616 that can be accessed through a window 1606 that appears on both the top and bottom of the handle 1601. The thumbwheel 1616 internally mates with a threaded insert (1627 in FIG. 18) that actuates the sheath catheter 1604, and the mechanics of this interaction will be explained in detail below.

Figure 18:
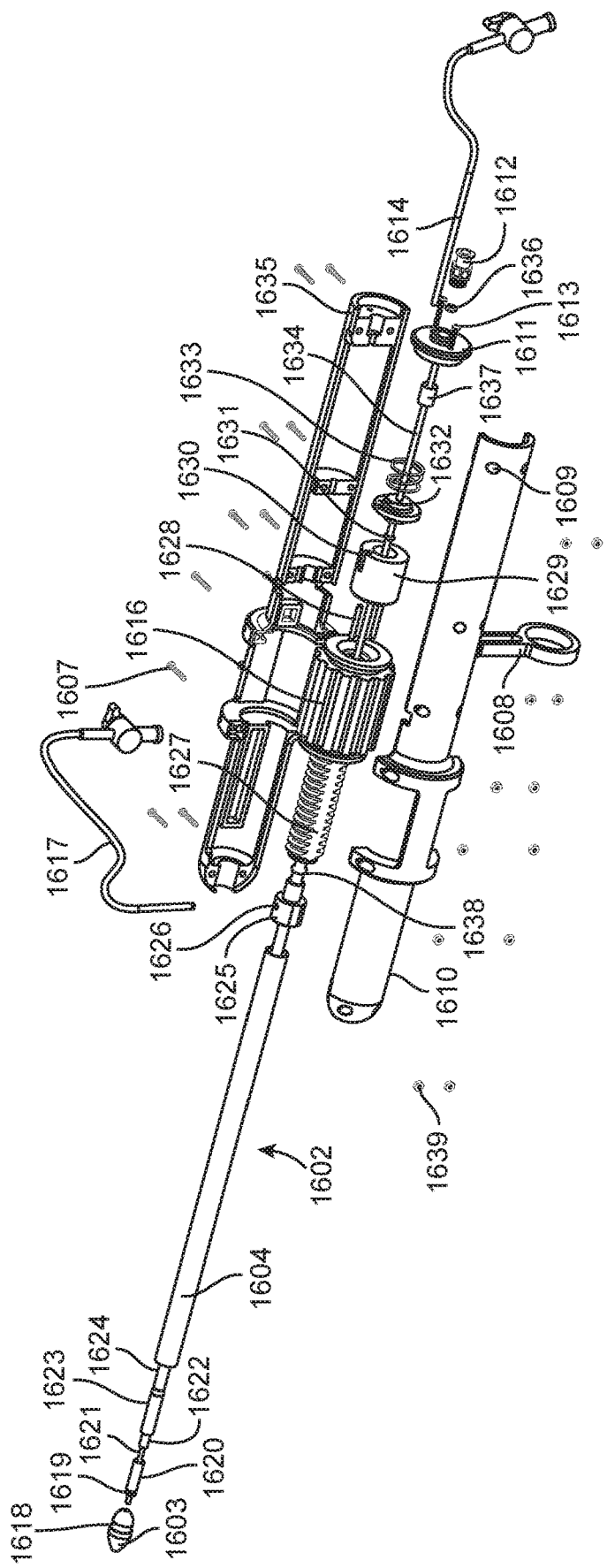
FIG. 18 is a perspective exploded view of the delivery device in FIG. 16.

FIG. 17 also shows a first hemostasis tube 1617 that is inserted internally through a slot 1605, and that mates with a first hemo-port through a hole (1625 and 1626 in FIG. 18 respectively). The first hemostasis tube 1617 allows for fluid purging between internal catheters. The position of the first hemostasis tube 1617 along the slot 1605 provides a visual indicator as to the position of the sheath catheter 1604, and relative deployment phase of a prosthetic mitral valve (not shown). The relationship between the connection of the first hemostasis tube 1617 and the sheath catheter 1604 will be described below.

As can also be seen in FIG. 17, a second hemostasis tube 1614 is inserted into the handle 1601 and mated to a second hemo-port (1629 in FIG. 18) in order to allow fluid purging between internal catheters, and details of this insertion will be described below. Finally, a pin lock 1608 provides a security measure against premature release of a prosthetic mitral valve, by acting as a physical barrier to translation between internal mechanisms. Pin lock prongs 1615 rely on spring force to retain the pin lock 1608 in the handle 1601, and a user must first pull out the pin lock 1608 before final deployment of a prosthetic valve.

FIG. 17 also shows how the handle 1601 is fastened together by use of threaded fasteners and nuts (1607 and 1639 of FIG. 18 respectively), and countersunk locator holes 1609 placed throughout the handle length.

Internal mechanisms of the delivery system are illustrated in detail in FIG. 18, and the following descriptions will reveal the interactions between individual components, and the manner in which those components combine in order to create a system that is able to deliver a prosthetic mitral valve preferably transapically.

As seen in FIG. 18, the flexible sheath 1602 is comprised of four concentrically nested catheters. In order from smallest to largest in diameter, the concentrically nested catheters will be described in detail. The innermost catheter is a guide-wire catheter 1621 that runs internally throughout the entire delivery system, beginning at the tip 1603 and terminating in the female threaded Luer adaptor 1612. The guide-wire catheter 1621 is composed of a lower durometer, single lumen Pebax extrusion and is stationary. It provides a channel through which a guidewire (not shown) can communicate with the delivery system. The next catheter is the hub catheter 1622 which provides support for the hub 1620 and is generally comprised of a higher durometer, single lumen PEEK extrusion. The hub catheter 1622 is in mating connection with both the hub 1622 at the distal end, and a stainless steel support rod 1634 at the proximal end. The stainless steel support rod 1634 is held fixed by virtue of a stopper 1637 that is encased in the handle 1601. The hub catheter 1622 is stationary, and provides support and axial rigidity to the concentrically nested catheters. The next catheter is the bell catheter 1624, which provides housing to the hub 1620 and is generally comprised of a medium durometer, single lumen Pebax extrusion, including internal steel braiding and lubricious liner, as well as a radiopaque marker band (not shown). The bell catheter 1624 translates axially, and can be advanced and retracted with respect to the hub 1620. The bell catheter 1624 is in mating connection with the second hemo-port 1629 at the proximal end, and hemostasis between the bell catheter 1624 and the stainless steel support rod 1634 can be achieved by purging the second hemostasis tube 1614. The bell catheter 1624 is bumped up to a larger diameter 1623 on the distal end in order to encapsulate the hub 1620. The outermost and final catheter is the sheath catheter 1604 which provides housing for a prosthetic mitral valve (not shown), and which is able to penetrate the apex of the heart (not shown), by supporting and directing a tip 1603 and assisting in the dilation of an incision in the heart wall muscle. The sheath catheter 1604 is generally comprised of a medium durometer, single lumen Pebax extrusion, including internal steel braiding and lubricious liner, as well as radiopaque marker band (not shown). The sheath catheter 1604 translates axially, and can be advanced and retracted with respect to the hub 1620. The sheath catheter 1604 is in mating connection with the first hemo-port 1625 at the proximal end, and hemostasis between the sheath catheter 1604 and the bell catheter 1624 can be achieved by purging the first hemostasis tube 1617.

As seen in FIG. 18, the proximal end of the sheath catheter 1604 is in mating contact with a first hemo-port 1625. The first hemo-port is in mating contact with a threaded insert 1627, and an O-ring 1638, which is entrapped between the first hemo-port 1625 and the threaded insert 1627 in order to compress against the bell catheter 1624, creating a hemostatic seal. As the thumbwheel 1616 is rotated, the screw insert 1627 will translate, and the sheath catheter 1624 can be retracted or advanced by virtue of attachment. In order to provide adequate stiffness to dilate heart wall tissue, the distal edge of the sheath catheter 1604 will abut against a shoulder 1618 located on the tip 1603. This communication allows the tip 1603 to remain secure and aligned with the sheath catheter 1604 during delivery, and creates piercing stiffness.

FIG. 18 also details the mechanism through which the bell catheter 1624 can be retracted or advanced with respect to the hub 1620. The thumbwheel 1616 can be rotated to such an extent that the screw insert 1627 will be brought into contact with two pins 1628 that are press fit into the second hemo-port 1629. As the bell catheter 1624 is in mating contact with the second hemo-port 1629, further rotation of the thumbwheel 1616 will cause the second hemo-port 1629 to translate and press against a spring 1633 by virtue of connection to a second hemo-port cap 1632. This advancement will cause the bumped larger diameter section 1623 of the bell catheter 1624 to be retracted from the hub 1620. As the thumbwheel 1616 is rotated in the opposite direction, restoring force produced by the spring 1633 will cause the second hemo-port 1629 to be pushed in the opposite direction, drawing the bumped larger diameter section 1623 of the bell catheter 1624 back over the hub 1620, an action that is necessary during the initial loading of a valve prosthesis.

FIG. 18 further details the manner in which hemostasis is achieved between the stainless steel support rod 1634 and the bell catheter 1624. An O-ring 1631 is compressed between the second hemo-port 1629 and the second hemo-port cap 1632, creating a seal against the stainless steel support rod 1634. Hemostasis between the bell catheter 1624 and the stainless steel support rod 1634 can be achieved by purging the second hemostasis tube 1614, which is in communication with the void to be purged through a slot and hole 1630.

Figure 19A:
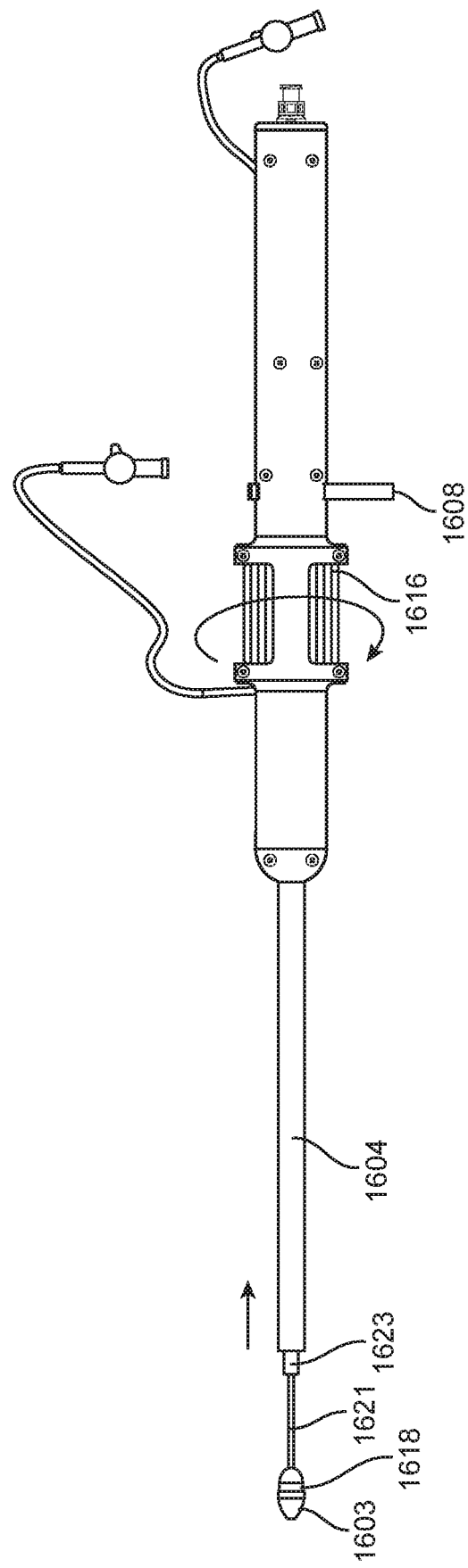
FIGS. 19A-19B are side views of the delivery device in FIG. 16 during various stages of operation.
Figure 19B:
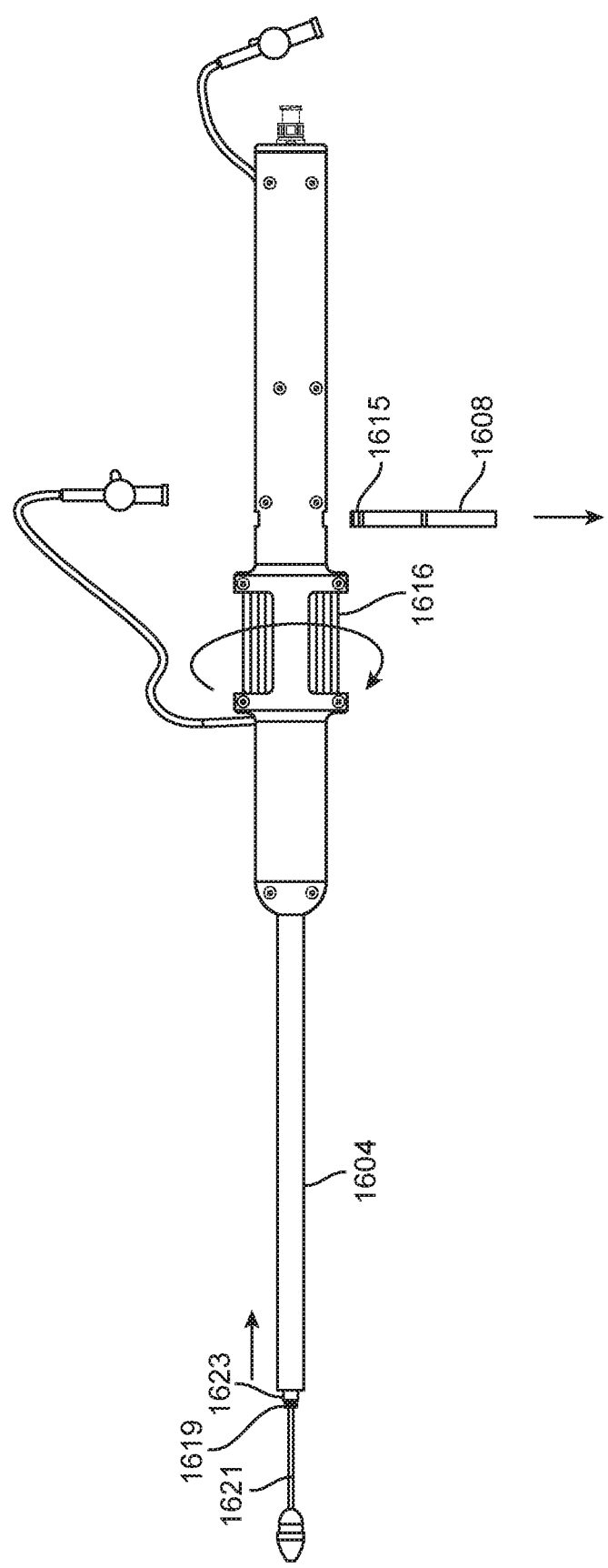

The deployment process and actions necessary to activate the mechanisms responsible for deployment are detailed in FIGS. 19A-19B. When performed in the reverse order, these actions also necessitate the first loading of a valve (not shown) prior to surgery.

As seen in FIG. 19A, manipulation of the thumbwheel 1616 will provide translational control of the sheath catheter 1604. In order to effect the deployment of a heart valve (not shown), the user must withdraw the sheath catheter 1604 from contact with the shoulder 1618 of the tip 1603 until it passes the larger diameter section 1623 of the bell catheter 1624. A heart valve (not shown) will reside concentrically above the guide-wire catheter 1621 in the position indicated by the leader for 1621 in FIG. 19A, similarly as to the embodiment illustrated in FIG. 13. The sheath catheter 1604 can be withdrawn until the screw insert 1627 comes into contact with the pin lock 1608. The pin lock 1608 must then be removed before further travel of the screw insert 1627 can be achieved.

As seen in FIG. 19B, the pin lock 1608 is removed from the handle 1601 in order to allow further translation of the sheath catheter 1604. When the sheath catheter 1604 is fully retracted, the larger diameter section 1623 of the bell catheter 1624 is also fully retracted, which completely frees the heart valve (not shown) from the delivery system. Three hub slots 1619, spaced circumferentially at 120.degree. from each other provide the anchoring mechanism and physical link between delivery system and heart valve. Once the larger diameter section 1623 of the bell catheter 1624 has been withdrawn, the hub slots 1619 become uncovered which allows the heart valve anchor (not shown) to fully expand.

Figure 16:
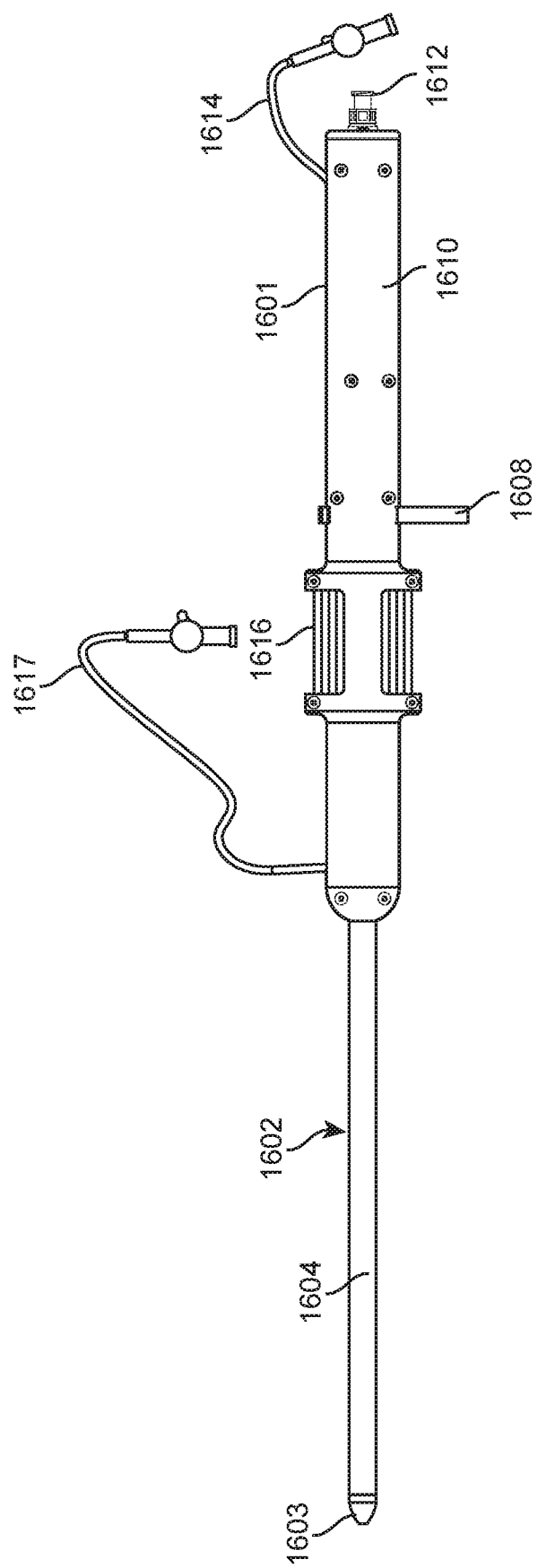
FIG. 16 is a side view of another exemplary embodiment of a delivery device for implantation of a prosthetic valve.
Figure 20:
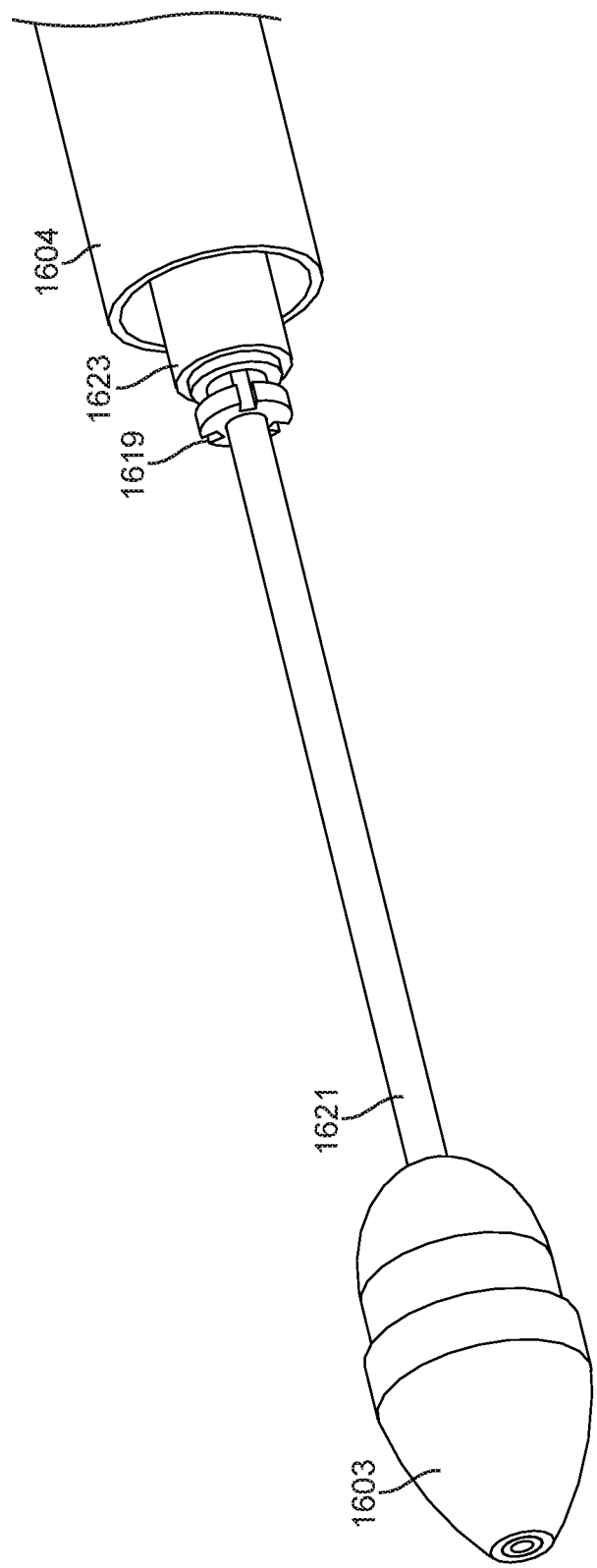
FIG. 20 illustrates a distal portion of the delivery device in FIG. 16 that is adapted to engage a portion of a prosthetic valve.

FIG. 20 illustrates a distal portion of the delivery device in FIG. 16. Three hub slots 1619 are slidably disposed distally relative to the large diameter tip 1623 of bell catheter 1624. These slots allow engagement with a prosthetic valve. The valve may be releasably held by the slots by disposing the commissure tabs or tabs 812 of the prosthetic valve into slots 1619 and then retracting the slots 1619 under tip 1623 of bell catheter 1624. The prosthetic valve may be released from the delivery catheter by advancing the slots distally relative to the bell catheter so that the loading anchors or tabs 812 may self-expand out of and away from slots 1619 when the constraint of tip 1623 on bell catheter 1624 has been removed.

Figure 21:
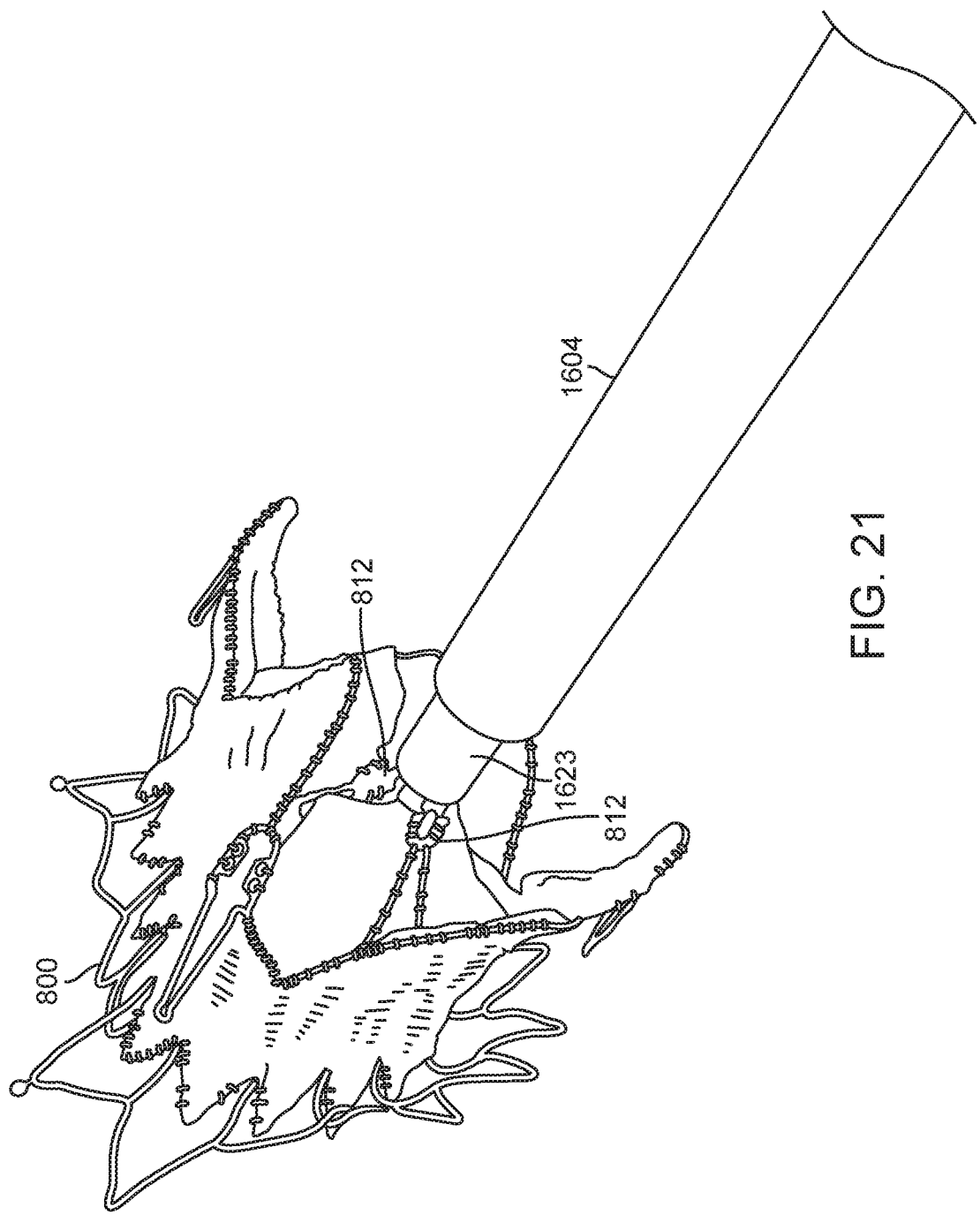
FIG. 21 illustrates engagement of the delivery device in FIG. 16 with the prosthetic valve of FIG. 8A.

FIG. 21 illustrates a prosthetic mitral valve 800 (as discussed above with reference to FIG. 8A) with the anchor tabs 812 disposed in the hub slots (not visible), and bell catheter 1623 advanced thereover. Thus, even though most of the prosthetic valve 800 has self-expanded into its expanded configuration, the valve commissures remain in a collapsed configuration with the tabs 812 captured in slots 1619. Once the constraint provided by bell catheter 1623 has been removed from the slots 1619, the tabs 812 may self-expand out of slots 1619, the commissures will open up to their unbiased position. The prosthetic valve is then disconnected and free from the delivery device.

Transapical Delivery Methods

Figure 22A:
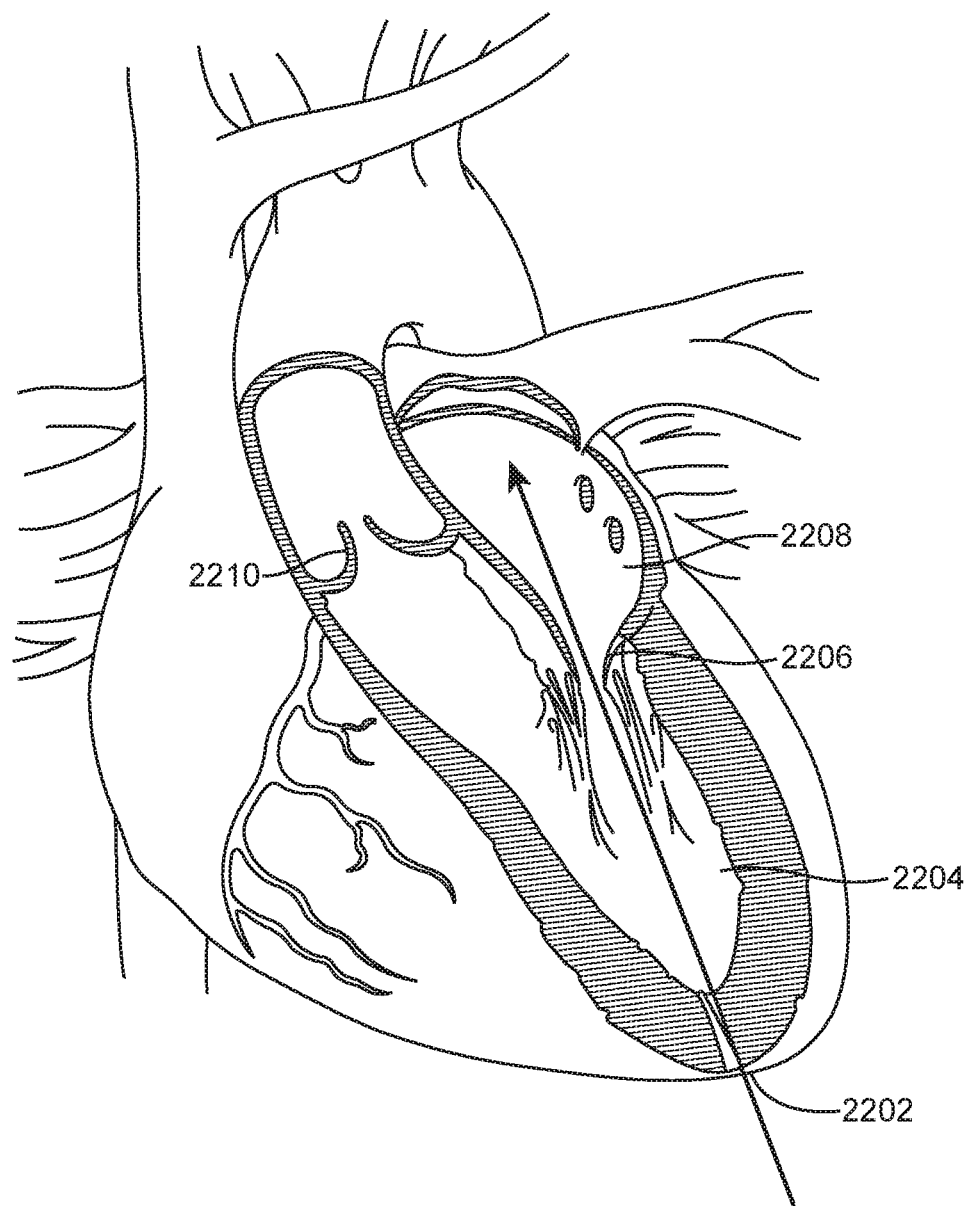
FIGS. 22A-22G illustrate an exemplary method of transapically delivering a prosthetic mitral valve.

FIGS. 22A-22G illustrate an exemplary method of transapically delivering a prosthetic mitral valve. This embodiment may use any of the prosthetic valves described herein, and may use any of the delivery devices described herein. FIG. 22A illustrates the general transapical pathway that is taken with entry into the heart at the apex 2202, through the left ventricle 2204, across the mitral valve 2206 and into the left atrium 2208. The aortic valve 2210 remains unaffected. Transapical delivery methods have been described in the patent and scientific literature, such as in International PCT Publication No. WO2009/134701, the entire contents of which are incorporated herein by reference.

Figure 22B:
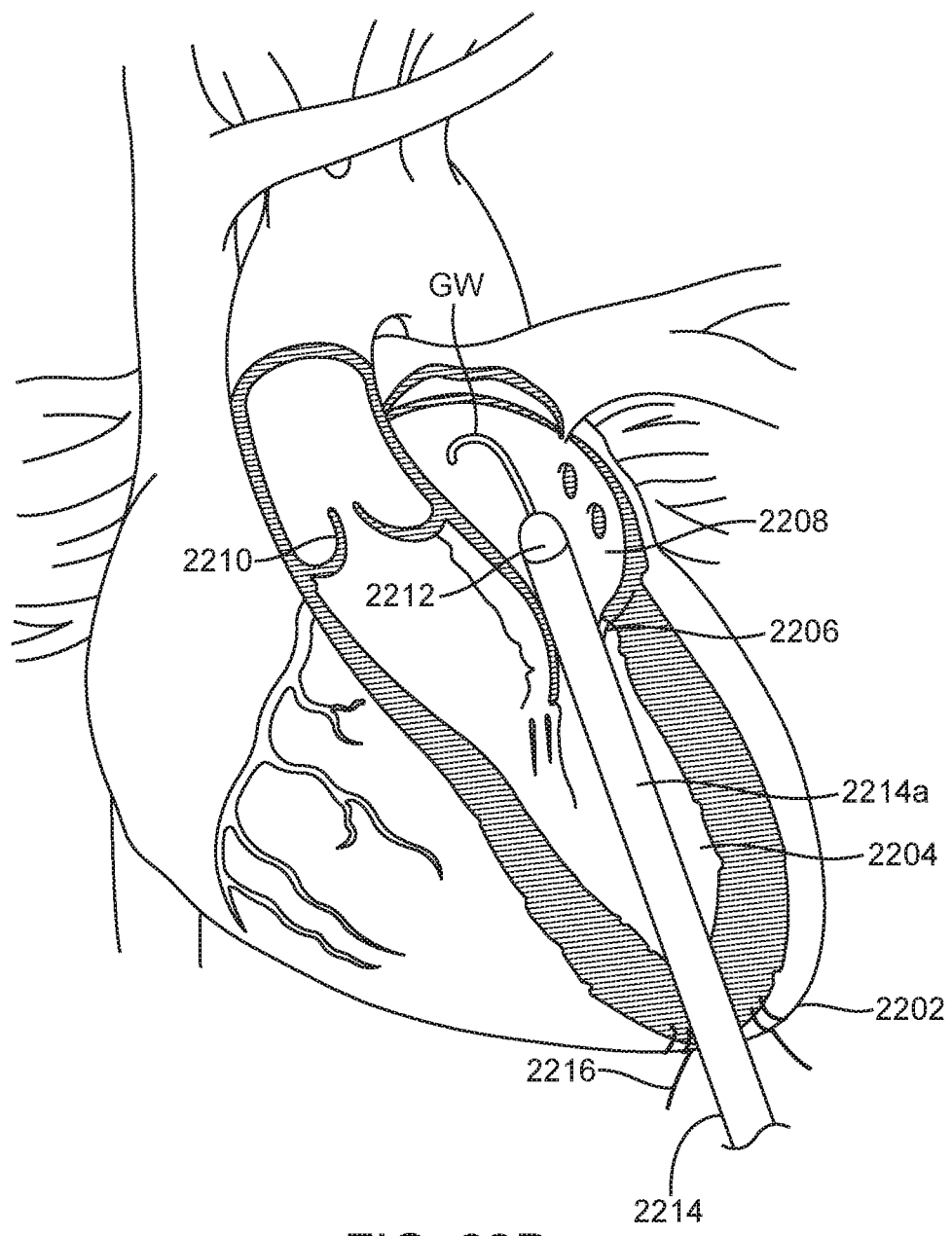

In FIG. 22B a delivery device 2214 is introduced through an incision in the apex 2202 and over a guidewire GW through the ventricle 2204, past the mitral valve 2206 with a distal portion of the delivery device 2214 disposed in the atrium 2208. The delivery device has a rounded tip 2212 that is configured to pass through and dilate the incision, and can be advanced through the heart without causing unwanted trauma to the mitral valve 2206 or adjacent tissue. Suture 2216 may be stitched around the delivery device 2214 at the apex 2202 using a purse string stitch or other patterns known in the art in order to prevent excessive bleeding and to help hold the delivery device in position.

Figure 22C:
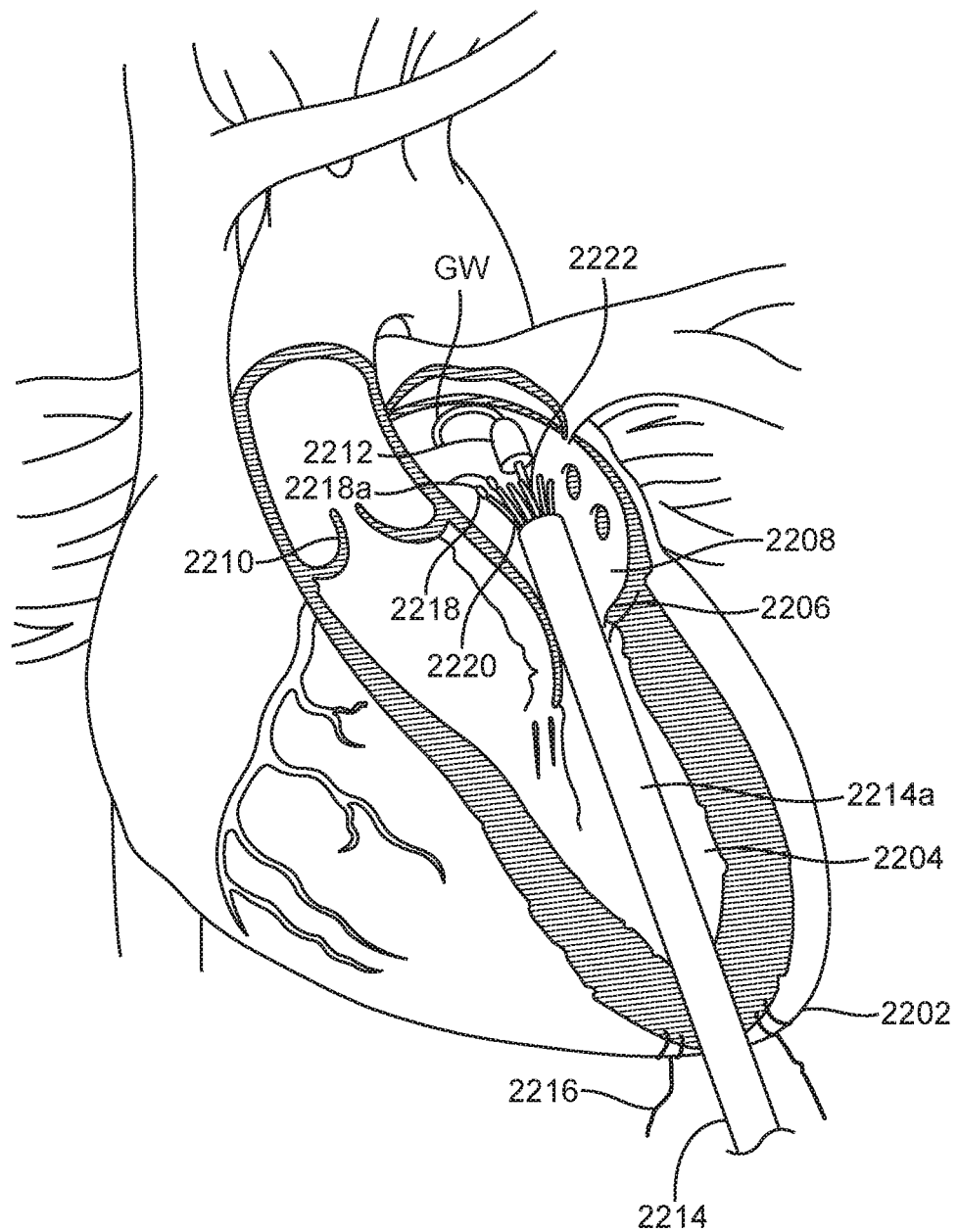

In FIG. 22C, the outer sheath 2214a of the delivery device 2214 is retracted proximally relative to the prosthetic mitral valve 2220 (or the prosthetic mitral valve is advanced distally relative to the outer sheath 2214a) to expose the alignment element 2218 and a portion of the atrial skirt region 2222 on the prosthetic mitral valve 2220 which allows the atrial skirt region 2222 to begin to partially radially expand outward and flare open. Alignment element 2218 may include a pair of radiopaque markers 2218a which facilitate visualization under fluoroscopy. The physician can then align the alignment element so that the radiopaque markers 2218a are disposed on either side of the anterior mitral valve leaflet. Delivery device 2214 may be rotated in order to help align the alignment element. The alignment element is preferably situated adjacent the aortic root and between the fibrous trigones of the native anterior leaflet.

Figure 22D:
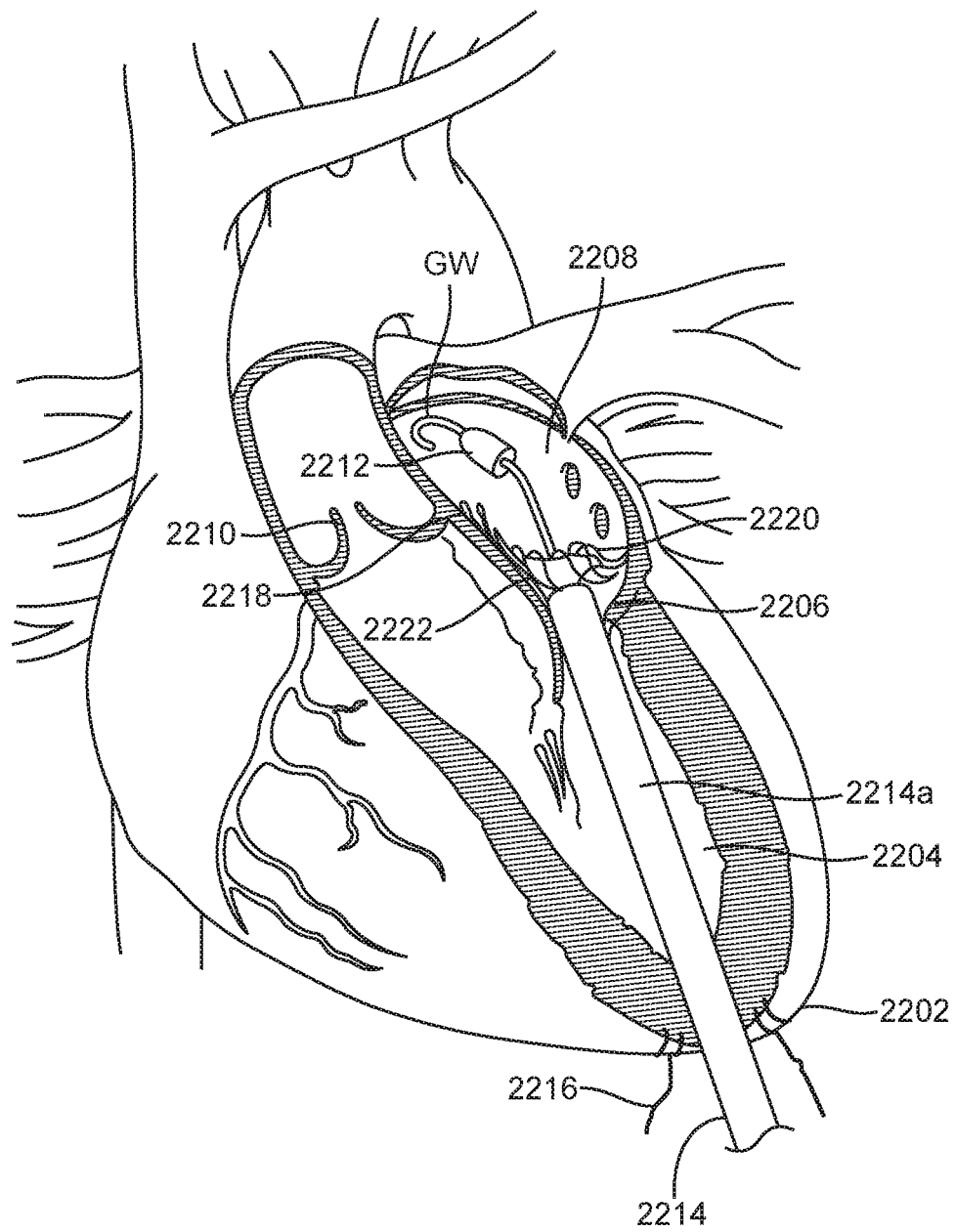

In FIG. 22D once alignment has been obtained, the sheath 2214a is further retracted proximally, allowing radial expansion of the atrial skirt 2222 which flares outward to form a flange. Proximal retraction of the delivery device 2214 and prosthetic valve 2220 seat the atrial skirt 2222 against an atrial surface adjacent the mitral valve 2206 thereby anchoring the prosthetic valve in a first position.

Figure 22E:
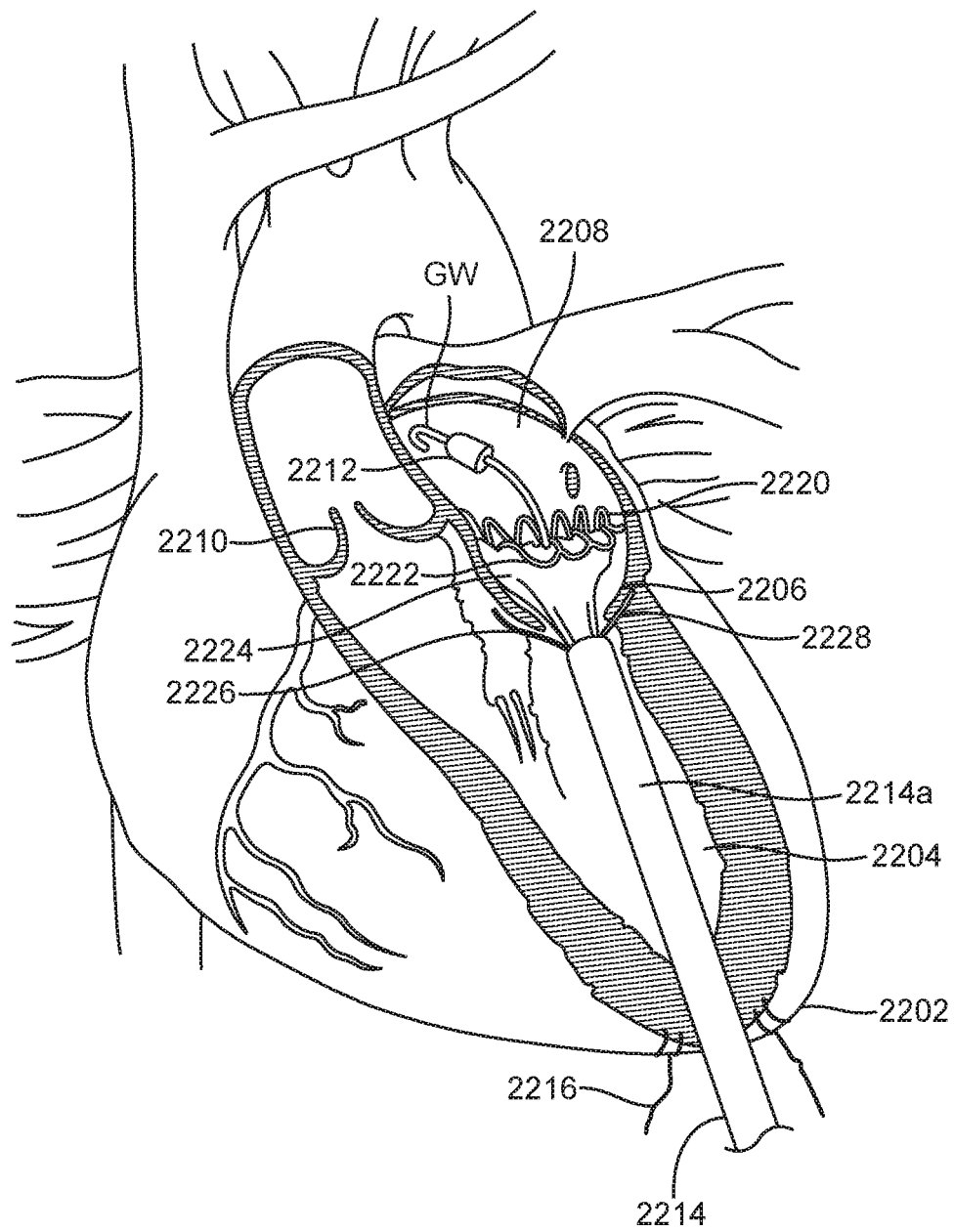

FIG. 22E shows that further proximal retraction of sheath 2214a exposes and axially removes additional constraint from the prosthetic valve 2220, thereby allowing more of the valve to self-expand. The annular region 2224 expands into engagement with the mitral valve annulus and the ventricular trigonal tabs 2226 and the posterior tab 2228 radially expand. Portions of the ventricular skirt serve as deployment control regions and prevent the entire ventricular skirt from expanding because they are still constrained. The tabs are captured between the anterior and posterior mitral valve leaflets and the ventricular wall. The posterior ventricular anchoring tab 2228 is preferably aligned in the middle of the posterior mitral valve leaflet where there is an absence of chordae attachments, and is passed over the posterior leaflet to seat between the posterior leaflet and the ventricular wall. The two ventricular trigonal anchoring tabs 2226 are positioned on either side of the anterior leaflet with their heads positioned at the fibrous trigones. Slight rotation and realignment of the prosthesis can occur at this time. As the prosthesis expands, the anterior trigonal tabs anchor against the fibrous trigones, capturing the native anterior leaflet and chordae between the tabs and the anterior surface of the prosthetic valve, and the posterior ventricular tab anchors between the ventricular wall and the posterior leaflet, capturing the posterior leaflet between the posterior anchoring tab and the posterior surface of the prosthetic valve assembly.

Figure 22F:
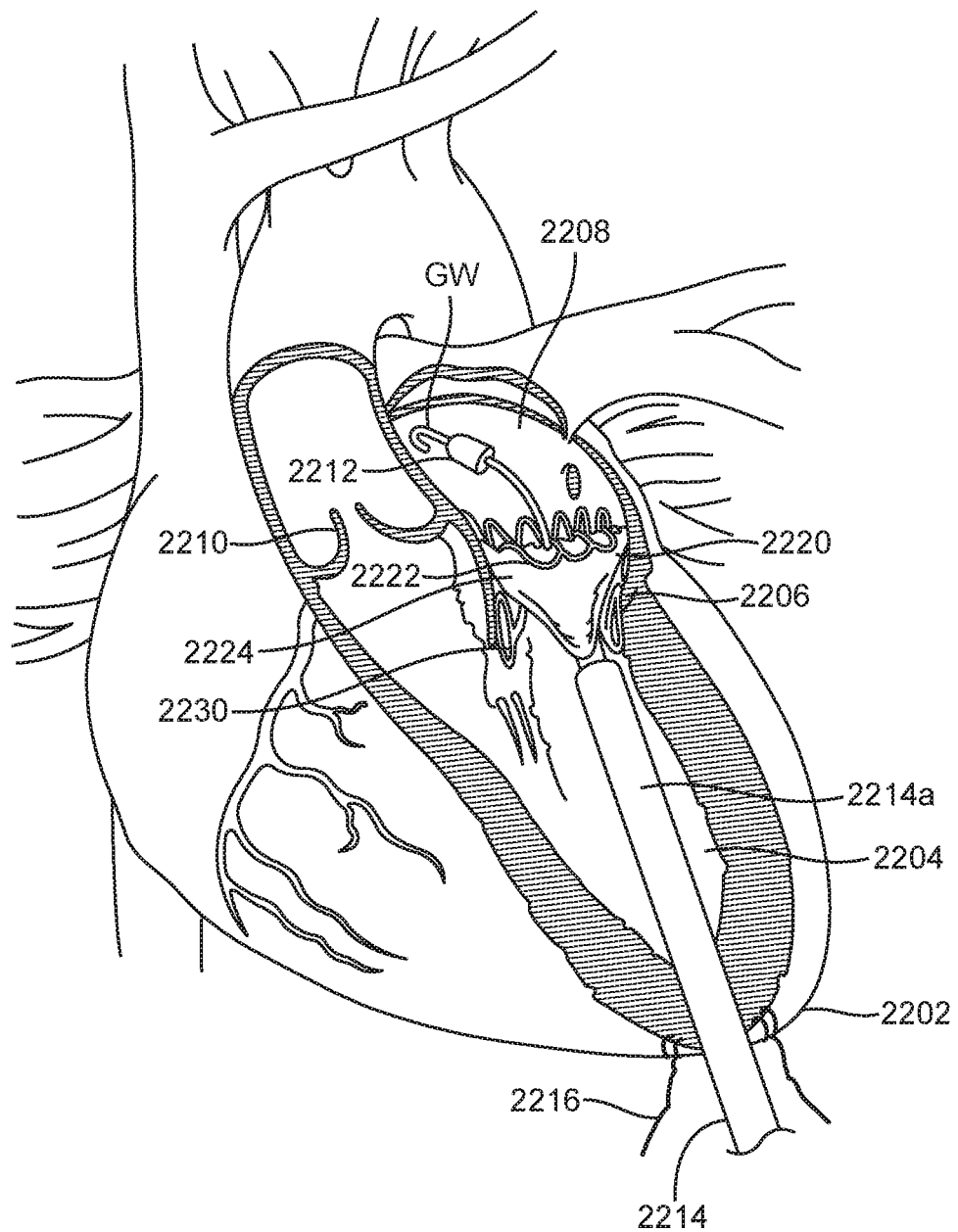
Figure 22G:
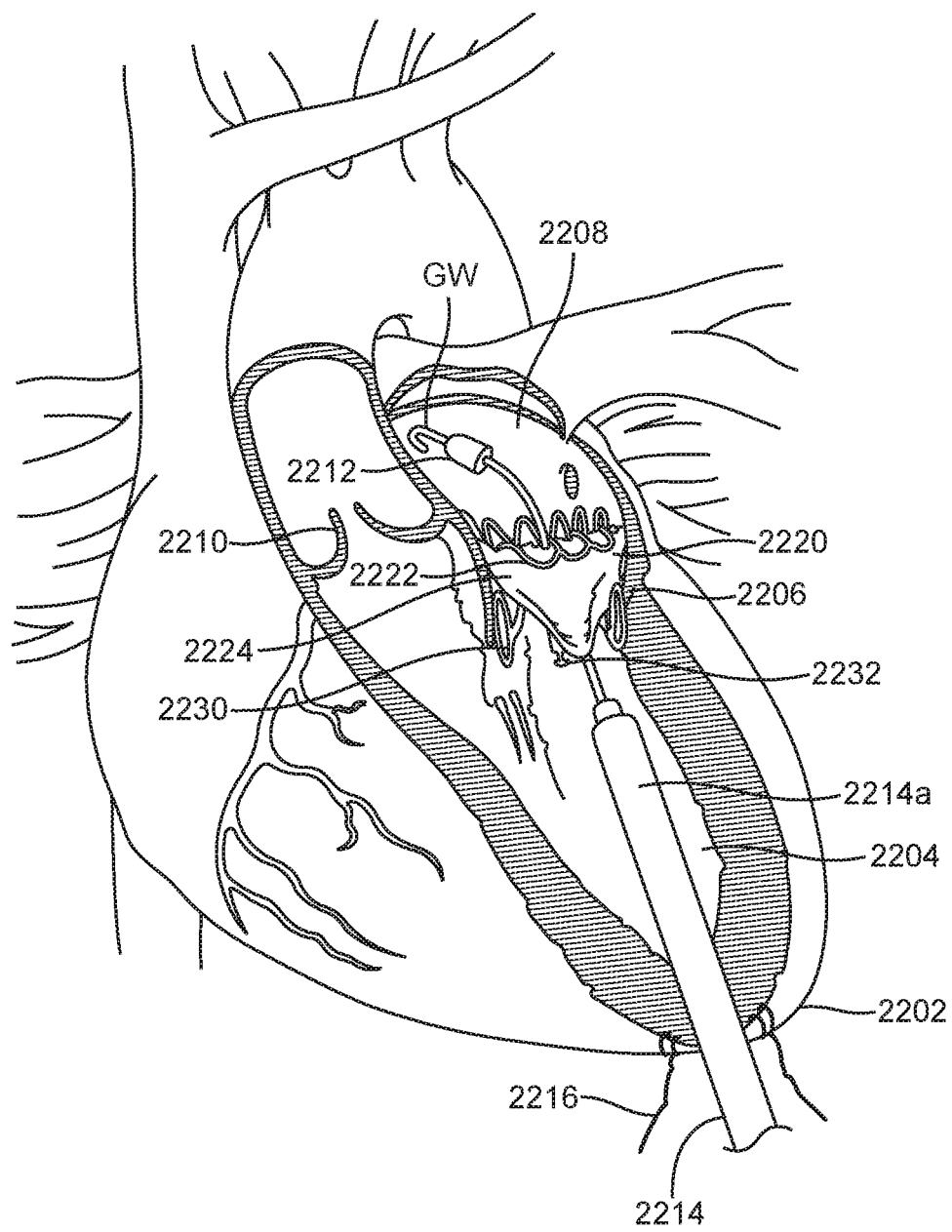

FIG. 22F shows that further retraction of sheath 2214a releases the ventricular trigonal tabs and the posterior tab and the deployment control regions of the ventricular skirt 2230 are also released and allowed to radially expand outward against the native mitral valve leaflets. This creates a sealing funnel within the native leaflets and helps direct blood flow through the prosthetic mitral valve. With the commissures of the prosthesis still captured within the delivery system, very minor adjustments may still be made to ensure accurate positioning, anchoring and sealing. The prosthetic valve is now anchored in four positions. The anchor tabs 2232 are then released from the delivery device by retraction of an inner shaft, allowing the tabs to self-expand out of slots on the delivery catheter as previously discussed above and shown in FIG. 22G. The prosthetic valve is now implanted in the patient's heart and takes over the native mitral valve. The delivery device 2214 may then be removed from the heart by proximally retracting it and removing it from the apex incision. The suture 2216 may then be tied off, sealing the puncture site.

Transseptal Delivery Methods

Figure 23A:
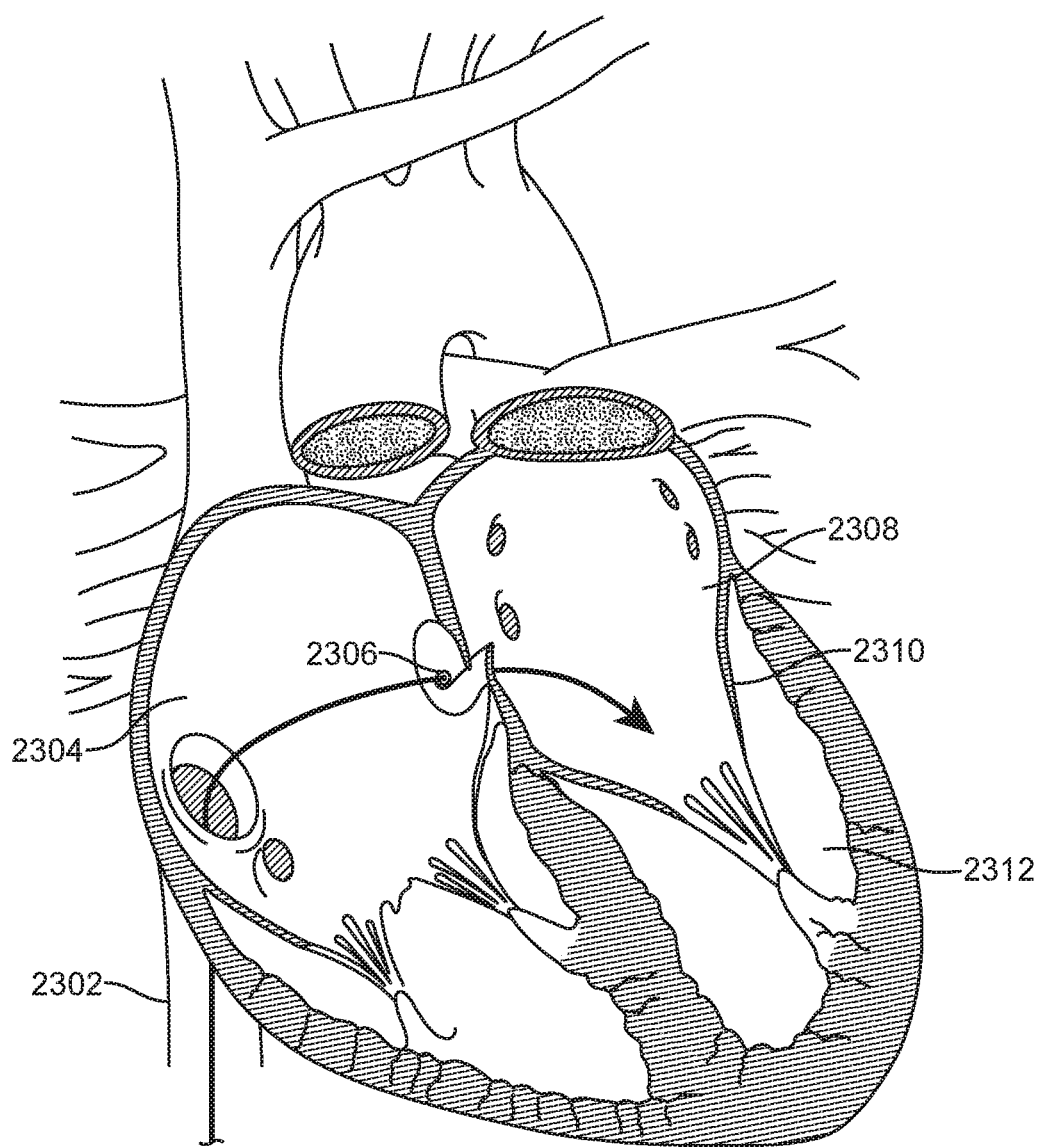
FIGS. 23A-23G illustrate an exemplary method of transseptally delivering a prosthetic mitral valve.

FIGS. 23A-23G illustrate an exemplary method of transseptally delivering a prosthetic mitral valve. This embodiment may use any of the prosthetic valves described herein, and may use any of the delivery devices described herein if modified appropriately. One of skill in the art will appreciate that relative motion of the various shafts in the delivery system embodiments disclosed above may need to be reversed in order to accommodate a transseptal approach. FIG. 23A illustrates the general transseptal pathway that is taken with the delivery device passing up the vena cava 2302 into the right atrium 2304. A transseptal puncture 2306 is created through the atrial septum, often through the foramen ovale, so that the device may be passed into the left atrium 2308, above the mitral valve 2310 and adjacent the left ventricle 2312. Transseptal techniques have been published in the patent and scientific literature, such as in U.S. Patent Publication No. 2004/0181238 to Zarbatany et al., the entire contents of which are incorporated herein by reference.

Figure 23B:
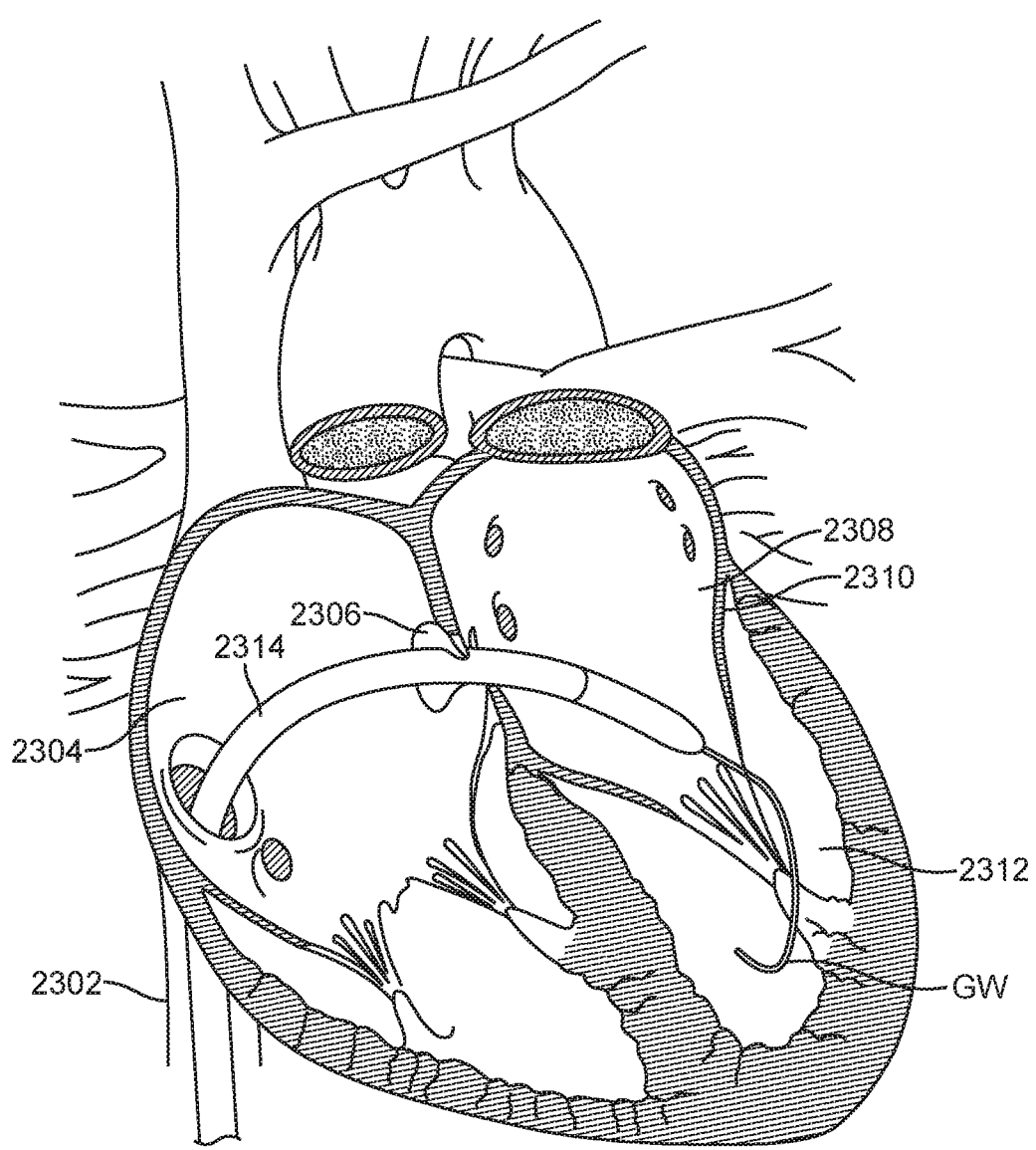

In FIG. 23B a delivery device 2314 is passed over a guidewire GW through the vena cava 2302 into the right atrium 2306. The delivery device 2314 is then transseptally passed through the atrial wall into the left atrium 2308 adjacent the mitral valve 2310. The guide-wire GW may be disposed across the mitral valve 2310 in the left ventricle 2312. The distal tip of the delivery device typically includes a nose cone or other atraumatic tip to prevent damaging the mitral valve or adjacent tissue.

Figure 23C:
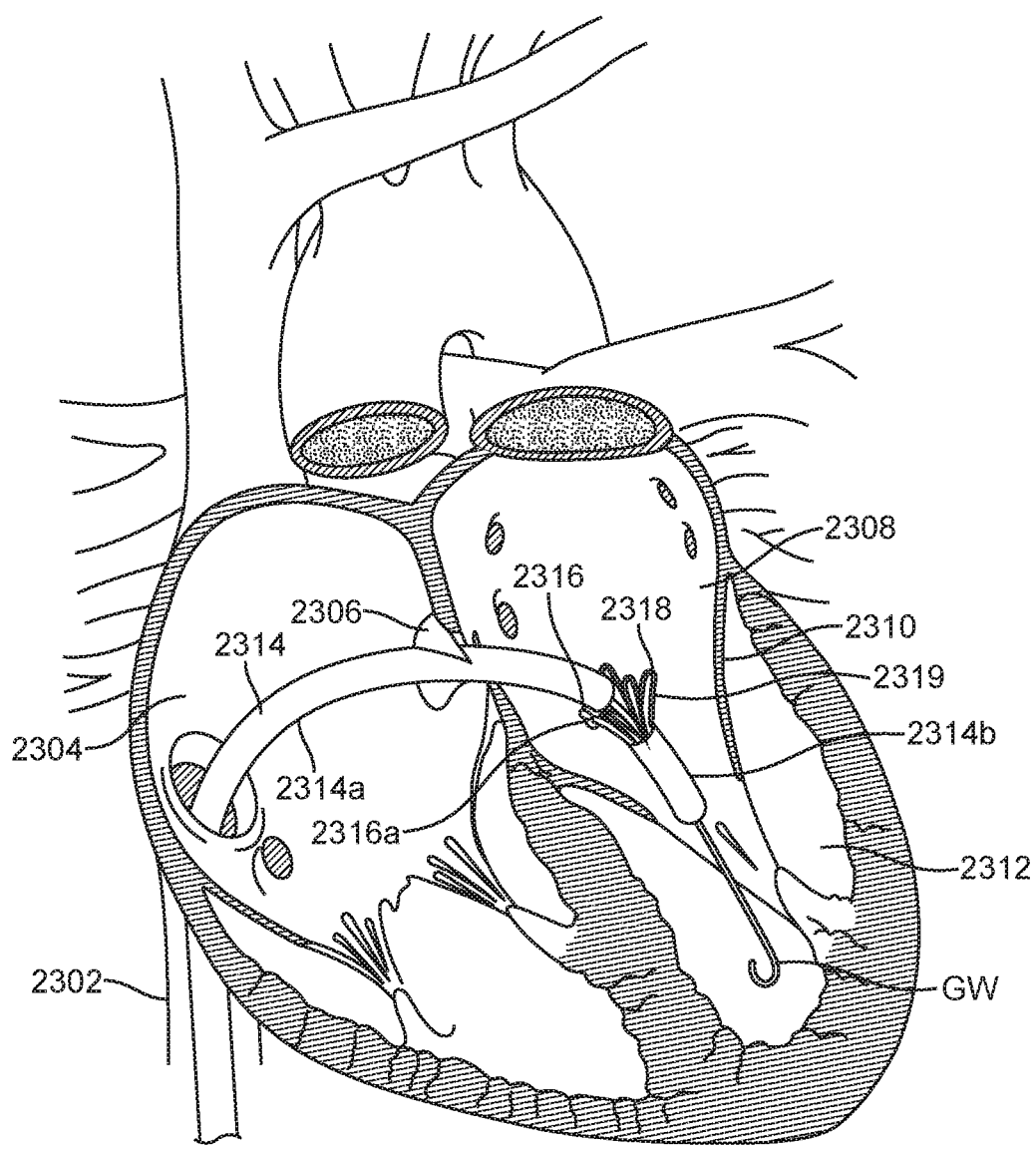

In FIG. 23C, the outer sheath 2214a of the delivery device 2214 is retracted proximally relative to the prosthetic mitral valve 2319. Alternatively, a distal portion 2314b of the delivery device 2214 may be advanced distally relative to the prosthetic valve 2319 to expose the alignment element 2316 and a portion of the atrial skirt region 2318 on the prosthetic mitral valve 2319 which allows the atrial skirt region 2318 to begin to partially radially expand outward and flare open. Alignment element 2316 may include a pair of radiopaque markers 2316a which facilitate visualization under fluoroscopy. The physician can then align the alignment element so that the radiopaque markers 2316a are disposed on either side of the anterior mitral valve leaflet. The alignment element is preferably situated adjacent the aortic root and between the fibrous trigones of the native anterior leaflet. Delivery device 2214 may be rotated in order to help align the alignment element.

Figure 23D:
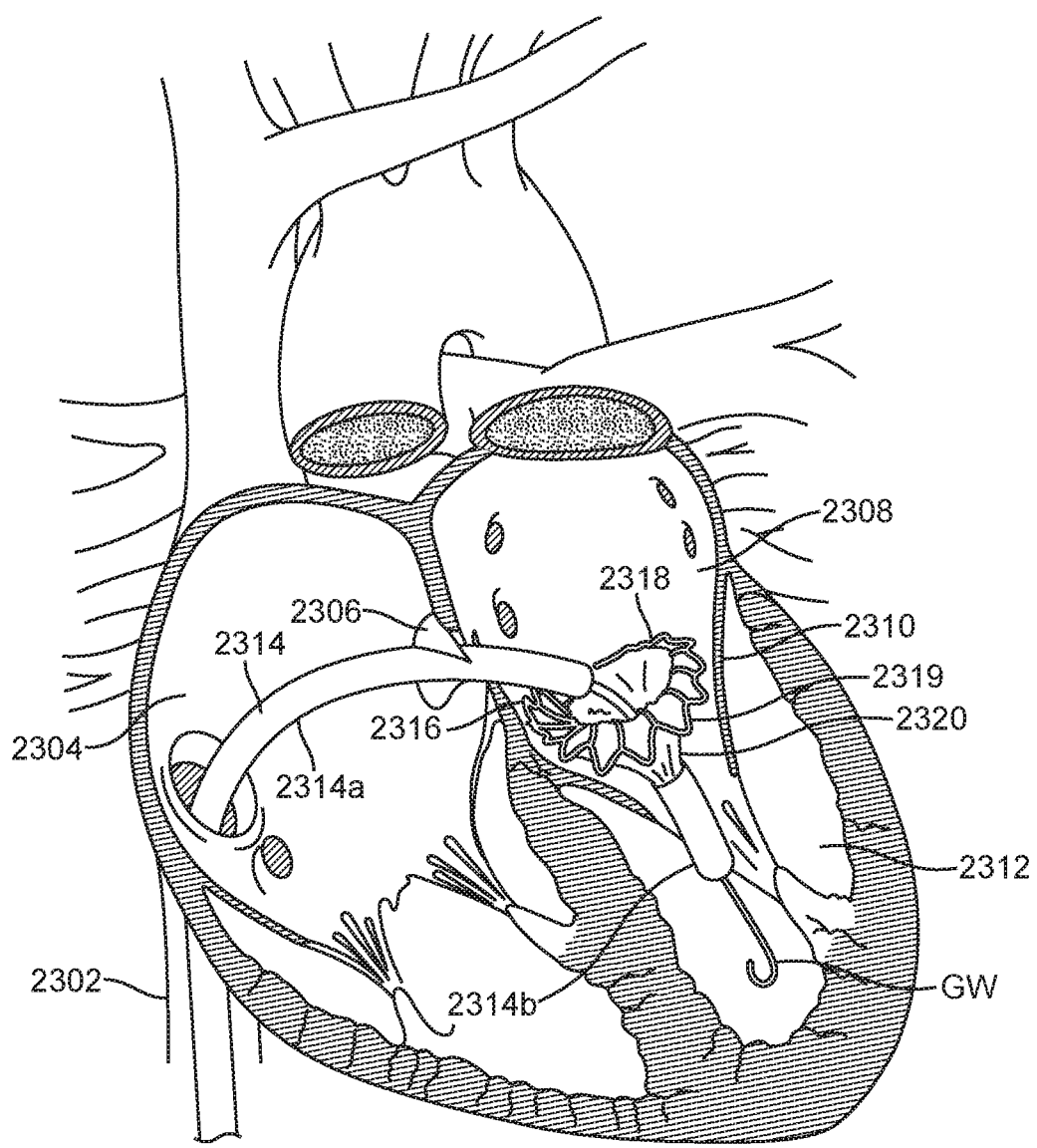

In FIG. 23D once alignment has been obtained, the distal portion 2314b is further advanced distally allowing radial expansion of the atrial skirt 2318 which flares outward to form a flange. Distally advancing the delivery device 2214 and prosthetic valve 2319 seats the atrial skirt 2318 against an atrial surface adjacent the mitral valve 2310 thereby anchoring the prosthetic valve in a first position.

Figure 23E:
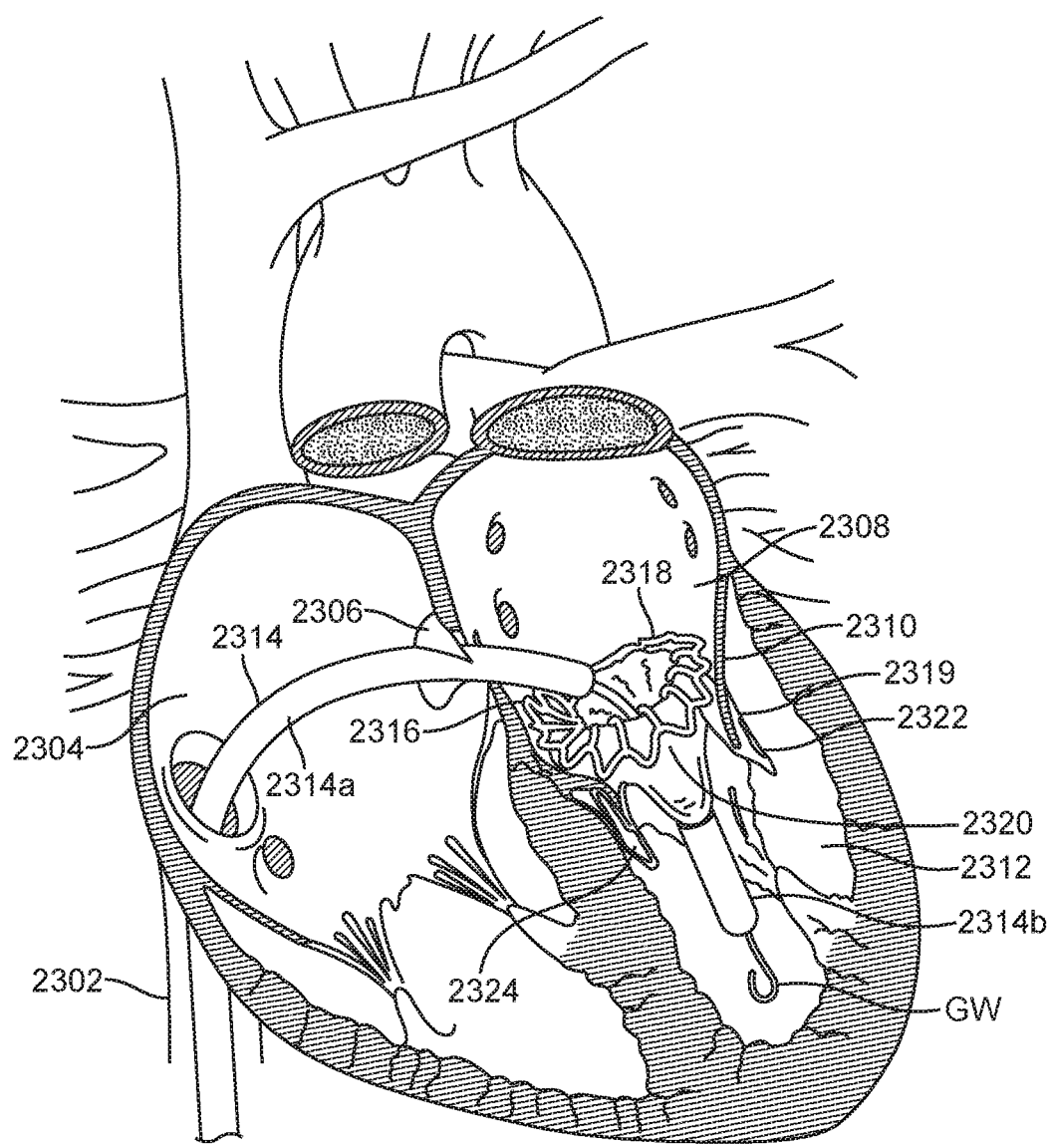

FIG. 23E shows that further distal advancement of distal portion 2314b exposes and axially removes additional constraint from the prosthetic valve 2319, thereby allowing more of the valve to self-expand. The annular region 2320 expands into engagement with the mitral valve annulus and the ventricular trigonal tabs 2324 and the posterior tab 2322 radially expand. Portions of the ventricular skirt serve as deployment control regions since they remain constrained and thus the entire ventricular skirt cannot expand. The tabs are captured between the anterior and posterior mitral valve leaflets and the ventricular wall. The posterior ventricular anchoring tab 2322 is preferably aligned in the middle of the posterior mitral valve leaflet where there is an absence of chordae attachments, and is passed over the posterior leaflet to seat between the posterior leaflet and the ventricular wall. The two ventricular trigonal anchoring tabs 2324 are positioned on either side of the anterior leaflet with their heads positioned at the fibrous trigones. Slight rotation and realignment of the prosthesis can occur at this time. As the prosthesis expands, the anterior trigonal tabs anchor against the fibrous trigones, capturing the native anterior leaflet and chordae between the tabs and the anterior surface of the prosthetic valve, and the posterior ventricular tab anchors between the ventricular wall and the posterior leaflet, capturing the posterior leaflet between the posterior anchoring tab and the posterior surface of the prosthetic valve assembly.

Figure 23F:
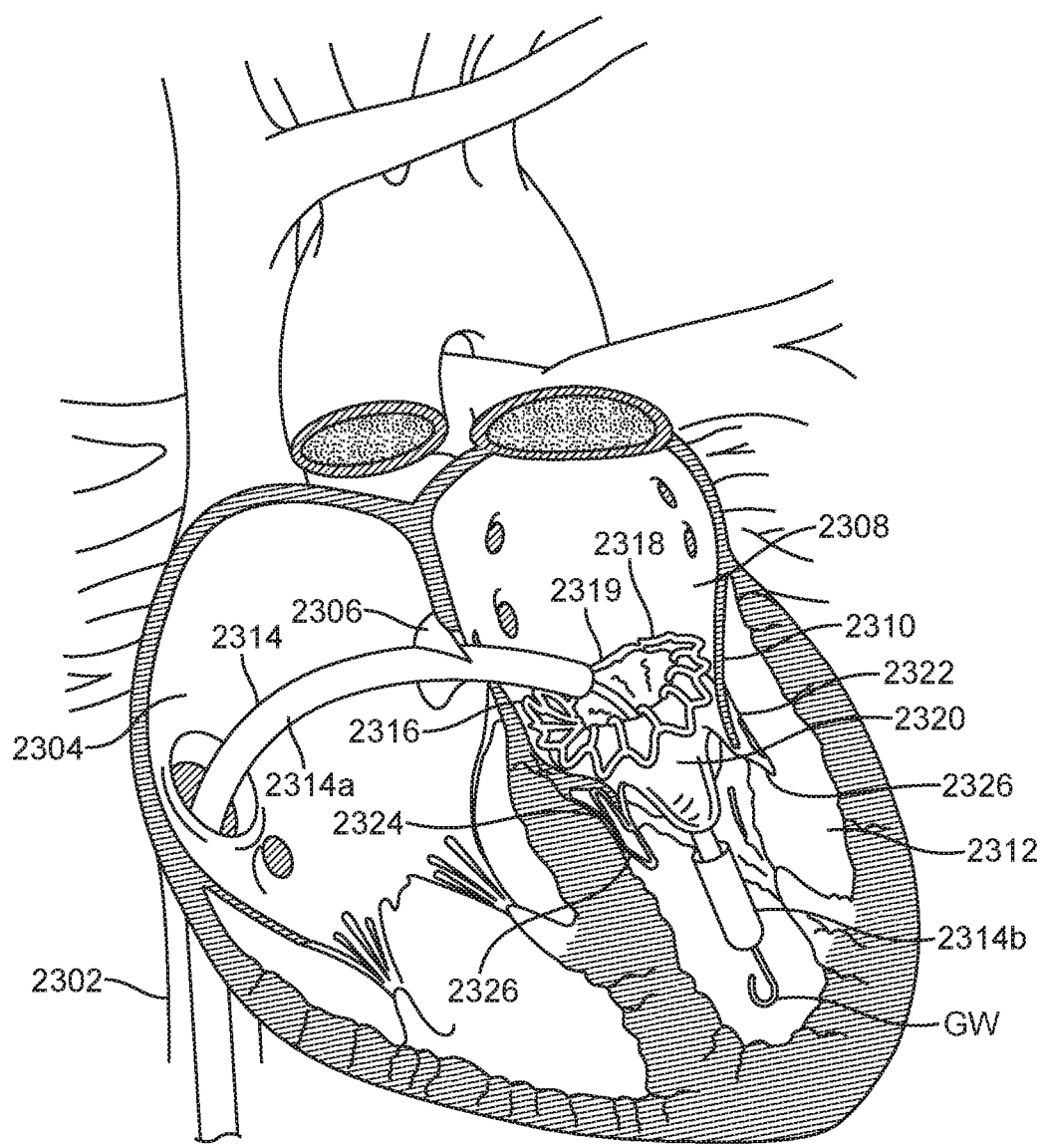
Figure 23G:
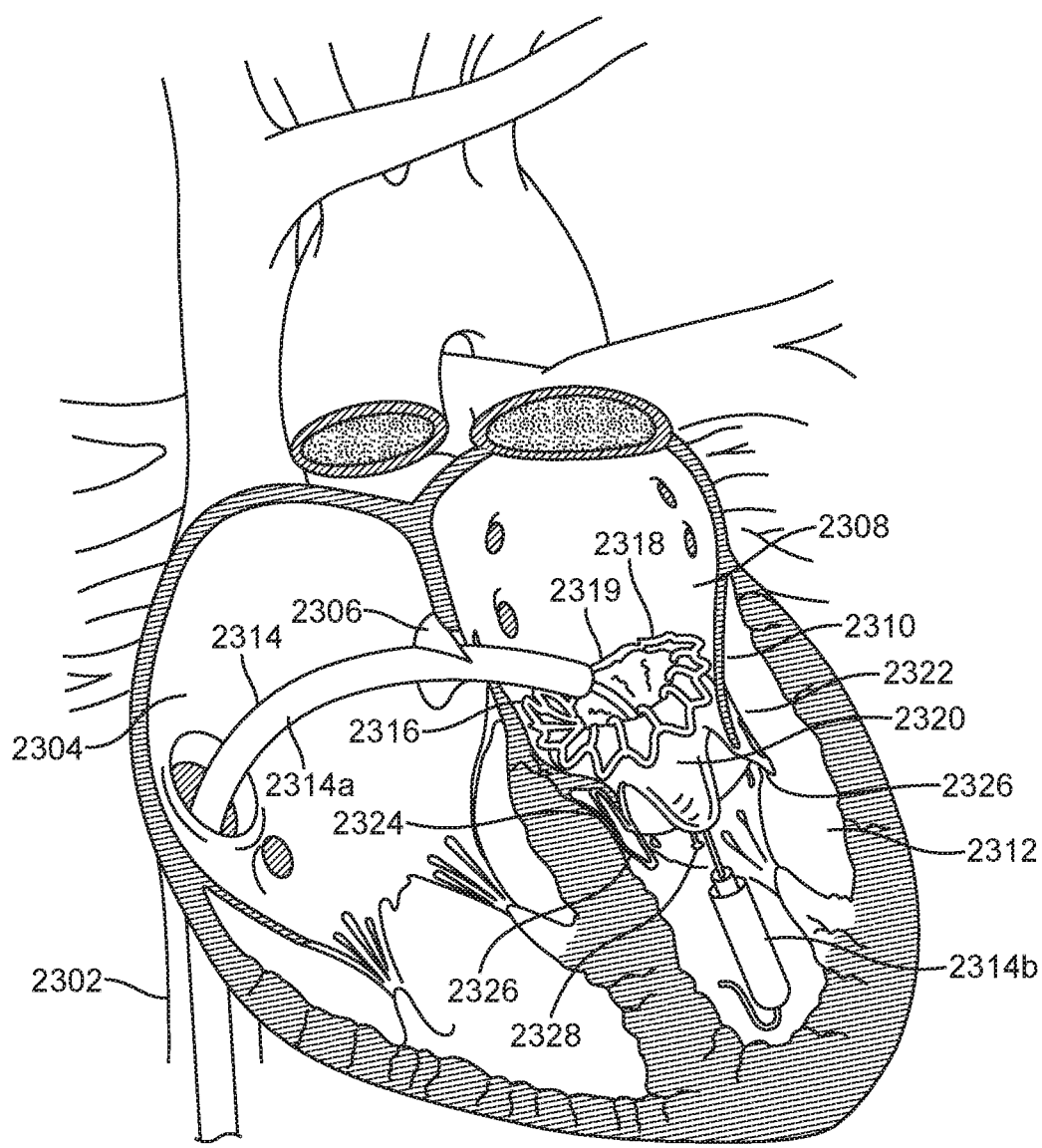

FIG. 23F shows that further distal advancement of distal portion 2314b releases the ventricular trigonal tabs and the posterior tab and the ventricular skirt 2326 is also released and allowed to radially expand outward against the native mitral valve leaflets without engaging the ventricular wall. This creates a sealing funnel within the native leaflets and helps funnel blood flow through the prosthetic valve. With the commissures of the prosthetic valve still captured by the delivery system, very minor adjustments may still be made to ensure accurate positioning, anchoring and sealing. The prosthetic valve is now anchored in four positions. The anchor tabs 2328 are then released from the delivery device by further advancement of an inner shaft, allowing the tabs to self-expand out of slots on the delivery catheter as previously discussed above and shown in FIG. 23G. The prosthetic valve is now implanted in the patient's heart and takes over the native mitral valve. The delivery device 2314 may then be removed from the heart by proximally retracting it back through the atrial septum, and out of the vena cava.

Figure 24:
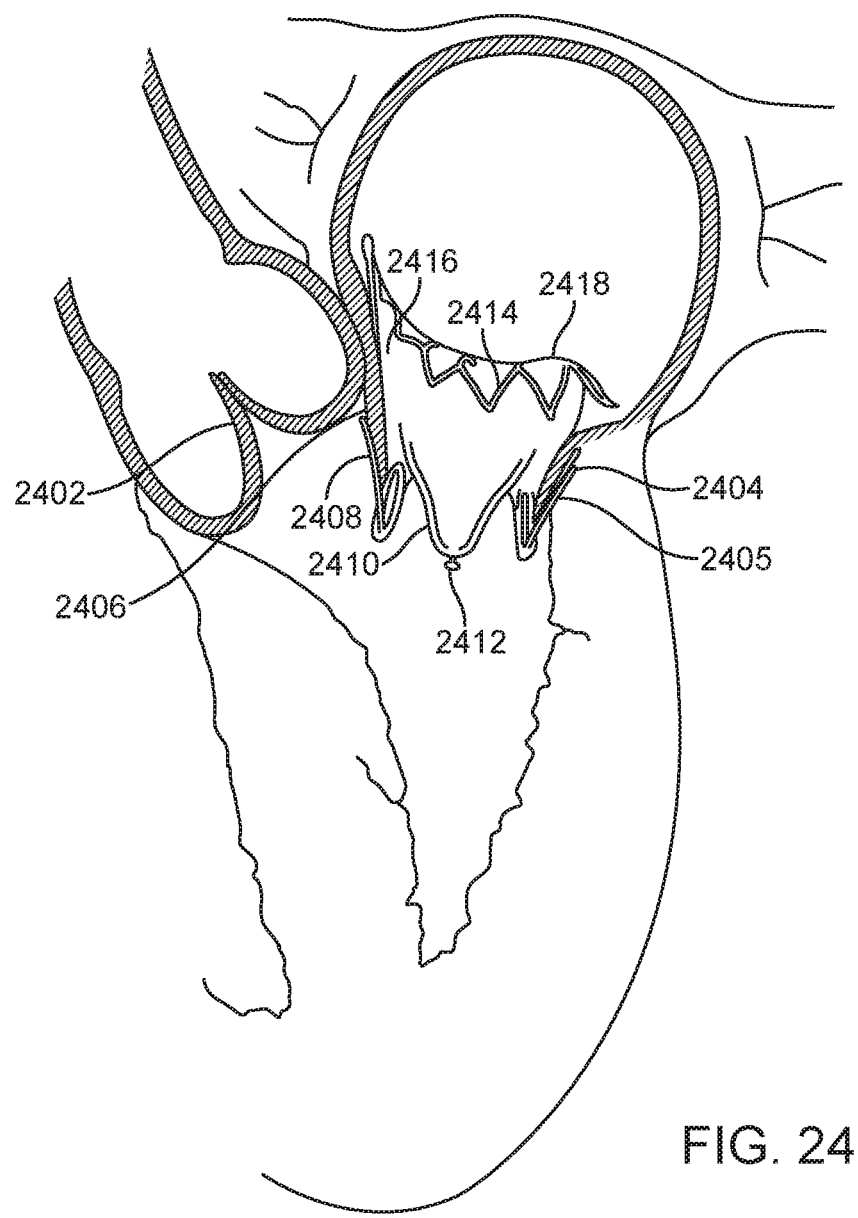
FIG. 24 illustrates a prosthetic mitral valve implanted in the mitral space.

FIG. 24 shows the prosthetic valve 2418 anchored in the mitral space after transapical or transseptal delivery. Prosthetic valve 2418 is preferably the prosthetic mitral valve illustrated in FIG. 8A, and delivered by methods shown in FIGS. 22A-22G or FIGS. 23A-23G. The prosthetic valve 2418 has radially self-expanded into engagement with the mitral valve to anchor it in position without obstructing other portions of the heart including the left ventricular outflow tract such as aortic valve 2402. The anterior trigonal tabs 2408 (only 1 seen in this view) and the posterior ventricular tab 2405 are radially expanded outward from the rest of the ventricular skirt 2410 and the anterior leaflet 2406 and posterior leaflet 2404 are captured between the respective tab and the ventricular skirt 2410 to form an anchor point. The ventricular skirt 2410 is also radially expanded outward to engage and press outwardly at least some of the chordae tendineae and papillary muscles but preferably without pressing against the ventricular wall. The annular region 2416 is expanded radially outward to engage and press against the mitral valve annulus, and the atrial skirt 2414 has also expanded outwardly to form a flange that rests on top of the mitral valve against the atrium. Thus, the prosthetic valve 2418 is anchored in four positions in the mitral space which prevents the prosthetic valve from migrating or dislodging during contraction of the heart. Moreover, using four anchor points lessens the anchoring pressure that is required to be applied in any given anchoring zone as compared to a prosthesis that is anchored in only a single anchoring zone, or in any combination of these four anchoring zones. The consequent reduction in radial force required to be exerted against the native structures in each zone minimizes the risk of obstruction or impingement of the nearby aortic valve or aortic root caused by the displacement of the native mitral valve apparatus. Valve leaflets 2420 form a tricuspid valve which opens with antegrade blood flow and closes with retrograde blood flow. Tab 2412 on a tip of the commissures 2421 (best seen in FIG. 25) remains free after disengagement from the delivery device.

Figure 25:
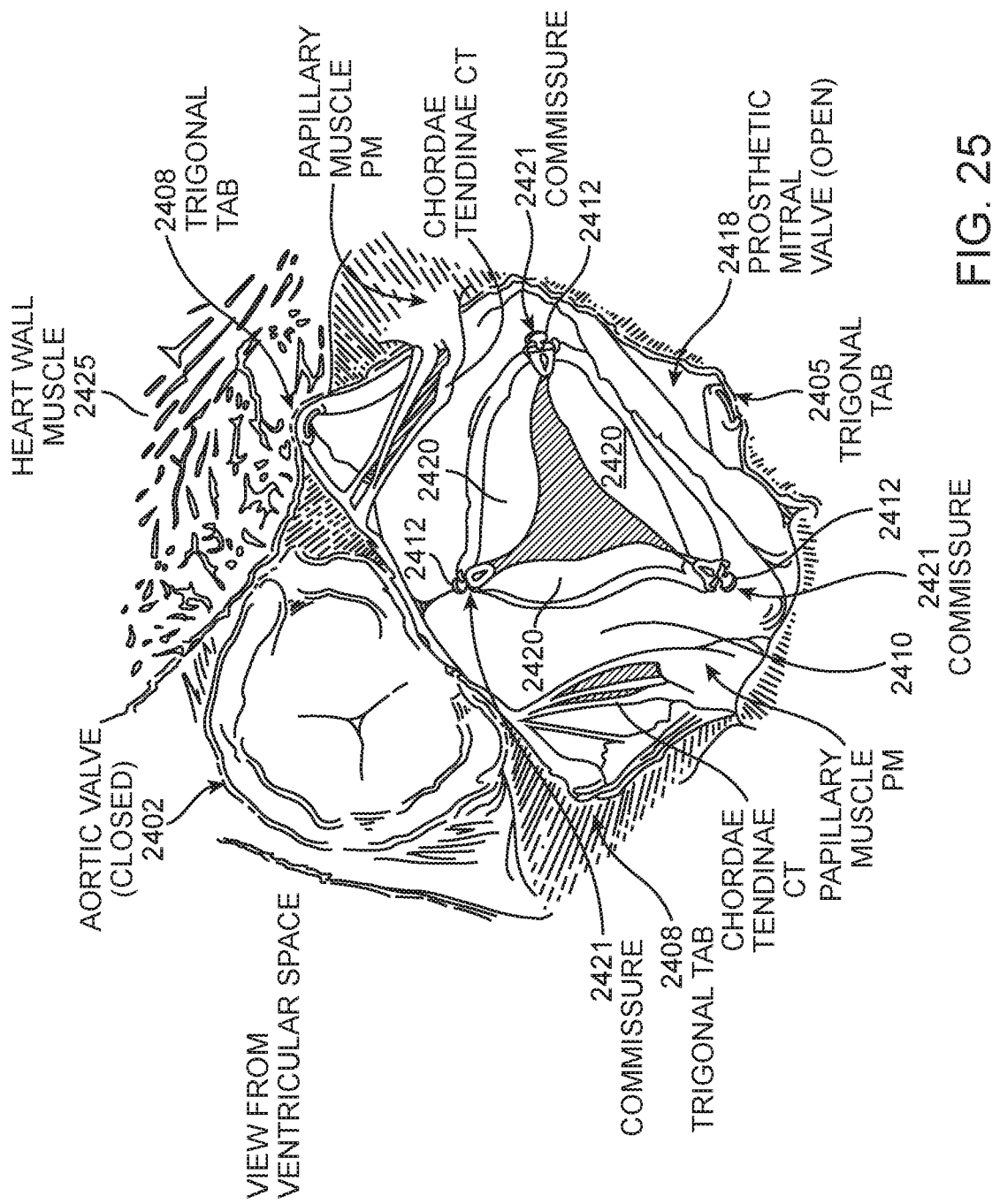
FIG. 25 illustrates a bottom view of a mitral valve implanted in the mitral space looking upward from the left ventricle.

FIG. 25 illustrates the prosthetic valve 2418 of FIG. 24 anchored in the mitral space and viewed from the left ventricle, looking upward toward the atrium. As previously mentioned, the prosthetic valve 2418 may be transapically or transsepally delivered and is preferably the prosthetic mitral valve illustrated in FIG. 8A, delivered by methods shown in FIGS. 22A-22G or FIGS. 23A-23G. This view more clearly illustrates anchoring and engagement of the prosthetic mitral valve 2418 with the adjacent tissue. For example, the three valve leaflets 2420 forming the tricuspid valve are shown in the open position, allowing blood flow therepast. Additionally, the anterior trigonal tabs 2408 and the posterior ventricular tab 2405 are shown radially expanded outward into engagement with the ventricular heart tissue 2425. The anterior portion of the prosthetic valve in between anterior trigonal tabs 2408 is approximately flat to match the corresponding flat anatomy as previously discussed above. The flat shape of the anterior portion of the prosthetic valve prevents the prosthetic valve from impinging on and obstructing adjacent anatomy such as the left ventricular outflow tract including the aortic valve. FIG. 25 also illustrates how the ventricular skirt 2410 expands radially outward against the native mitral valve leaflets.

Drug Delivery

Any of the prosthetic valves disclosed herein may also be used as a drug delivery device for localized drug elution. The therapeutic agent may be a coated on the prosthetic valve, on the tissue covering the anchor, on both, or otherwise carried by the prosthetic valve and controllably eluted therefrom after implantation. Exemplary drugs include anti-calcification drugs, antibiotics, anti-platelet aggregation drugs, anti-inflammatory drugs, drugs which inhibit tissue rejection, anti-restenosis drugs, anti-thrombogenic drugs, thrombolytic drugs, etc. Drugs which have these therapeutic effects are well known to those of skill in the art.

Transseptal Delivery System

Figure 26:
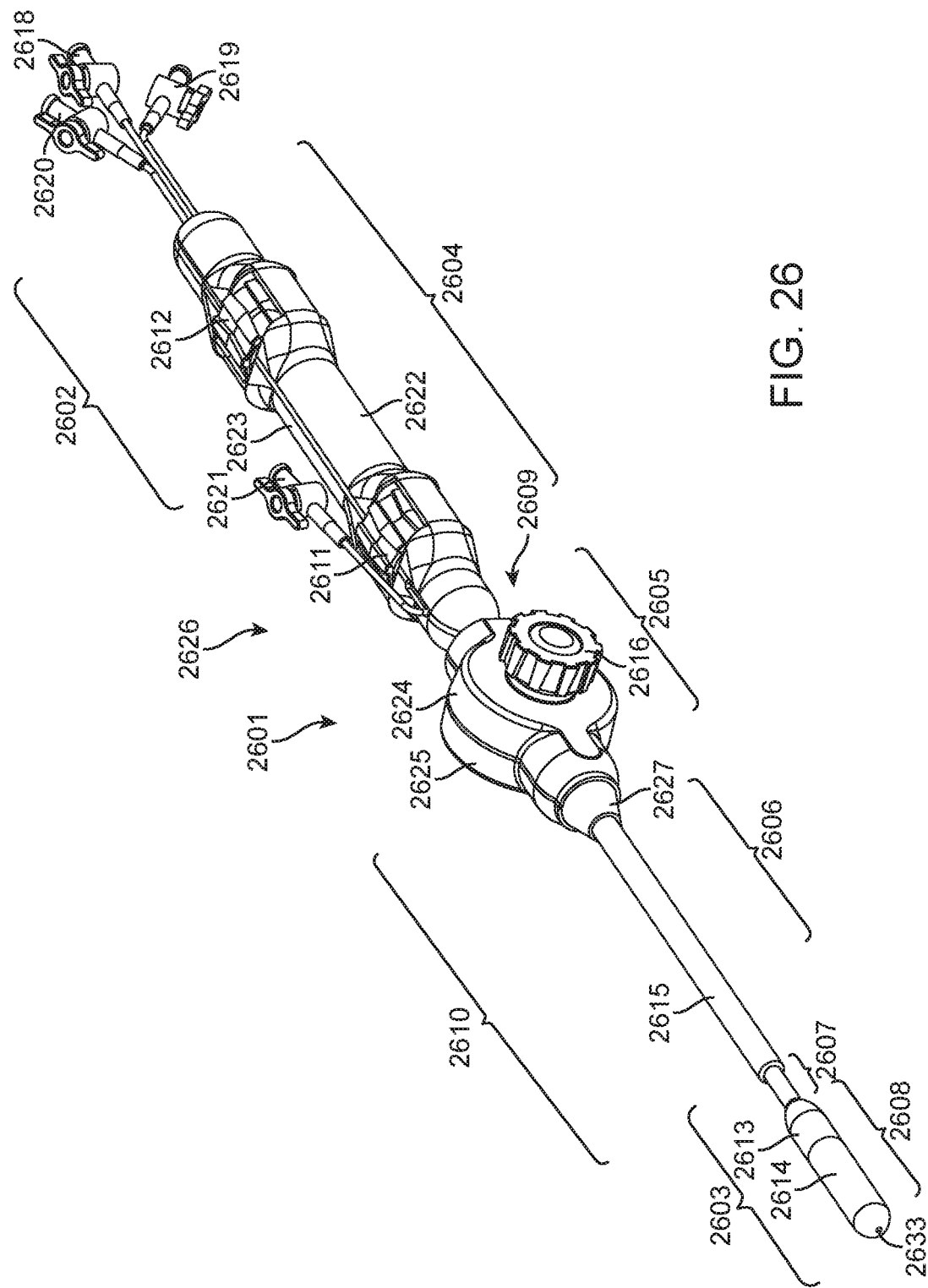
FIG. 26 is a perspective view of a transseptal delivery system for a prosthetic heart valve.

Referring to FIG. 26, one example of a transseptal delivery system for transcatheter heart valve delivery is depicted generally as 2601. In the drawings and in the descriptions which follow, the term "proximal" will refer to the end 2602 of the delivery system that is closest to the user, while the term "distal" will refer to the end 2603 that is farthest from the user. The transseptal delivery system 2601 can comprise a prosthesis such as a prosthesis capsule or valve capsule assembly 2608, a delivery catheter assembly 2607, a steering guide 2610, a delivery handle assembly 2604, and an interface 2609 between the delivery handle 2604 and steering handle 2605. The steering guide 2610 can be comprised of a steerable catheter assembly 2606 and a steering handle 2605. The valve capsule assembly 2608 can be in operable communication with the delivery handle assembly 2604 by way of the delivery catheter assembly 2607 which extends therebetween. The translational position and angular attitude of the prosthesis or valve capsule assembly 2608 can be operably controlled by the steering handle 2605 and in communication by way of the steerable catheter assembly 2606 which extends therebetween. The interface 2609 can be comprised of a slidable seal, such as an O-ring type seal. The interface 2609 can further function to allow the delivery handle or delivery catheter to translate within the steering handle while maintaining some stiction, thus preventing blood or other fluid from seeping out of the steering handle should such blood or fluid make its way up the steering catheter assembly.

Further details of a transcatheter mitral valve or any prosthesis that may be used with any of the delivery devices described herein, along with other related delivery catheters are described herein and in commonly owned U.S. Pat. No. 8,579,964 to Lane et. al., the entire contents of which are incorporated by reference herein.

Generally, delivery handle assembly 2604 includes a distal actuator such as a thumbwheel 2611 and a proximal actuator such as a thumbwheel 2612, both of which are integrally associated with the delivery handle assembly 2604, which is comprised of an A-side deli very handle housing 2622, and a B-side delivery handle housing 2623. Distal thumbweel 2611 and proximal thumbwheel 2612 are also rotatably positionable with respect to the delivery handle assembly 2604, serving as actuators by way of internal threads (not shown) and enabling translational control of various catheters within the delivery catheter assembly 2607, further evidence of which will be detailed in a later section. The delivery handle assembly 2604 is operatively coupled to the valve capsule assembly 2608 via the delivery catheter assembly 2607, which functions in one aspect as a motion translation agent. In some embodiments, the delivery handle assembly 2604, delivery catheter assembly 2607 and valve capsule assembly 2608 can form a delivery system 2626. In some embodiments, the steering handle 2605 and steerable catheter assembly 2607 can form a steering guide 2610, which provides a path through which the delivery system 2626 can translate and rotate, and from which it may take its shape in order to traverse tortuous vasculature during implantation. Taken altogether, the delivery system 2626 and steering guide 2610 can form the transseptal delivery system 2601.

Valve capsule assembly 2608 may exhibit various constructions. For example, the distal capsule 2614 and proximal capsule 2613 may be formed from substantially rigid, stainless steel, polymer, metal or otherwise rigid tubing, from collapsible, flexible tubing, or from shape-settable exotic metal alloys which exhibit shape memory characteristics and are actuated by temperature gradients inherent to the human physiology, such as nitinol. Presently, portions of the valve capsule assembly 2608 can be translatably controlled by the turning of either the distal thumbwheel 2611, or the proximal thumbwheel 2612, located in the delivery handle assembly 2604. By rotating the distal thumbwheel 2611, the proximal capsule 2614 can be translatably positioned along the axis of the capsule assembly 2608 in order to reveal certain portions of the prosthesis such as a prosthetic mitral valve for example, that is entrained within. By rotating the proximal thumbwheel 2612, the proximal capsule 2613 can be translatably positioned along the axis of the valve capsule assembly 2608, again preferably revealing and releasing certain portions of the prosthetic valve (not shown). Capsule variations will be described in detail in a later section.

Figure 32:
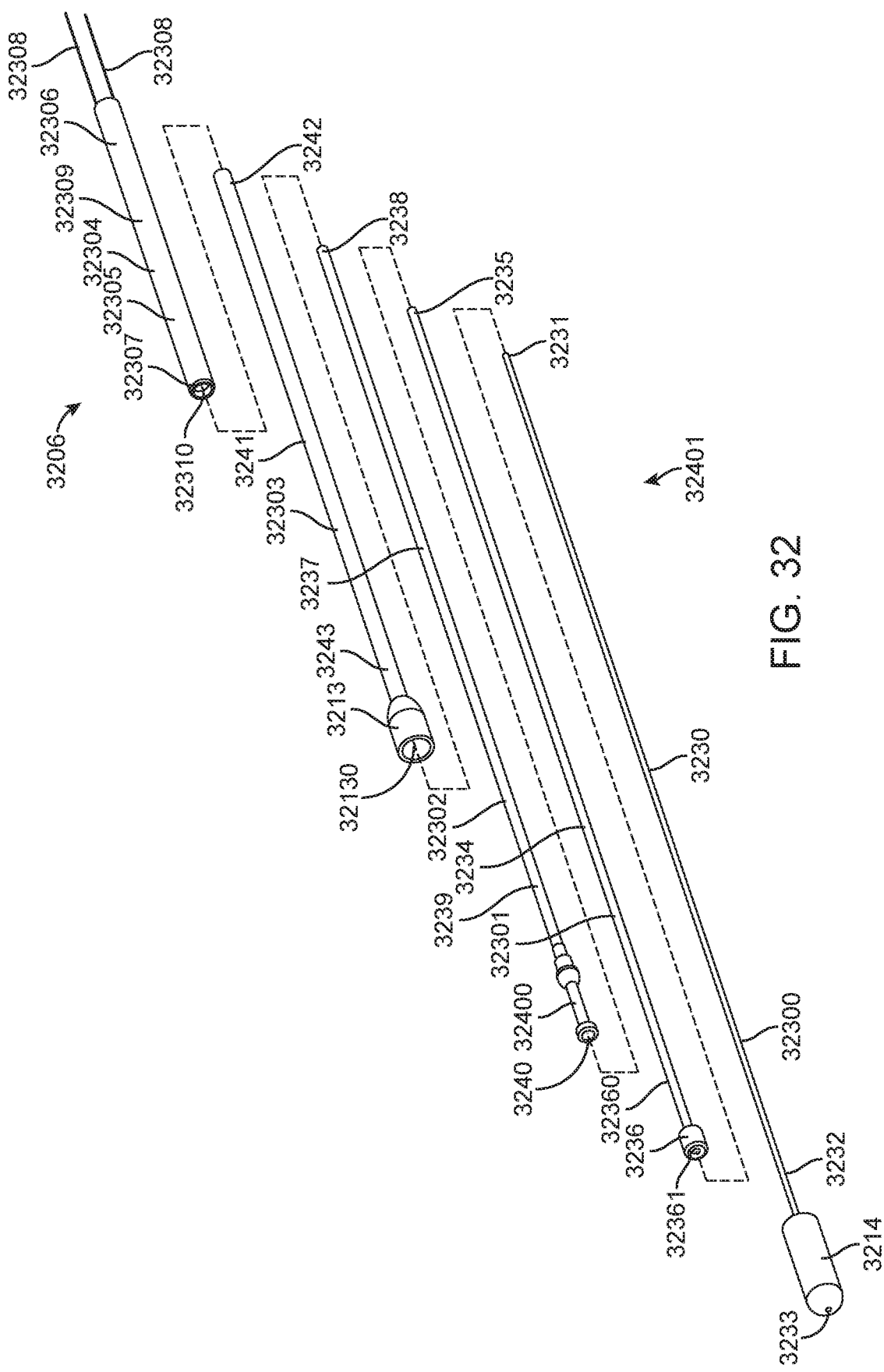
FIG. 32 is an assembly view of the delivery catheter portion of the delivery system seen in FIG. 26.

With reference to FIG. 32, the delivery catheter assembly 3206 is generally comprised of a family of nested catheters concentrically and slidably disposed over one another. The innermost catheter in the family of nested catheters is the guidewire catheter 3230 which has a distal section 3232 that is coupled to the distal capsule 3214, and a proximal section 3231, with a guidewire lumen 3233 that is generally sized to accept a guidewire running therebetween. The guidewire catheter 3230 has a constant outer diameter and a constant inner diameter throughout its entire length, as well as a flexible section 32300 which allows for articulation. The guidewire catheter 3230 is generally configured to be able to fit inside of and translate slidably with respect to the bell catheter 3234. The bell catheter 3234 has a distal section 32360 that is coupled to a bell 3236, wherein the bell can be generally cylindrically shaped having a diameter larger than the bell catheter, and a proximal section 3235, with an inner lumen 32361 that is generally sized to accept the guidewire catheter 3230 running therebetween. The bell catheter 3234 has a constant outer diameter and a constant inner diameter throughout its entire length, as well as a flexible section 32301 which allows for articulation. The bell catheter 3234 is generally configured to be able to fit inside of and slidably translate with respect to the anchoring catheter 3237. The anchoring catheter 3237 has a distal section 3239 that is coupled to an anchor 32400, wherein the anchor can be generally cylindrically shaped and have a plurality of anchoring slots circumferentially positioned to receive valve commissure anchoring portions (not shown), and a proximal section 3238, with an inner lumen 3240 that is generally sized to accept the bell catheter 3234 running therebetween. The anchoring catheter 3237 has a constant outer diameter and a constant inner diameter throughout its entire length, as well as a flexible section 32302 which allows for articulation. The anchoring catheter 3237 is generally configured to be able to fit inside of and translate with respect to the sheath catheter 3241. The sheath catheter 3241 has a distal section 3243 that is coupled to the proximal capsule 3213, wherein the proximal capsule can have a cylindrical portion terminating in a cap portion, and wherein the cap portion can have a rounded dome-like surface, and a proximal section 3242, with an inner lumen 32130 that is generally sized to accept the anchoring catheter 3237 running therebetween. The sheath catheter 3241 has a constant outer diameter and a constant inner diameter throughout its entire length, as well as a flexible section 32303 which allows for articulation. The sheath catheter 3241 is generally configured to be able to fit inside of and slidably translate with respect to the steering catheter assembly 3206. The steering catheter assembly 3206 is comprised of a steerable catheter 32309, a pull ring 32307, wherein the pull ring can have a circular ring-like shape located at the distal section 32305 of the catheter, a plurality of pull wires 32308 located at the proximal section of the catheter, a flexible section 32304 that allows for articulation, and an inner lumen 32310 running throughout the entire length. For each pull wire 32308 there is a corresponding lumen (not shown) that runs the entirety of the steerable catheter 32309.

Generally, the steering guide 2610 includes an interface section 2609 that is comprised of an O-ring type interface of cylindrical shape similar to a gasket, which is embedded within A and B side steering handle housings 2624 and 2625 respectively, the A-side steering handle housing 2624, the B-side steering handle housing 2625, an actuator such as a steering thumbwheel 2616, wherein the steering thumbwheel can have a generally cylindrical shape, a catheter strain relief 2627, and a steerable catheter assembly 2606. The steering thumbwheel can additionally include one or more protrusions separated by one or more recesses or slots to provide a surface to facilitate grasping and turning the wheel. In some embodiments, the steering thumbwheel can have a textured surface with ribs to facilitate grasping and turning the wheel. The interface section 2609 provides a dynamic seal between the steering handle 2605 and the delivery catheter assembly 2607 thus allowing for slidably sealed catheter translation thereby; the delivery catheter assembly thus may traverse therethrough and exit towards the distal end of the steering guide 2610 at the terminal, articulated end 2615 of the steerable catheter assembly 2606. While the interface section 2609 provides a dynamic seal, the delivery catheter assembly 2607 may still translate and rotate within the steering guide 2610, in order to define accurate positioning within a patient, at the target implant site. Detail regarding the implant procedure and target implant site will be discussed in a later section. In order to actuate the steerable portion of the steering catheter assembly 2606, the steering thumbwheel 2616 must be turned. When the steering thumbwheel 2616 is turned, the articulated end 2615 of the steerable catheter assembly 2606 will bend in the same direction as the direction of thumbwheel turning. This motion translation is achieved through the use of internal pull wires 32308, as depicted for example in FIG. 32, that are distally in mated connection (such as a welded connection, or using fasteners, or adhesives, or any suitable method of fastening) with a pull ring 32307, and proximally connectably communicate with the internal mechanisms which are inherent to the steering handle 2605 and will be described in further detail in a later section.

Figures 27A, 27B, 27C:
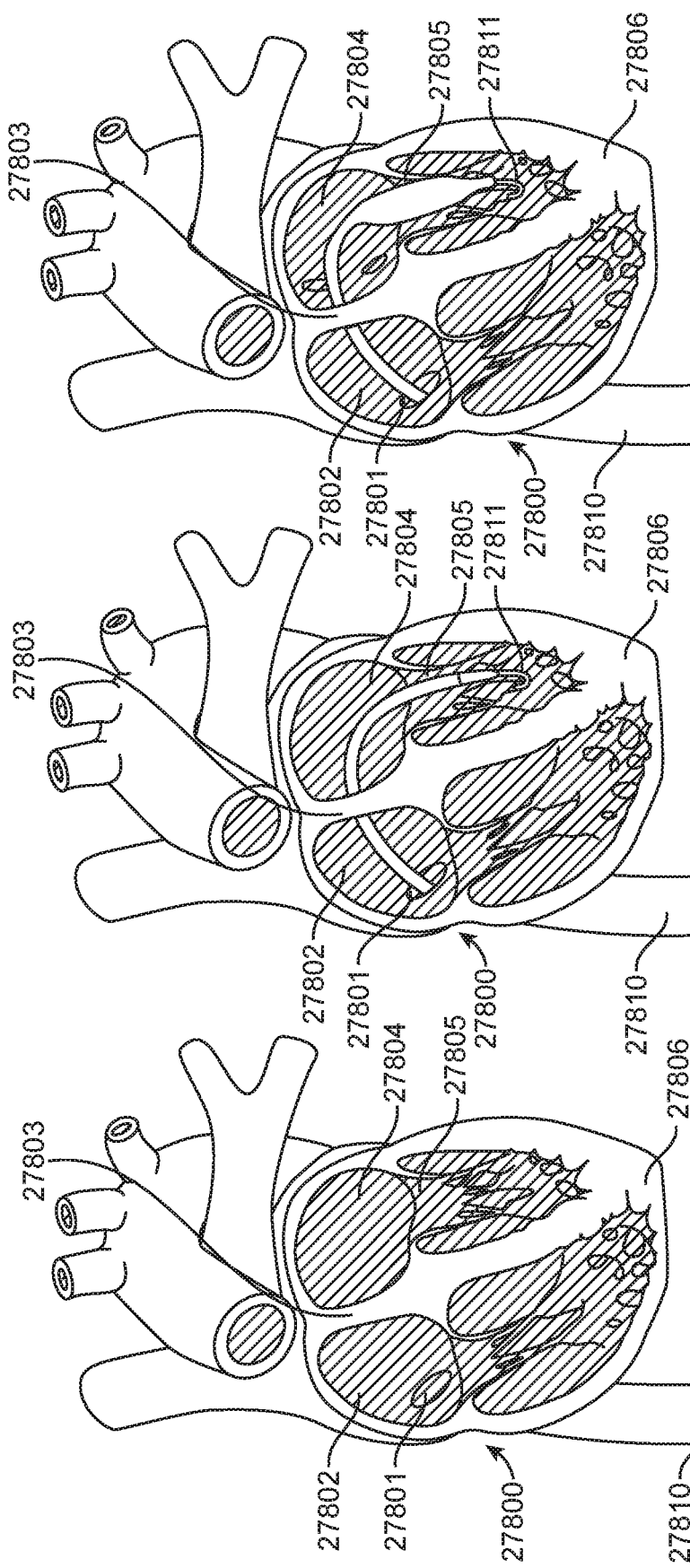

Turning now to FIGS. 27A-27F, the sequence of steps generally followed during a transseptal valve implantation are incorporated for reference. FIG. 27A describes a general depiction of a partial view (with anterior ventricular surface, pulmonary trunk, and aorta removed) of a human heart 27800. The steering guide 2607 will follow a guidewire 27811 that has previously been placed in order to provide a path that leads to the target implant site. During a typical procedure, the steering guide 2607 will enter the inferior vena cava 27810 by way of the descending inferior vena cava (not shown) and first an incision at the femoral vein near the groin (not shown). The steering guide 2607 will then exit the inferior vena cava 27810 through a caval foramen 27801 which acts as an inlet to the right atrium 27802 (FIG. 27B). Once in the right atrium 27802, the steering guide 2607 will then penetrate the foramen ovale 27803 in the septal wall and gain access to the left atrium 27804. At the left atrium 27804 (FIG. 27C), the steering guide 2610 will be aimed towards the mitral annulus 27805 in order to provide a direct channel towards the implant site (mitral annulus 27805) for the delivery catheter 27812 (FIG. 27D) to operate within. Once at the target implant site (FIG. 27E), the delivery catheter 27812 will operate to deploy the prosthetic valve 27808. Once the valve 27808 has been deployed, the delivery catheter 27812 can be fully removed (FIG. 27F).

Again turning, now to FIGS. 28A-28D, the sequence of steps generally followed during a transaortic valve implantation are incorporated for reference. FIG. 28A describes a general depiction of a partial view (with anterior ventricular surface, pulmonary trunk, and aortic root surface removed) of a human heart 28800. The steering guide 2607 will again follow a guidewire 28811 that has previously been placed in order to provide a path that leads to the target implant site. During a typical procedure, the steering guide 2607 will enter the descending aorta 28813 by way of an incision at the femoral artery near the groin (not shown). The steering guide 2607 will then continue up the descending aorta 28813 and cross the aortic arch 28814 before passing through the aortic valve 28815 and descending into the left ventricular outflow tract 28816 (LVOT). After emerging from the LVOT 28816, and entering the left ventricle 28817, the steering guide 2607 must then make a sharp turn and point upward and towards the mitral annulus 28805. At this point, the delivery catheter 28812 may be advanced within the steering guide 287 in order to approach the target implant site (mitral annulus 28805). Once at the target implant site (FIG. 27E), the delivery catheter 28812 will operate to deploy the prosthetic valve 28808. Once the valve 28808 has been deployed, the delivery catheter 28812 can be fully removed (FIG. 27F).

Figure 29:
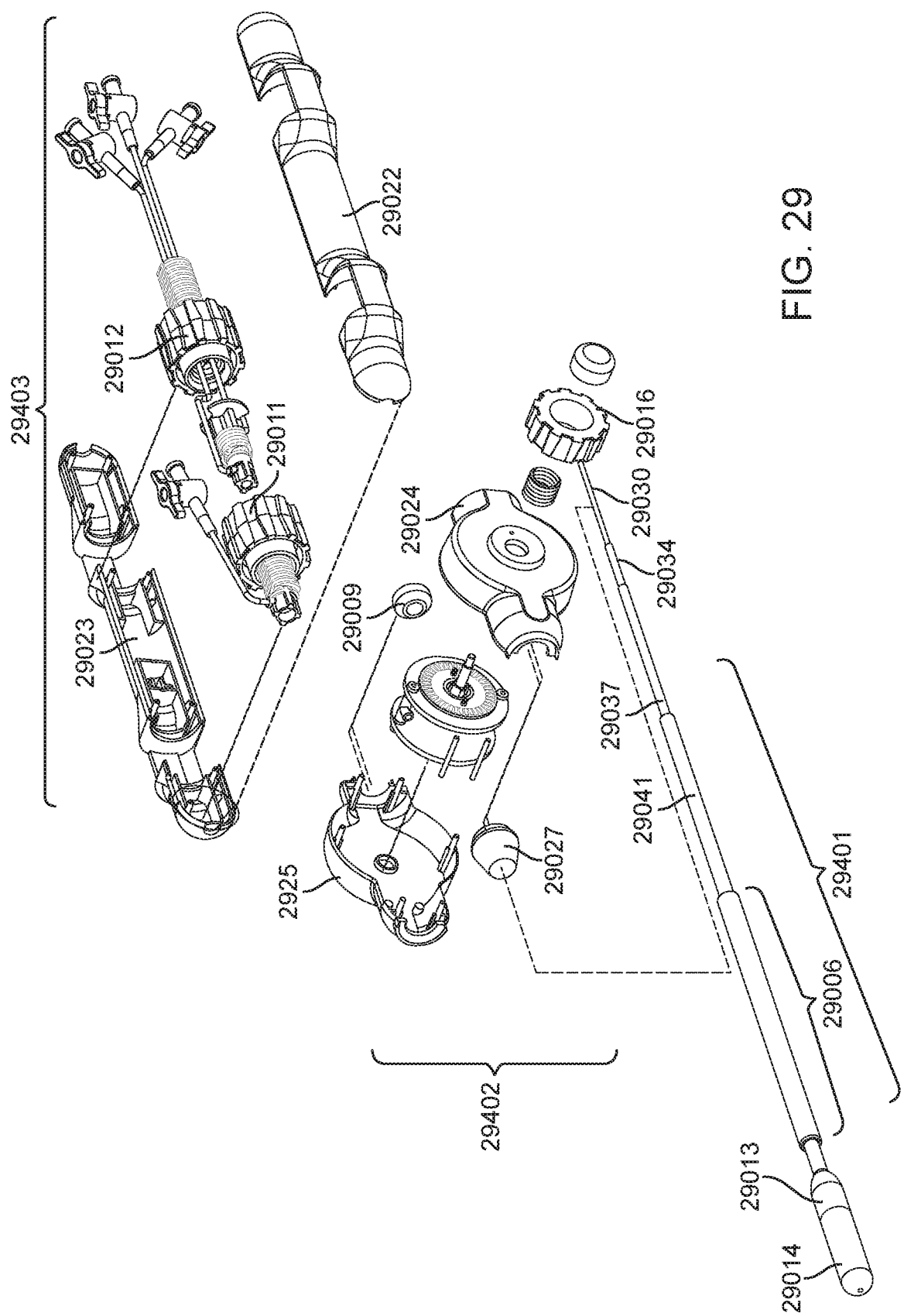
FIG. 29 is an assembly view of the delivery system seen in FIG. 26.

With particular reference to FIGS. 29-32, the internal mechanisms of the transseptal delivery system 2601 that permit functionality will be described. Specifically, FIG. 29 illustrates an example of an assembly of a transseptal delivery system 2601 shown in exploded view. The transseptal delivery system 2601 is displayed in sections in order to make description of the internal parts more easily understood. Delivery handle section 29403 will be described in further detail below with reference to FIG. 30. Steering handle section 29402 will be described in further detail below with reference to FIG. 31. Finally, delivery catheter section 29401 has previously been described above with reference to FIG. 32.

Figure 30:
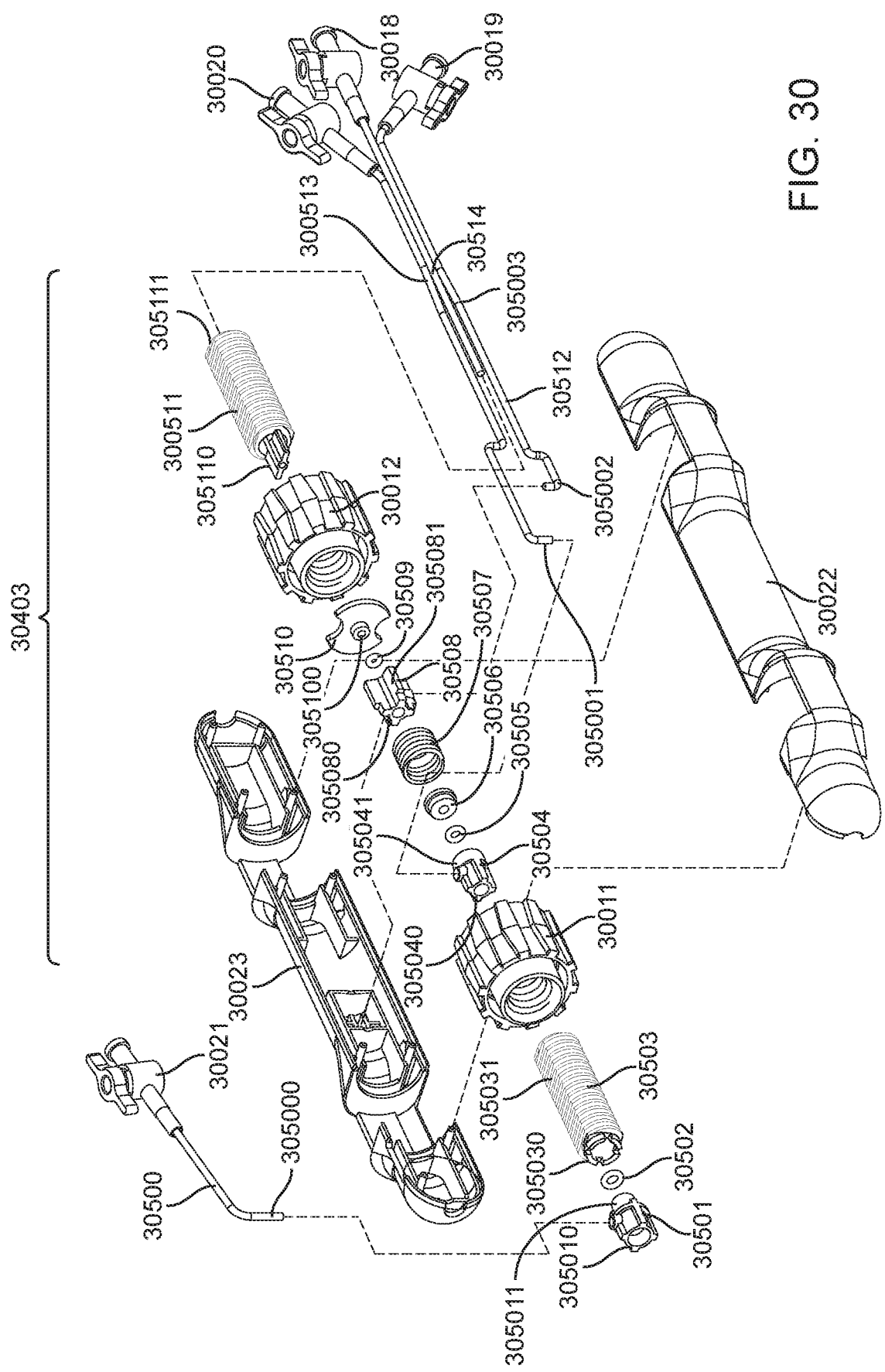
FIG. 30 is an assembly view of the delivery handle portion of the delivery system seen in FIG. 26.

Referring now to FIG. 30, the delivery handle section 30403 is generally comprised of an A-side delivery handle housing 30022 that is in mating connection with a B-side delivery handle housing 30023, actuators such as a plurality of thumbwheels (distal thumbwheel 2611 and proximal thumbwheel 2612), a plurality of force transferring leadscrews (distal leadscrew 30503 and proximal leadscrew 30511) that may translate proximally or distally depending on the rotation of the thumbwheel within said plurality of thumbwheels, a plurality of hemostatic ports and related tubing (hemo port A 2621, hemo port B 2620, hemo port C 2618 and hemo port D 2619) which provide the ability to remove entrained air boluses from concentrically nested catheters within the system, and various other components and fasteners that shall be described in further detail. Referring specifically to the motion transferring elements of the delivery handle section 30403, a distal leadscrew 30503 is in threaded connection with a distal thumbwheel 30011 and by turning said distal thumbwheel 30011, translational motion is imparted upon the distal leadscrew 30503. The motion of the distal leadscrew 30503 is transferred to the sheath catheter 3241 by way of a connection between the proximal end 3242 of the sheath catheter 3241 and the distal end 305010 of the distal leadscrew cap 30501, which itself is mated with adhesive (medical grade UV cure adhesive, or medical grade cyanoacrylate adhesive, or any suitable medical grade adhesive for plastics or polymers, etc.) to the distal leadscrew 30503. The distal leadscrew cap 30501 also permits the ejection of air by way of a sealed interface (distal O-ring 30502) between the sheath catheter 3241 and the anchoring catheter 3237, and an outlet hemo port A 2621. A stationary screw cap 30504 is entrained within the A and B side handle housings 30022, 30023 respectively, and provides location and retention for the anchoring catheter 3237, whereby the proximal end 3238 of the anchoring catheter 3237 is in mated connection (medical grade UV cure adhesive, or medical grade cyanoacrylate adhesive, or any suitable medical grade adhesive for plastics or polymers, or by way of fastening mechanical threads) with the distal end 305040 of the stationary screw cap 30504. The stationary screw cap 30504 also permits the ejection of air by way of a sealed interface (medial O-ring 30505) between the anchoring catheter 3237 and the bell catheter 3234, and an outlet hemo port B 2620. A proximal leadscrew 300511 is in threaded connection with a proximal thumbwheel 30012 and by turning said proximal thumbwheel 30012, translational motion is imparted upon the proximal leadscrew 300511. The motion of the proximal leadscrew 300511 is transferred to the guidewire catheter 3230 by way of a connection between the proximal end 3231 of the guidewire catheter 3230 and the distal end 305110 of the proximal leadscrew 300511. Proximal leadscrew 300511 motion is also transferred to the bell catheter 3234 by way of a slidable interference between the distal end 305110 of the proximal leadscrew 300511 and the proximal leadscrew plate 30510, whereby the proximal leadscrew plate 30510 is in mated connection with the proximal leadscrew cap 30508, and the proximal leadscrew cap 30508 houses the proximal end 3235 of the bell catheter 3234. The proximal leadscrew cap 30508 also permits the ejection of air by way of a sealed interface (proximal O-ring 30509) between the bell catheter 3234 and the guidewire catheter 3230, and an outlet hemo port C 2619. The proximal leadscrew 300511 permits the ejection of air by way of an outlet hemo port D 2618 which is in mated connection with the proximal leadscrew 300511.

Figure 31:
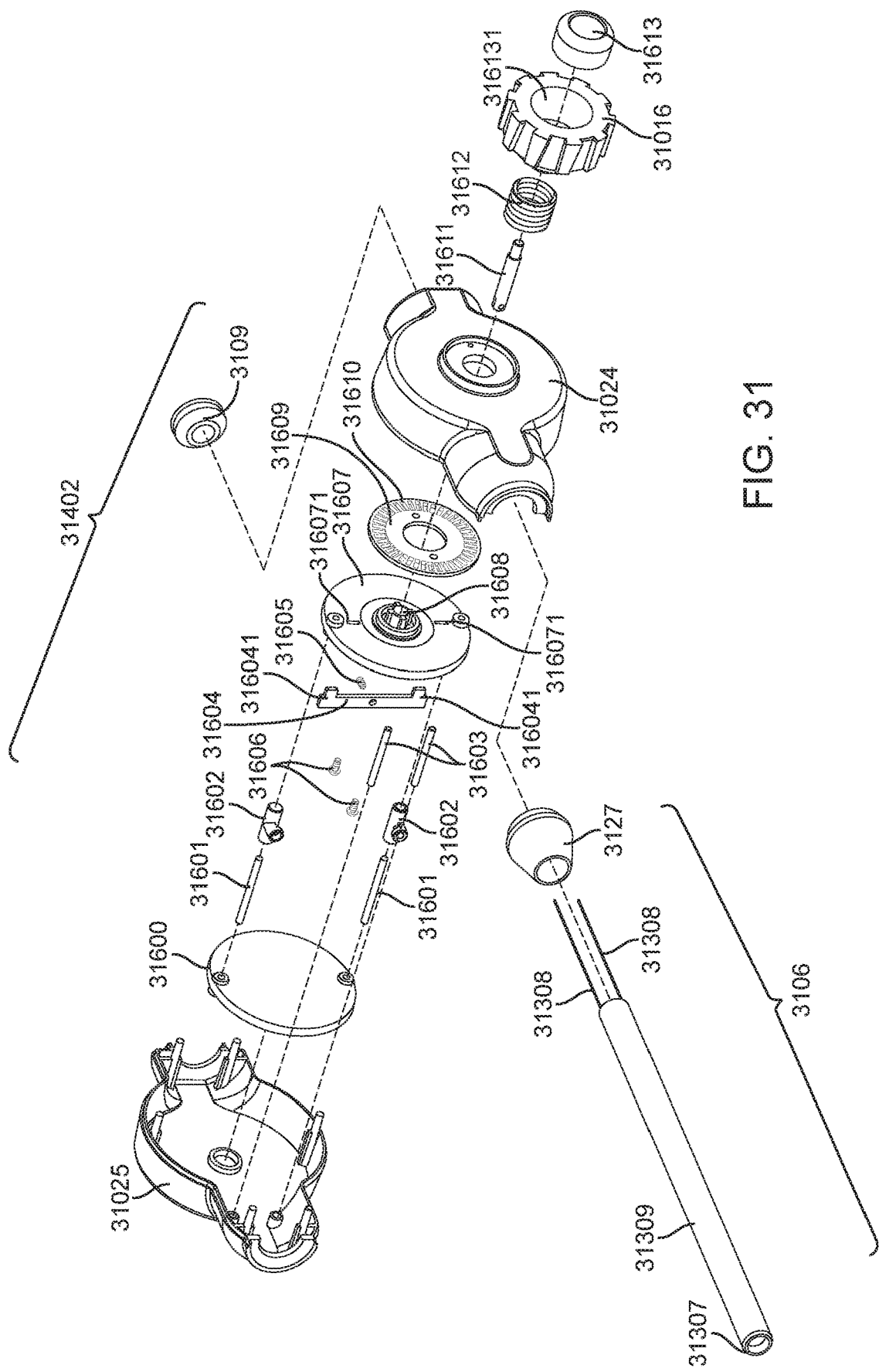
FIG. 31 is an assembly view of the steering guide portion of the delivery system seen in FIG. 26.

Referring now to FIG. 31, the steering handle section 31402 is generally comprised of an A-side steering handle housing 31024 that is in mating connection with a B-side steering handle housing 31025, a steerable catheter assembly 2606 that is in mating connection with a catheter strain relief 2627, an interface 2609, a plurality of rotatable disks (B-side rotatable disk 31600 and A-side rotatable disk 31607), a steering thumbwheel 31016, a push button 31613, and various other components and fasteners that shall be described in further detail. Referring specifically to the steering elements of the steering handle section 31402, a steering thumbwheel 31016 is in mating connection with a locking hub 31608 that is centered within the A-side rotatable disk 31607. The A-side rotatable disk 31607 and B-side rotatable disk 31600 are coupled together by way of a plurality of carrier rods 31601, and work mechanically to spin within the handle housing that is comprised of the A-side steering handle housing 31024 and B-side steering handle housing 31025. Since the A-side rotatable disk 31607 is connected to the steering thumbwheel 31016, rotation of the steering thumbwheel 31016 causes rotation of the A-side rotatable disk 31607. A specific function of the plurality of rotatable disks (B-side rotatable disk 31600 and A-side rotatable disk 31607) is to actuate the plurality of pull wires 31308 by way of tensioning hinges 31602 that may spin freely on the carrier rods 31601 and that are also connected to the pull wires 31308 and also apply tension to them when turned. Referring now specifically to the locking elements of the steering handle section 31402, a push button 31613 is in threaded connection with a push button pin 31611 that acts as a shaft. The push button 31613 is located within a cavity 316131 that allows for direct translation when the button is depressed. A push button spring 31612 is housed between the inside surface of the push button 31613, and the bottom of the cavity 316131 and provides return force for when the depressed push button 31613 is released. Motion from the push button 31613 is transferred along the push button pin 31611 directly to a cross bar 31604 that is fastened to the push button pin 31611 by way of a setscrew 31605. When the push button pin 31611 translates as the push button 31613 is depressed, the cross bar 31604 also translates and a plurality of cross bar pegs 316041 that are located on the ends of the cross bar 31604 thus translate as well. When in an un-depressed state, the cross-bar pegs 316041 are seated within a plurality of slots 316071 that appear on the periphery of the A-side rotatable disk 31607. The cross bar pegs 316041 then also project through the slots 316071 and may rest within any of the circumferential slits 31610 that appear in an array about the periphery of a position disk 31609 that is mounted to the inside surface of the A-side steering handle housing 31024 by threaded fasteners 31606. When in a depressed state, the cross bar pegs 316041 are moved away from the circumferential slits 31610 until clearance is achieved, and the locking mechanism enables free rotation of the cross bar 31604, as well as all aspects that are directly connected to the A-side rotatable disk 31607. Further detail regarding the mechanics behind the locking mechanism can be seen in FIG. 34, which is incorporated herein for reference.

By way of cross-sectional illustration, FIGS. 33A-33D show specific internal features of the devices described herein, and will now be relied upon to reveal further detail. FIG. 33A depicts the entire transseptal delivery system 3301 comprised of a distal end 333, a steerable catheter assembly 3306, a steering handle 335, and a delivery handle assembly 334 therebetween the distal end 333 and the proximal end 3302. At the distal end 333 of the transseptal delivery system 3301 is located the distal 3314 and proximal 3313 capsules, which entrain a prosthetic valve therein. An articulated end 3315 of the steerable catheter assembly 3306 is in mating connection with the distal-most portion of the steering handle 335, which locates and controls it thereby. The steering thumbwheel 3316 provides actuation control of the articulated end 3315 of the steerable catheter assembly 3306. Continuing proximally, the delivery handle assembly 334 is depicted, which houses the distal 3311 and proximal 3312 thumbwheels, each being responsible for the translation of the proximal 3313 and distal 3314 capsules, respectively. A hemo port A 3321 is provided and housed by the a-side delivery handle housing 3322 and b-side delivery handle housing 3323 (not shown). Further hemo ports B, C, and D (3320, 3319, and 3318 respectively) are also provided, the functions of which being described in greater detail in previous sections.

FIG. 33B introduces a cross-sectional view AA of the aforementioned depiction in FIG. 33A, which reveals the internal mechanisms of the distal end 333, the steering handle 335, and the delivery handle assembly 334. Cross-section AA of FIG. 33B shows the internal surfaces of the distal capsule 3314, and the proximal capsule 3313, as well as the articulated end 3315 of the steerable catheter assembly 3306, all of whose mechanical interactions have been described previously above. Also depicted is an internal view of the steering handle 335, and the delivery handle assembly 334 which displays the elements distal 3311 and proximal 3312 thumbwheels, and a-side delivery handle housing 3322. A detail section C 33250 is provided, whereby the enlarged illustration of the contents of detail section C 33250 appear in FIG. 33C.

As mentioned, FIG. 33C is the enlarged illustration of the contents of detail section C 33250 of FIG. 33B, and further detail of the internal features of the valve capsule assembly 3308 are hereby provided. It can be seen that the distal capsule 3314 is internally threaded at a threaded portion 33460, which provides mating means for a guidewire catheter threaded insert 33490 that is embedded near the distal end 3332 of the guidewire catheter 3230. Similarly, the bell 3236 is internally threaded at a threaded portion 33470, which provides mating means for a bell catheter threaded insert 33500 that is embedded near the distal end 33360 of the bell catheter 3234. Similarly, the anchor 33400 is internally threaded at a threaded portion 33480, which provides mating means for an anchoring catheter threaded insert 33510 that is embedded near the distal end 3339 of the anchoring catheter 3337. Further regarding the bell 3236, it can be seen that the bell 3236 is shown in position and concentrically oriented to the distal most portion 33450 of the anchor 33400, over which it may translate when actuated accordingly by the delivery handle assembly 334 (not shown). It should be apparent that the connected pair that is comprised of the distal capsule 3314 and guidewire catheter 3230 may move in tandem concentrically within the similarly connected pair that is comprised of the bell 3236 and bell catheter 3234, which may also move in tandem concentrically within the similarly connected pair that is comprised of the anchor 33400 and anchoring catheter 3237 which are stationary, but inherently flexible by virtue of their construction. The proximal capsule 3313 by way of attachment to the sheath catheter 3241 also form a connected pair that may move in tandem concentrically over the previously discussed catheters.

FIG. 33D depicts the result of the cross-section B-B introduced in FIG. 33A. As previously described, a plurality of handle housings, A-side 3324 and B-side 3325 are in mated connection and form the entirety of the housing which comprises the steering handle 335. Within this cross-section B-B of FIG. 33D can also be seen a plurality of carrier rods 33601 that matingly pin together the A-side 33607 and B-side 33600 rotatable disks. Also shown are the cross bar 33604, push-button pin 33611, and setscrew 33605 that fasten said bar and said pin together in mating connection. The steering thumbwheel 3316, which houses the push button 33613 and by extension the push button spring 33612 is further revealed, additionally.

Figure 34A:
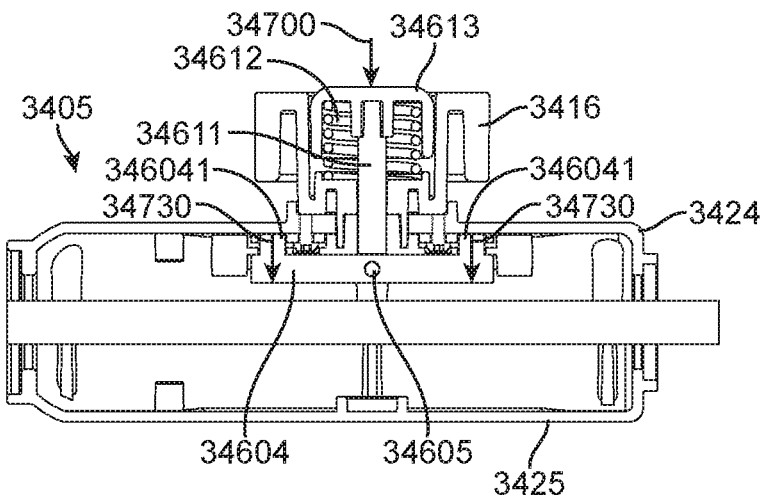
FIGS. 34A-34C are cross-sectional views of the steering handle portion taken along the line A-A in FIG. 33A.
Figure 34B:
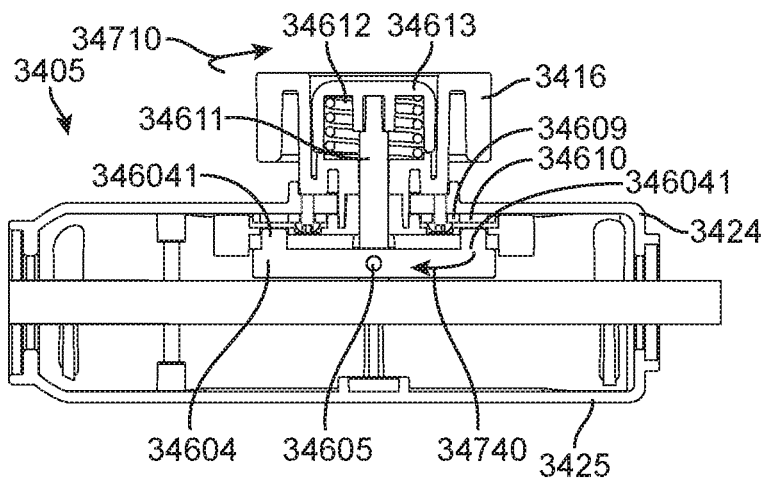
Figure 34C:
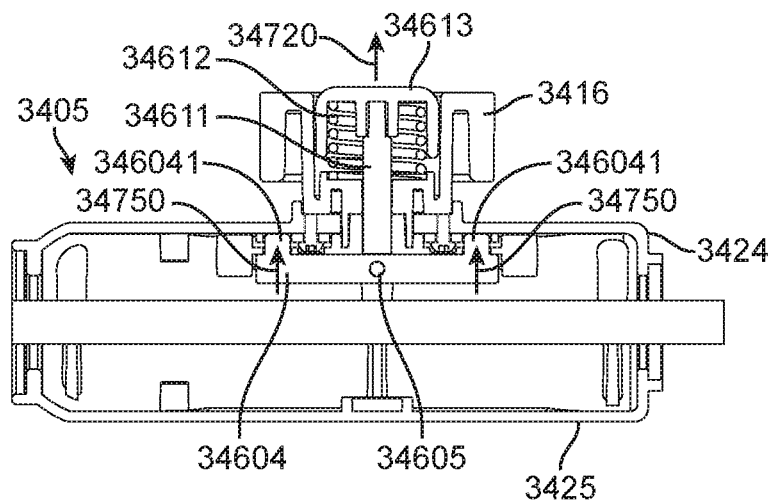

FIGS. 34A-34C illustrate the internal mechanics of the locking mechanism that is inherent to the steering handle 335 (of which these figures provide a cross-sectional view), and further illustrate the dynamic relationships between the components, and the manner in which they may be operated. Beginning with FIG. 34A, the sequence of operation that comprises pushing a button, turning a knob, and then releasing the button while maintaining an achieved angular position by the button is set forth. Specifically, FIG. 34A depicts the depression (arrow indicating translation 34700) of the push button 34613 that is mounted within the steering thumbwheel 3416 and biased internally by the opposing force of the push button spring 34612. As the push button 34613 is matingly connected to the cross bar 34604 by way of the push button pin 34611 and the setscrew 34605, when the push button 34613 is translated through depression, the cross bar 34604 is also translated (arrows indicating translation 34730) in the same direction as the push button 34613. Once the cross bar 34604 is fully translated, a plurality of cross bar pegs 346041 described on the ends of the cross bar 34604 become disengaged from circumferential slits 34610 (FIG. 34B) that are provided by the position disk 34609 (FIG. 34B).

Continuing within FIG. 34B, once the cross bar 34604 is unconstrained it is thus free to rotate (arrows indicating rotation 34740) by the application of a torque to the steering thumbwheel 3416 (arrows indicating rotation 34710).

FIG. 34C provides the final step in the operation of the push button 34613 mechanism of the steering thumbwheel 3416 for steering and positional lockout. After the appropriate rotational position is achieved with the steering thumbwheel 3416, the push button 34613 is released. This allows for translation in the opposite direction (arrows indicating translation 34720) to that experienced when the push button 34613 is depressed, due to the biasing force of the push button spring 34612. Releasing the push button 34613 also allows the cross bar 34604 to translate (arrows indicating translation 34750) and by extension, the cross bar pegs 346041 may thus achieve re-engagement with the circumferential slits 34610 (FIG. 9B) and provide lockout against further rotation of the steering thumbwheel 3416 and by extension disruption of position of the steerable catheter 34309 (not shown).

Turning now to FIGS. 35A-35D, a sequence of images is provided which depict the rotation of the steering thumbwheel 3516 and the ensuing effect at the valve capsule end of the system. Beginning with FIG. 35A, when a torque is applied to the steering thumbwheel 3516, rotational motion is transferred to the A-side rotatable disk 35607, which is in communication with a plurality of pull wires 35308 that are further internally embedded at the articulated end 3515 of the steerable catheter assembly 356. The pull wires act to preferentially pull the articulated end 3515 of the steerable catheter assembly 356 in the direction of steering thumbwheel 3516 rotation. Further application of torque (FIG. 35B-35D) results in a further rotation of the steering thumbwheel 3516 and yet further bending of the articulated end 3515 of the steerable catheter assembly 3106.

Now with specific reference to FIGS. 36A-36D, a particular example of a valve capsule assembly 3608, and general deployment sequence of a transcatheter valve prosthesis are herein illustrated. Details regarding the transcatheter valve prosthesis referenced herein may be any of the prostheses disclosed herein and are described in commonly owned U.S. Pat. No. 8,579,964 to Lane et. al. As depicted in FIG. 36B, a transcatheter valve prosthesis 361100 is entrained within the valve capsule assembly 3608, after having been preferentially crimped (details regarding the loading device used to crimp the transcatheter valve prosthetic are described in commonly owned U.S. Pat. Publication. No. 2014/0155990, the entire contents of which are incorporated herein by reference, and loaded therein. The valve capsule assembly 3608 can comprise a generally cylindrical structure having a proximal end and a distal end, wherein each of the proximal and distal ends terminates in a rounded dome-like surface. As shown in FIGS. 36A, the valve capsule assembly can comprise a proximal capsule 3613 and a distal capsule 3614, wherein the proximal capsule 3613 is disposed at a proximal end of the valve capsule assembly, and the distal capsule 3614 is disposed at a distal end of the valve capsule assembly. Each of the proximal capsule 3613 and the distal capsule 3614 can have a cylindrical portion with one end of the cylindrical portion having an open circular shape and the other end having a cap portion that can have a rounded dome-like surface. As shown in FIG. 36B, the open circular shape of proximal capsule 3613 can be configured to meet with or abut against the open circular shape of distal capsule 3614, with the cap portion of the proximal capsule forming the proximal end of the valve capsule assembly, and the cap portion of the distal capsule forming the distal end of the valve capsule assembly.

FIG. 36C illustrates the valve 361100 in staged deployment after the proximal capsule 3613 has been translated away from the valve 361100, and the atrial skirt 361101 has been revealed and allowed to self-expand.

FIG. 36D illustrates the valve 361100 with the atrial skirt 361101 fully expanded, after the distal capsule 3614 has been translated away from the valve 361100. A plurality of trigonal anchoring tabs 361102 have also been revealed by the movement of the distal capsule 3614.

FIG. 36E illustrates final deployment of the valve 361100, whereby the distal capsule 3614 has translated to its maximum displacement, and the bell 3636 on the bell catheter has also translated maximally in order to release anchoring features of the valve (not shown) until finally full release of the valve from the delivery device has been achieved, and the valve 361100 is no longer anchored to any part of the valve capsule assembly 3608.

User Interface Stops

In some situations, it may be desirable to provide user interface stops on the delivery system so that the operator does not inadvertently deploy the prosthesis prematurely. Various stopping mechanisms may be incorporated into the delivery system.

A first stopping mechanism may be included in the delivery system to prevent the operator from inadvertently releasing the elbows on a prosthetic mitral valve. The elbows are the inferior portion of the ventricular anchor tabs adjacent to the connection point of the ventricular anchor tab with the ventricular skirt. In any of the delivery systems disclosed herein, an outer sheath is retracted from the prosthesis and the superior tips of the ventricular anchor tabs (anterior and posterior) initially self-expand radially outward and in a transverse position relative to the longitudinal axis of the prosthesis. The transverse position is horizontal or nearly horizontal relative to the longitudinal axis of the prosthesis. With further retraction of the sheath, the elbows become unconstrained and the ventricular anchor tabs spring fully open and the tab returns to an inferior/superior orientation that is substantially vertical or substantially parallel to the longitudinal axis of the prosthesis. Once the elbow is unconstrained, it is challenging and may not be possible to resheath and recover the ventricular anchor tabs in case they were improperly deployed. Also once the ventricular anchor tabs are released and fully deployed it becomes challenging or may no longer be possible to resheath the remainder of the prosthesis in case delivery needs to be aborted or the prosthesis requires repositioning.

FIGS. 37A-37I disclose a hard stop mechanism that may be included on any of the delivery system handles disclosed herein, or elsewhere to prevent the operator from inadvertently retracting the sheath far enough to fully release the elbows. As the operator retracts the sheath, the hard stop will prevent further retraction until the operator actuates a release mechanism such as a button, switch or other mechanism to allow further retraction of the sheath and eventual release of the elbows. Thus, once the operator is confident that he/she is ready to fully release the ventricular anchor tabs, the release mechanism may be actuated thereby allowing the operator to continue retracting the outer sheath and releasing the elbows on the ventricular anchor tabs.

Optionally, a second stop may also be included in any of the delivery systems disclosed herein. Again, operation of delivery systems allow the operator to continue to deploy the prosthesis. After deployment of the ventricular anchors, further deployment allows the operator to retract the bell catheter which then removes a constraint from the commissure tabs thereby allowing the commissure tabs to uncoupled from the hub catheter slots and then the prosthesis is fully uncoupled from the delivery catheter. At this point it is challenging or may not be possible to retrieve the commissure tabs or the prosthesis if needed. The second stop therefore similarly prevents the operator from releasing the commissure tabs before the operator is certain that he/she wishes to proceed and this may help prosthesis retrieval or resheathing if needed.

The second stop may be any number of stop mechanisms which can be actuated to allow the operator to proceed with release of the commissure tabs. The stop mechanism may be a button, switch or any other mechanism.

Figure 37A:
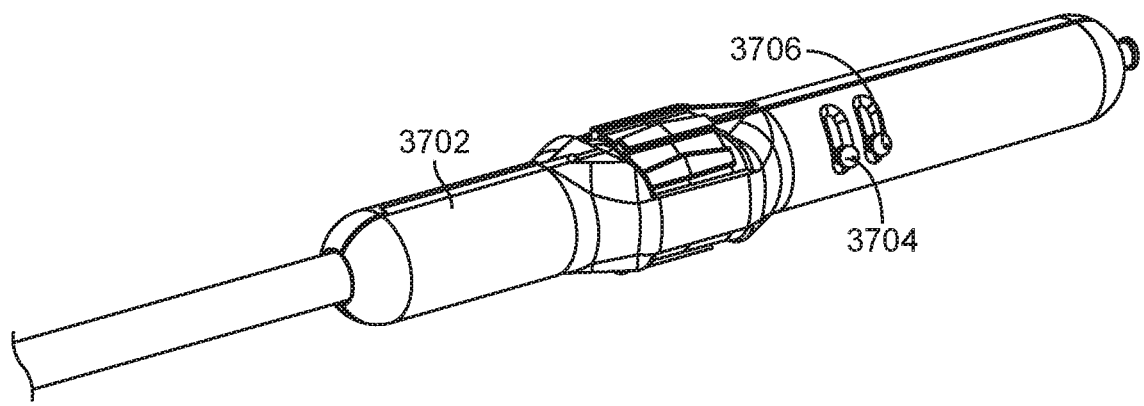
FIGS. 37A-37I show the use of stops to control actuation of a delivery catheter.

FIG. 37A shows a handle 3702 of a delivery system that may be the handle in any delivery system disclosed herein. The handle 3702 includes one or both hard stops 3704, 3706 which each have a locked position and an unlocked position. Here, both hard stops or switches 3704, 3706 are in the down or locked position which will prevent certain actuation of the handle.

Figure 37B:
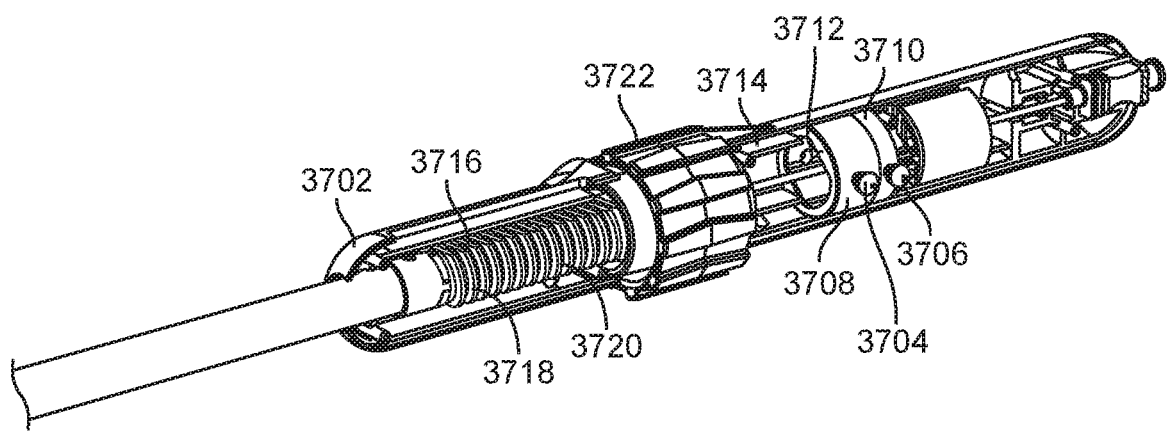

FIG. 37B shows a partial cutaway of the handle 3702 in FIG. 37A. Here, similar as to the other delivery mechanisms disclosed herein, a lead screw 3720 is actuated by rotation of a wheel or knob 3722 such that rotation of wheel 3722 is translated into axial movement of lead screw 3720 to move the various shafts as described previously. The lead screw is contoured to have a flat surface 3716 and a rounded surface 3718. Two blocks 3708 and 3710 are actuated by movement of switches 3704, 3706 to allow or prevent motion. Here, both blocks 3708, 3710 also have a rounded interior surface 3714 and a flat surface 3712 to match the rounded and flat surfaces 3718, 3716 on the lead screw. However, when the switches 3704, 3706 are in the locked position, the rounded and flat surfaces of the blocks are not registered with the rounded and flat surfaces of the lead screw and thus the lead screw will be unable to move through and past either block 3708, 3710. However, rotation of wheel 3722 will retract the lead screw proximally until the proximal end of the lead screw abuts the distal end of block 3708. This motion is enough to allow the atrial flange on the prosthesis to deploy as described previously.

Figure 37C:
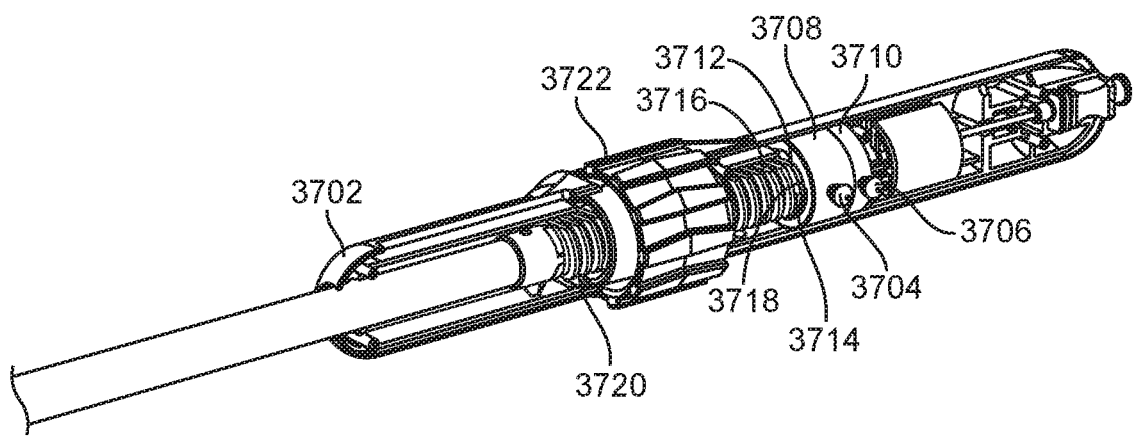

FIG. 37C shows the lead screw 3720 proximally retracted until its proximal end abuts the distal end of block 3708 and stops, thereby retracting the outer sheath and allowing the atrial flange to deploy on the prosthesis.

Figure 37D:
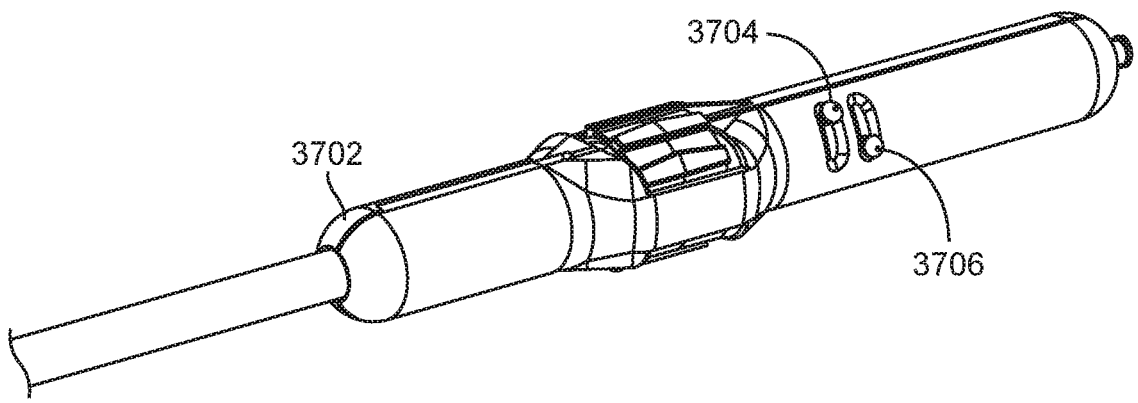

In FIG. 37D switch 3704 is flipped to the unlocked position while switch 3706 remains in the locked position.

Figure 37E:
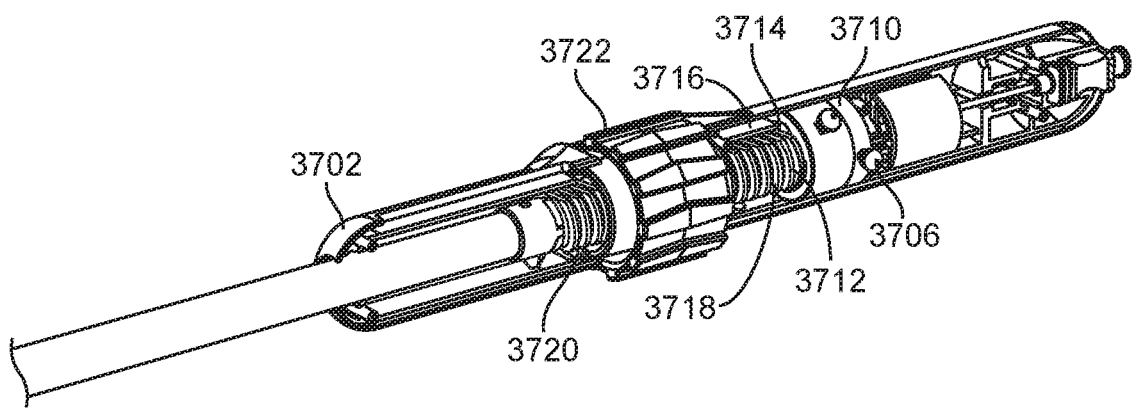

FIG. 37E shows the flat and rounded portions 3716, 3718 of the lead screw 3720 aligned with the flat and rounded portions 3714, 3712 on the distal block 3708 so that the rotation of wheel 3722 retracts the lead screw further into block 3708.

Figure 37F:
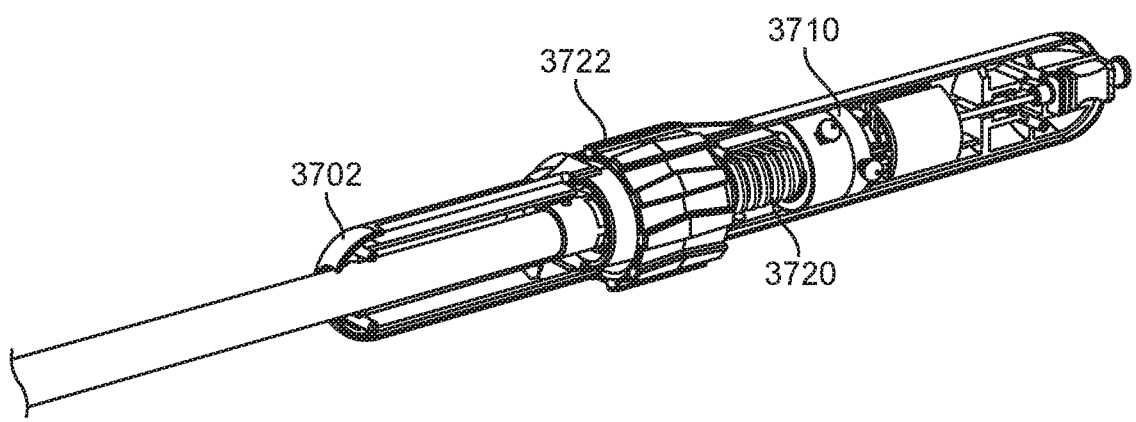

FIG. 37F shows the lead screw fully retracted until the proximal end of the lead screw abuts the distal end of block 3710 which is not registered with the lead screw since the switch is in the locked position. This further retracts the sheath and deploys the prosthesis. Here the annular region and ventricular skirt region deploy as well as the ventricular anchor tabs partially deploy.

Figure 37G:
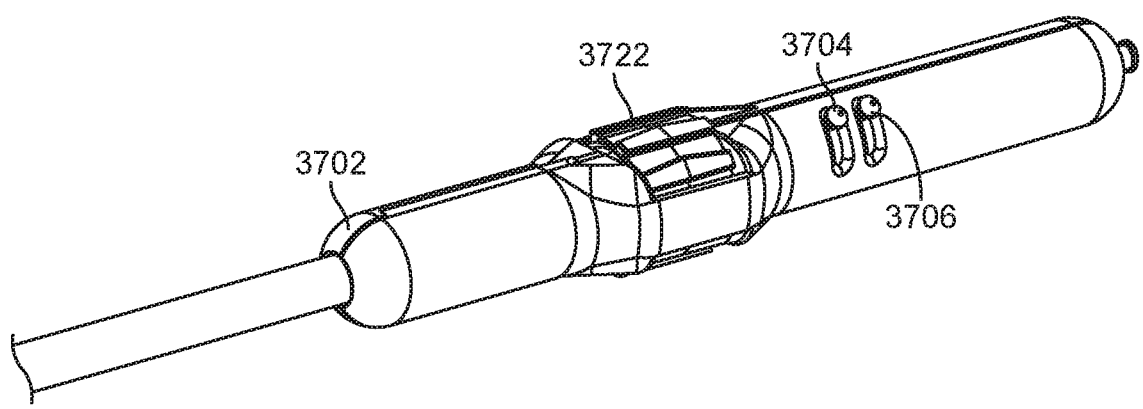

In FIG. 37G both switches 3704, 3706 are now disposed in the unlocked position.

Figure 37H:
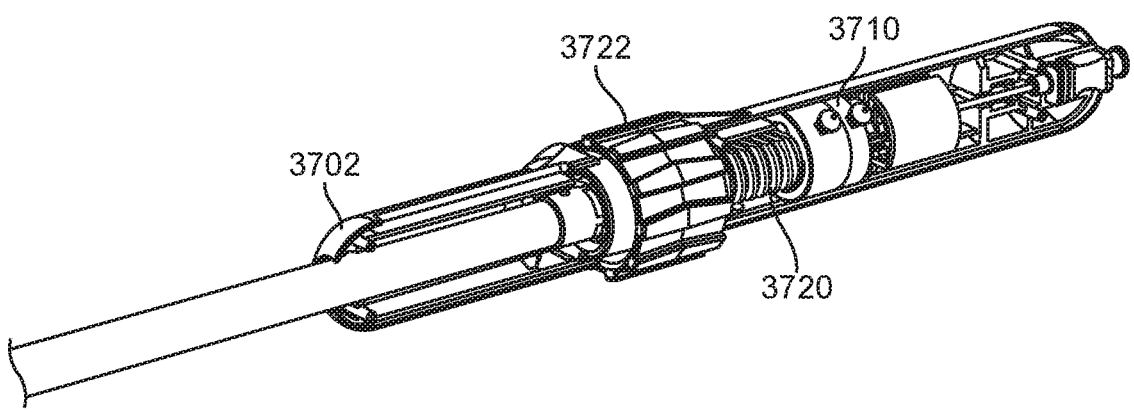

In FIG. 37H rotation of wheel 3722 continues to move the lead screw into block 3710 further retracting the sheath and releasing the elbows of the anchor tabs and allowing them to fully deploy.

Figure 37I:
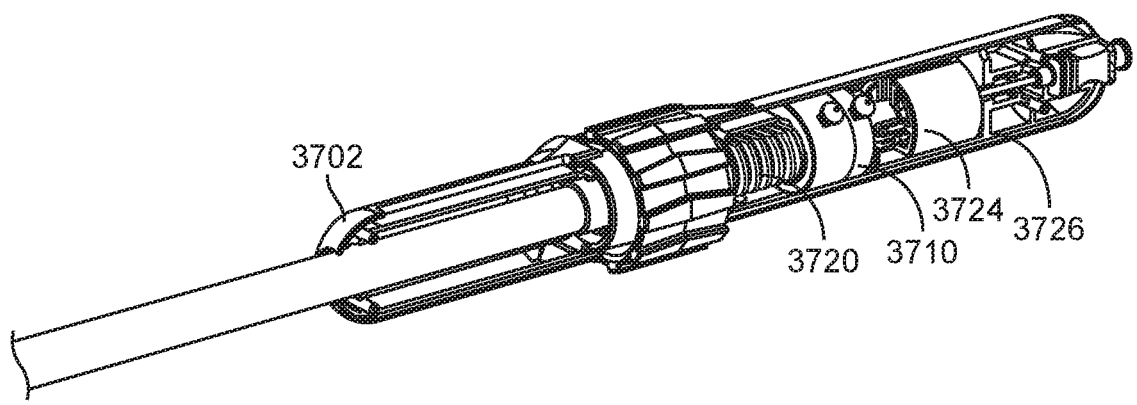

In FIG. 37I, the lead screw 3720 passes through block 3710 and pushes the bell slider 3724 back proximally until it abuts against a stop wall 3726. At this point the sheath is fully retracted and the bell catheter is fully retracted thereby allowing the prosthesis to fully release from the delivery catheter as the commissure tabs release from slots in the hub or anchor element.

Optionally in any example, the delivery system may include a third or more stops. For example, the first stop may be used to control deployment of one or both anterior ventricular anchor tabs, a second stop may be used to control deployment of the posterior ventricular anchor tab, and a third stop may be used to control deployment of the commissure tabs. In another example, a first stop may be used to control deployment of one anterior ventricular anchor tab, a second stop may be used to control deployment of a second anterior ventricular anchor tab, a third stop may be used to control deployment of the posterior anchor tab, and a fourth stop may be used to control deployment of the commissures. Optionally, in any example, there may be a hard stop on other stages of prosthesis deployment, such as during the initial deployment of the atrial skirt. The optional hard stop may be any of the mechanisms disclosed herein or otherwise known in the art. Therefore any number of stops may be used to control deployment of any of the various portions of the prosthesis.

Retrievability

In some circumstances is may be desirable to retrieve the prosthesis from a partially or fully deployed state in order to adjust position of the prosthesis, abandon the procedure, or for other reasons.

The retrieval mechanisms allow the operator to fully recapture the prosthesis after the elbows have been deployed and prior to release of the commissure tabs. Control cables or tethers may be disposed in the delivery system handle and allow individual tensioning of each elbow. The control cables or tethers may be coupled directly to the prosthesis or to a deployment control mechanism operably coupled to one or more of the elbows in the prosthesis. The deployment control mechanism may be used to control deployment of the elbow and retrieval of the prosthesis. In other examples, a catheter may be used that has attachments to the tethers at the very distal end of the delivery system. The tensioning can be individual or group controlled depending on the mechanism and desired behavior.

Tension may be adjusted individually, or in unison. The tension control cables also may allow tension control in the crescents in unison. The crescents are portions of the ventricular skirt on the prosthesis frame just superior to the commissure tabs.

In one example, upon deployment of the prosthesis, no other materials other than the prosthesis are left behind in the patient. Any of the examples disclosed herein may be used with the transapical or transseptal delivery systems disclosed herein.

The cables or tethers may be a single filament (three for the elbows, and three for the crescents), or the cables maybe comprise two filaments for each elbow and each crescent, where the two filaments are formed from a single filament looped around the elbow or crescent allowing them to be removed post implant or to tack them at the apex of the heart if required by retracting one of the free ends of the filament. Any of the tethers disclosed herein may also be a single filament with a closed loop. Both strands in the closed loop pass through the elbow and attach to the post or tab on the anchor element. When the capsule is deployed and the loop is allowed off the post, then the whole closed loop pulls back through the elbows and the loop is retracted into the delivery system.

In another example, the tethers may remain attached to the prosthesis thereby providing another opportunity for the tethers to be manipulated. For example, in the situation when the prosthesis has not been properly deployed and retrieval was not successful, the tethers may still be anchored at the location where the delivery device was inserted into the heart, thereby providing supplemental anchoring of the prosthesis. Therefore, some or all of the tethers may be removed from the prosthesis or some or all of the tethers may remain connected to the prosthesis after delivery and deployment.

FIGS. 38A-38C illustrate an example that uses tethers to control prosthesis deployment.

In FIG. 38A the prosthesis 3802 is partially deployed as previously described above with the atrial flange, annular region and ventricular anchors 3804 (anterior and posterior) partially deployed. The elbows 3806 of the ventricular anchors are still partially constrained by the distal capsule 3808.

In FIG. 38B the elbows 3812 are released from the distal capsule and allowed to spring fully open into a substantially vertical configuration. Tethers 3810 remain coupled to the elbows, thus if needed tension may be applied to the tethers to collapse and recapture the elbows so that the entire prosthesis may be recaptured in the sheath/capsules and then either repositioned and redeployed, or the procedure may be abandoned and the catheter with prosthesis withdrawn from the patient. The tethers may be suture material, wires, or other elongate filaments than span the length of the catheter and can be controlled at the proximal end of the delivery device from the handle or any other tether control mechanism. Additionally, when the elbows are disposed in the capsule, the capsule helps prevent release of the tethers from the elbows.

FIG. 38C shows release of the tethers 3810 from the elbows after the prosthesis is properly positioned and then the commissure tabs may be released from the anchor hub. The tethers may be retracted from the patient at the same time the catheter is withdrawn from the patient, or the tethers may be retracted first independently of catheter withdrawal. Here, three tethers are used, one for the two anterior anchors and one for the posterior anchor. The filament may form a large elongate loop and one free end of the tether may be released allowing the filament to be pulled through the elbow and back out the proximal end of the catheter thereby releasing the filament from the prosthesis. Or, tension may be released from the tether allowing the elbows to spring open and release from the looped part of the filament.

Moreover, using tethers coupled to the elbows allows the sequence of deployment of the elbows to be controlled by controlling tension on the tethers. For example, all elbows maybe deployed simultaneously, or they may be deployed in a desired sequence. For example, both anterior elbows maybe deployed first simultaneously followed by the posterior elbow. Or the posterior elbow may be deployed first, followed the anterior elbows either both together or one after the other. Or, one anterior elbow may be deployed first, followed by the second anterior elbow, followed by the posterior elbow. Or one anterior elbow may deploy first followed by the posterior elbow followed by the other anterior elbow. Or all three elbows may be deployed simultaneously.

Figure 39A:
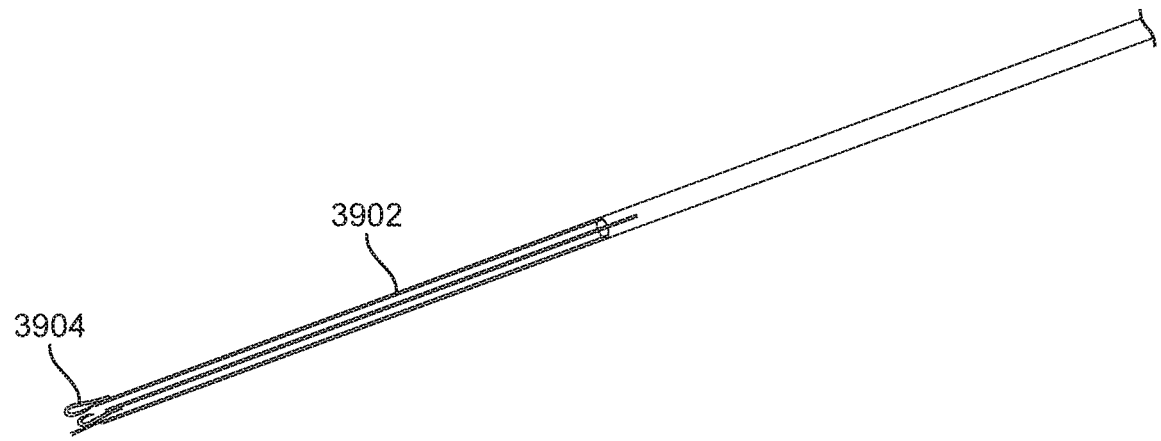
FIGS. 39A-39C show stylets.

In addition to tethers such as sutures, elongate wire filaments may be used to control prosthesis deployment and recapture. For example, in FIG. 39A, three elongate wires 3902 (also referred to as stylets) with looped ends 3904 may extend the length of the catheter and the looped ends 3904 may be coupled to the elbows. Or, the elongate wires may be used and the looped ends 3904 may be coupled to a suture or other filament that is coupled to the elbows. Using elongate suture running the length of the catheter can create significant friction which may make it difficult to manipulate the suture tethers and thus a partial suture and part wire tether may reduce friction and create a more optimal tether.

The elongate wires may extend from an internal catheter running a short distance, most of the distance, or the entire distance of the delivery system to further reduce friction. Or, in other examples the suture may be attached directly to an attachment element on an elbow control catheter.

Figure 39B:
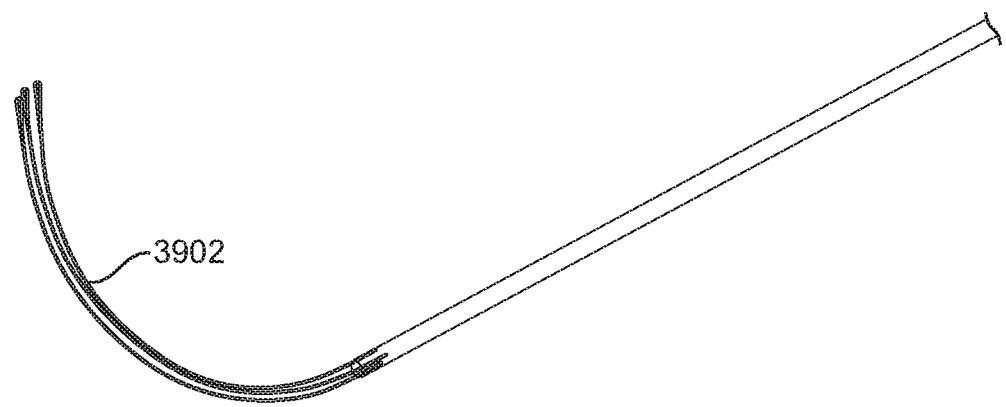
Figure 39C:
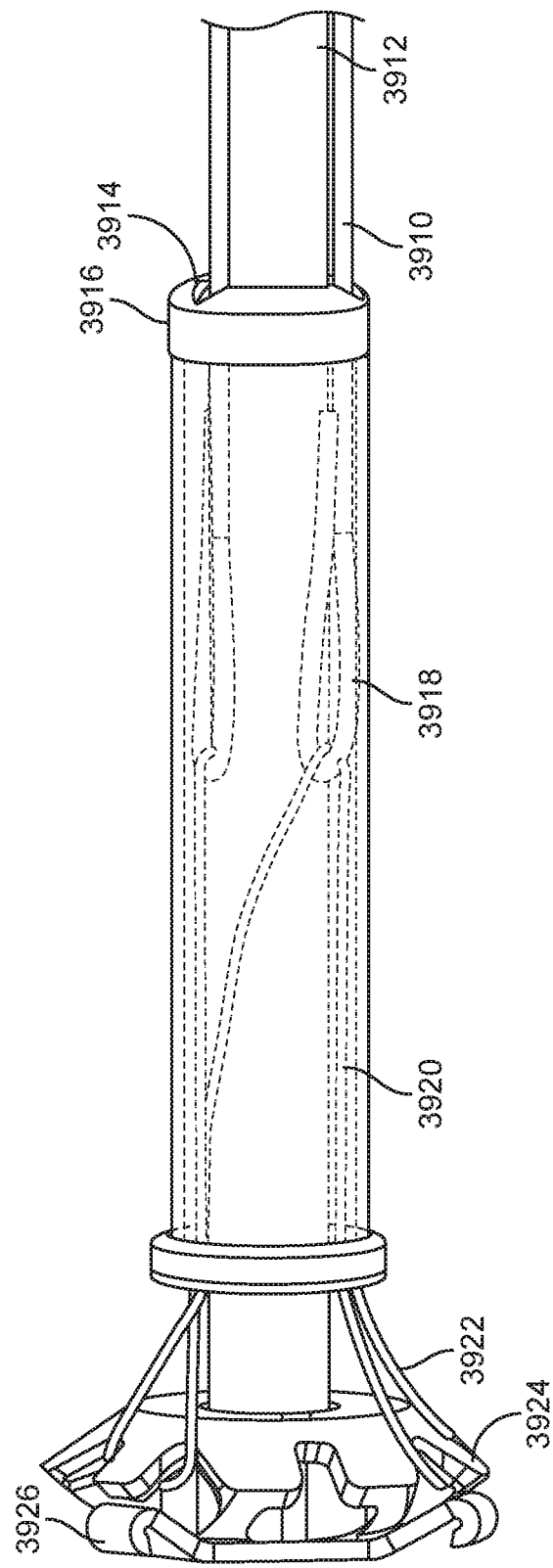

FIG. 39C illustrates an example of sytlets 3910 with looped ends 3918 are coupled to suture filaments 3920. The suture filaments 3920 are looped 3922 around the tabs or posts 3924 on the anchor element to constrain and control an elbow. An optional anchor plate 3926 may also be used and additional disclosure about this element is provided below. A cable guard 3916 having several channels or lumens 3914 extending through the cable guard allow the filaments and/or sytlets to pass through the cable guard which ensures there is no entanglement and also helps to minimize friction. The cable guard 3916 may be disposed over the anchor catheter 3912.

FIG. 39B shows the tethers are flexible and can bend with the catheter during delivery or during steering.

Equal adjustment of tension in tethers may be desirable in order to control deployment or control recapture of the prosthesis. FIG. 40 shows an example of a tension equalizer that may be used with any example of delivery system disclosed herein.

In FIG. 40, the plurality of tethers 4002 are coupled to the anchor element (sometimes also referred to herein as a hub) and then the anchor elbows are coupled to the looped ends of the tethers. And optional anchor plate is coupled to the anchor. This will be described in greater detail below. The tethers may extend along the length of the delivery catheter and converge to a single point 4004 on a proximal portion of the delivery catheter, often in the handle. A tension control mechanism 4006, here a screw winds the tethers around a shaft increasing tension unwinds the tethers from the shaft, decreasing tension. This helps ensure that a uniform tension is applied to each tether.

Figure 41A:
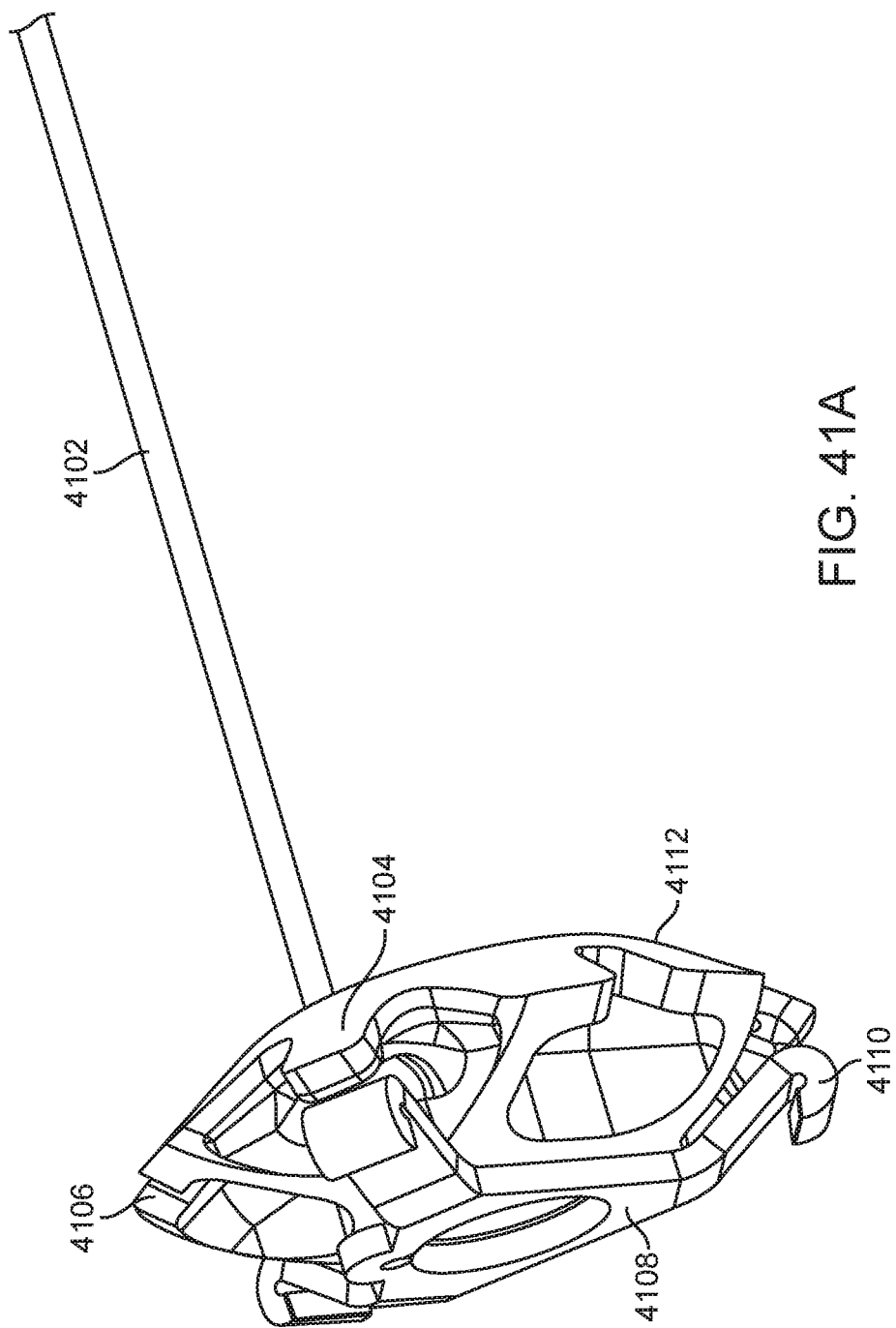
FIGS. 41A-41B show an anchor element and anchor plate.
Figure 41B:
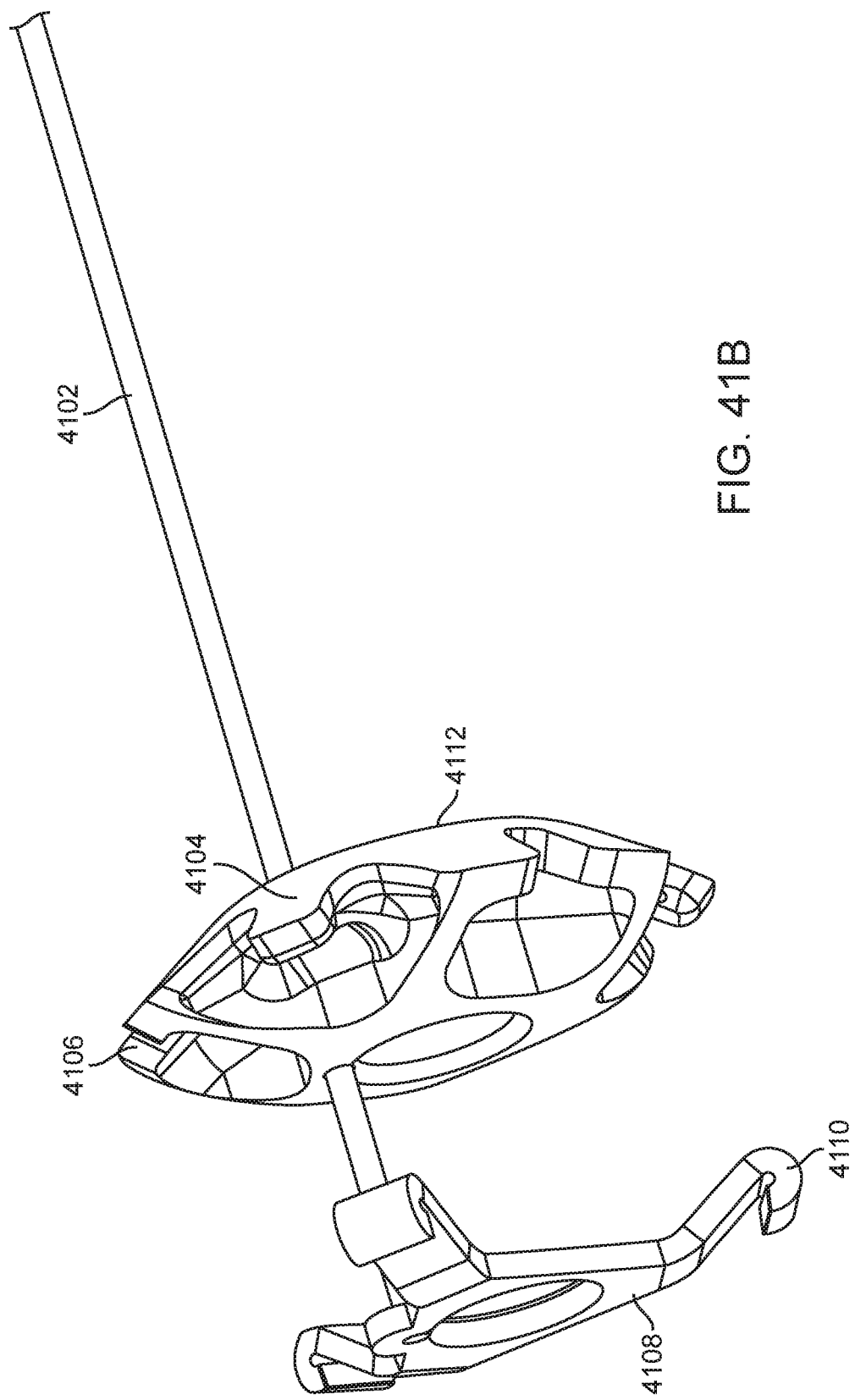

Optionally, in any example, the hub or anchor element may be modified as shown in FIGS. 41A-41B to facilitate capture and release of the commissures as well as the tethers.

FIG. 41A shows the anchor element 4112 (also referred to as a hub) which may be used in any delivery catheter. It is a generally disc-shaped element having a plurality of slanted tabs 4104 that extend radially outward. Additionally, there are slots 4106 which are also slanted. An optional anchor plate 4108 with radially extending arms 4110 that cooperate with the tabs 4104. A push rod 4102 is coupled to the anchor plate.

The tabs and the slots are sloped or slanted downward in the distal direction so that the commissure tabs can easily slide off and disengage from the slots, and similarly so that the looped ends of the tethers can also release from the tabbed regions.

In use, tension is applied to the push rod so that the anchor plate abuts the anchor element and the arms 4110 cooperate with the tabs 4104 to help capture the tethers therebetween, and when the operator wishes to release the tethers, the push rod maybe pushed distally to move the anchor plate away from the anchor element increasing the gap between the arms 4110 and the tabs 4104 to allow the looped ends of the tether to release. In other examples, a small gap remains from between the arms and the tabs and the tether may simply pass through the gap automatically when tension on the tethers is released, therefore the push rod is optional.

FIG. 41B shows the anchor plate 4108 disengaged from the anchor element when the push rod is pushed distally. The push rod may extend along the length of the catheter to the proximal end of the device and it may be actuated by a control on the handle. As discussed previously, the handle may include a hard stop such as those previously discussed above to lock or unlock a control that allows actuation of the push rod or any mechanism that controls engagement of the anchor plate with the anchor.

Optionally in any example with an anchor plate (sometimes also referred to as an elbow retention plate or J-plate) a passive release mechanism includes a spring element that biases the anchor plate against the anchor to hold the filament loops. When the prosthesis self-expands the spring force of the expanding prosthesis overcomes the spring force holding the anchor plate against the anchor and pulls the filament loops out from the anchor permitting release of the elbows. This is in contrast to the active release mechanism in FIG. 41B which uses a push rod.

Soft Edge

A soft edge on the delivery catheter helps minimize tissue trauma and this element may also help facilitate management of the large number of catheter shafts, tethers, wires, or other tubes and rods which may be used in a delivery system.

Figure 42:
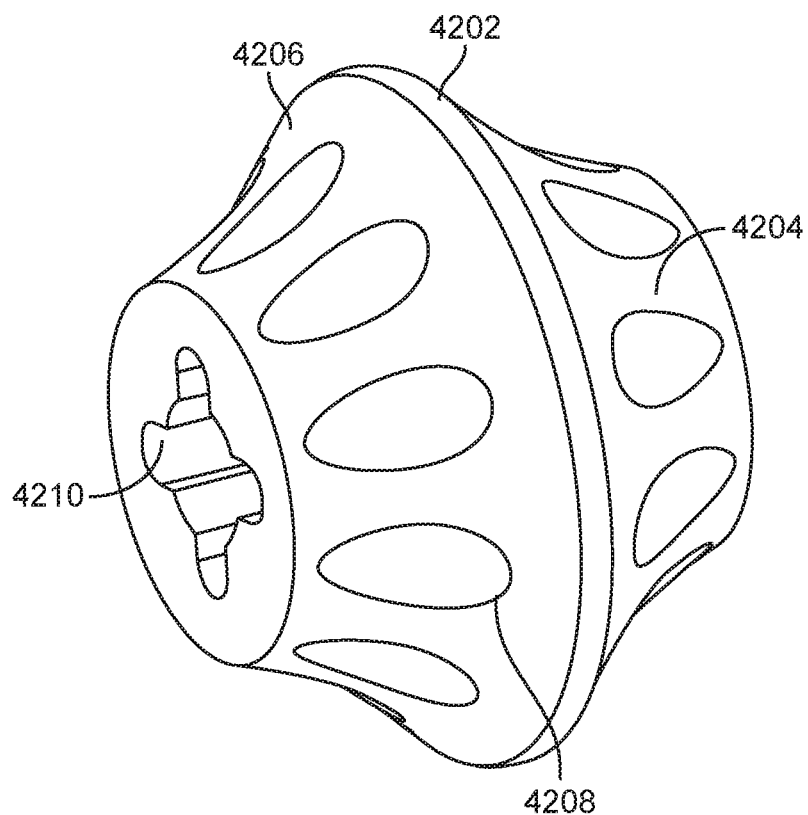
FIG. 42 shows a centering and tether management element.

FIG. 42 shows an example of a soft edge 4202. It may be attached to the centering catheter and provides a soft edge proximal to the capsule/prosthetic valve on the end of the delivery system. This aids in valve retrievability by minimizing risk of damage to patient anatomy.

It is a round disc-like resilient component with a plurality of through holes 4208 that allow the disc to be compressed to a smaller outer diameter since the disc may be larger than the inner diameter of the capsule so it needs to be compressible in order to fit in the capsule. Oversizing the disc accounts for any deformation/flaring of the capsule during tracking, deployment, or resheathing. Both the proximal and distal ends 4204, 4206 are beveled or angled to help center components which interact with the soft edge 4202 and also to facilitate smooth passage of the delivery device thorough a vessel or other anatomy. A central channel 4210 may be formed to allow tethers, or other catheter shafts to pass through the soft edge element. For example, here the central channel is cross shaped with discrete slots separated from one another and sized to accommodate the anchor catheter and any tethers. The soft edge may be disposed over the anchor catheter and may be disposed axially proximal of the capsule that houses the prosthesis. However, this is not limiting and it maybe disposed anywhere along the delivery catheter as desired. The soft edge may be coupled to the next adjacent shaft that is over the anchor catheter.

Other management elements similar to the tether management element may also be used. For example, an annular ring with a plurality of slots on an inner diameter of the ring maybe adjacent of and on a proximal end of the anchor element. Tethers or wires may pass through the annular ring in the slotted regions and this helps prevent entanglement. This element is not illustrated due to its simplicity.

Optional Features

Any of the delivery systems disclosed herein may also include any of the following optional features.

As previously discussed, the commissures are anchored to slots in an anchor element or hub. When a constraint is release, the commissures are free to expand and release from the slots. Optionally in any example, an O-ring or other resilient member may be disposed around the circumference of the anchor element between the commissures and the anchor element so that when the bell element is disposed over the commissures and constrains the commissures, the O-ring will compress. When the bell is removed from the commissures, the commissures will expand out of the slots aided by the resilient O-ring also expanding. Therefore the O-ring helps facilitate release of the commissures from the anchor element.

The anchor catheter may also have an optional steering mechanism. Any of the tethers coupled to the anchor element to control the anchor elbows or additional tethers may be coupled to the anchor element and when tension is applied to those anchors, they will bend or steer the anchor catheter. Opposite tethers may be used to steer the anchor catheter in one direction or the opposite direction depending on which tether is tensioned. Any number of tethers may be used to steer the anchor catheter in any number of directions.

Any example of delivery catheter may also include additional cable organizer elements. For example one, two, three, or more cylindrical elements may be disposed along the anchor catheter with slots, channels or though holes to allow tethers, wires, stylets, or any other filaments to pass through. This keeps the filaments extending in a linear untangled manner along the length of the catheter proximally toward the handle.

NOTES AND EXAMPLES

The following, non-limiting examples, detail certain aspects of the present subject matter to solve the challenges and provide the benefits discussed herein, among others.

Example 1 is a prosthetic delivery system comprising a delivery catheter having a plurality of concentric shafts; an actuator mechanism coupled to one or more of the plurality of concentric shafts, wherein actuation of the actuator mechanism advances or retracts the one or more of the plurality of concentric shafts; and a first stop mechanism operably coupled to the actuation mechanism, wherein the stop mechanism prevents advancement or retraction of the one or more of the plurality of concentric shafts beyond a predetermined position unless the stop mechanism is released thereby allowing full advancement or retraction of the one or more of the plurality of concentric shafts.

Example 2 is the delivery system of Example 1, further comprising a second stop mechanism operably coupled to the actuation mechanism, wherein the second stop mechanism prevents advancement or retraction of another of the plurality of concentric shafts beyond a predetermined position unless the second stop mechanism is released thereby allowing full advancement or retraction of the another of the plurality of concentric shafts.

Example 3 is any of the delivery systems of Examples 1-2, further comprising a second stop mechanism, wherein the first stop mechanism controls deployment of a first anterior anchor tab on the prosthesis, and wherein the second stop mechanism controls deployment of either a second anterior anchor tab or a posterior anchor tab on the prosthesis.

Example 4 is any of the delivery systems of Examples 1-3, wherein the stop mechanism comprises a block having an inner channel shaped to receive a lead screw in a handle of the delivery system, wherein the stop mechanism rotates the block in a first direction so that the inner channel is misaligned with the lead screw in a first position to prevent movement of the lead screw through the channel, and wherein the stop mechanism rotates the block in a second direction opposite the first direction so that the inner channel is registered with the lead screw allowing movement of the lead screw through the channel.

Example 5 is a prosthetic delivery system comprising a delivery catheter having a plurality of concentric shafts; a capsule having a proximal end and a distal end, the capsule sized to hold a prosthesis and operably coupled to at least one of the plurality of shafts; and a chamfer element having a proximal beveled end and a distal beveled end, the distal beveled end engageable with the proximal end of the capsule to provide smooth transition between the capsule and an adjacent shaft, the proximal and distal bevels also configured to center the capsule when engaged therewith or to center at least some of the plurality of concentric shafts when engaged therewith, and wherein the proximal and distal beveled ends are configured to minimize or prevent trauma to tissue as the delivery catheter is advanced or retraced.

Example 6 is the delivery system of Example 5, wherein the chamfer element comprises a plurality of apertures disposed around a perimeter of the chamfer element, the plurality of apertures configured to allow compression and expansion of the chamfer element.

Example 7 is any of the delivery systems of Examples 5-6, wherein the chamfer element comprises an aperture extending through a central portion of the chamfer element, the aperture configured to permit one or more of the plurality of concentric shafts to slidably pass through the aperture, or wherein the aperture is configured to permit one or more tethers to slidably pass through the aperture.

Example 8 is a prosthetic delivery system comprising a delivery catheter having a plurality of concentric shafts, wherein the plurality of concentric shafts comprises an anchor catheter having an anchor element adjacent a distal end thereof, the anchor element configured to engage and hold anchors on a prosthesis.

Example 9 is the delivery system of Example 8, wherein the anchor element comprises a plurality of tether pegs configured to engage and hold one or more tethers.

Example 10 is any of the delivery systems of Examples 8-9, wherein the anchor element comprises a plurality of slots configured to receive the anchors on the prosthesis.

Example 11 is any of the delivery systems of Examples 8-10, wherein a surface surrounding at least some of the plurality of slots is inclined to facilitate release of the anchors on the prosthesis from the plurality of slots.

Example 12 is any of the delivery systems of Examples 8-11, further comprising an anchor shaft guide element proximal of the anchor element, the anchor shaft guide comprising a plurality of internal slots on an inner perimeter of the anchor shaft guide, the plurality of internal slots configured to receive tethers.

Example 13 is any of the delivery systems of Examples 8-12, wherein the anchor element comprises a resilient material configured to expand and contract, wherein in the expanded configuration, the anchors on the prosthesis are pushed radially outward away from the slots.

Example 14 is any of the delivery systems of Examples 8-13, further comprising one or more steering tethers coupled to the anchor element, wherein tension applied to the steering tethers steers the anchor catheter.

Example 15 is any of the delivery systems of Examples 8-14, further comprising a plurality of tethers coupled to the anchor element and the anchors on the prosthesis, the plurality of tethers configured to control deployment of one or more elbow regions on the anchors of the prosthesis.

Example 16 is any of the delivery systems of Examples 8-15, further comprising a capsule and a plurality of tethers, the capsule coupled to at least one of the plurality of concentric shafts and configured to carry the prosthesis, wherein the plurality of tethers are configured to control deployment of one or more elbow regions on the anchors of the prosthesis, and wherein the capsule constrains release of the plurality of tethers from the anchor when the anchor is disposed in the capsule.

Example 17 is any of the delivery systems of Examples 8-16, further comprising a plurality of tethers releasably coupled to a plurality of elbow regions on the anchors of the prosthesis, and wherein actuation of the plurality of tethers controls displacement of the plurality of elbow regions.

Example 18 is any of the delivery systems of Examples 8-17, further comprising a stylet coupled to at least some of the plurality of tethers.

Example 19 is any of the delivery systems of Examples 8-18, wherein the anchors on the prosthesis are configured to reengage with the anchor element when tension is applied to the plurality of tethers after the anchors on the prosthesis are radially expanded outward.

Example 20 is any of the delivery systems in Examples 8-19, further comprising a guide element coupled to the anchor catheter and disposed proximal of the anchor element, the guide element having a plurality of slots therein or channels therethrough, the plurality of slots or channels configures to guide wires, filaments, stylets passing therethrough.

Example 21 is any of the delivery systems in Examples 8-20, further comprising a plurality of tethers coupled to the anchors of the prosthesis to hold the prosthesis, wherein the plurality of tethers converge together onto a tension equalizer element configured to apply equal tension to each of the plurality of tethers.

Example 22 is any of the delivery systems in Examples 8-21, further comprising an elbow retention plate adjacent the anchor element.

Example 23 is a method of delivering a prosthesis, said method comprising advancing a delivery catheter carrying a prosthesis to a target treatment area; actuating an actuator on the delivery catheter to advance or retract a shaft in the delivery catheter thereby removing a constraint from the prosthesis until a stop mechanism in the delivery catheter prevents further advancement or retraction of the shaft beyond a predetermined position; and releasing the stop mechanism thereby allowing further advancement or retraction of the shaft beyond the predetermined position.

Example 24 is the method of Example 23, further comprising: further actuating the actuator to advance or retract a second shaft in the delivery catheter thereby removing a second constraint from the prosthesis until a second stop mechanism in the delivery catheter prevents further advancement or retraction of the second shaft beyond a second predetermined position; and releasing the second stop mechanism thereby allowing further advancement or retraction of the second shaft beyond the second predetermined position.

Example 25 is the method of any of Examples 23-24, wherein the delivery catheter further comprises a second stop mechanism, the method further comprising wherein releasing the stop mechanism and further movement of the shaft removes a constraint from the prosthesis thereby allowing radial expansion of a first ventricular anchor tab on the prosthesis; and wherein releasing the second stop mechanism allows radial expansion of a second ventricular anchor tab or a posterior anchor tab on the prosthesis.

Example 26 is a method for delivering a prosthesis, said method comprising providing a prosthesis carried on a delivery catheter; at least partially deploying the prosthesis from the delivery catheter; and retrieving the prosthesis back into the delivery catheter by actuating a plurality of filaments coupled to the prosthesis.

Example 27 is the method of Example 26, further comprising steering the delivery catheter by actuating a tether coupled to the delivery catheter.

In Example 28, the apparatuses or methods of any one or any combination of Examples 1-27 can optionally be configured such that all elements or options recited are available to use or selection from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A method for delivering a prosthesis, said method comprising:
providing a prosthesis carried on a delivery catheter within a capsule, the delivery catheter comprising:
an anchor catheter connected to the prosthesis;
a guidewire catheter extending concentrically with the anchor catheter to connect to the capsule; and
a steerable catheter at least partially surrounding the anchor catheter and the guidewire catheter;
at least partially deploying the prosthesis from the capsule by actuating the guidewire catheter to cause translation between the capsule and the prosthesis; and
retrieving the prosthesis back into the capsule of the delivery catheter by actuating a plurality of filaments coupled to the prosthesis;
wherein the capsule comprises proximal and distal sections that can be axially translated away from each other to deploy the prosthesis, and the proximal and distal sections of the capsule have an outer profile size that is larger than the delivery catheter.

2. The method of claim 1, further comprising steering the delivery catheter by actuating a tether coupled to the delivery catheter.

3. The method of claim 1, further comprising adjusting tension on a plurality of stylets connected to the plurality of filaments to control deployment of the prosthesis from the delivery catheter.

4. The method of claim 1, wherein retrieving the prosthesis back into the capsule of the delivery catheter by actuating a plurality of filaments coupled to the prosthesis comprises operating a tension equalizer to simultaneously control tension on each of the plurality of filaments.

5. The method of claim 1, wherein at least partially deploying the prosthesis from the capsule comprises fully deploying elbows of ventricular anchors extending from the prosthesis such that the elbows expand radially outward of the capsule by moving the capsule distally with the guidewire catheter.

6. The method of claim 5, wherein retrieving the prosthesis back into the capsule of the delivery catheter by actuating the plurality of filaments coupled to the prosthesis comprises pulling the elbows radially inward of the capsule by pulling the plurality of filaments proximally, wherein proximal pulling of the plurality of filaments produces radial movement of the elbows that is discrete from axial movement of the prosthesis.

7. The method of claim 5, wherein the plurality of filaments are attached to the elbows via a single tether extending through loops of each filament and the elbows.

8. The method of claim 1, further comprising releasing the plurality of filaments to allow full deployment of the prosthesis.

9. The method of claim 8, wherein releasing the plurality of filaments comprises releasing tension in the plurality of filaments such that opening of the prosthesis via spring action pulls the plurality of filaments from the prosthesis.

10. The method of claim 8, wherein all of the plurality of filaments are connected in a single loop and releasing the plurality of filaments comprises pulling the single loop from the prosthesis.

11. The method of claim 8, wherein:
the delivery catheter comprises a handle located at a proximal end of the steerable catheter; and
the capsule is located distally of the steerable catheter and axially translatable relative to the steerable catheter.

12. The method of claim 8, wherein releasing the plurality of filaments comprises:
moving an anchor plate connected to the prosthesis away from a plurality of slanted tabs around which each of the plurality of filaments is attached, the plurality of slanted tabs extending from an anchor element attached to the delivery catheter, wherein each of the plurality of filaments is trapped between one of the plurality of slanted tabs and the anchor plate;
expanding the prosthesis via spring action to pull the plurality of filaments along the plurality of slanted tabs; and
allowing each of the plurality of filaments to slip off a slanted tab of the plurality of slanted tabs at a gap between the plurality of slanted tabs and the anchor plate due to the spring action.

13. The method of claim 12, wherein pushing the anchor plate connected to the prosthesis away from each of the slanted tabs to release the plurality of filaments comprises actively pushing the anchor plate with a push rod.

14. The method of claim 12, wherein pushing the anchor plate connected to the prosthesis away from each of the slanted tabs to release the plurality of filaments comprises passively pushing the anchor plate with a spring.

15. The method of claim 1, wherein the capsule comprises a rigid body defining an enclosure having an internal space in which the prosthesis is disposed separated from an internal space of the steerable catheter.

16. A method for delivering a mitral valve prosthesis, said method comprising:
   partially deploying the mitral valve prosthesis while being carried on a delivery catheter by sliding a sheath away from the mitral valve prosthesis to progressively expose an anchor portion of the mitral valve prosthesis;
   deploying from the sheath elbows of ventricular anchors extending from the anchor portion of the mitral valve prosthesis by allowing the elbows to radially expand beyond the anchor portion and the sheath independent of axial movement of the anchor portion; and
   applying tension to a plurality of filaments attached to the elbows to collapse the elbows radially inward toward the anchor portion independent of axial movement of the anchor portion and then sliding the sheath toward the mitral valve prosthesis to retrieve the mitral valve prosthesis back into the sheath, wherein the plurality of filaments are attached to the elbows via a single tether extending through loops of each filament and the elbows.

17. The method of claim 16, further comprising:
   fully deploying the mitral valve prosthesis from the catheter;
   releasing tension on the plurality of filaments; and
   detaching the delivery catheter form the mitral valve prosthesis.

18. The method of claim 17, further comprising allowing the mitral valve prosthesis to spring open to detach the plurality of filaments from the mitral valve prosthesis, wherein the elbows comprise inferior portions of the ventricular anchors adjacent to connection points of the ventricular anchors with a ventricular skirt extending from the anchor portion, and wherein the ventricular anchors are configured to spring radially outward of the anchor portion of the mitral valve prosthesis when deployed.

19. The method of claim 17, further comprising operating an anchor device to allow the plurality of filaments to detach from the mitral valve prosthesis.

20. The method of claim 17, wherein releasing tension on the plurality of filaments comprises:
   moving an anchor plate away from a plurality of slanted tabs around which each of the plurality of filaments is attached, the plurality of slanted tabs extending from an anchor element attached to the delivery catheter, wherein each of the plurality of filaments is trapped between one of the plurality of slanted tabs and the anchor plate;
   expanding the mitral valve prosthesis via spring action to pull the plurality of filaments along the plurality of slanted tabs; and
   allowing each of the plurality of filaments to slip off a slanted tab of the plurality of slanted tabs at a gap between the plurality of slanted tabs and the anchor plate due to the spring action.

21. The method of claim 16, wherein applying tension to a plurality of filaments attached to the elbows comprises pulling the elbows radially toward a longitudinal axis of the delivery catheter with radially extending portions the plurality of filaments.

22. The method of claim 16, wherein applying tension to a plurality of filaments attached to the elbows comprises operating an equalizer device to apply tension to each of the plurality of filaments simultaneously.

* * * * *